(12) United States Patent
Lopez et al.

(10) Patent No.: US 9,511,989 B2
(45) Date of Patent: Dec. 6, 2016

(54) FLUID TRANSFER DEVICES AND METHODS OF USE

(71) Applicant: ICU MEDICAL, INC., San Clemente, CA (US)

(72) Inventors: George A. Lopez, Laguna Beach, CA (US); Thomas F. Fangrow, Mission Viejo, CA (US); Peter Leissling, Schalksmuehle (DE); Matthias Janssen, Meinerzhagen (DE)

(73) Assignee: ICU Medical, Inc., San Clemente, CA (US)

( * ) Notice: Subject to any disclaimer, the term of this patent is extended or adjusted under 35 U.S.C. 154(b) by 230 days.

(21) Appl. No.: 14/189,920

(22) Filed: Feb. 25, 2014

(65) Prior Publication Data

US 2014/0174596 A1    Jun. 26, 2014

Related U.S. Application Data

(63) Continuation of application No. 13/937,127, filed on Jul. 8, 2013, now Pat. No. 8,973,622, which is a continuation of application No. 12/845,548, filed on Jul. 28, 2010, now Pat. No. 8,522,832.

(60) Provisional application No. 61/229,701, filed on Jul. 29, 2009, provisional application No. 61/354,648, filed on Jun. 14, 2010.

(51) Int. Cl.
  *B67D 3/00* (2006.01)
  *A61J 1/20* (2006.01)

(52) U.S. Cl.
  CPC ............ *B67D 3/0003* (2013.01); *A61J 1/2058* (2015.05); *A61J 1/2062* (2015.05); *A61J 1/2089* (2013.01); *A61J 1/2096* (2013.01); *Y10S 604/905* (2013.01); *Y10T 29/49826* (2015.01)

(58) Field of Classification Search
  CPC ..... A61J 1/2062; A61J 1/2058; A61M 39/26
  USPC ............... 141/9, 23–27, 301–302, 329–330; 604/407, 408, 410, 411, 416, 905
  See application file for complete search history.

(56) References Cited

U.S. PATENT DOCUMENTS

| 1,923,501 A | 8/1933 | Perry |
| 4,005,710 A | 2/1977 | Zeddies et al. |

(Continued)

FOREIGN PATENT DOCUMENTS

| DE | 20 2004 014 868 | 11/2004 |
| EP | 1 563 819 | 8/2005 |

(Continued)

OTHER PUBLICATIONS

Autoyec 50, from KRZ, Dec. 6, 2007.

(Continued)

*Primary Examiner* — Mark A Laurenzi
*Assistant Examiner* — Timothy P Kelly
(74) *Attorney, Agent, or Firm* — Knobbe, Martens, Olson & Bear, LLP

(57) ABSTRACT

Some embodiments disclosed herein related to a device for transferring precise amounts of fluid from at least one source container to a at least one target container. In some embodiments, the fluid is first transferred from the source container (e.g., a vial) through a connector to an intermediate measuring container (e.g., a syringe). In some embodiments air can pass through an air inlet and enter the vial to compensate for the volume of fluid withdrawn from the vial. An air check valve or a bag or a filter can prevent the fluid from escaping through the air inlet. The precisely measured amount of fluid can then be transferred from the intermediate measuring container to the target container (e.g., an IV bag). In some embodiments the connector can include a source check valve and a target check valve to direct fluid first from the source container to the intermediate measuring container and then from the intermediate measuring container to the target container. Some embodiments of the device can include a motor and a controller for automatically actuating a plunger of the syringe to transfer the desired amount of fluid.

23 Claims, 107 Drawing Sheets

(56) References Cited

U.S. PATENT DOCUMENTS

| | | |
|---|---|---|
| 4,084,606 A | 4/1978 | Mittleman |
| 4,190,048 A | 2/1980 | Sampson |
| 4,306,705 A | 12/1981 | Svensson |
| 4,559,043 A | 12/1985 | Whitehouse et al. |
| 4,561,856 A | 12/1985 | Cochran |
| 4,666,429 A | 5/1987 | Stone |
| 4,670,007 A | 6/1987 | Wheeldon et al. |
| 4,683,916 A | 8/1987 | Raines |
| 4,755,172 A | 7/1988 | Baldwin |
| 4,778,450 A | 10/1988 | Kamen |
| 4,819,684 A | 4/1989 | Zaugg et al. |
| 4,863,429 A | 9/1989 | Baldwin |
| 4,922,975 A | 5/1990 | Polaschegg |
| 4,969,874 A | 11/1990 | Michel et al. |
| 4,976,590 A | 12/1990 | Baldwin |
| 4,995,268 A | 2/1991 | Ash et al. |
| 5,024,347 A | 6/1991 | Baldwin |
| 5,037,390 A | 8/1991 | Raines et al. |
| 5,114,580 A | 5/1992 | Ahmad et al. |
| 5,176,658 A | 1/1993 | Ranford |
| 5,256,155 A | 10/1993 | Yerlikaya et al. |
| 5,300,044 A | 4/1994 | Classey et al. |
| 5,334,211 A | 8/1994 | Shiber |
| 5,336,201 A | 8/1994 | von der Decken |
| 5,423,791 A | 6/1995 | Bartlett |
| 5,431,201 A | 7/1995 | Torchia et al. |
| 5,439,451 A | 8/1995 | Collinson et al. |
| 5,609,572 A | 3/1997 | Lang |
| 5,645,538 A | 7/1997 | Richmond |
| 5,676,346 A | 10/1997 | Leinsing |
| 5,685,866 A | 11/1997 | Lopez |
| 5,782,816 A | 7/1998 | Werschmidt et al. |
| 5,807,312 A | 9/1998 | Dzwonkiewicz |
| 5,871,500 A | 2/1999 | Jepson et al. |
| 5,897,526 A | 4/1999 | Vaillancourt |
| 5,904,666 A | 5/1999 | DeDecker et al. |
| 5,935,106 A | 8/1999 | Olsen |
| 5,947,951 A | 9/1999 | Ortiz et al. |
| 5,968,014 A | 10/1999 | Neftel et al. |
| 5,989,237 A | 11/1999 | Fowles et al. |
| 6,059,747 A | 5/2000 | Bruggeman et al. |
| 6,110,153 A | 8/2000 | Davis et al. |
| RE36,871 E | 9/2000 | Epstein et al. |
| 6,123,685 A | 9/2000 | Reynolds |
| 6,132,404 A | 10/2000 | Lopez |
| 6,152,900 A | 11/2000 | Mayer |
| 6,179,823 B1 | 1/2001 | Niedospial, Jr. |
| 6,221,041 B1 | 4/2001 | Russo |
| 6,245,048 B1 | 6/2001 | Fangrow, Jr. et al. |
| 6,302,864 B1 | 10/2001 | Nowosielski |
| 6,425,497 B1 | 7/2002 | Chu et al. |
| 6,474,375 B2 | 11/2002 | Spero et al. |
| 6,485,472 B1 | 11/2002 | Richmond |
| 6,585,229 B2 | 7/2003 | Cote, Sr. et al. |
| 6,590,167 B2 | 7/2003 | Clare |
| 6,599,273 B1 | 7/2003 | Lopez |
| 6,623,455 B2 | 9/2003 | Small et al. |
| 6,629,956 B1 | 10/2003 | Polidoro et al. |
| 6,651,956 B2 | 11/2003 | Miller |
| 6,663,586 B2 | 12/2003 | Verkaart et al. |
| 6,689,108 B2 | 2/2004 | Lavi et al. |
| 6,726,672 B1 | 4/2004 | Hanly et al. |
| 6,793,651 B1 | 9/2004 | Bennett et al. |
| 6,813,868 B2 | 11/2004 | Baldwin et al. |
| 6,854,620 B2 | 2/2005 | Ramet |
| 6,877,530 B2 | 4/2005 | Osborne et al. |
| 6,908,459 B2 | 6/2005 | Harding et al. |
| 6,915,823 B2 | 7/2005 | Osborne et al. |
| 6,948,522 B2 | 9/2005 | Newbrough et al. |
| 6,953,450 B2 | 10/2005 | Baldwin et al. |
| 6,985,870 B2 | 1/2006 | Martucci et al. |
| 6,991,002 B2 | 1/2006 | Osborne et al. |
| 6,994,315 B2 | 2/2006 | Ryan et al. |
| 7,017,623 B2 | 3/2006 | Tribble et al. |
| 7,117,902 B2 | 10/2006 | Osborne |
| 7,128,105 B2 | 10/2006 | Tribble et al. |
| 7,163,035 B2 | 1/2007 | Khan et al. |
| 7,194,336 B2 | 3/2007 | DiGianfilippo et al. |
| 7,317,967 B2 | 1/2008 | DiGianfilippo et al. |
| 7,343,224 B2 | 3/2008 | DiGianfilippo et al. |
| 7,343,943 B2 | 3/2008 | Khan et al. |
| 7,351,226 B1 | 4/2008 | Herskowitz |
| 7,392,638 B2 | 7/2008 | Baldwin et al. |
| 7,396,051 B2 | 7/2008 | Baldwin et al. |
| 7,418,981 B2 | 9/2008 | Baker et al. |
| 7,442,186 B2 | 10/2008 | Blomquist |
| 7,499,581 B2 | 3/2009 | Tribble et al. |
| 7,538,858 B2 | 5/2009 | Mackey |
| 7,566,326 B2 | 7/2009 | Duchon et al. |
| 7,610,115 B2 | 10/2009 | Rob et al. |
| 7,654,976 B2 | 2/2010 | Peterson et al. |
| 7,681,606 B2 | 3/2010 | Khan et al. |
| 7,703,483 B2 | 4/2010 | Hartman et al. |
| 7,789,850 B2 | 9/2010 | Roger |
| 7,814,731 B2 | 10/2010 | Bender et al. |
| 7,850,051 B2 | 12/2010 | Py et al. |
| 7,882,863 B2 | 2/2011 | Pestotnik et al. |
| 7,900,658 B2 | 3/2011 | Osborne et al. |
| 7,913,720 B2 | 3/2011 | Tribble et al. |
| 7,967,202 B2 | 6/2011 | Durrell et al. |
| 7,981,381 B2 | 7/2011 | Lurvey et al. |
| 7,997,304 B2 | 8/2011 | Ranalletta et al. |
| 8,091,860 B2 | 1/2012 | Thompson et al. |
| 8,104,644 B2 | 1/2012 | Py et al. |
| 8,140,351 B2 | 3/2012 | Tribble et al. |
| 8,151,835 B2 | 4/2012 | Khan et al. |
| 8,162,903 B2 | 4/2012 | Reilly et al. |
| 8,220,504 B2 | 7/2012 | Hartman et al. |
| 8,225,824 B2 | 7/2012 | Eliuk et al. |
| 8,267,912 B2 | 9/2012 | Ferris |
| 8,328,082 B1 | 12/2012 | Bochenko et al. |
| 8,414,554 B2 | 4/2013 | Garfield et al. |
| 8,425,487 B2 | 4/2013 | Beiriger et al. |
| 8,522,832 B2 | 9/2013 | Lopez et al. |
| 8,551,037 B2 | 10/2013 | Suchecki et al. |
| 8,562,584 B2 | 10/2013 | Beiriger et al. |
| 8,567,235 B2 | 10/2013 | Bojan et al. |
| 8,602,067 B2 | 12/2013 | Kuhni et al. |
| 8,679,075 B2 | 3/2014 | Lurvey et al. |
| 8,720,496 B2 | 5/2014 | Huwiler et al. |
| 8,926,554 B2 | 1/2015 | Okuda et al. |
| 8,973,622 B2 | 3/2015 | Lopez et al. |
| 9,043,019 B2 | 5/2015 | Eliuk et al. |
| 9,056,164 B2 | 6/2015 | Tate et al. |
| 9,057,370 B2 | 6/2015 | Mundt et al. |
| 2002/0179544 A1 | 12/2002 | Johnson et al. |
| 2004/0035743 A1 | 2/2004 | Tighe et al. |
| 2004/0087888 A1 | 5/2004 | Digianfilippo et al. |
| 2004/0116891 A1 | 6/2004 | Curutcharry |
| 2005/0059952 A1 | 3/2005 | Giuliano et al. |
| 2005/0096627 A1 | 5/2005 | Howard |
| 2005/0131357 A1 | 6/2005 | Denton et al. |
| 2005/0230575 A1 | 10/2005 | Zelenski et al. |
| 2005/0252574 A1 | 11/2005 | Khan et al. |
| 2006/0064053 A1 | 3/2006 | Bollish et al. |
| 2006/0259195 A1 | 11/2006 | Eliuk et al. |
| 2007/0007478 A1 | 1/2007 | Leinsing et al. |
| 2007/0088252 A1 | 4/2007 | Pestotnik et al. |
| 2007/0106244 A1 | 5/2007 | Mosler et al. |
| 2008/0065006 A1 | 3/2008 | Roger et al. |
| 2008/0114328 A1 | 5/2008 | Doherty et al. |
| 2008/0125897 A1 | 5/2008 | DiGianfilippo et al. |
| 2008/0169043 A1 | 7/2008 | Osborne et al. |
| 2008/0169044 A1 | 7/2008 | Osborne et al. |
| 2008/0177222 A1 | 7/2008 | Roger |
| 2008/0195416 A1 | 8/2008 | Tribble et al. |
| 2008/0199353 A1 | 8/2008 | Mlodzinski et al. |
| 2008/0287920 A1 | 11/2008 | Fangrow et al. |
| 2009/0012449 A1 | 1/2009 | Lee et al. |
| 2009/0050216 A1 | 2/2009 | Trocki et al. |
| 2009/0067973 A1 | 3/2009 | Eliuk et al. |
| 2009/0069743 A1 | 3/2009 | Krishnamoorthy et al. |
| 2009/0082649 A1 | 3/2009 | Muller et al. |
| 2009/0088687 A1 | 4/2009 | Yardimci et al. |

(56) References Cited

U.S. PATENT DOCUMENTS

| | | |
|---|---|---|
| 2009/0099547 A1 | 4/2009 | Radmer |
| 2009/0101576 A1 | 4/2009 | Rohde et al. |
| 2009/0126825 A1 | 5/2009 | Eliuk et al. |
| 2009/0145509 A1 | 6/2009 | Baker et al. |
| 2009/0149743 A1 | 6/2009 | Barron et al. |
| 2009/0163860 A1 | 6/2009 | Patrick et al. |
| 2009/0177149 A1 | 7/2009 | Childers et al. |
| 2009/0198215 A1 | 8/2009 | Chong et al. |
| 2009/0254031 A1 | 10/2009 | Lee |
| 2009/0306621 A1 | 12/2009 | Thome, Jr. et al. |
| 2010/0049157 A1 | 2/2010 | Fangrow |
| 2010/0245056 A1 | 9/2010 | Braun et al. |
| 2010/0276034 A1 | 11/2010 | Gonnelli et al. |
| 2010/0280430 A1 | 11/2010 | Caleffi et al. |
| 2011/0062703 A1 | 3/2011 | Lopez et al. |
| 2011/0087164 A1 | 4/2011 | Mosler et al. |
| 2011/0112501 A1 | 5/2011 | Garfield et al. |
| 2011/0178493 A1 | 7/2011 | Okiyama |
| 2011/0196304 A1 | 8/2011 | Kramer et al. |
| 2012/0041391 A1 | 2/2012 | Fangrow et al. |
| 2012/0078091 A1 | 3/2012 | Suchecki et al. |
| 2012/0197184 A1 | 8/2012 | Okuda et al. |
| 2013/0006214 A1 | 1/2013 | Garfield et al. |
| 2013/0292002 A1 | 11/2013 | Lopez |
| 2014/0124092 A1 | 5/2014 | Gonnelli et al. |
| 2014/0299221 A1 | 10/2014 | Lopez |
| 2015/0068640 A1 | 3/2015 | Garfield et al. |
| 2015/0101707 A1 | 4/2015 | Ranalletta et al. |
| 2015/0161354 A1 | 6/2015 | Blomquist |
| 2015/0283322 A1 | 10/2015 | Hachey et al. |

FOREIGN PATENT DOCUMENTS

| | | |
|---|---|---|
| EP | 1 997 471 | 12/2008 |
| JP | 2002-355318 | 12/2002 |
| JP | 2003-144546 | 5/2003 |
| WO | WO 97/14493 | 4/1997 |
| WO | WO 99/63547 | 12/1999 |
| WO | WO 01/03757 | 1/2001 |
| WO | WO 2005/123162 | 12/2005 |
| WO | WO 2007/061424 | 5/2007 |
| WO | WO 2007/079305 | 7/2007 |
| WO | WO 2008/128074 | 10/2008 |
| WO | WO 2013/096911 | 6/2013 |

OTHER PUBLICATIONS

Cato (Computer Aided Therapy for Oncology)—Reference Manual—Vienna, May 2005, 255 pgs.
CytoCare, by Health Robotics, Brochure, Date Unknown, downloaded on May 25, 2012 from http://www.health-robotics.com/smartedit/downloads/en/cytocare7.pdf, 6 pages.
Exacta-Mix 2400, from Baxa, which appears to have a date of 2007, 2 pages.
Flickinger, Bruce, "Misperceptions Cloud the Issue of Sterile Drug Compounding," Jun. 2007.
Fox, Brent I., "Pharmacy Automation and Technology: Automated Intravenous Preparation: Robots for the Pharmacy," Hospital Pharmacy, vol. 44, Mar. 2009, pp. 255-257.
Integra Brochure, from Eurospital, Brochure acquired in Mar. 2012.
International Report on Patentability and Written Opinion re PCT Application No. PCT/US2010/043451, mailed Feb. 9, 2012.
International Search Report and Written Opinion re PCT Application No. PCT/US2010/043451, mailed Nov. 30, 2011.
International Search Report and Written Opinion re PCT Application No. PCT/US2012/071493, mailed Feb. 19, 2013.
Pinnacle TPN Management System, from B Braun, downloaded May 5, 2009 from http://www.bbraunusa.com/index.cfm?uuid=7386ADF065B05CD0D22AF700339AA4092, 1 page.
Product detail for "NAMIC® Closed Fluid Systems" from Navilyst Medical, downloaded on May 11, 2010 from http://www.navilystmedical.com/Products/index.cfm/19, 2 pages.
Product detail for "RapidFill™ Automated Syringe Filler," from Baxa, downloaded on Mar. 31, 2010 from http://www.baxa.com/PharmacyProducts/AutomatedFillingSystems/ProductDetail/?id=B1, 2 pages.
Product detail for "Summit Medical DirectFlow" micro infusion extension set from Summit Medical Technologies, downloaded on May 10, 2010 from http://summitmedtech.com/p6line.php, 1 page.
Riva, downloaded in Apr. 2009 from http://www.rivasystem.com, 6 pages.
Smith, "Lifesaving Cancer Drugs May Put Workers' Lives at Risk," downloaded on Jul. 12, 2010 from http://www.msnbc.msn.com/id/38114586/ns/health-cancer, 7 pages.
Technical Data sheet for Analog Amplifiers Type VA, models V8-C and V8-D, STM Sensors dated Dec. 2007, 4 pages.
Technical Data sheet for Through Beam Sensors Type G2, 1480 nm, STM Sensors dated Dec. 2009, 2 pages.
Technical Data sheet for Through Beam Sensors Type G2, 645 nm, STM Sensors dated Sep. 2008, 2 pages.
User Guide for medOC 1xx Basic, Neo Care Medical Products GmbH, Version 06.2008, 23 pages.
User Manual for medOC 3xx /6xx /8xx, Neo Care Medical Products GmbH, Version 05.2008, 44 pages.
U.S. Appl. No. 15/156,257, filed May 16, 2016, Fangrow, Including its prosecution history.
Spiros—Closed Male Connector, published Jan. 22, 2008.
Neo Care Medical Products: Product Catalog, dated Jun. 2008, in 38 pages.
B. Braun Medical Inc. Two-Bag Irrigation Set, Two Non-vented Spikes, dated Jul. 2012, in 1 page.
Clearlink Needleless IV Access System, dated Aug. 2007, in 2 pages.
International Search Report and Written Opinion for International PCT Patent Application No. PCT/US2014/065972, dated Feb. 24, 2015.
SmartSite Safety Disposables, with copyright notice dated 2004.
International Search Report and Written Opinion for International PCT Patent Application No. PCT/US2014/066645, dated Apr. 15, 2015.
International Search Report and Written Opinion for International PCT Patent Application No. PCT/US2015/040174, dated Dec. 30, 2015.

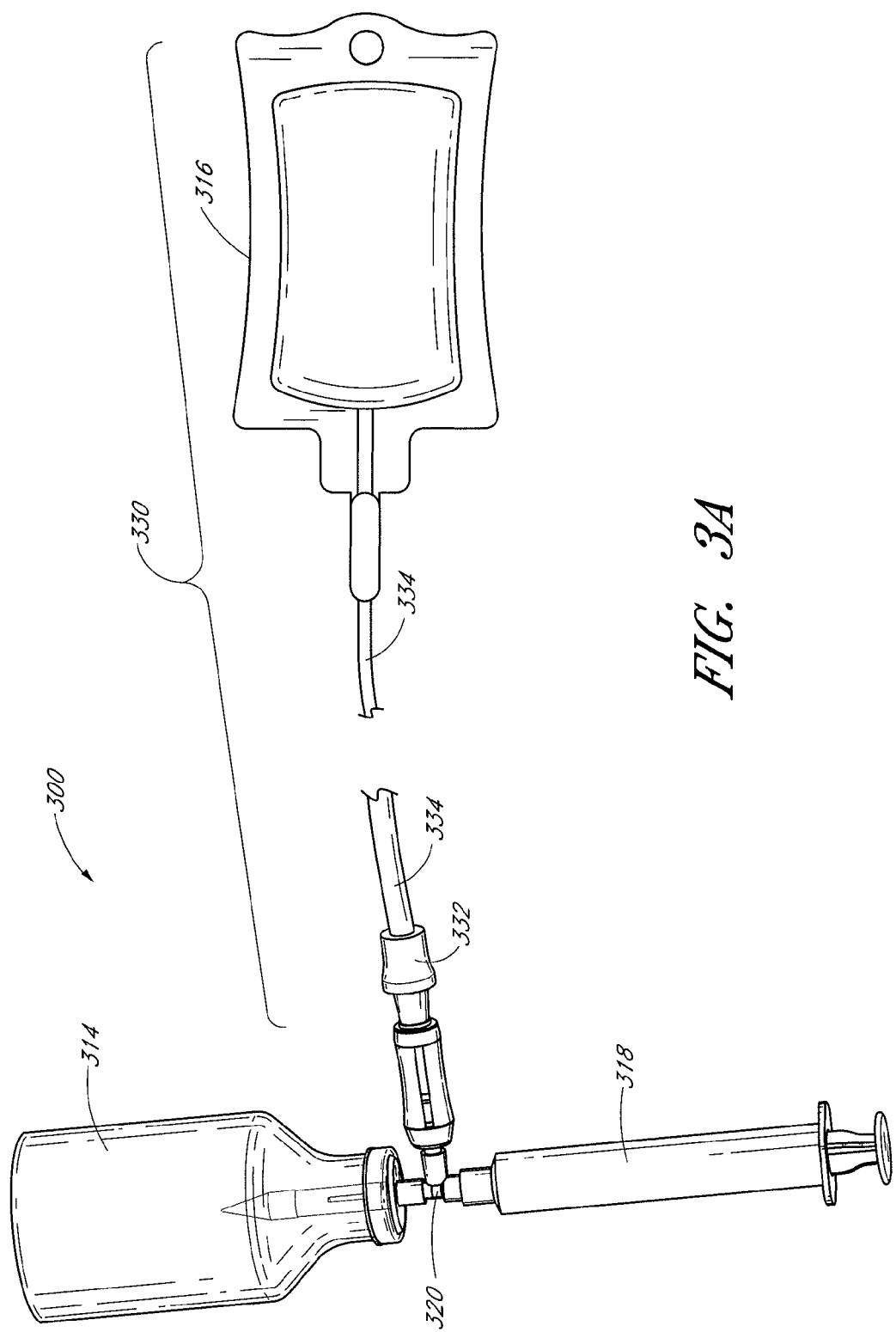

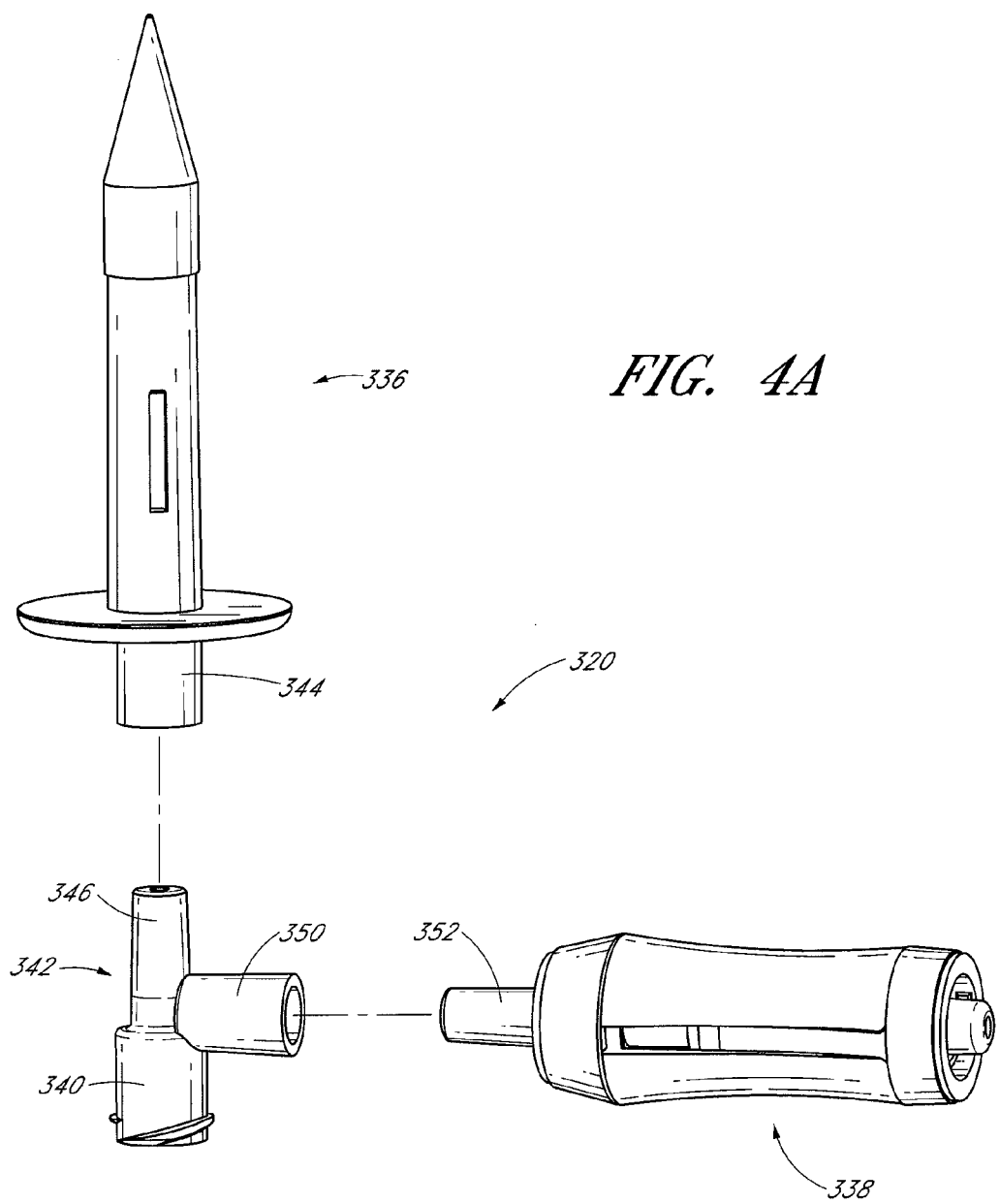

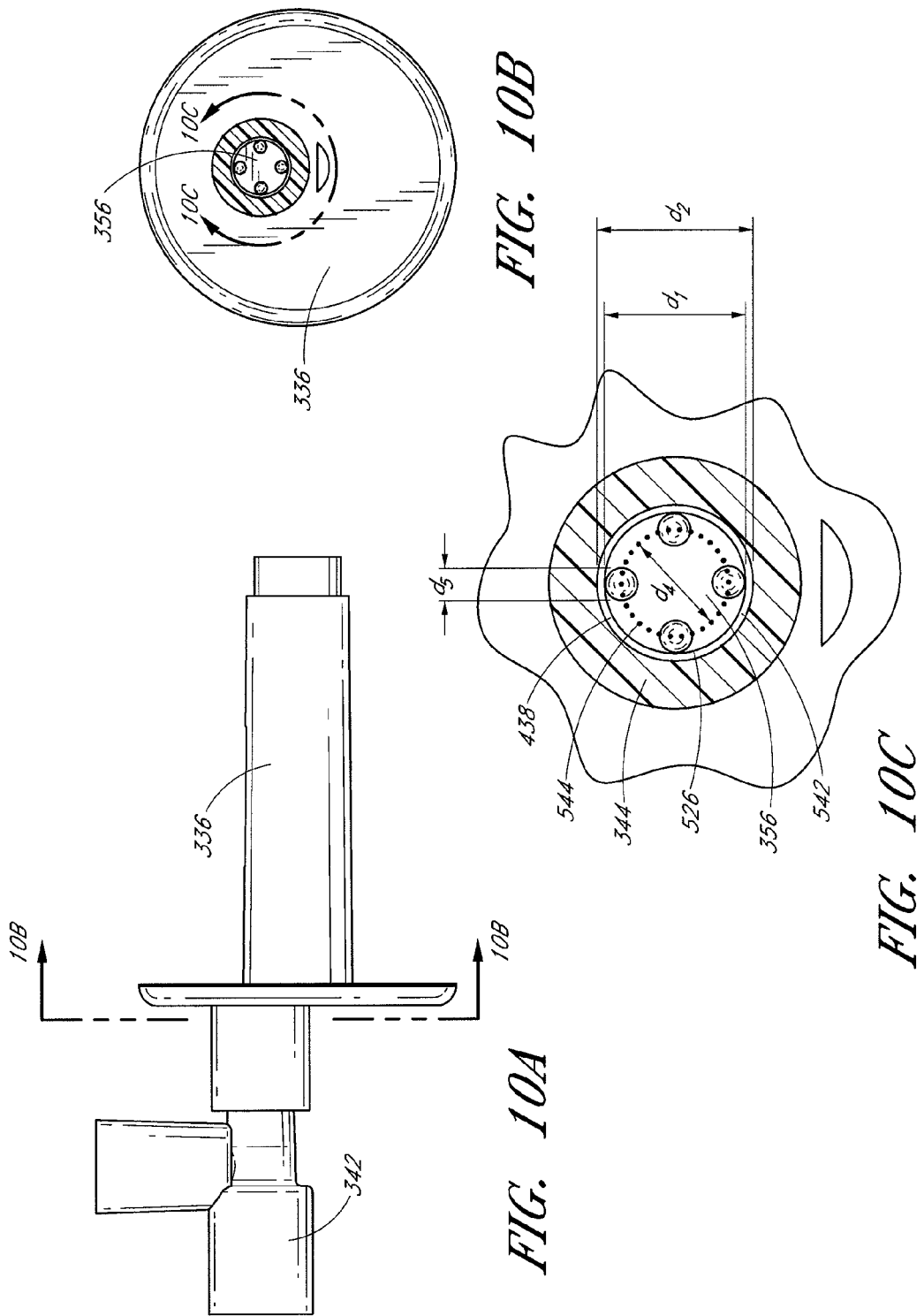

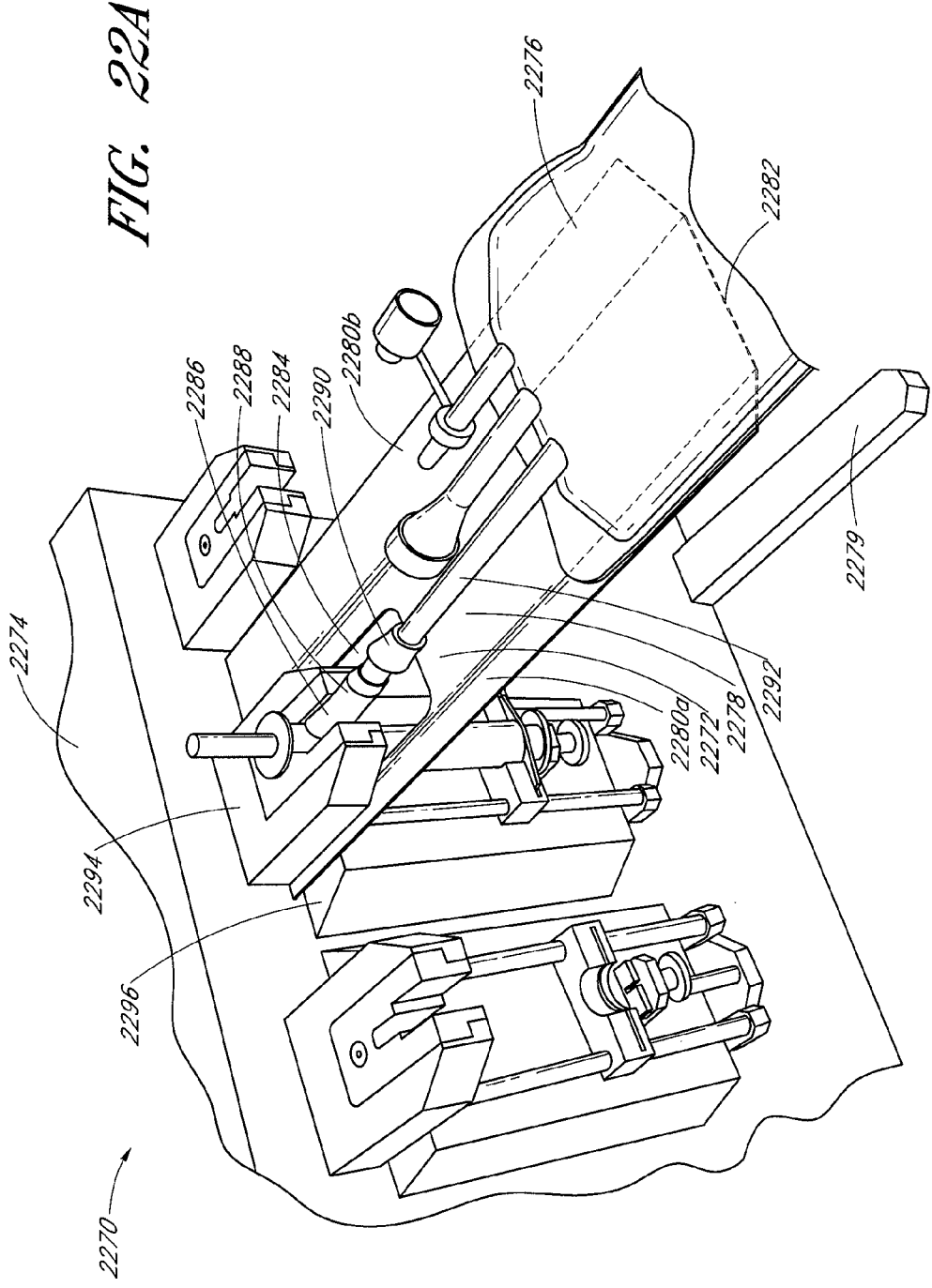

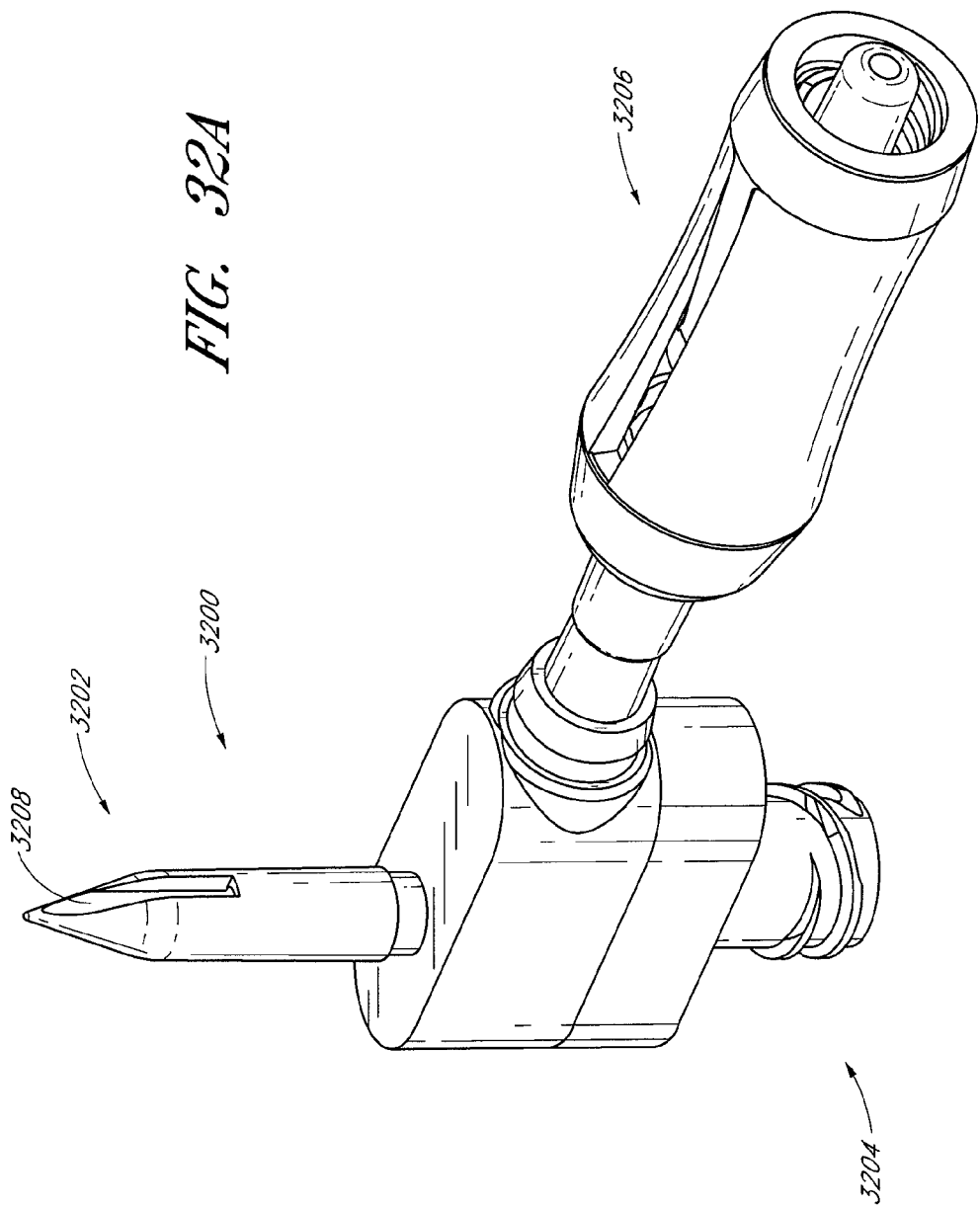

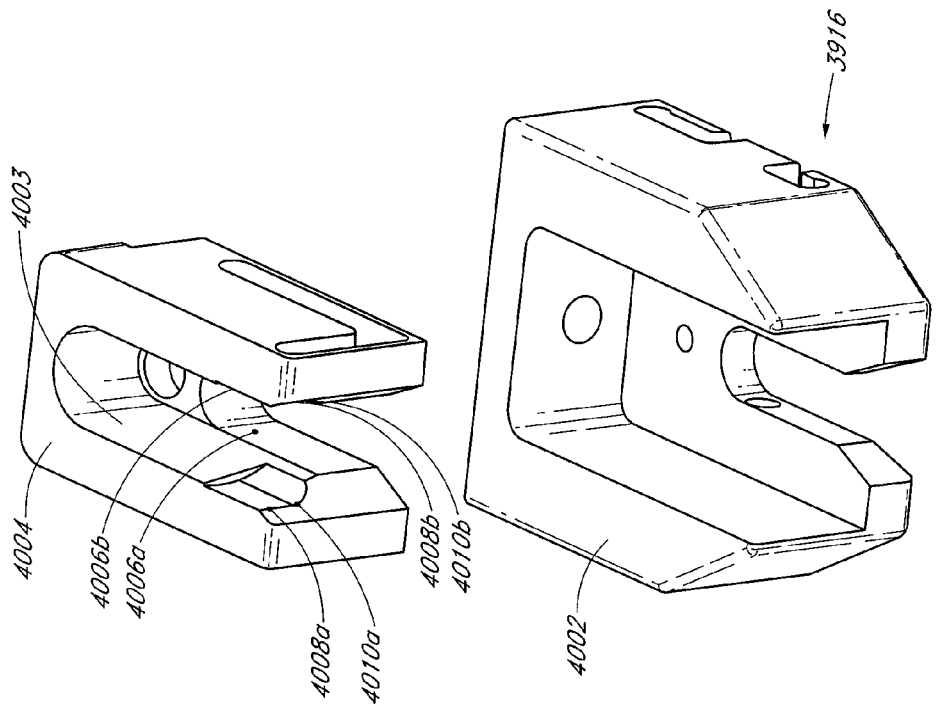
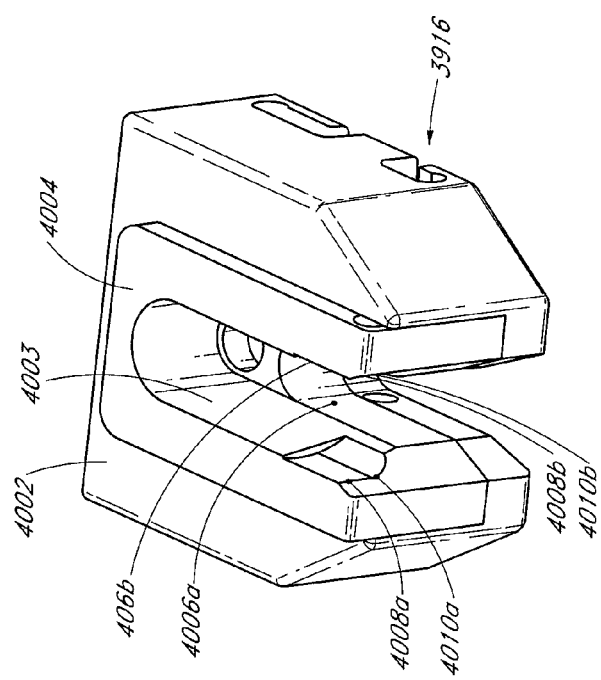

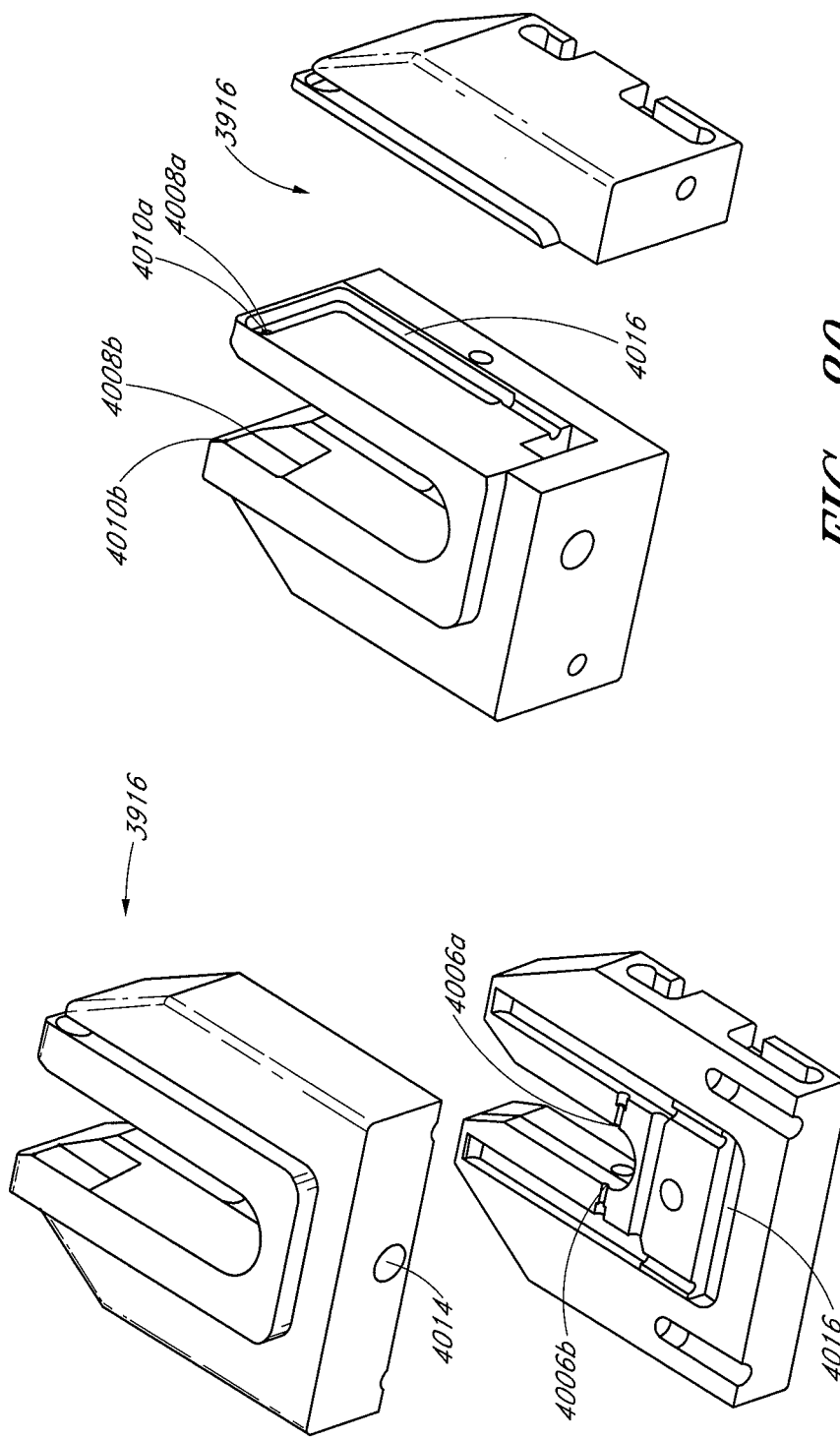

FLUID TRANSFER DEVICES AND METHODS OF USE

RELATED APPLICATIONS

This application is a continuation of U.S. patent application Ser. No. 13/937,127, filed Jul. 8, 2013, which is a continuation of U.S. patent application Ser. No. 12/845,548, filed Jul. 28, 2010, now U.S. Pat. No. 8,522,832, and entitled FLUID TRANSFER DEVICES AND METHODS OF USE, which claims the benefit under 35 U.S.C. §119(e) of U.S. Provisional Patent Application No. 61/229,701, filed Jul. 29, 2009, and entitled FLUID TRANSFER DEVICE, and U.S. Provisional Patent Application No. 61/354,648, filed Jun. 14, 2010, and entitled FLUID TRANSFER DEVICE. The entire contents of each of the above-identified applications are hereby incorporated by reference herein and made part of this specification for all that they disclose.

BACKGROUND OF THE DISCLOSURE

Field of the Disclosure

Some embodiments of the invention relate generally to devices and methods for transferring fluid and specifically to devices and method for transferring medical fluids.

Background of the Disclosure

In some circumstances it can be desirable to transfer one or more fluids between containers. In the medical field, it is often desirable to dispense fluids in precise amounts and to store and to transport potentially dangerous fluids. Current fluid transfer devices and methods in the medical field suffer from various drawbacks, including high cost, low efficiency, intensive labor demands, and excessive fluid or vapor leakage. Some embodiments disclosed herein overcome one or more of these disadvantages.

SUMMARY OF SOME EMBODIMENTS

Some embodiments disclosed herein related to devices for transferring precise amounts of fluid from a source container to a target container. In some embodiments, the fluid is first transferred from the source container through a connector to an intermediate measuring container (e.g., a syringe). The precisely measured amount of fluid can then be transferred from the intermediate measuring container to the target container.

In some embodiments, methods and devices for providing a substantially entirely closed system for the transfer of medical fluids between or among different medical fluid containers include a fluid transfer module that can be removably attached to an electronically controlled fluid dispensing system. The fluid transfer module can comprise first and second interfaces connected respectively to fluid source and fluid destination containers. The first and second interfaces can comprise selectively openable and closeable apertures that can substantially entirely prevent fluid within the fluid transfer module from escaping through the apertures when closed. An intermediate container can be part of or connected to the fluid transfer module. One or more valves within the fluid transfer module can permit fluid to move from the fluid source to the intermediate container, but can generally obstruct the fluid from moving from the intermediate container to the fluid source, and can permit fluid to move from the intermediate container to the fluid destination, but can generally obstruct the fluid from moving from the fluid destination to the intermediate container. In some embodiments, the fluid transfer module can be attached to an electronically controlled fluid dispensing system, and the fluid transfer module can include an interaction portion configured to permit the electronically controlled fluid dispensing system to indicate that at least a portion of the fluid transfer module is attached to the electronically controlled fluid dispensing system. In some embodiments, the electronically controlled fluid dispensing system can include an interactive user interface and can be configured to dispense precise amounts of medical fluid.

BRIEF DESCRIPTION OF THE DRAWINGS

Certain embodiments of the invention will now be discussed in detail with reference to the following figures. These figures are provided for illustrative purposes only, and the embodiments are not limited to the subject matter illustrated in the figures.

FIG. 3A is a perspective view of a subsystem for transferring fluid.

FIG. 4A is an exploded perspective view of the connector of FIG. 3A.

FIG. 10A is a side view of the main body coupled to the source connector portion of FIG. 4A.

FIG. 10B is a cross sectional view of the source connector portion of FIG. 4A and the source check valve of FIG. 8A disposed therein.

FIG. 10C is a partial cross-sectional view of the source connector and source check valve shown in FIG. 10B.

FIG. 22A is a perspective view of a fluid transfer system that includes a support tray for supporting an IV bag.

FIG. 32A is a perspective view of another embodiment of a connector for transferring fluid.

FIG. 58 is a perspective view of a top connector of the system of FIG. 39.

FIG. 59 is a perspective exploded view of the top connector of FIG. 58.

FIG. 79-81 are perspective views of the top connector that are cut and separated to illustrate the interior of the top connector.

FIG. 109 is a cross sectional view of the target connector portion of the connector of FIG. 107 with the valve member in the open position and an obstructed light path.

FIG. 110 is a cross sectional view of the target connector portion of the connector of FIG. 107 with the valve member in the closed position and an obstructed light path.

FIG. 111 is a cross sectional view of the target connector portion of the connector of FIG. 107 with the valve member in the open position and an unobstructed light path.

DETAILED DESCRIPTION OF SOME EXAMPLE EMBODIMENTS

The following detailed description is now directed to certain specific example embodiments of the disclosure. In this description, reference is made to the drawings wherein like parts are designated with like numerals throughout the description and the drawings.

In many circumstances fluid is transferred from a source container to a target container. In some instances, it can be desirable to transfer precise amounts of a fluid such as a medication into the target container. For example, in some embodiments a medication can be stored in a vial or other container, and a precise dosage amount of the medication can be extracted and transferred to a target device so that the dosage amount can be delivered to a patient. In some embodiments, fluid from multiple source containers can be combined, or compounded, into a single target container. For example, in some embodiments a mixture of medications can be created in the target container, or a concentrated medication can be combined with a diluent in the target container. To achieve the desired proportions of fluids, it can be desirable to precisely measure the amounts of fluids transferred into the target container. Also, precisely measuring the amount of fluid transferred from the source container to the target container can reduce the amount of fluid wasted (e.g., when more fluid than necessary is withdrawn from the source container). Reduction of waste is desirable because in some instances the fluid being transferred can be expensive.

Some embodiments disclosed herein provide a fluid transfer device for transferring precise amounts of fluid from one or more source containers into one or more target containers.

In some embodiments, it can be desirable to transfer fluids from a source container to a target container using a sealed system. In some embodiments, exposing the fluid to ambient air can allow contaminants to enter the fluid or cause an undesirable reaction with the fluid. Some medications (e.g., chemotherapy medications) can be harmful to a healthy individual. Therefore, it can be desirable to prevent or reduce exposure of the fluid being transferred to the ambient air or area outside the fluid transfer system. In some embodiments, a fluid transfer system that prevents or reduces exposure of the fluid to the area outside the fluid transfer system can render other expensive equipment (e.g., a clean room) unnecessary, thereby reducing the cost associated with transferring the fluids.

Some embodiments disclosed herein provide a fluid transfer device for transferring fluid while preventing, reducing, or minimizing the amount of contact the fluid has with the ambient air or area outside the fluid transfer system.

Figure 1:
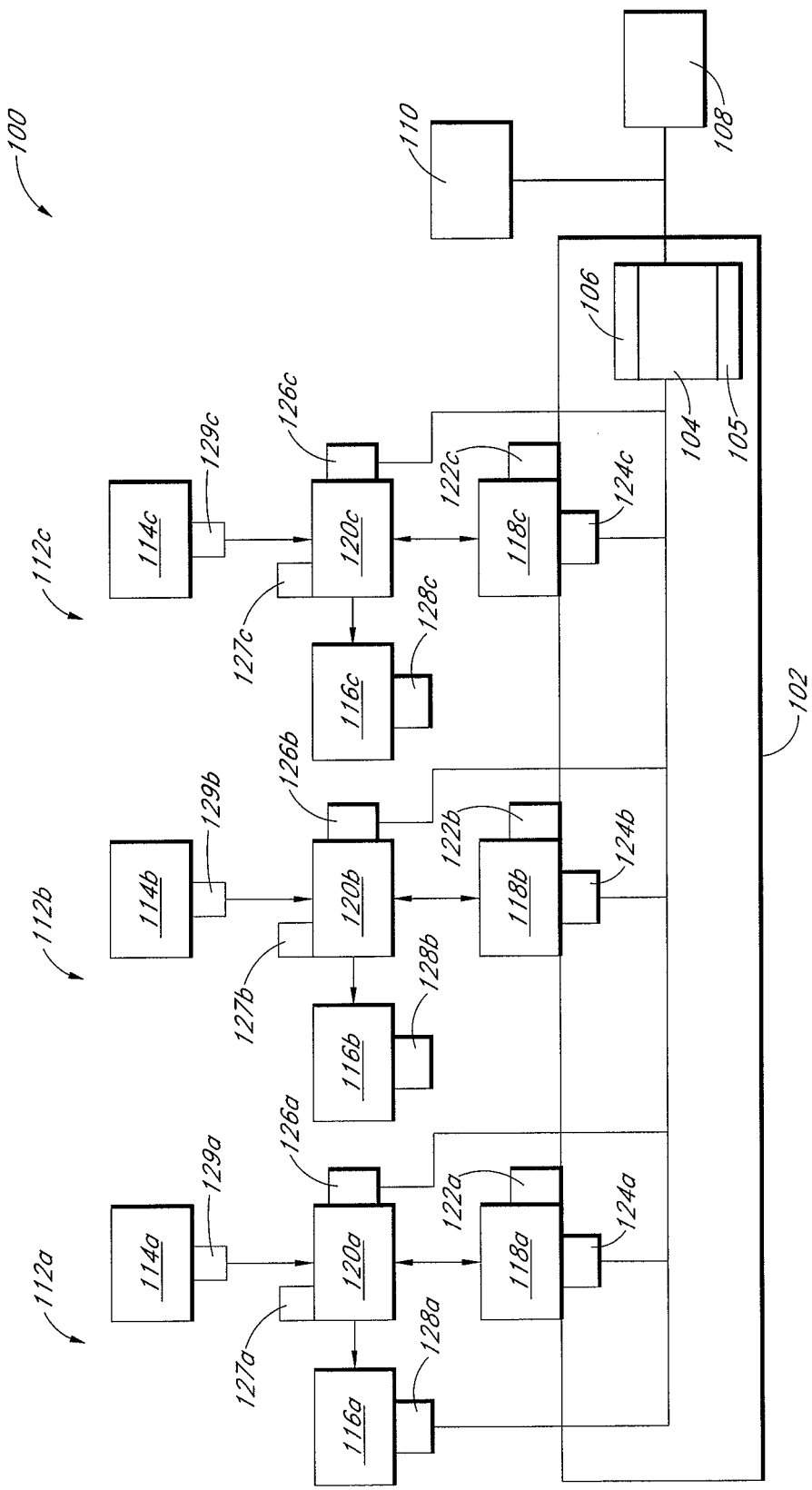
FIG. 1 schematically shows an embodiment of an automated system for transferring precise amounts of fluid.

FIG. 1 schematically shows an embodiment of an automated fluid transfer system 100. The system 100 can include a housing 102 enclosing a controller 104 and a memory module 106. The system 100 can also include a user interface 108, which can be, for example, external to the housing 102. The user interface 108 can also be integrated into the housing 102 in some cases. The user interface 108 can include, for example, a display, a keypad, and/or a touch screen display. The user interface 108 can be configured to receive instructions from the user, for example, regarding the amounts of fluid to be transferred and the types of fluids to be transferred. The user interface can also be configured to provide information to the user, such as error messages, alerts, or instructions (e.g., to replace an empty vial). The system 100 can also include a bar code scanner 110 in communication with the controller 104. Although in the embodiment shown, the controller 104 and memory module 106 are contained within the housing 102, a variety of other configurations are possible. For example, controller 104 can be external to the housing 102, and can be, for example contained within a second housing which also contains the user interface 108. In some embodiments, the system 100 can include a communication interface 105 configured to receive information (e.g., instructions) from a remote source such as a terminal or an automated management system, etc. In some embodiments, the communication interface can also send information (e.g., results or alerts) to the remote source. In some embodiments, the system 100 does not include a communication interface 105 and does not communicate with a remote source.

The system 100 can include multiple transfer stations 112a-c. In the embodiment shown, the system 100 includes three transfer stations 112a-c, but a different number of transfer stations can be used. For example, in some embodiments, the system may include a single transfer station. In other embodiments, the system may include two, four, five, six, seven, eight, or more transfer stations depending on the number of different fluid types the system is designed to handle and the amount of fluid to be transferred.

Each transfer station 112a-c can include a fluid source container 114a-c, which can be, for example, a medical vial or other suitable container such as a bag, a bottle, or a vat, etc. Although many embodiments disclosed herein discuss using a vial as the source container, it will be understood the other containers can be used even when not specifically mentioned. In some embodiments, each of the source containers 114a-c can contain a unique fluid, providing a variety of fluids that the user can select for transfer. In other embodiments, two or more of the source containers 114a-c can contain the same fluid. In some embodiments, the source containers 114a-c include bar codes that identify the types of fluid contained therein. The bar codes can be scanned by the scanner 110 so that the identities of the fluids contained by source containers 114a-c can be stored within memory module 106. In some embodiments, the fluid transfer stations 112a-c are configured to transfer precise amounts of fluid from source containers 114a-c to target containers 116a-c, which can be, for example IV bags. It will be understood that in various embodiments described herein, a different type of target connector or destination container can be used instead of an IV bag (e.g., a syringe, a bottle, a vial, etc.) even when not specifically mentioned. In some embodiments the fluid can first be transferred from source containers 114a-c to intermediate measuring containers 118a-c so that a precise amount of fluid can be measured. The intermediate measuring containers 118a-c can be, for example, syringes. After being measured, the fluid can be transferred from intermediate measuring containers 118a-c to the target containers 116a-c. In some embodiments, one or more of the transfer stations 112a-c can include one or more pairs of male and female fluid connectors configured to be attached to each other to selectively permit the passage of fluid. When fluid transfer is completed, the connectors can be detached or disconnected. In some embodiments, the connectors can be configured to automatically close. The fluid module can be removed while retaining substantially entirely or entirely all of the remaining interior fluid within the respective connectors and the rest of the fluid module, thus permitting the transfer to occur in a substantially entirely or entirely closed system, thereby diminishing the risk of damage caused by liquid or vapor leakage from the fluid module after disconnection and from the fluid source and the fluid destination after disconnection.

In some embodiments, the system 100 can be configured to be compatible with a variety of sizes of syringes. For example, larger volume syringes can be used to transfer larger volumes of fluid in shorter amounts of time. Smaller volume syringes can be used to increase the accuracy and precision with which amounts of fluid can be transferred. In some embodiments, the syringes can include a bar code which identifies the volume of the syringe. The bar code can be scanned by a bar code scanner 110, so that the sizes of the syringes used by the different transfer stations 112a-c can be stored within memory module 106 for use by the controller 104.

In some embodiments, connectors 120a-c connect the source containers 114a-c, the intermediate containers 118a-c, and the target containers 116a-c. In some embodiments, the connectors 120a-c can include first check valves (not shown) configured to allow fluid to flow from the source containers 114a-c into the connector 120a-c, and block fluid from flowing connector 120a-c into the source containers 114a-c, as shown by single-headed arrows. The connectors 120a-c can also include second check valves (not shown) configured to allow fluid to flow from connectors 120a-c into target containers 116a-c, but block fluid from flowing from target containers 116a-c into connectors 120a-c, as shown by single-headed arrows. In some embodiments, the connectors 120a-c can be in two-way fluid communication with the intermediate containers 118a-c, as shown by double-headed arrows.

In some embodiments, the system 100 can include mounting modules 122a-c for mounting the transfer stations 112a-c onto the housing 102. For example, in some embodiments the mounting modules 122a-c can be configured to securely receive intermediate measuring containers 118a-c as shown in FIG. 1. The system 100 can also include motors 124a-c, which can be for example, contained within housing 102. The motors 104a-c can be configured to actuate the plungers on the syringes 118a-c to draw fluid into the syringes and to dispel fluid therefrom. The motors 124a-c can be in communication with the controller 104, and can receive actuation instructions from the controller 104.

In some embodiments, the system can include fluid detectors 126a-c configured to detect a presence or absence of fluid in connectors 120a-c. The fluid detectors 126a-c can be in communication with the controller 104 so that when the detectors 126a-c detect an absence of fluid in connectors 120a-c, indicating that source fluid containers 114a-c have run dry, they can send a signal to controller 104 that a source container 114a-c needs to be replaced. The fluid detectors 126a-c can be for example an infrared LED and photo detector, or other type of electronic eye, as will be discussed in more detail below. In the embodiment shown, fluid detectors 126a-c are shown connected to connectors 128a-c, but other configurations are possible. For example, fluid detectors 126a-c can be connected to fluid source containers 114a-c themselves.

In some embodiments, the system 100 can include compatibility mechanisms 127a-c for ensuring that an approved connector 120a-c has been placed in communication with the system 100 to ensure the accuracy of the amount of fluid transferred. The compatibility mechanisms 127a-c can be, for example, a specifically shaped mounting feature configured to correspond to a portion of the connector 120a-c.

In some embodiments, the system 100 can include source adapters 129a-c configured to receive the source containers 114a-c and removably connect to the connectors 120a-c. Thus, when a source container 114a-c runs out of fluid, the empty source container 114a-c and its corresponding adapter 129a-c can be removed and replaced without removing the associated connector 120a-c from the system 100. In some embodiments, source adapters 129a-c can be omitted, and the source containers 114a-c can be directly received by the connectors 120a-c.

In some embodiments the system 100 can include sensors 128a-c for detecting the presence of target containers 116a-c. Sensors 128a-c can be in communication with the controller 104 so as to prevent the system 100 from attempting to transfer fluid when no target container 116a-c is connected. A variety of sensor types can be used for sensors 128a-c. For example, sensors 128a-c can be weight sensors or infrared sensors or other form of electronic eye. In some embodiments, weight sensors 128a-c can also be used to measure the weight of the target containers 116a-c after fluid has been transferred. The final weight of a target container 116a-c can be compared to an expected weight by the controller 104 to confirm that the proper amount of fluid was transferred into the target container 116a-c. Sensors 128a-c can be a variety of other sensor types, for example sensor pads or other sensor types able to detect the presence of target containers 116a-c.

Figure 2:
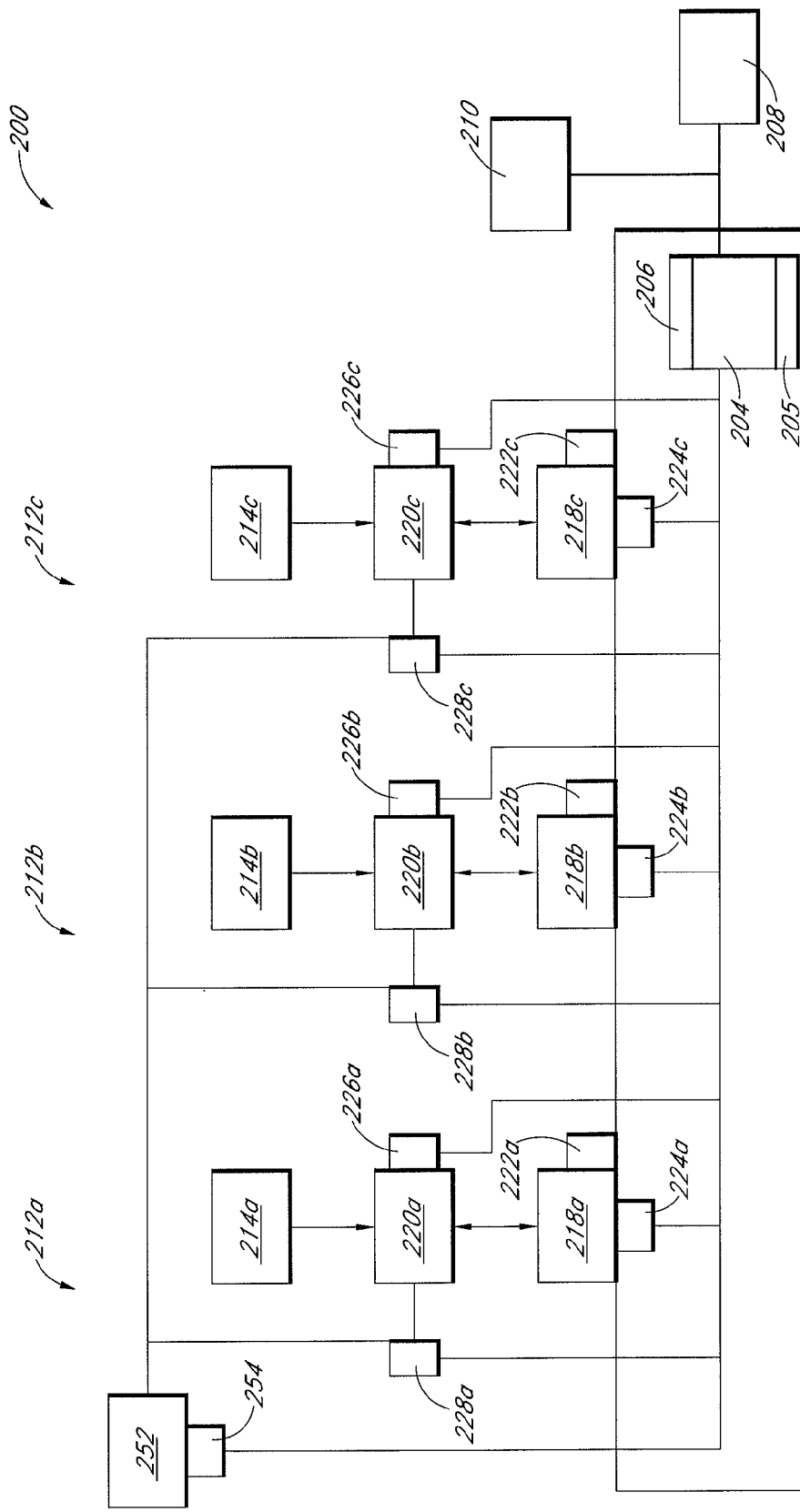
FIG. 2 schematically shows an embodiment of an automated system for compounding mixtures of precise amounts of fluid.

FIG. 2 schematically illustrates a system 200 for automated precise transfer of fluids. System 200 can be the same as or similar to the system 100 in some regards. Some features shown in FIG. 1, such as the adapters 129a-c and compatibility mechanisms 127a-c, are not shown specifically in the system 200, but it will be understood that system 200 can include corresponding features. The system 200 can include a housing 202, a controller 204, a memory 206, a user interface 208, a scanner 210, and a communication interface 205, similar to those describe above in connection with the system 100. System 100 is configured to transfer individual fluids from the source containers 114a-c to target containers 116a-c. System 200, on the other hand, is configured to transfer and combine fluids from source containers 214a-c into a common target container 216. Thus, system 200 can be used for compounding mixtures of fluids. In some embodiments, a single system can be configured both for compounding mixtures of fluids and for the transfer of individual fluids from a single-source container to a single-target container. For example, a system containing six fluid transfer stations can be configured so that transfer stations 1-3 are dedicated to compounding mixtures of fluids into a single common target container, while fluid transfer stations 4-6 can be configured to each transfer fluid from a single source container to a single target container. Other configurations are possible. In the embodiment shown in FIG. 2, the system 200 can include sensors 228a-c for detecting whether or not the connectors 220a-c are connected to the common target container 216. The system 200 can also include a sensor 229 for detecting the presence of the common target container 216. In some embodiments, the sensor 229 can measure the weight of the common target container 216 and can report the weight to the controller 104. The controller 104 is then able to compare the final weight of the common target container 216 with an expected weight to confirm that the common target container 152 was filled with the correct amount of fluids.

Figure 3B:
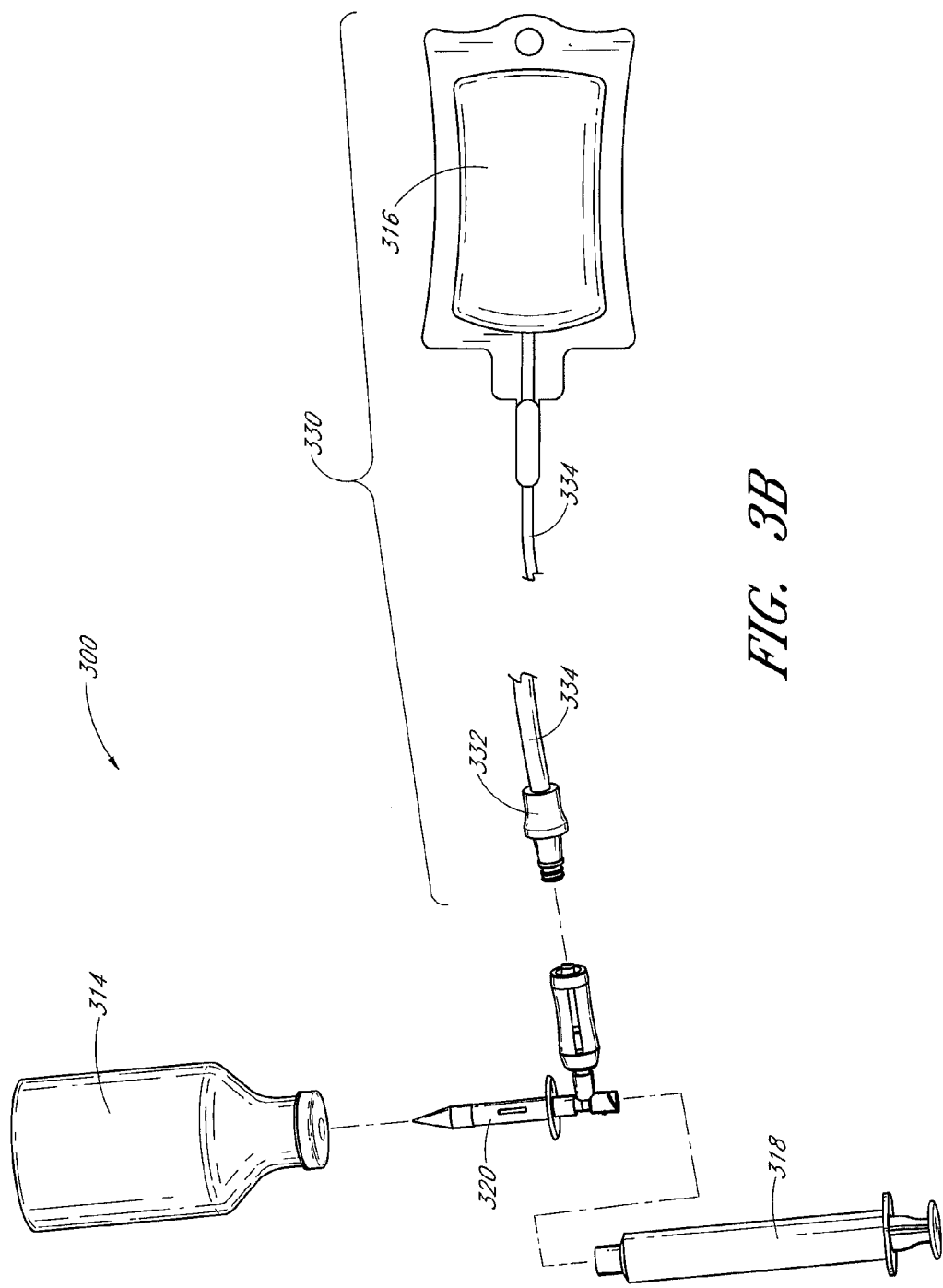
FIG. 3B is an exploded perspective view of the subsystem of FIG. 3A.

FIGS. 3A and 3B show a subsystem, or fluidics assembly, 300 for transferring precise amounts of fluid from a medical vial 314 to an IV bag 316. FIG. 3A is a perspective view of subsystem 300, and FIG. 3B is an exploded perspective view of subsystem 300. The subsystem 300 can include a syringe 318 for measuring precise amounts of fluid to be transferred. In some embodiments, the system includes an IV bag assembly 330. The IV bag assembly 330 can include the IV bag 316, a connector 332, and a piece of tubing 334 connecting the IV bag 316 to the connector 332. The connector 332 can be, for example, a female medical connector. The connector 332 illustrated in FIGS. 3A-B is a version of the Clave® connector manufactured by ICU Medical, Inc., of San Clemente, Calif. Various embodiments of a connector of this type are described in U.S. Pat. No. 5,685,866 (the "'866 patent"), the entirety of which is incorporated herein by reference. The subsystem 300 can also include a connector 320, for interconnecting the vial 314, the syringe 318, and the IV bag assembly 330.

Figure 4B:
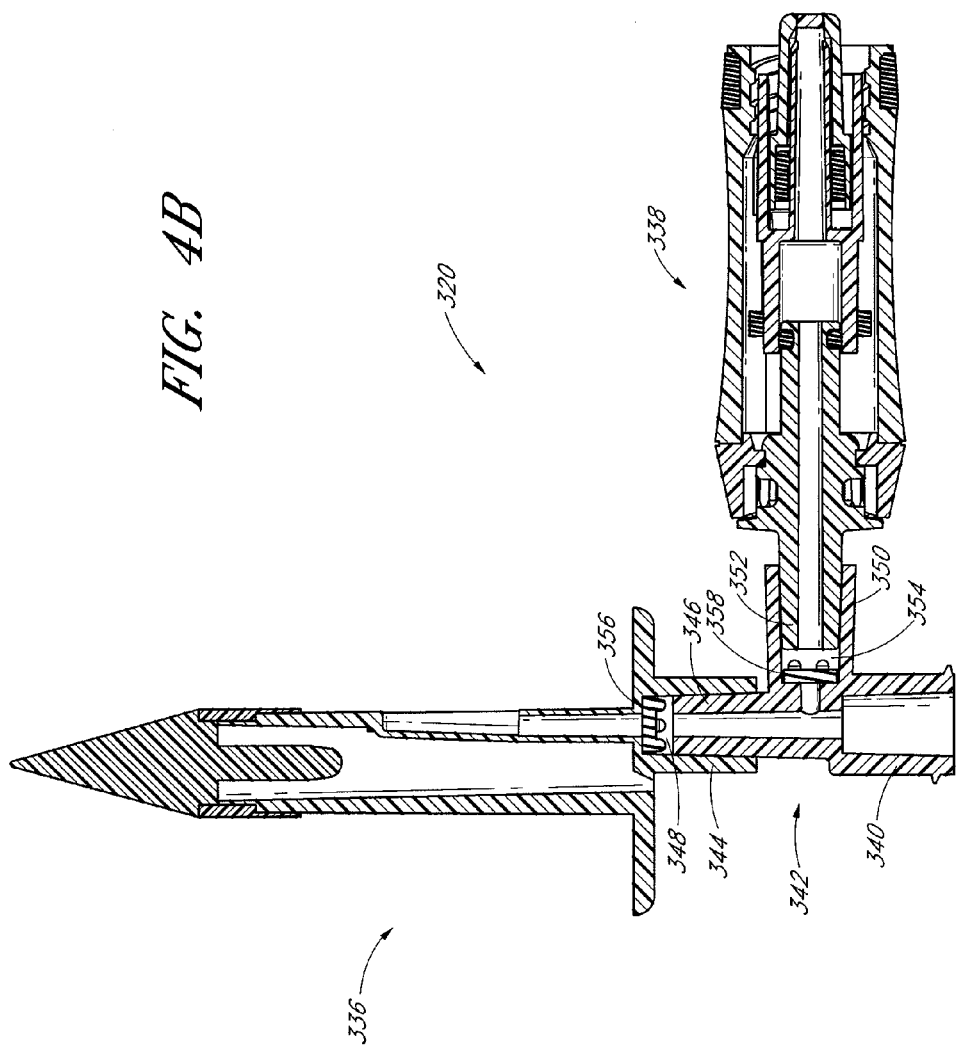
FIG. 4B is a cross sectional view of the connector of FIG. 4A.

Turning now to FIGS. 4A and 4B, FIG. 4A shows an exploded perspective view of a fluid transfer module in the form of connector 320, and FIG. 4B shows a cross-sectional view of the connector 320. The connector 320 can include a first interface or source connector portion 336 configured to provide fluid communication between the connector 320 and the vial 314, a second interface of target connector portion 338 configured to provide fluid communication between the connector 320 and the IV bag assembly 330, and an intermediate connector portion 340 configured to provide fluid communication between the connector 320 and the syringe 318. The connector can also include a main body 342. In the embodiment shown in FIGS. 4A-B, the intermediate connector portion 340 is integrally formed as part of the main body 342.

In some embodiments, the connector 320 can be a T-connector. In the embodiment shown, the fluid path leading to the IV bag assembly 330 is substantially perpendicular to the fluid path between the vial 314 and the syringe 318. A variety of other configurations are possible. For example, the fluid pathways can be arranged to intersect at an oblique angle.

In some embodiments, the source connector portion 336 includes a female connector portion 344 having a slightly tapered internal surface. The main body 342 of the connector can have a corresponding male connector portion 346 having a similarly tapered outer surface. The female connector portion 344 and male connector portion 346 can be configured such that when the male connector portion 346 is fully inserted into the female connector portion 344 (i.e., the tapered surfaces prevents further insertion), a chamber 348 is defined between the end of the male connector portion 346 and the base of the female connector portion 344. The male connector portion 346 can be secured to the female connector portion 344 by applying a plastic welding adhesive (such as Dichloromethane) to the outer surface of the male connector portion 346 and/or to the inner surface of the female connector portion 344 before insertion. The Dichloromethane can chemically weld the outer surface of the male connector portion 346 to the inner surface of the female connector portion 344. Other methods can be used to connect the male connector portion 346 to the female connector portion 344, such as sonic welding, threading, adhesives, etc. In some embodiments, the connection between the main body 342 and the source connector portion 336 is hermetically sealed, and in some embodiments includes a sealing member (not shown), such as an O-ring, to provide the hermetic seal.

In some embodiments, the target connector portion 338 can be similarly attached to the main body 342. The main body 342 can include a female connector portion 350 with a tapered inner surface, and the target connector portion 338 can include a male connector portion 352 with a tapered outer surface. When the male connector portion 352 is inserted fully into the female connector portion 350 (i.e., the tapered surfaces prevent further insertion), a chamber 354 is defined between the end of the male connector portion 352 and the base of the female connector portion 350. The connector portions 350, 352 can be secured to one another using Dichloromethane or any of the other methods discussed above. In some embodiments, the connection between the main body 342 and the target connector portion 338 is hermetically sealed, and in some embodiments, the connection can include a sealing member.

The connector 320 can include a source check valve 356 disposed inside the chamber 348. The check valve 356 can be configured to allow fluid to flow from the vial 314 into the connector 320, but block fluid from flowing from the connector 320 into the vial 314. The connector can also include a target check valve 358 disposed inside chamber 354. Check valve 358 can be configured to allow fluid to flow from the connector 320 into the IV bag assembly, but blocks fluid from flowing from the IV bag assembly into the connector 320. The check valves 356, 358 will be discussed in greater detail below.

The main body 342 can be constructed from a variety of materials. The main body 342 can be constructed from a rigid material such as polycarbonate or other polymeric materials. In some embodiments, at least a portion of the main body 342 can be formed from a substantially transparent material as discussed below.

Figure 5A:
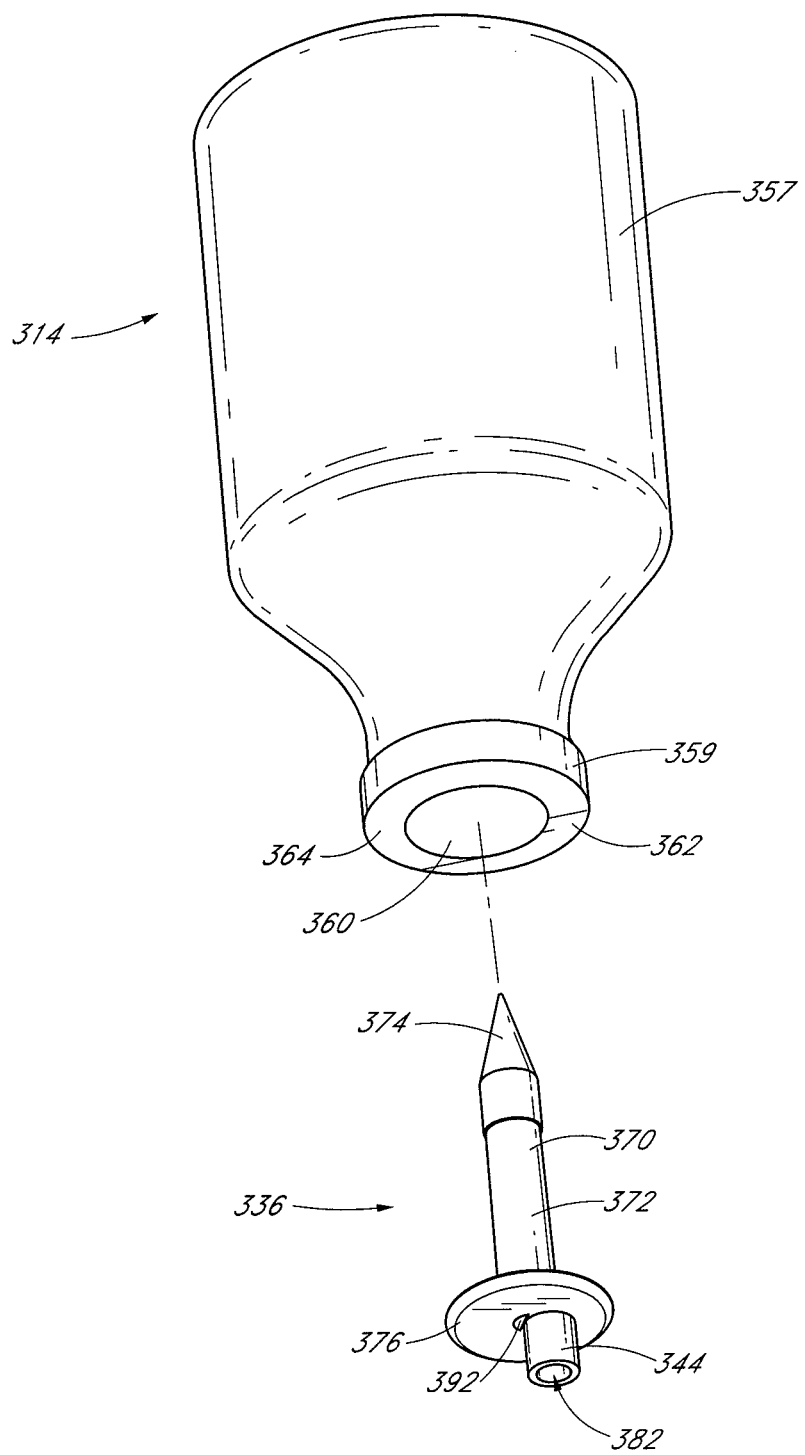
FIG. 5A is a perspective view of the source connector portion of FIG. 4A adjacent to the vial of FIG. 3A.
Figure 5B:
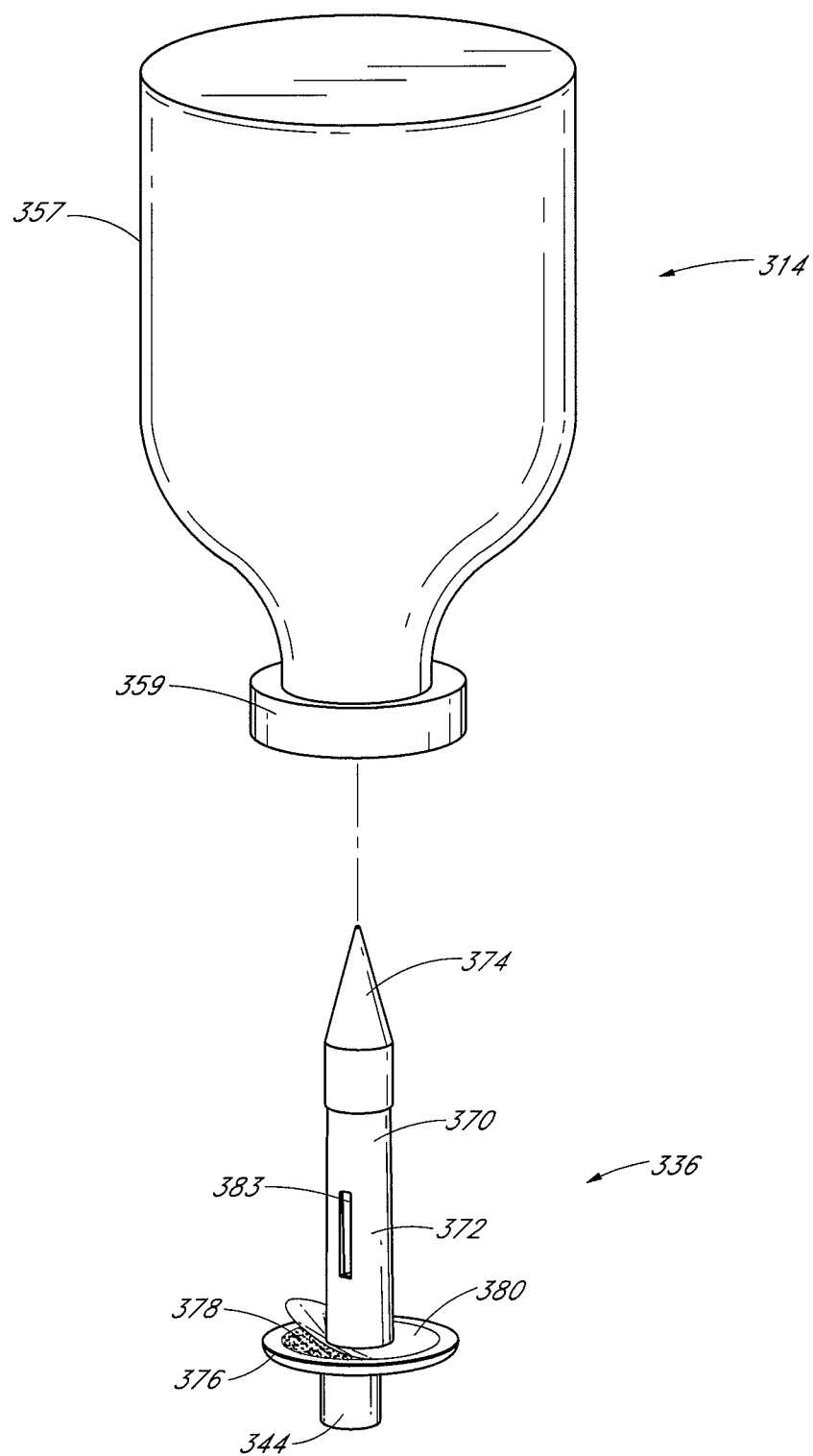
FIG. 5B is another perspective view of the source connector portion of FIG. 4A and the vial of FIG. 3A.
Figure 5C:
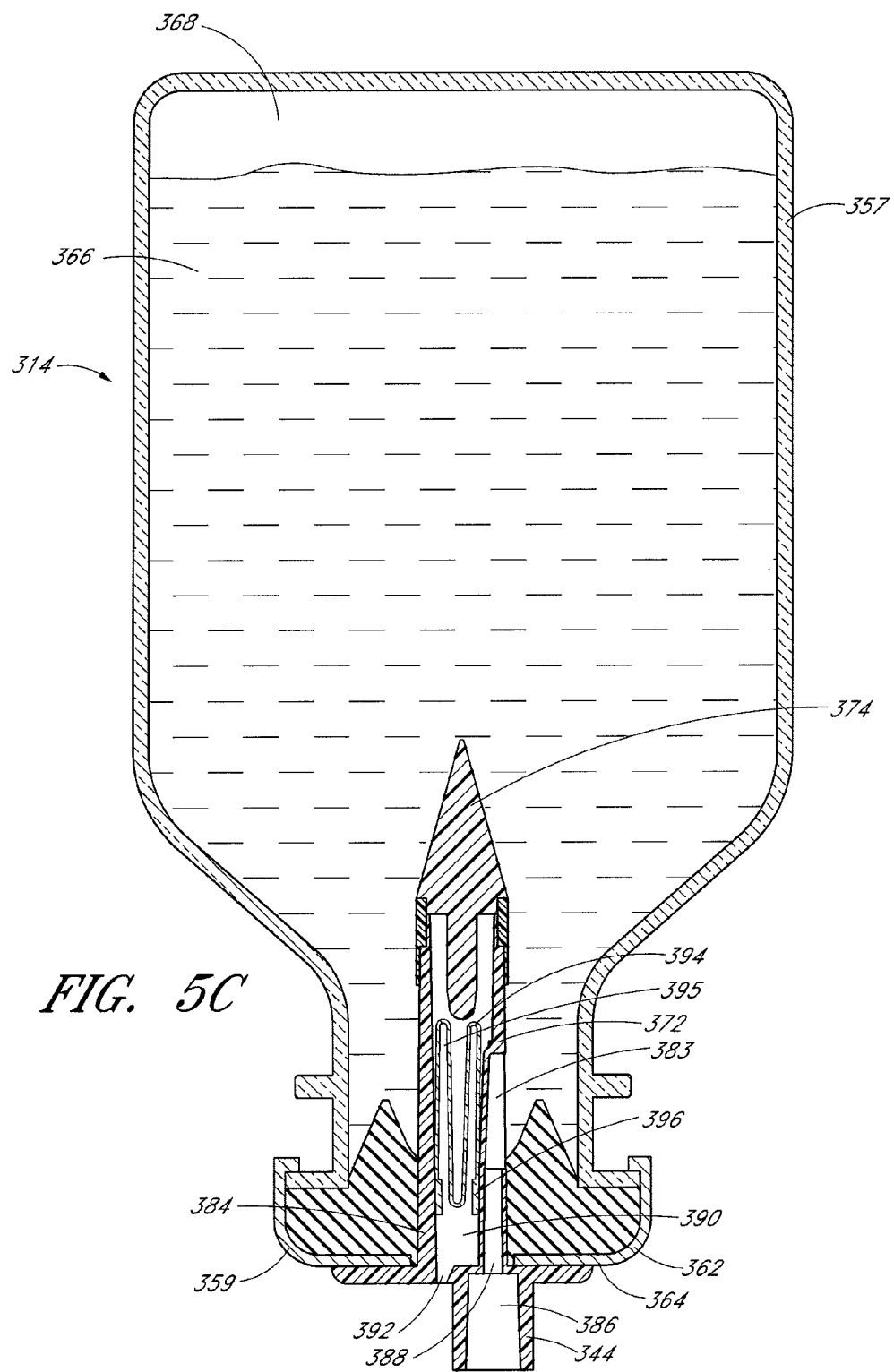
FIG. 5C is a cross-sectional view of the source connector portion and vial of FIG. 5A in engagement.
Figure 5D:
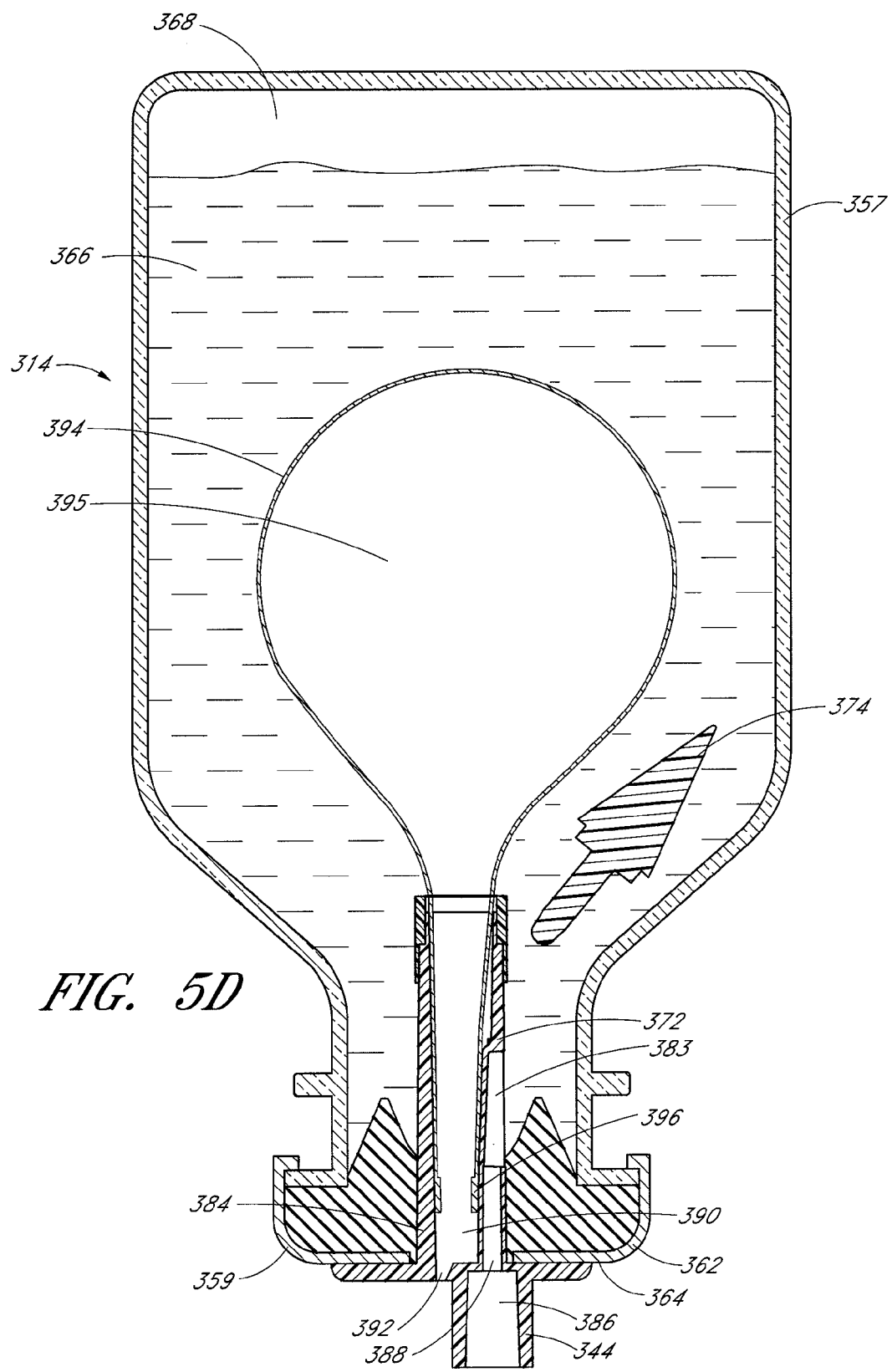
FIG. 5D is a cross-sectional view of the source connector portion and vial of FIG. 5B in a subsequent stage.

FIG. 5A shows a perspective view of the source connector portion 336 and vial 314 in an unengaged configuration. FIG. 5B is another perspective view of the source connector portion 336 and vial 314, also in an unengaged configuration. FIG. 5C is a cross-sectional view of the source connector portion 336 and vial 314 in an engaged configuration. FIG. 5D is a cross-sectional view of the source connector portion 336 and vial 314 after a portion of the fluid has been withdrawn from the vial 314. Although FIGS. 5A-5D shown the source connector portion 336 of the connector 320 separated from the remainder of the connector 320 for simplicity, it should be understood that the source connector portion 336 can be connected to the remainder of the connector 320 when in use.

With reference now to FIGS. 5A-D, the vial 314 can comprise any suitable container for storing medical fluids, and can be for example a medical vial such as those produced by Abbott Laboratories of Abbott Park, Ill. In some embodiments, the vial 314 includes a body 357 and a cap 359. In some instances, the vial 314 can be configured to be hermetically sealed. The body 357 can comprise a rigid substantially impervious material such as plastic or glass. In some embodiments the cap 359 includes a septum 360 and casing 362. The septum 360 can be made of an elastomeric material capable of deforming in such a way that when punctured by an item, it forms a substantially airtight seal around that item. For example, in some instances the septum 360 comprises silicone rubber or butyl rubber. The casing 362 can surround the septum 360 and can be made from any suitable material for sealing the vial 314. In some instances, the casing 362 comprises a metal that is crimped around the septum 360 and an end portion of the vial body 357 in order to form an airtight seal between the septum 360 and the vial body 357. In some embodiments, casing 362 can include a substantially flat mounting surface 364. The vial 314 can include a fluid 366, such as a medical fluid (e.g., a chemotherapy drug) contained within its internal volume. The vial 314 can also include a relatively small amount of sterilized air 368 also contained within the internal volume.

The source connector portion 336 can include a piercing member 370 which can comprise a sheath 372 and a pointed tip 374. The sheath 372 can be cylindrical in shape, or it can be a variety of other suitable shapes. For example, in some embodiments, the sheath 372 can be generally conical in shape and taper toward the pointed tip 374. The piercing member 370 can comprise a rigid material such as metal or plastic, suitable for insertion through the septum 360, such as a polycarbonate plastic. In some instances the pointed tip 374 is separable from the sheath 372. In other embodiments, the pointed tip 374 and sheath 372 can be integrally formed or permanently joined. The pointed tip 374 can be configured to facilitate piercing of the septum 360. The source connector portion 336 can also include a cap connector 376 configured to secure the source connector portion 336 to the vial 314. In some embodiments, the cap connector 376 can include an adhesive 378, such as a double-sided tape, disposed on the surface of the cap connector 376. A removable covering 380 (shown partially pealed away in FIG. 5B) can be disposed over the adhesive 378 until it is ready to be used. The vial 314 can be secured to the cap connector 376 by removing the covering 380 from the adhesive 378 and pressing the vial 314 down onto the source connector portion 336 so that the piercing member 370 pierces the septum 360 and the mounting surface 364 comes into contact with the adhesive 378. A variety of other connection types can be used to secure the vial 314 to the source connection portion 336 of the connector 220.

In some embodiments, the source connector portion 336 can be configured to automatically equalize pressure within the vial 314 as fluid 366 is withdrawn. For example, the source connector portion 336 can be a version of the Genie® closed vial access device manufactured by ICU Medical, Inc. of San Clemente, Calif. Certain embodiments of closed vial access devices of this type are disclosed in U.S. Provisional Patent Application No. 61/090,561 (the "'561 application"), the entirety of which is herein incorporated by reference. For example, the '561 application discloses other methods by which the vial 314 can be connected to the source connector portion 336.

In some embodiments, the source connection portion 336 can include a fluid extraction channel 382. The fluid extraction channel 382 can include an upper portion 384 that extends from an extraction aperture 383 formed in the side wall of the piercing member 370 through a portion of the piercing member 370. The fluid extraction channel 382 can also include and a lower portion 386 that extends through the female connection portion 344. In certain embodiments, the lower portion 386 can be wider than the upper portion 384, defining a shoulder 388 at the transition from the lower portion 386 to the upper portion 384.

In some embodiments, the sheath 372 can be hollow defining a regulator channel 390 that extends through the sheath 372 and through the cap connector 376 to a regulator aperture 392 formed on a position of the source connector portion 344 that remains exposed to the ambient air when the vial 324 is secured to the source connector portion 336. In some embodiments, a bag 394 can be enclosed within the regulator channel 390. The bag can define an inner volume 395 that is in fluid communication with the regulator channel 390. In some embodiments, the bag can include a connection region 396 that forms an airtight seal with the walls of the regulator channel 390 so that air cannot move past the connection region 396 unless it enters the inner volume 395 of the bag 394. In some embodiments, the connection region 396 of the bag 394 can be secured to the sheath 372 by an adhesive, or by any other suitable manner.

The bag 394 can be folded up inside the regulator channel 390 so that it occupies a relatively small volume compared to its unfolded state. The bag 394 can be configured to be able to fill all, or a substantial portion, of the internal volume of the vial 314. In some embodiments, the bag 394 can comprise a elastomeric material, such as Mylar®, polyester, polyethylene, polypropylene, saran, latex rubber, polyisoprene, silicone rubber, polyurethane, and latex-free silicone that can allow the bag 394 to unfold, expand, and/or contract. In some embodiments, the bag 394 can comprise a non-expandable material that is flexible enough to allow the bag to unfold. In some circumstances, the bag 394 can comprise a material that is impervious to liquid and air and inert with respect to the fluid 366.

FIG. 5C illustrates an embodiment of the source connector portion 336 coupled to the vial 314 at a stage before any of the fluid 366 is extracted. By comparison, FIG. 5D illustrates an embodiment of the source connector portion 336 coupled to the vial 314 at a stage with the bag 394 deployed after some of the fluid 366 has been extracted. Although not shown in FIGS. 5C and 5D, the fluid extraction channel 382 of the source connector portion 336 can be in fluid communication with the syringe 318 or other medical instrument capable of creating a negative pressure to extract fluid 366 from the vial 314. In some circumstances, a volume of the fluid 366 can be withdrawn from the vial 314 by the syringe causing the pressure within the vial 314 to drop. The reduced pressure in the vial can cause the tip 374 to disengage from the sheath 372, so that the bag 394 is free to emerge from the sheath 372. As the fluid 366 flows out of the vial 314 and toward the syringe 318, ambient air flows into the inner volume 395 of the bag 394 by way of the regulator channel 390 and the regulator aperture 392. In some circumstances the inner volume 395 of the bag 394 expands (by the bag unfolding and/or expanding) to compensate for the reduced pressure inside the vial 314.

Thus, the source connector portion 336 can be configured to allow the fluid 366 to be withdrawn from the vial 314 while regulating the pressure within the vial 314. In some embodiments, the source connector portion 336 maintains a substantially constant pressure within the vial 314 as the fluid 366 is withdrawn therefrom. In some embodiments, the pressure within the vial 314 changes by no more than about 1-5 psi as the fluid 366 is withdrawn. The '561 application discloses additional details and various alternatives that can be applied to the source connector portion 336 and vial 314.

Figure 6A:
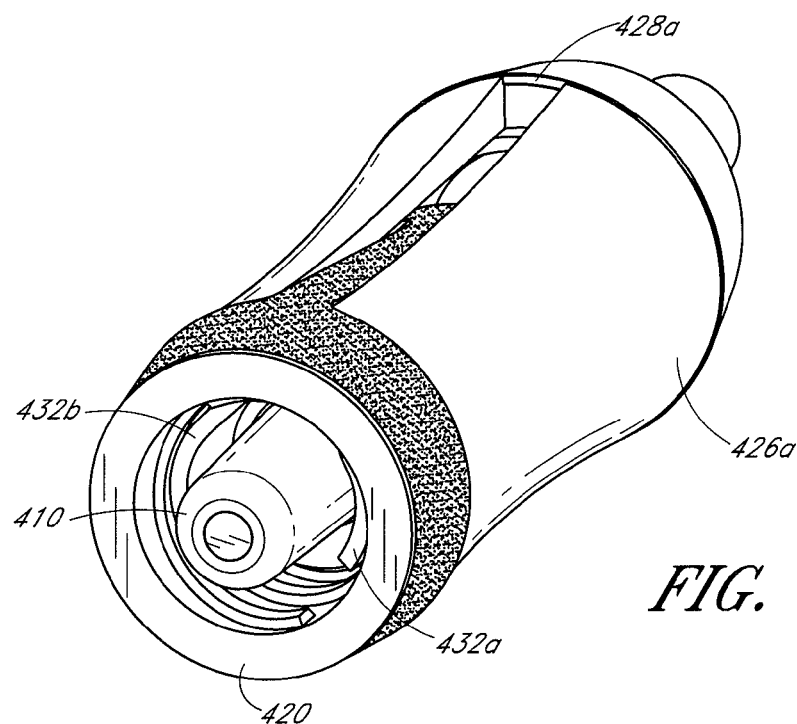
FIG. 6A is a perspective view of the target connector portion of FIG. 4A.
Figure 6C:
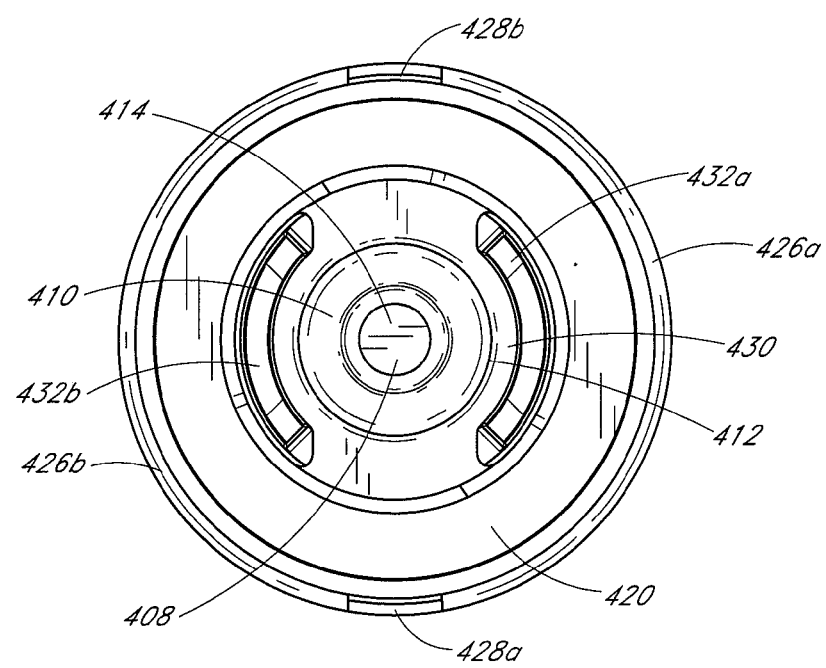
FIG. 6C is a top view of a housing portion of the target connector portion.
Figure 6B:
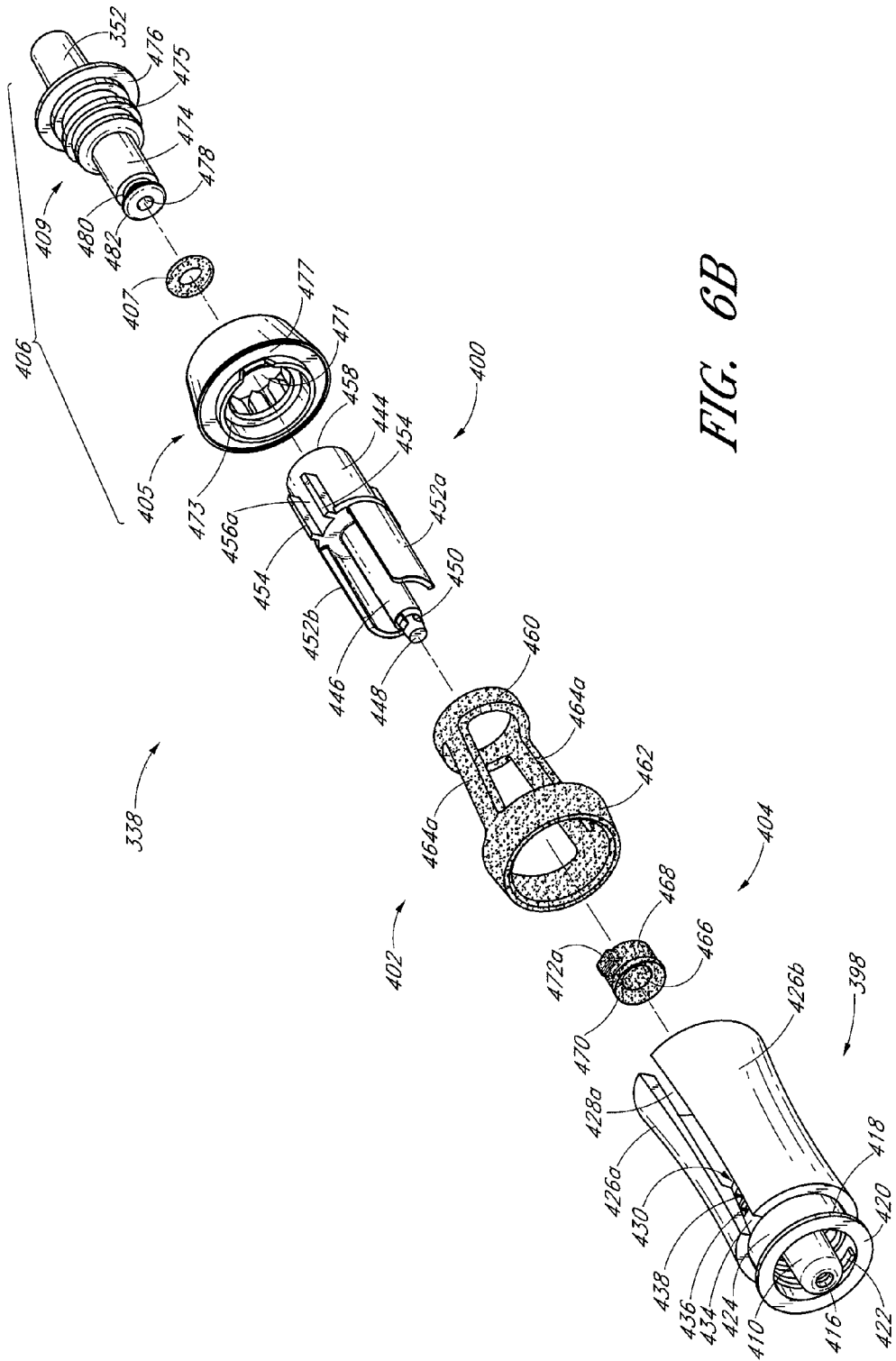
FIG. 6B is an exploded perspective view of the target connector portion of FIG. 6A.
Figure 6D:
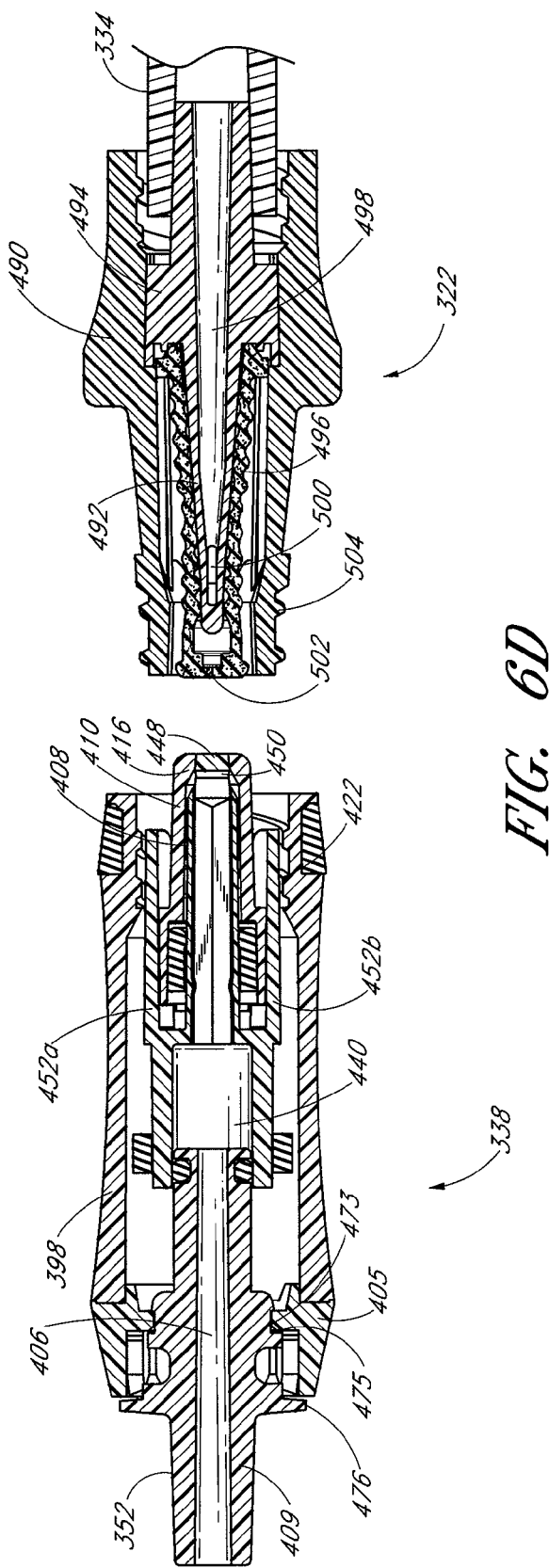
FIG. 6D is a cross-sectional view of the target connector portion and the female connector in an unengaged configuration.
Figure 6E:
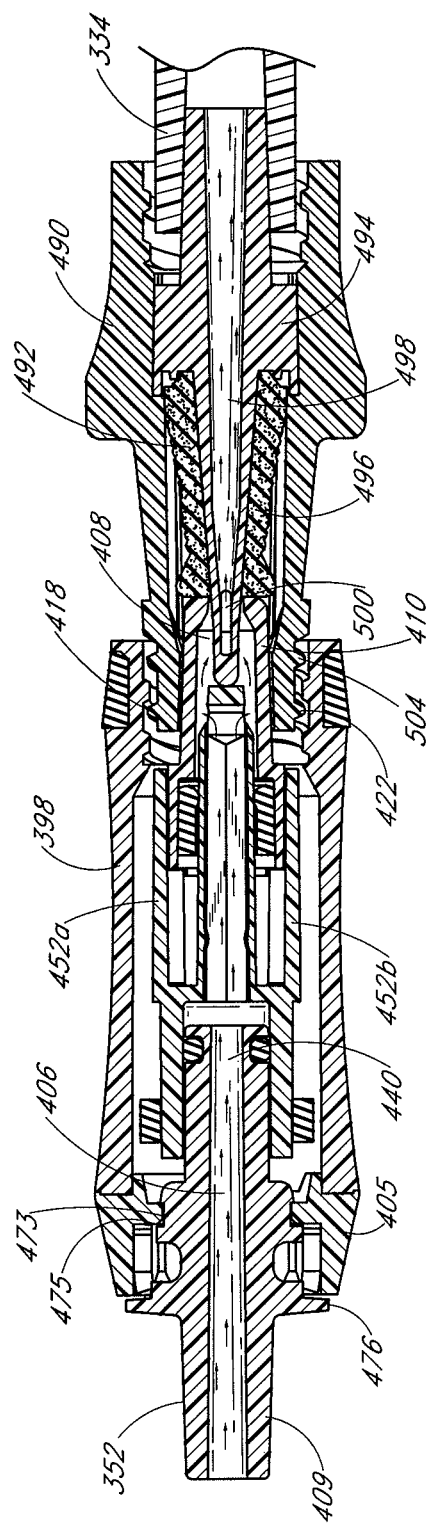
FIG. 6E is a cross-sectional detail view of the target connector portion and the female connector in an engaged configuration.

FIG. 6A shows a perspective view of the target connector portion 388. FIG. 6B is an exploded perspective view of the target connector portion 388. FIG. 6C shows a top view of a housing portion of the target connector portion 388. FIG. 6D shows a cross-sectional view of the target connector portion 388 and the female connector 332 in an unengaged configuration. FIG. 6E shows a cross-sectional view of the target portion 338 and the female connector 332 in an engaged configuration. Although the target connector portion 338 is shown separated from the remainder of the connector 320 in FIGS. 6A-6E, it should be understood that the target connector portion 338 can be connected to the remainder of the connector 320 when in use.

With reference now to FIGS. 6A-6E, the target connector portion 338 of the connector 320 can be a closeable male luer connector that is configured to prevent fluid from escaping from or entering into the connector when it is not engaged with a corresponding female connector, but allow fluid to flow when it is engaged with a corresponding female connector 332. In the embodiments shown, the target connector portion 338 can be a version of the Spiros® closeable male connector manufactured by ICU Medical, Inc., of San Clemente, Calif. Various embodiments of connectors of this type are described in U.S. Patent Publication No. 2008/0287920 (the "'920 Publication"), the entirety of which is incorporated herein by reference. Although the embodiments illustrated in FIGS. 6A-6E show the connector 332 as being a female connector and the target connector portion 338 as being a male connector, it should be noted that other configurations are possible. For example, the connector 332 can be a male connector while the target connector portion 338 can be a female connector. In some embodiments, a substantially entirely or entirely closed system can be achieved, at least in part, by providing corresponding automatically closeable male and female connectors at various (or all) connection points within the fluid transfer system 100, thereby causing the stationary fluid to substantially entirely remain within the fluid source, the fluid module, and the fluid target, respectively, upon disconnection and to not generally leak or vaporize outside of the system. For example, in some embodiments, corresponding pairs of automatically closing connectors (e.g., male and female connectors) can be provided at the interfaces between the fluid source and the fluid module, the fluid module and the intermediate container, and/or the fluid module and the destination or target container.

The target connector portion 338 can include a housing 398, a valve member 400, a resilient member 402, a sealing ring 404, an end cap 406, and an O-ring 407. The housing 398 can be generally tubular in shape, and can include a passageway 408 that extends axially through the housing. As illustrated, the passageway 408 includes apertures on each side of the connector. The housing 398 can include a male luer tip 410 that connects to the rest of the housing 398 at a base 412. The luer tip 410 can be generally tubular in shape so that a portion of the passageway 408 is defined therein, and the luer tip 410 can include a hole 414 at its end providing access to the passageway 408. In some embodiments, the luer tip 410 includes a shelf 416 that extends radially inwardly toward the axis of the passageway 408. The shelf 416 can be located adjacent to the hole 414, so that the passageway 408 is narrowed at the end of the luer tip 410. In some embodiments, the surface of the shelf 416 that faces radially inwardly is tapered so that the passageway 408 is narrowest immediately adjacent to the hole 414. In some circumstances, the shelf 416 can be configured to seal the passageway when a portion of the valve member 400 is abutted against it. As illustrated, in some embodiments, connectors can be used to substantially entirely prevent fluid therein to leak, vaporize, or otherwise escape through apertures in the fluid pathway when the connectors are closed.

The luer tip 410 can be surrounded by a shroud 418. In some embodiments, the luer tip 410 extends some distance beyond the edge 420 of the shroud. The shroud 418 can include inner threads 422 on its interior surface. The inner threads 422 can be used for securing a female connector 332. The shroud can include an indented portion 424 that has a smaller outer diameter than the other portions of the housing. The indented portion 424 can be configured to engage a portion of the resilient member 402.

The housing 398 can include two wall sections 426a, 426b separated by two gaps 428a, 428b. The gaps 428a, 428b can be configured to receive portions of the resilient member 402. The wall sections 426a, 426b can be configured to engage the end cap 406.

In some embodiments, the housing 398 includes a middle portion 430 located substantially between the wall sections 426a, 426b, and connected to the wall sections 426a, 426b near the gaps 428a, 428b. In some embodiments, holes 432a, 432b are defined between the middle portion 430 and the wall sections 426a, 426b (as shown in FIG. 6C). In some embodiments, the luer tip 410 connects to the middle portion 430 at its base 412. In some embodiments, the middle portion defines a portion of the passageway 408 therein. In some embodiments, portions 434 of the outer surface of the middle portion 430 are exposed by the gaps 428a, 428b. The portions 434 can include notches 436a, 436b and through-holes 438a, 438b. The notches 436a, 436b can be generally rectangular in shape, and can be tapered such that the notches 436a, 436b are narrower near their bases than near their surfaces. The through-holes 438a, 438b can also be generally rectangular in shape.

The housing 398 can be constructed from a variety of materials. The housing 398 can be constructed from a rigid material such as polycarbonate or other polymeric materials. In some embodiments, the housing 398 can be constructed from a hydrophobic material such as Bayer Makrolon, or any other suitable material. In some embodiments, the housing 398 can be formed from a substantially transparent material.

The valve member 400 can include a fluid passageway 440 extending axially from an opening formed in a base portion 444 and into a tube 446. In some embodiments, the passageway 440 can be wider in the base portion 444 than in the tube 446. In some embodiments, the tube 446 includes a narrowed tip 448. In some embodiments, the tip 448 can have a tapered outer surface. The tip 448 can be tapered to substantially the same degree as the radially inwardly facing surface of the shelf 416 and can be sized so that the tip 448 can form a fluid seal with the shelf 416 when abutted against it. In some embodiments, the tip 448 can be made from a flexible or compressible material, such as silicone rubber to facilitate formation of the fluid seal between the tip 448 and the shelf 416. In some embodiments, the tube can include one or more holes 450 for providing access to the fluid passageway 440. The holes 450 can be formed, for example, in the tip 448 of the tube 446.

In some embodiments, the valve member 400 can include two struts 452a, 452b extending out from the base 444 and positioned on either side of tube 446, so that an open space is defined on either side of the tube. In some embodiments, the tube 446 can extend axially past the ends of the struts 452a, 452b.

The base 444 of the valve member 400 can include a plurality of protrusions 454 extending radially outwardly from its external surface. In some embodiments, the protrusions 454 can be positioned so as to define two channels 456a, 456b therebetween. In some embodiments, the protrusions 454 do not extend across the full length of the base 444, leaving a lower portion 458 of the base 444 that has a substantially smooth outer surface.

The valve member 400 can be constructed from a variety of materials, such as polycarbonate or other polymeric materials. In some embodiments, the valve member 400 can be constructed from the same material as the housing 398. In some embodiments, the valve member 400 and housing 398 can be constructed from different materials. In some embodiments, the valve member 400 can be constructed from multiple materials or from multiple pieces. For example, the tip 448 can be constructed from a material that is more flexible than the remainder of the valve member 400. In some embodiments, the valve member 400 can be formed from a substantially opaque material.

The resilient member 402 can include a first ring 460 and a second ring 462 connected to each other by elastic members 464a, 464b. The elastic members 464a, 464b can be made from an elastic material that exerts a restoring force when stretched, such as silicon rubber. Thus, if the rings 460, 462 are pulled apart, the elastic members 464a, 464b function to restore the rings 460, 462 to their relaxed configuration. In some embodiments, the rings 460, 462 are also constructed from an elastic material, such as the same material used to form the elastic members 464a, 464b. In some embodiments, the second ring 462 can have a greater diameter than the first ring 460. In some embodiments, the second ring 462 can have a tapered outer surface so that the end of the second ring 462 that is closest to the first ring 460 is wider than the end of the second ring 462 that is furthest from the first ring 460.

The sealing ring 404 can be generally cylindrical in shape, and can have a bore 466 extending axially therethrough. The sealing ring 404 can have a cylindrical body section 468 and an O-ring 470 located at one end of the body section 468. In some embodiments, the thickest portion of the O-ring 470 can be thicker than the body section 468 so that the thickest portion of the O-ring 470 extends radially inwardly toward the axis of the bore 466 a distance past the inner surface of the body section 468. Thus, the bore 466 can be narrower at the thickest part of the O-ring 470 than in the body section 468. In some embodiments, the thickest portion of the O-ring 470 also extends radially outwardly a distance past the outer surface of the body section 468. The sealing ring 404 can include two protrusions 472a, 472b that extend radially outwardly from the body section 468. In some embodiments, the protrusions 472a, 472b can be generally rectangular in shape.

The sealing ring 404 can be constructed from a variety of materials. In some embodiments, the sealing ring 404 can be constructed from a deformable or elastic material such as a silicone rubber. In some embodiments, the sealing ring 404 can be constructed from the same material used for form the resilient member 402. In some embodiments, the sealing ring 404 can be constructed from a material capable of forming a fluid seal against a rigid plastic or other rigid polymeric material.

The end cap 406 can include a first end cap member 405 and a second end cap member 409. The second end cap member 409 can include a male connector 352, a plunger 474, and a disk portion 476 located between the male connector 352 and the plunger 474. The second end cap member 409 can have a fluid passageway 478 axially positioned therein. In some embodiments, the plunger 474 can be generally tubular in shape. In some embodiments, the outer surface of the plunger 474 includes an indented region 480, which can be configured to receive the O-ring 407 therein. The O-ring 407 can be constructed from an elastic material such as silicone rubber so that it can be stretched over the edge 482 of the plunger 474 and be seated in the indented region 480. In some embodiments, the O-ring 407 can be constructed from the same material as the resilient member 402 and/or the sealing ring 404. In some embodiments, the O-ring 407 can be sized so that when seated in the indented region 480, the thickest portion of the O-ring 407 extends radially outwardly a distance past the outer surface of the plunger 474.

In some embodiments, the passageway 478 can have a substantially constant width throughout the second end cap member 409. In some embodiments, the passageway 478 can be tapered so that it is wider in the male connector 352 than in the plunger 474. In some embodiments, the passageway 478 can narrow near the end of the plunger 474, for example, to accommodate the indented region 480.

The first end cap member 405 can be generally frusto-conical in shape and can have a central opening 471 therein. When assembled, the plunger 474 can extend through the central opening 471. A ridge 473 can extend inward into the central opening 471. The ridge 473 can be received into a channel 475 formed between the base of the plunger 474 and the disk portion 476 on the second end cap member 409 to secure the first end cap member 405 to the second end cap member 409. The ridge 473 and corresponding channel 475 can allow the first end cap member 405 to rotate about a longitudinal axis with respect to the second end cap member 409. Thus, the first end cap member 405 and the second end cap member 409 can join to form the end cap 406.

The valve end cap 406 can be constructed from a variety of materials, such as polycarbonate or other rigid polymeric materials. In some embodiments, the end cap 406 can be constructed from the same material as the housing 398 and/or the valve member 400.

In some embodiments, the end cap 406 can be constructed from a different material than the valve member 400 and/or the housing 398. The first end cap member 405 can be formed from the same material as the second end cap member 409, or different materials can be used. In some embodiments, the first end cap member 405 or the second end cap member 409 or both can be substantially transparent.

Certain interconnections between various parts of the target connector portion 338 will now be discussed in further detail. The sealing ring 404 can be positioned inside the middle portion 430 of the housing 398. The protrusions 472a, 472b can be sized and positioned so that they engage the through-holes 438a, 438b. Thus, the sealing ring 404 can be secured to the housing 398 so that it does not rotate or move axially with respect to the tube 446.

The valve member 400 can be slidably inserted into the housing 398 so that the tube 446 enters the passageway 408. The narrowed tip 448 of the tube 446 can pass through the bore 466 of the sealing ring 404 and into the male luer tip 410 until it abuts against the shelf 416. The tube 446 can have a width that substantially fills the bore 446 and presses against the O-ring 470 portion of the sealing ring 404 to form a fluid seal therebetween. The struts 452a, 452b can pass through the holes 432a, 432b in the housing 398 respectively, so that the struts 452a, 452b are positioned between the male luer tip 410 and the shroud 418.

The resilient member 402 can function to bias the valve member 400 against the housing 398. The first ring 460 can fit onto the lower portion 458 of the base 444 of the valve member 400, so that a surface of the ring 460 abuts against the protrusions 454. The second ring 462 can fit into the indented portion 424 of the housing. The elastic members 464a, 464b can be positioned in the channels 456a, 456b respectively, and can pass through the respective gaps 428a, 428b between the wall sections 426a, 426b of the housing 398.

The O-ring 407 can be seated onto the indented region 480 of the end cap 406, as discussed above, and the plunger 474 can be slidably inserted at least partially into the passageway 440 of the valve member. In some embodiments, the thickest portion of the O-ring 407 can be wider than the portion of the passageway 440 formed in the base 444 of the valve member 400, so that the O-ring 407 forms a fluid seal against the inner surface of the passageway 440. The plunger 474 can be inserted into the valve member 400 until the disk portion 476 of the end cap 406 comes into contact with the ends of the wall sections 426a, 426b of the housing 398.

In some embodiments, the wall sections 426a, 426b can be secured to the top surface 477 of the first end cap member 405 by sonic welding, snap fit structures (not shown), a pressure or friction fitting, or other suitable connection type. As mentioned above, the first end cap member 405 can be secured to the second end cap member 409 in a manner that allows the first end cap member 405 to rotate relative to the second end cap member 409. Thus, once the target connector portion 338 is assembled, the housing 398, sealing ring 404, resilient member 402, valve member 400, and first end cap member 405 can rotate relative to the second end cap member 409 about the longitudinal axis.

With reference now to FIGS. 6D-6E, the target connector portion 338 can be configured to engage a female connector 332. A variety of types of female connectors 332 can be used. The female connector 332 shown is a closable female luer connector that includes a housing 490, a spike 492, a base 494, and a resilient seal element 496. A fluid passageway 498 can pass through the base 494 and through the spike 492. The spike 492 can include one or more holes 500 providing fluid communication between the passageway 498 and the area outside the spike 492. The seal element 496 can be shaped and positioned to substantially surround the spike 492. The seal element 496 can include a closable aperture 502 or slit that can open to allow the tip of the spike 492 to pass through then end of the seal element 496 when the seal element 496 is compressed (as shown in FIG. 6E). The housing can include external threads 504 configured to engage the inner threads 422 on the housing 398 of the target connector portion 338. An end of the tubing 334 can be connected to the end of the female connector 332 by an adhesive, clamp, friction or pressure fitting, or other suitable manner to form a fluid tight connection.

As discussed above, in some embodiments, the housing 398, sealing ring 404, resilient member 402, valve member 400, and first end cap member 405 can rotate about the longitudinal axis with respect to the second end cap member 409. Thus, as the female connector 332 of the IV bag assembly is attached to the target connector portion 338, the female connector 332 can be held still while the housing 398 of the target connector portion 338 can rotate causing the threads 504, 422 to engage. Because the female connector 322 is not required to rotate during engagement and disengagement with the target connector portion 338, the tubing 334 can avoid being twisted or kinked and the user is not required to twist the IV Bag to accommodate rotation of the female connector 322. Embodiments of the connectors with this rotational capability are disclosed in greater detail in the '920 Publication incorporated by reference herein in its entirety.

When not engaged with the female connector 332 (as shown in FIG. 6D), the target connector portion 338 can be sealed. In some embodiments, fluid can enter the target connector portion 338 at the male connector 352 and pass through the passageway 478 of the end cap 406, through the passageway 440 of the valve member 400, through the holes 450, and into the portion of the passageway 408 defined by the male luer tip 410. But the fluid seal created by the tip 448 of the valve member 400 pressing against the shelf 416 of the male luer tip 410 prevents the fluid from exiting the target connector portion 338. In some embodiments, an increase in pressure, such as when additional fluid is forced into the target connector portion 338, causes the tip 448 to press more firmly against the shelf 416, thereby improving the fluid seal.

When the target connector portion 338 is engaged with the female connector 332 (as shown in FIG. 6E), the external threads 504 of the female luer connector 332 can engage the inner threads 422 on the shroud 418, securing the female connector 332 to the target connector portion 338. The edge of the male luer tip 410 can press against and compress the resilient seal element 496 so that the spike 492 passes through the aperture 502 until the holes 500 are exposed. The end of the housing 490 of the female luer connector 332 can enter the space between the male luer tip 410 and the shroud 418 until it contacts the struts 452a, 452b. As the female luer connector 332 further engages the target connector portion 338, it can push on the struts 452a, 452b causing the entire valve member 400 to retract. As the valve member 400 retracts, the elastic members 464a, 464b of the resilient member 402 stretch. When the valve member 400 retracts, the tip 448 disengages from the shelf 416, breaking the fluid seal and allowing fluid pass from the passageway 408 in the housing 398 of the target connector portion 338 to the passageway 498 in the female connector 332 via the holes 500. When engaged, the resilient seal element 496 exerts a restoring force toward the target connector portion 338 that presses the end of the seal element 496 against the end of the male luer tip 410, forming a fluid seal therebetween. Thus, the fluid can be kept isolated from the external environment while it is transferred from the target connector portion 338 to the female connector 332.

The female connector 332 can be disengaged from the target connector portion 338. The restoring force exerted by the resilient seal element 496 of the female connector 332 causes it to return to its closed position, sealing off its passageway 498. The elastic members 464a, 464b of the resilient member 402 exert a restoring force on the valve member 400, causing the valve member 400 to return to its closed position with its tip 448 abutted against the shelf 416 as the female connector 332 is disengaged.

The '920 Publication discloses additional details and various alternatives that can be applied to the target connector portion 338 of the connector 320.

Figure 7A:
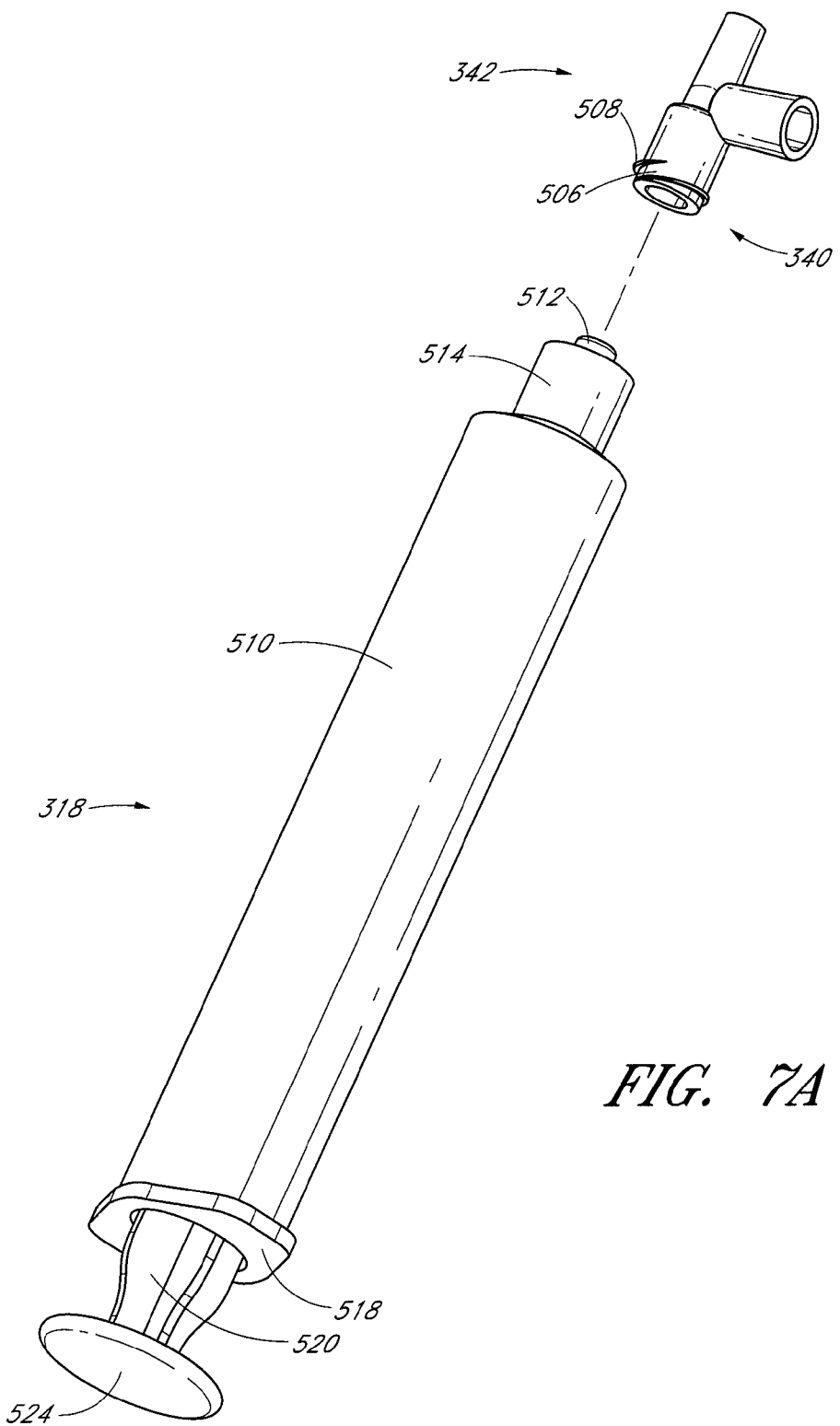
FIG. 7A is a perspective view of the syringe connector portion of FIG. 4A adjacent to the syringe of FIG. 3A.
Figures 7B, 7C:
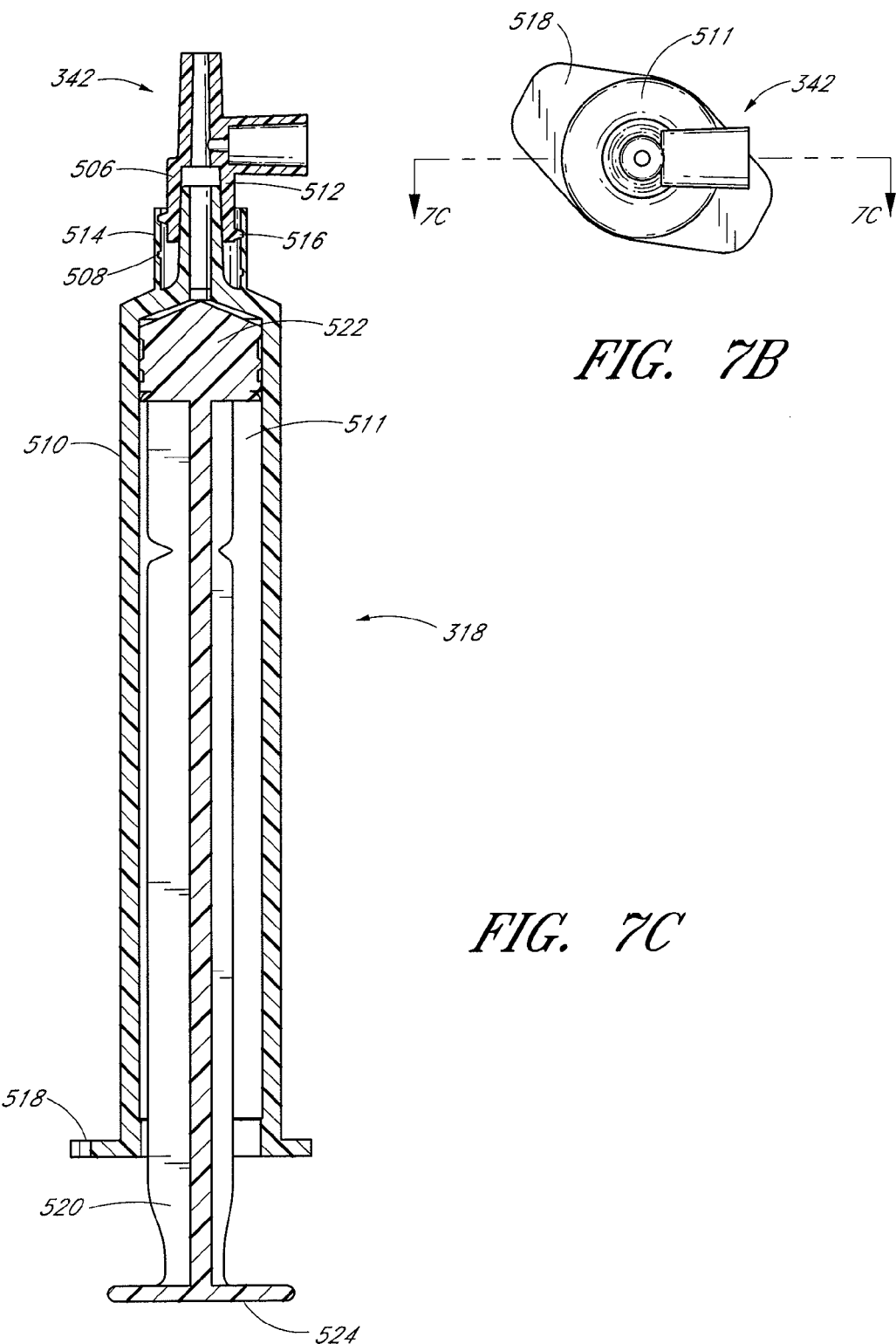
FIG. 7B is a top view of the syringe connector portion and the syringe of FIG. 7A in engagement.
FIG. 7C is a cross-sectional view of the syringe connector portion and syringe of FIG. 7A in engagement.

FIG. 7A shows a perspective view of the syringe 318 and the intermediate connector portion 340 of the connector 320 in an unengaged configuration. FIG. 7B is a top view of the syringe 318 and intermediate connector portion in an engaged configuration. FIG. 7C is a cross-sectional view of the syringe 318 and intermediate connector portion 340 in an engaged configuration. Although FIGS. 7A-7C show the main body 342 of the connector 320 separated from the remainder of the connector 320 for simplicity, it should be understood that the main body 342 can be connected to the remainder of the connector 320 when in use.

In the embodiment shown, the intermediate connector portion 340 is an integral part of the main body 342 of the connector 320. Other configurations are possible. For example, in some embodiments, the intermediate connector portion 340 can a separate piece connected to the main body 342. The intermediate connector portion 340 can include a female connector 506. In some embodiments, the female connector 506 can have a tapered inner surface. The external surface of the female connector 506 can include external threads 508.

The syringe 318 can have a hollow syringe body 510 defining an internal volume 511. The syringe can include a male luer tip 512 at one end and a shroud 514 surrounding the male luer tip 512. The shroud 514 can have internal threads 516. The male luer tip 512 and threaded shroud 514 can be configured to securely mate with the female connector 506 on the intermediate connector portion 340 of the connector 320, forming a fluid tight connection therebetween. The syringe body 510 can include a body flange 518 positioned at the end of the body opposite the male luer tip 512. The syringe also includes a plunger 520 that can be slidably received into the internal volume of the syringe body 510. The plunger 522 can include a stopper 522 or other sealing member configured to form a fluid tight seal against the inner surface of the syringe body 510. A plunger flange 524 can be positioned on the plunger 520 at the end opposite the stopper 522.

In some embodiments, the female connector 506 and the male luer tip 512 can be open to the atmosphere when unengaged. Other configurations are possible. For example, in some embodiments, the female connector 506 can be a sealing female connector similar to the female connector 332 described above, and can be for example a version of the Clave® connector. Similarly, the syringe 318 can include a sealing male connector, or a sealing male connector can be connected between the syringe 318 and the female connector 506. In some embodiments the sealing male connector can be a version of the Spiros™ connector. Thus, in some embodiments, the fluid in the syringe 318 and in the connector 320 can be isolated from the environment even when they are disengaged from each other.

In some embodiments, when the syringe 318 is engaged with the connector 320 (as shown in FIG. 7B) the internal volume 511 of the syringe 318 can be in two way fluid communication with the connector 320. Thus, as the plunger 520 is retracted a fluid can be drawn from the connector 320 into the internal volume 511 of the syringe 318. Then as the plunger 520 is advanced the fluid can be directed out of the internal volume 511 and into the connector 320.

As discussed briefly above, the connector 320 can include a source check valve 356 and a target check valve 358. The check valves 356, 358 can function so that when the plunger 520 is retracted the source check valve 356 opens and the target check valve 358 closes, allowing fluid to flow from the vial 314 through the connector 320 and into the syringe 318. Then, when the plunger 520 is advanced the source check valve 356 can close and the target check valve 358 can open, allowing fluid to flow from the syringe 318 through the connector 320 and into the IV bag 316.

Figure 8B:
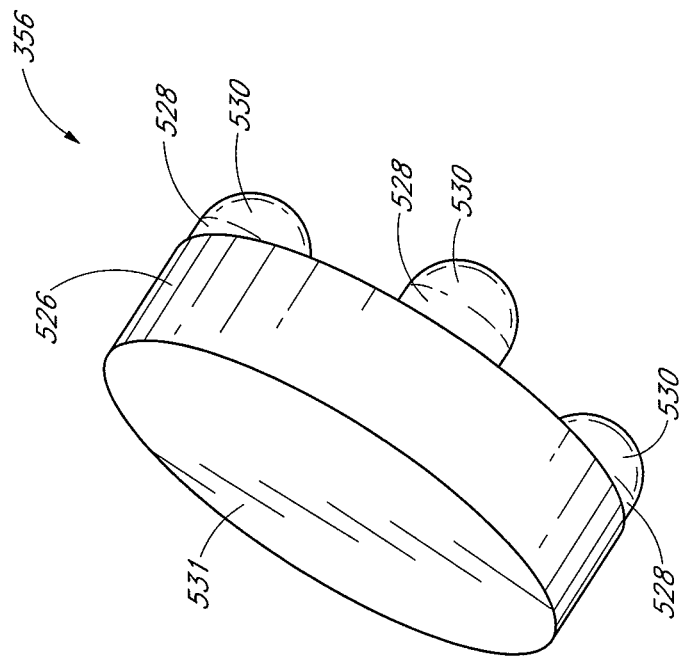
FIG. 8B is another perspective view of the source check valve of FIG. 8A.
Figure 8A:
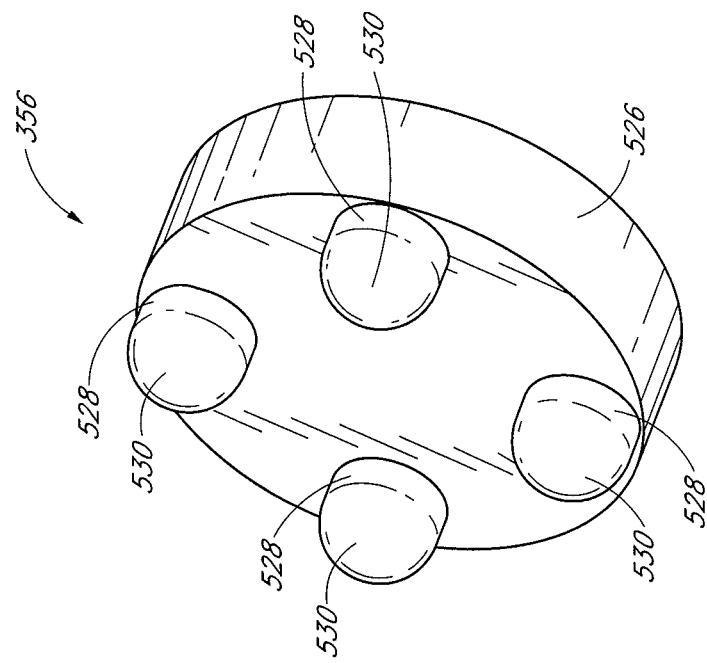
FIG. 8A is a perspective view of the source check valve of FIG. 4B.

FIG. 8A is a perspective view showing the source check valve 356. FIG. 8B is another perspective view showing the source check valve 356 from a different angle. The source check valve 356 can include a disk shaped base 526. A plurality of feet 528 can extend axially from one side of the base 526. In the embodiment shown, the source check valve 356 includes four feet 528, but other numbers of feet 528 can be used, such as three feet, or five feet, or another suitable number of feet 528. In some embodiments, the feet 528 can each be generally cylindrical in shape and can each include a rounded tip 530. Other shapes and configurations are possible. The source check valve 356 can have a sealing surface 531 located on the side opposite the feet 528.

Figure 9A:
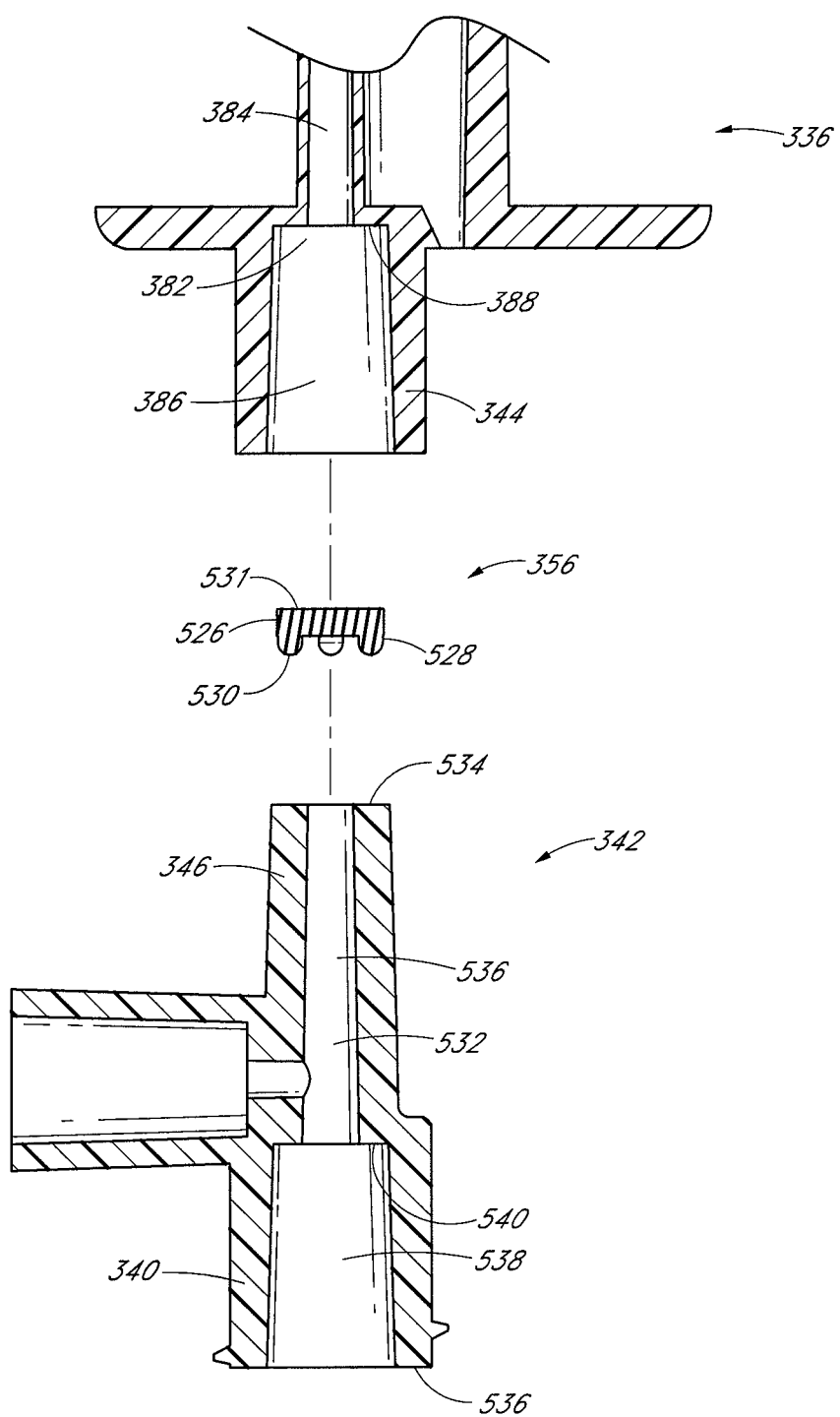
FIG. 9A is an exploded cross sectional view of the source connector portion and main body of FIG. 4A and the source check valve of FIG. 8A.
Figure 9B:
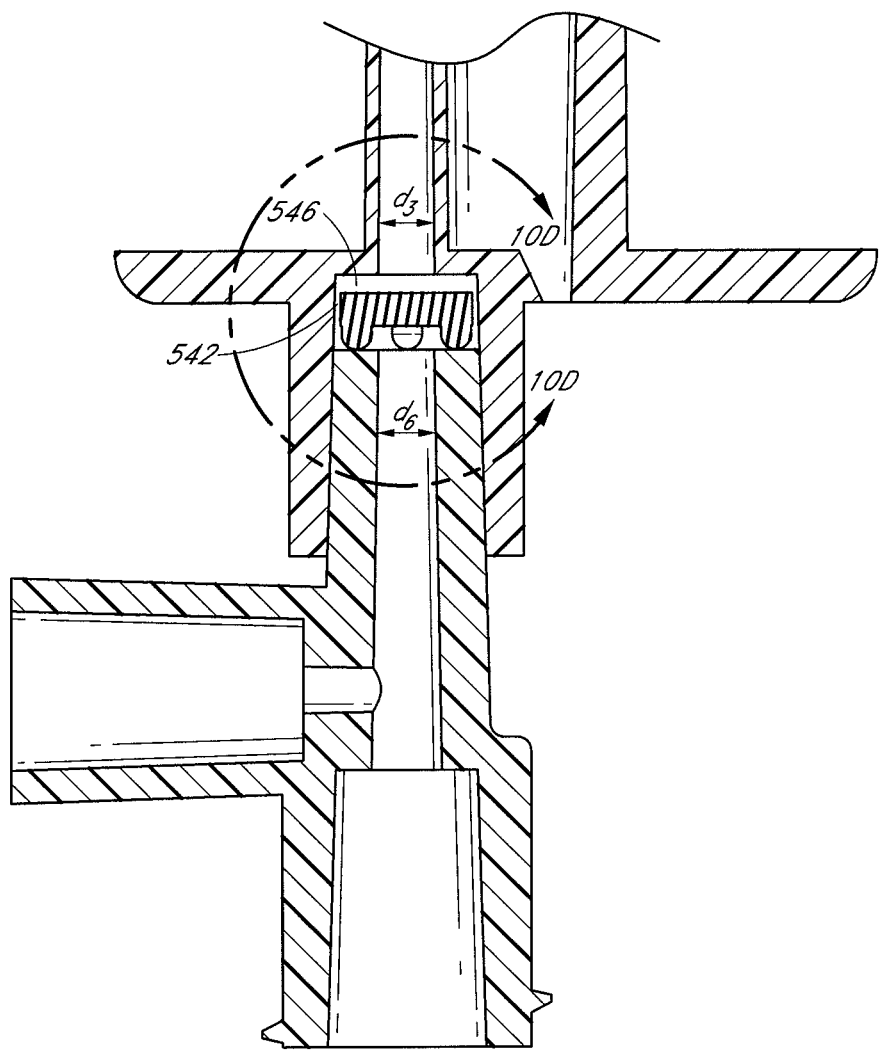
FIG. 9B is a cross sectional view of the source connector portion, main body, and source check valve shown in FIG. 9A in an assembled configuration.

FIG. 9A shows the source connector portion 336, the source check valve 356, and the main body 342 in an exploded cross-sectional view. FIG. 9B is a cross-sectional view of the source connector portion 336, the source check valve 356, and the main body 342 in an assembled configuration with the check valve 356 in an open position. As discussed above, the source connector portion 336 can include a fluid extraction channel 382 having an upper, narrow portion 384 and a lower, wide portion 386. A shoulder 388 can be defined at the transition from the upper portion 384 to the lower portion 386 of the fluid extraction channel 382. In some embodiments, the lower portion 386 of the extraction channel 382 can have a tapered inner surface, so that the lower portion 386 narrows near the shoulder 388. The upper portion 384 can also have a tapered inner surface, so that the upper portion 384 widens near the shoulder 388. In some embodiments, the upper portion 384 and/or the lower portion 386 can be substantially cylindrical or can assume a variety of other shapes having a substantially uniform cross-sectional area.

The main body 342 can include a first fluid passageway 532 leading from the end 534 of the male connector 346 to the end 534 of the intermediate connector portion 340. The first fluid passageway 532 can include an upper portion 536 and a lower portion 538. The lower portion 538 can be wider than the upper portion 536 defining a shoulder 540. The upper portion 536 and lower portion 538 can have tapered or untapered inner surfaces. When assembled, the source check valve 356 can be positioned in the chamber 348 located between the end 534 of the male connector 346 and the shoulder 388 of the fluid extraction channel 382. The source check valve 356 can be positioned so that the feet 528 face toward the end 534 of the male connector 346, while the sealing surface 531 can face toward the shoulder 388. In some configurations, when the pressure in the fluid passageway 332 is sufficiently higher than the pressure in the extraction channel 382, such as when the plunger 520 of the syringe 318 is advanced forcing fluid into the fluid passageway 332, the source check valve 356 is pushed away from the main body 342 and the sealing surface 531 engages the shoulder 388 forming a fluid tight seal that prevents fluid from flowing from the first fluid passageway 532 into the upper portion 384 of the extraction channel 382. In some configurations, when the pressure in the fluid passageway 332 is sufficiently lower than the pressure in the extraction channel 382, such as when the plunger 520 of the syringe 318 is retracted drawing fluid out of the fluid passageway 332, the source check valve 356 is pulled away from the shoulder 388 and the feet 528 rest against the end 534 of the male connector 346 in an open position.

Figure 10D:
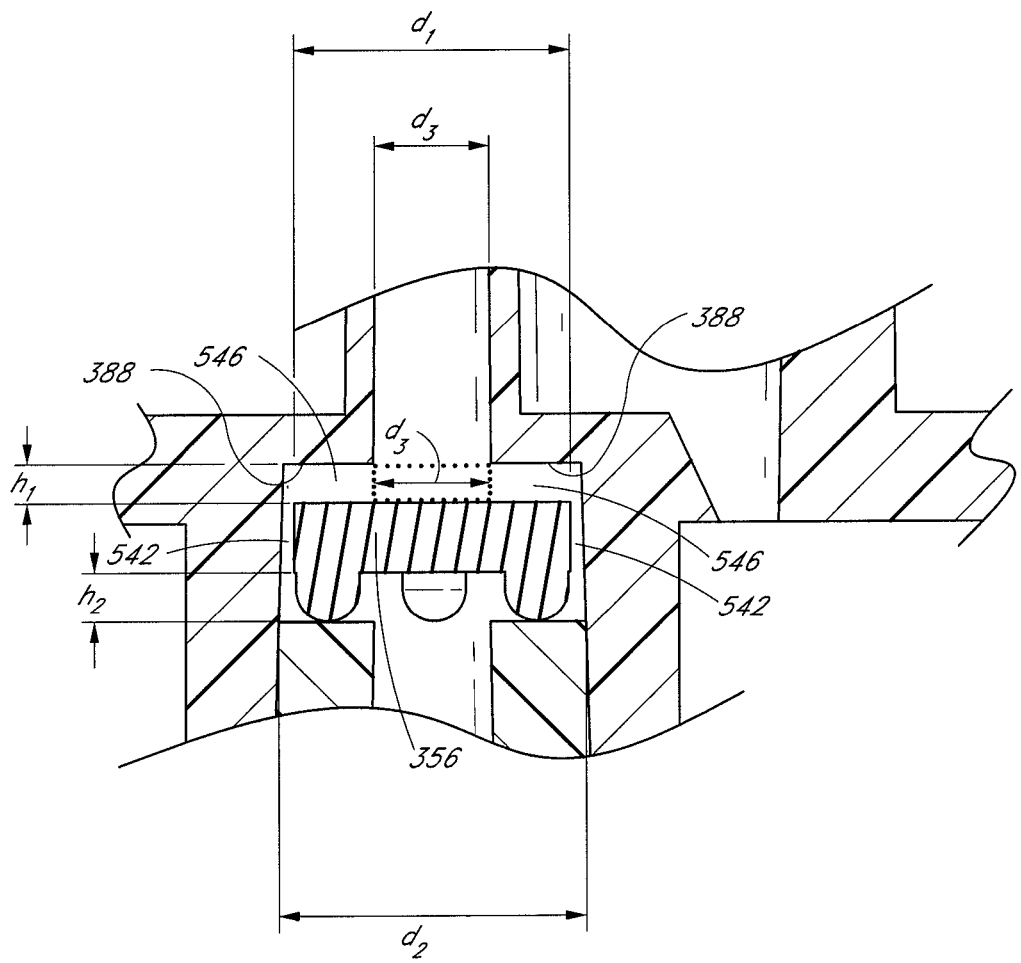
FIG. 10D is a side cross sectional view showing the source connector portion and the source check valve of FIG. 10B.

FIG. 10A is a side view of the main body 342 coupled to the source connector portion 336 of the connector 320. FIG. 10B is a cross sectional view of the source connector portion 336 of the connector 320 and the source check valve 356 disposed therein. FIG. 10C is a partial cross-sectional view showing the source check valve 356 positioned in a chamber 348 defined radially by the walls of the female connector 344. FIG. 10D is another cross sectional view showing the source check valve 356 positioned in the chamber 348.

With reference to FIGS. 10A-10D, the base 526 of the source check valve 356 can be disk shaped and can have a diameter $d_1$ that is less than the diameter $d_2$ of the chamber 438, defining a space 542 between the side edges of the source check valve 356 and the inner walls of the chamber 348 through which fluid can pass. Also, the feet 528 can be spaced so that open areas 544 are defined between adjacent feet 528.

Thus, when the source check valve 356 is in the open position, fluid can flow from the upper portion 384 of the extraction channel 382, into the chamber 348, through the space 542 between the side edges of the source check valve 356 and the inner walls of the chamber 348, through the open areas 544 between the feet 528, and into the upper portion 536 of the first fluid passageway 532.

In some embodiments, the source check valve 356 can be configured to allow a substantially open flow around the check valve 356 without significant bottlenecking. For example, the space 542 between the side edges of the source check valve 356 and the inner walls of the chamber 348 can have a cross-sectional area $A_1$ that is at least large as the cross-sectional area $A_2$ of the upper portion 483 of the extraction channel 382 taken near the chamber 348. This relationship can be expressed as equation (1) below.

$$A_1 \geq A_2 \tag{1}$$

In some embodiments, the chamber 348 and the source check valve 356 can both be substantially cylindrical, having diameters $d_2$ and $d_1$ respectively (as shown in FIGS. 10C and 10D). The cross sectional area $A_1$ of the space the space 542 between the side edges of the source check valve 356 and the inner walls of the chamber 348 can then be defined by equation (2) below.

$$A_1 = \pi\left(\frac{d_2}{2}\right)^2 - \pi\left(\frac{d_1}{2}\right)^2 \tag{2}$$

In some embodiments, the upper portion 483 of the extraction channel 382 taken near the chamber 348 can be substantially cylindrical and can have a diameter $d_3$ (as shown in FIG. 10D). The area $A_2$ can then be defined by equation (3) below.

$$A_2 = \pi\left(\frac{d_3}{2}\right)^2 \tag{3}$$

By substituting equations (2) and (3), equation (1) can be rewritten as equation (4) below.

$$\pi\left(\frac{d_2}{2}\right)^2 - \pi\left(\frac{d_1}{2}\right)^2 \geq \pi\left(\frac{d_3}{2}\right)^2 \tag{4}$$

By solving equation (4) for $d_1$, equation (4) can be rewritten as equation (5) below.

$$d_1 \leq \sqrt{d_2^2 - d_3^2} \tag{5}$$

Thus, when the diameter $d_2$ of the chamber 348 and the diameter $d_3$ of the upper portion 483 of the extraction channel 382 are known, the source check valve 356 can be having a diameter that satisfies equation (5) to avoid bottlenecking of fluid as it flows through the space 542.

As shown in FIG. 10D, in some embodiments, when the source check valve 356 is in the open position a space 546 having a height $h_1$ is defined between the sealing surface 531 and the shoulder 388. The space 546 can allow fluid to flow therethrough. In some embodiments, the source check valve 356 and the chamber 348 can be configured to prevent bottlenecking as fluid flows through the space 546. For example, in the embodiment shown, the smallest area of the space 546 through which the fluid flows can be described as an open an imaginary open cylinder (shown by dotted lines in FIG. 10D) having a height of $h_1$, a diameter of $d_3$, and a surface area $A_3$. If the surface area $A_3$ of the imaginary cylinder is at least as great as the cross-sectional area $A_2$ of the upper portion 483 of the extraction channel 382 taken near the chamber 348, bottlenecking can be reduced. This relationship can be expressed as equation (6) below.

$$A_3 \geq A_2 \quad (6)$$

The surface area $A_3$ of the imaginary open cylinder can be expressed as equation (7) below.

$$A_3 = \pi d_3 h_1 \quad (7)$$

By substituting equations (3) and (7), equation (6) can be rewritten as equation (8) below.

$$\pi d_3 h_1 \geq \pi \left(\frac{d_3}{2}\right)^2 \quad (8)$$

By solving for $h_1$, equation (8) can be rewritten as equation (9) below.

$$h_1 \geq \frac{d_3}{4} \quad (9)$$

Thus, when the diameter $d_3$ of the upper portion 483 of the extraction channel 382 is known, the source check valve 356 can be made to have a total height that is shorter than the height of the chamber 348 by at least $$\frac{d_3}{4}$$

to reduce bottlenecking as the fluid flows from the upper portion 483 of the extraction channel 382 into the space 546 between the source check valve 356 and the shoulder 388.

The source check valve 356 can be configured to reduce bottlenecking of the fluid as it flows through the open areas 544 (shown in FIG. 10C) between the feet 528. For example, if the total area $A_4$ of the open areas 544 between the feet 528 is at least as great as the cross-sectional area $A_2$ of the upper portion 483 of the extraction channel 382 taken near the chamber 348, bottlenecking can be reduced as the fluid flows from the extraction channel 382 and around the check valve 356. This relationship can be expressed by equation (10) below.

$$A_4 \geq A_2 \quad (10)$$

In the embodiment shown, the feet 528 are arranged so that an imaginary open cylinder (shown by a dotted line in FIG. 10C) can be placed so that its edge intersects each of the feet 528. The feet 528 can be positioned so that the imaginary cylinder has a diameter $d_4$. In some embodiments, the source check valve 356 includes a number n of feet that each have substantially equal diameters $d_5$ and substantially equal heights $h_2$. The area total area $A_4$ of the open areas 544 can be defined by equation (11) below. It should be noted that because the feet 528 have rounded tips 530, the area $A_4$ can be slightly greater than represented by equation (11). In some embodiments, the feet 528 do not have rounded tips and can be substantially cylindrical.

$$A_4 = \pi d_4 h_2 - n d_5 \quad (11)$$

By substituting equations (3) and (11), equation (10) can be rewritten as equation (12) below.

$$\pi d_4 h_2 - n d_5 \geq \pi \left(\frac{d_3}{2}\right)^2 \quad (12)$$

By using feet 528 that satisfy equation (12), bottlenecking can be reduced. For example, if the number n of feed or the diameter $d_5$ is increased, the height $h_2$ of the feet can be increased, or the feet can be moved closer to the peripheral edge (increasing $d_4$) to compensate.

In some embodiments, the source check valve 356 can be configured to provide a substantially uniform flow of fluid. For example, the space 542 between the side edges of the source check valve 356 and the inner walls of the chamber 348 can have a cross-sectional area $A_1$ that is substantially equal to the cross-sectional area $A_2$ of the upper portion 483 of the extraction channel 382 taken near the chamber 348. Similarly, the surface area $A_3$ of the first imaginary cylinder can be substantially equal to the cross-sectional area $A_2$ of the upper portion 483 of the extraction channel 382 taken near the chamber 348. Likewise, the total area $A_4$ of the open areas 544 between the feet 528 can be substantially equal to the cross-sectional area $A_2$ of the upper portion 483 of the extraction channel 382 taken near the chamber 348. The source check valve 356 and chamber 348 can be configured so that other areas of flow also have an area that is substantially equal to the cross-sectional area $A_2$ of the upper portion 483 of the extraction channel 382 taken near the chamber 348. For example, in some embodiments, the shoulder 388 or the sealing surface 531 of the check valve 356 can be tapered so that the height of the space 546 is smaller near the side space 542 than near the upper portion 483 of the extraction channel 382. In some embodiments, the areas discussed herein can be considered to be substantially equal if they vary by an amount less than an acceptable tolerance T. In some embodiments, the acceptable tolerance T can be less than about 1 mm, 0.5 mm, 0.1 mm, 0.05 mm, or 0.01 mm. In some embodiments, the flow areas around the check valve 356 (e.g., $A_1$, $A_3$, and $A_4$) can be smaller than $A_2$ by an amount no larger than tolerance T. Thus, in some embodiments, a small but acceptable amount of bottlenecking can occur as the fluid flows around the source check valve 356.

Figure 11:
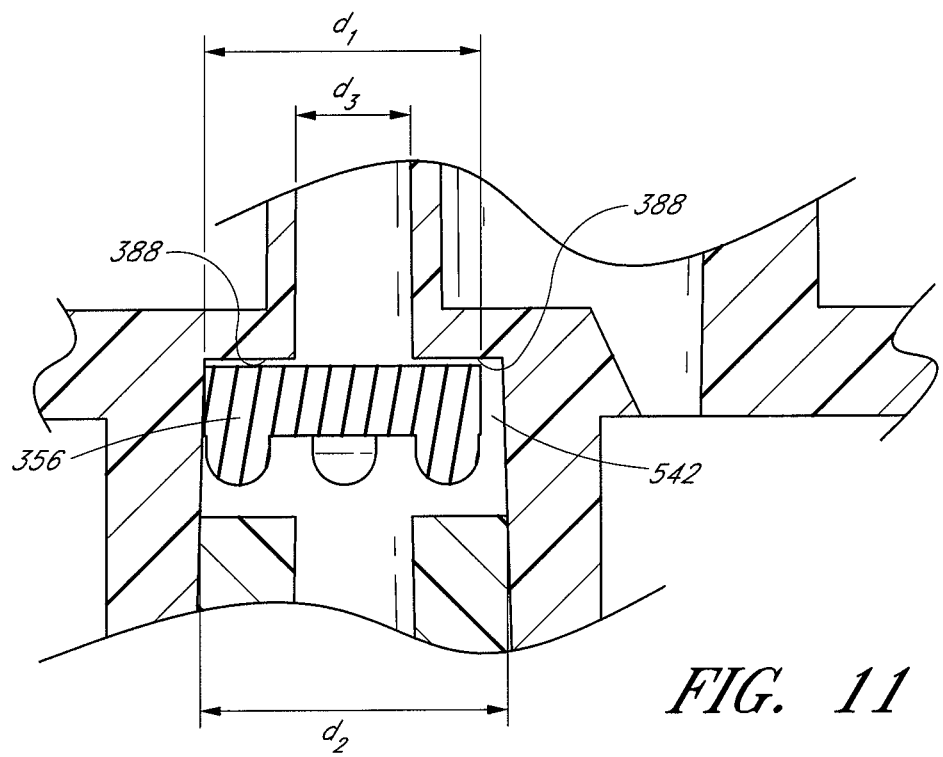
FIG. 11 is a side cross sectional view of the source check valve of FIG. 10B positioned against a side wall of a chamber.

In embodiments where the diameter $d_2$ of the chamber 348 is greater than the diameter $d_1$ of the source check valve 356, the source check valve 356 can move not only axially within the chamber, but also radially within the chamber. For example, FIG. 11 shows a cross-sectional view of the source check valve 356 positioned against one side of the chamber 348 when in a closed position. The diameter $d_1$ of the check valve 356 can be large enough to allow the check valve 356 to adequately seal off the chamber 348 when positioned against one side of the chamber 348. For example, in some embodiments, the chamber 348 can be generally symmetrical so that the shoulder 388 has a substantially uniform width, and the diameter $d_1$ of the check valve 356 can be chosen to satisfy the equation (13) below.

$$d_1 > \frac{d_2}{2} + \frac{d_3}{2} \tag{13}$$

Figure 12:
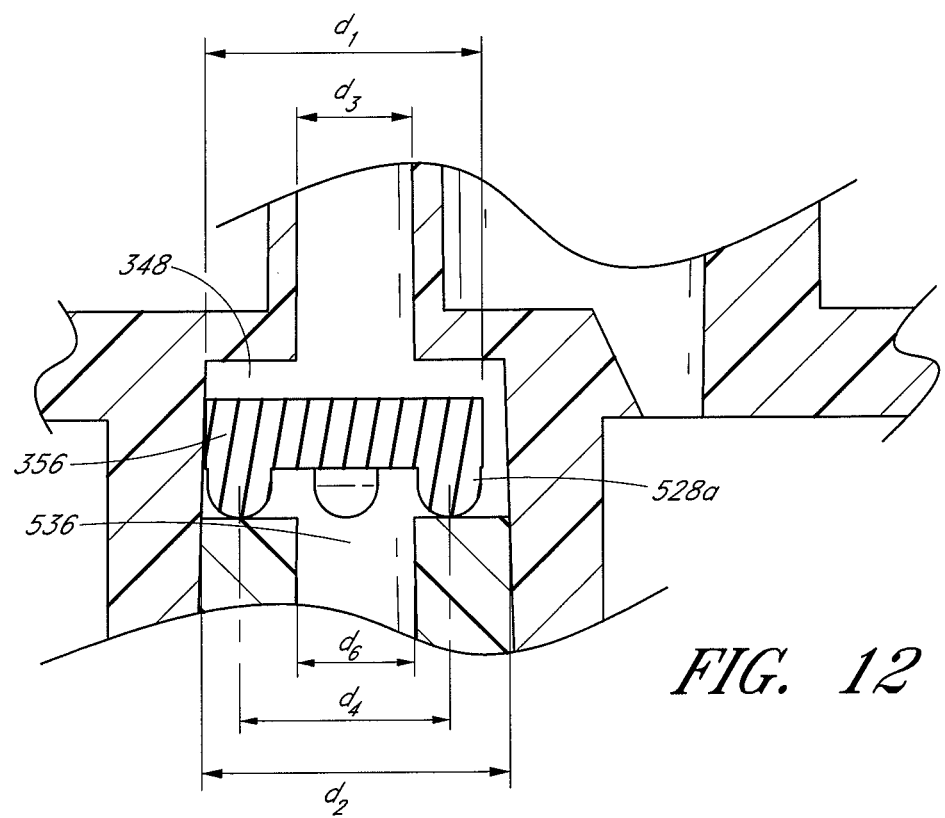
FIG. 12 is another side cross sectional view of the source check valve of FIG. 10B positioned against a side wall of a chamber.

In some embodiments, the upper portion 536 of the first fluid passageway 532 can be generally cylindrical in shape and can have a diameter $d_6$. In some embodiments, the feet 528 are positioned near enough to the peripheral edges of the check valve 356 so the feet do not drop into the upper portion 536 of the first fluid passageway 532 when the check valve 356 is positioned against the side of the chamber 348. For example, FIG. 12 shows a cross-sectional view of the source check valve 356 positioned against one side of the chamber 348 in an open position. The feet 528 are positioned so that when the check valve 356 is positioned against one side of the chamber 348 the foot 528a closest to the first passageway 532 does not drop down into the first passageway 532. In some embodiments, the feet 528 can be positioned along a circle concentric with the check valve 356, the circle having a diameter $d_4$ that satisfies the equation (14) below.

$$d_4 \geq d_6 + d_2 - d_1 \tag{14}$$

In some embodiments, the source check valve 356 can have a diameter of about 2 mm to about 20 mm, although diameters outside this range can also be used. A variety of other configurations are possible. For example, the source check valve 356, the chamber 348, the extraction channel 382 and/or the first fluid passageway 532 can have non-circular cross sections.

Figure 13A:
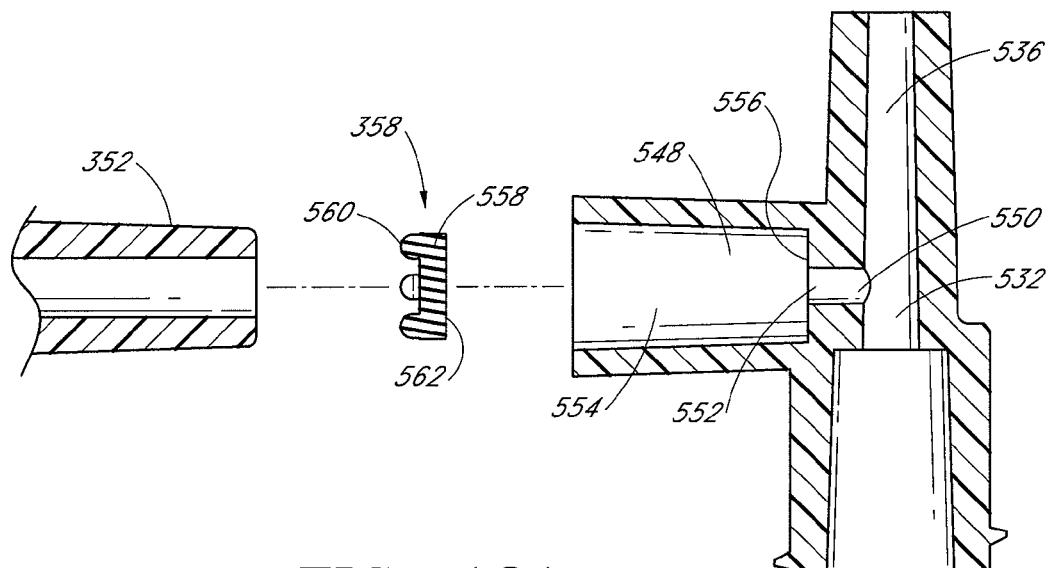
FIG. 13A is an exploded cross sectional view of the main body, target connector portion, and target check valve of FIG. 4B.
Figure 13B:
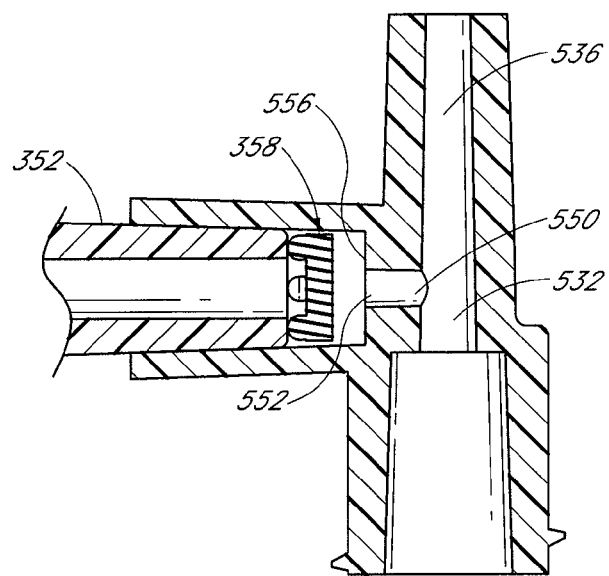
FIG. 13B is a cross sectional view of the main body, target connector portion, and target check valve of FIG. 13A.

Turning now to FIGS. 13A-B, FIG. 13A shows an exploded cross-sectional view of the target connector portion 338, the target check valve 358, and the main body 342. FIG. 13B shows a cross-sectional view of the target connector portion 338, the target check valve 358, and the main body 342 in an assembled configuration with the target check valve 358 in an open position. The main body 342 can include a second fluid passageway 548 that intersects the first fluid passageway 532 at a junction 550. In some embodiments, the second fluid passageway 548 can intersect the upper portion 536 of the first fluid passageway 532. In the embodiment shown the second fluid passageway 548 intersects the first fluid passageway 532 at a substantially right angle. Other configurations are also possible. For example, the fluid passageways 532, 548 can intersect at an oblique angle. The second fluid passageway 548 can have a narrow portion 552 and a wide portion 554 that define a shoulder 556. In some embodiments, the narrow portion 552 can have a width that is substantially the same as the width of the upper portion 536 of the first fluid passageway 532 near the junction 550, while in other embodiments the narrow portion 552 can have a width that is smaller or larger than the width of the upper portion 536 of the first fluid passageway 532 near the junction 550. In some embodiments, the narrow portion 552 and/or the wide portion 554 of the second fluid passageway 548 can have tapered interior surfaces. For example, the wide portion 554 can be tapered so as to receive a tapered male connector 352, as discussed above.

When assembled, the target check valve 358 can be positioned in the chamber 354 formed between the male connector 352 and the shoulder 556. In some embodiments, the target check valve 358 can be similar to the source check valve 356 described above, having a disk shaped base 558, a plurality of feet 560, and a sealing surface 562. The target check valve 358 can be positioned with the feet 560 facing the male connector 352 and the sealing surface 562 facing the shoulder 556. Thus, when the pressure in the second fluid passageway 548 is sufficiently higher than the pressure inside the male connector 352, such as when the plunger 520 of the syringe 318 is advanced forcing fluid into the main body 342, the target check valve 358 can be pushed toward the male connector 352 so that the feet 560 rest against the end of the male connector 352 in an open position. When the pressure in the second fluid passageway 548 is sufficiently lower than the pressure inside the male connector 352, such as when the plunger 520 of the syringe 318 is retracted drawing fluid out of the main body 342, the target check valve 358 can be pulled away from the main body 342 so that the sealing surface 562 engages the shoulder 556 forming a fluid tight seal that prevents fluid from flowing from the chamber 354 into the narrow portion 552 of the second fluid channel 548.

In some embodiments, the target check valve 358 and the chamber 354 can be configured to reduce bottlenecking as fluid flows around the target check valve 358 in its open position. For example, the target check valve 358 and chamber 354 can be configured similarly in many ways to the source check valve 358 and chamber 348 described above.

Figure 14A:
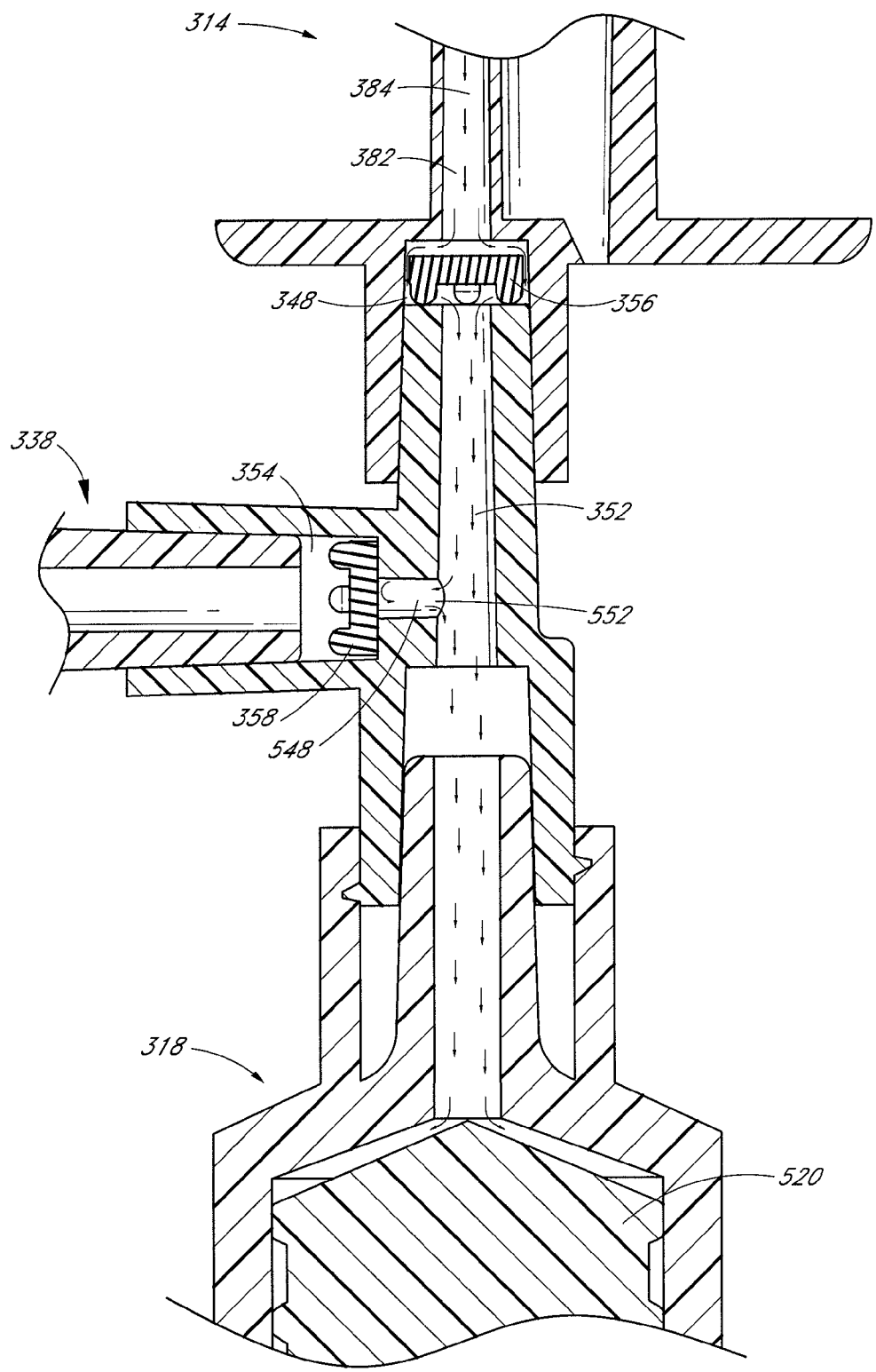
FIG. 14A is a cross sectional view of the fluid transfer system of FIG. 3A with the source check valve in an open configuration and the target check valve in a closed configuration.

The check valves 356, 358 can work together to direct fluid through the system. FIG. 14A shows the flow of fluid (by flow lines) as the plunger 520 is retracted. Fluid is drawn out of the vial 314 through the upper portion 384 of the fluid extraction channel 382. The fluid flows into the chamber 348 and around the source check valve 356, which is in the open position. The fluid flows through the first fluid passageway 532 and into the syringe 318. The fluid can enter the narrow portion 552 of the second fluid passageway 548, but the target check valve 358 is in the closed position and prevents the fluid from entering the chamber 354.

Figure 14B:
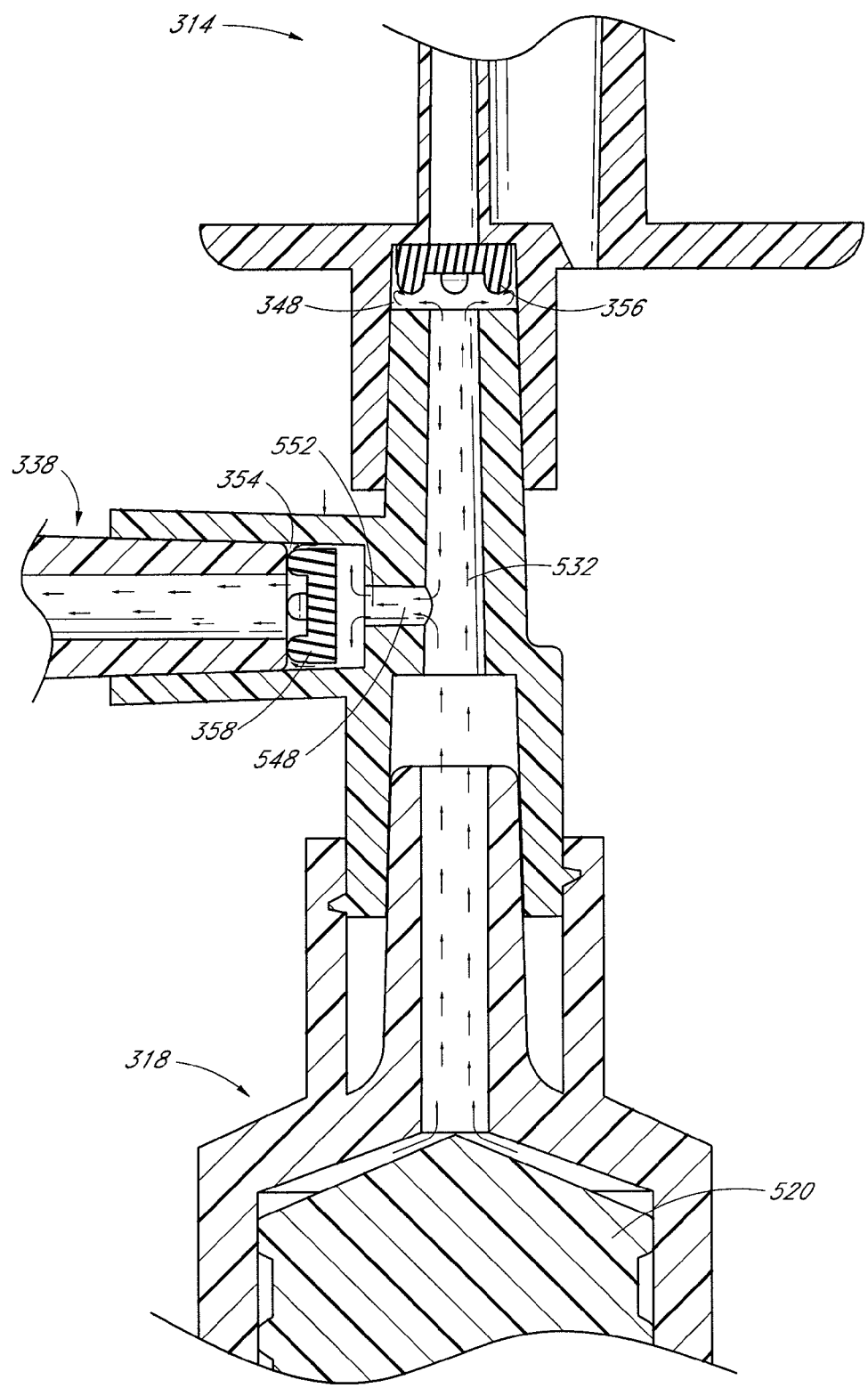
FIG. 14B is a cross sectional view of the fluid transfer system of FIG. 3A with the source check valve in a closed configuration and the target check valve in an open configuration.

FIG. 14B shows the flow of fluid (by flow lines) as the plunger 520 is advanced. Fluid is expelled from the syringe 318, into the first fluid passageway 532, through the narrow portion 552 of the second fluid passageway 548, into the chamber 354, around the target check valve 358 (which is in the open position), through the target connector portion 338, toward the IV bag 316. The fluid can travel up the first fluid passageway 532 and into the chamber 348, but the source check valve 356 is in the closed position and prevents the fluid from advancing back into the vial 314. In some embodiments, the force of the fluid pressing against the source check valve 356 is strong enough the overcome the force of gravity pulling the source check valve 356 downward so as to maintain the source check valve 356 in the closed position.

The check valves 356, 358 can be formed from rigid, semi-rigid, or deformable materials. In some embodiments, at least the sealing surfaces 531, 562 of the check valves 356, 358 can be formed from a material capable of forming a fluid tight seal against a plastic or other rigid material. In some embodiments, the check valves can include a silicon-based deformable material, or a rubber. In some embodiments, the feet 528, 560 can be formed from different material than the disk shaped base 526, 558. In some embodiments, the feet 528, 560 can be formed from a rigid polycarbonate or other polymeric material.

Figure 15:
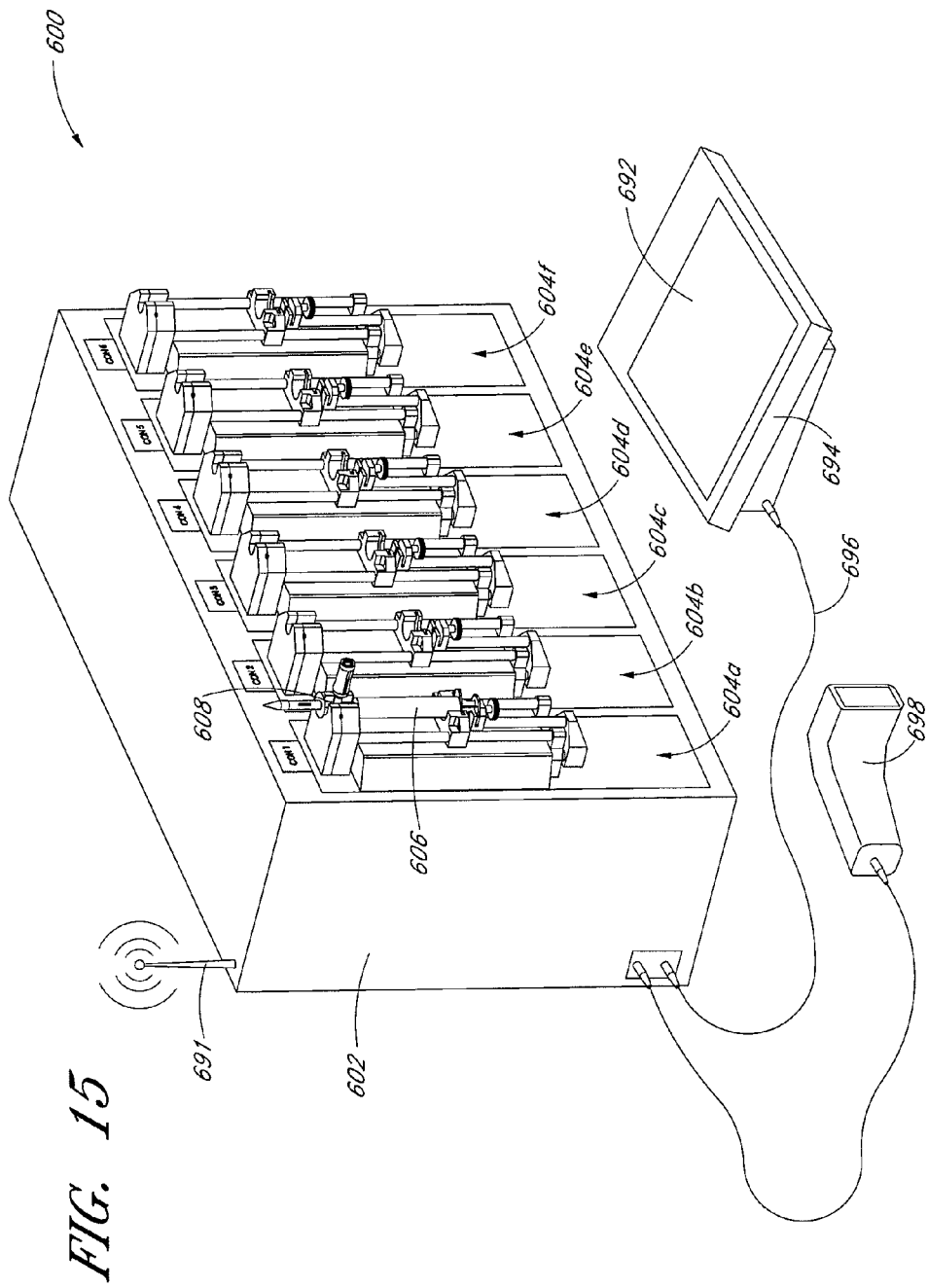
FIG. 15 is a perspective view of an automated system for transferring fluid having multiple transfer stations.

FIG. 15 is a perspective view of an automated system 600 for transferring fluid, which can be similar to or the same as the other automated fluid transfer systems (e.g., 100, 200) disclosed herein. The system 600 can include a base housing 602, and six transfer stations 604a-f, located on a front side of the base housing 602. In some embodiments, the system 600 can include a different number of transfer stations 604a-f (e.g., one, two, four, five, eight, or more transfer stations). In some embodiments, the transfer stations 604a-f can be distributed on multiple sides of the base housing 602. Transfer stations 604b-f are shown in an empty state having no syringe attached thereto. Transfer station 604a is shown having a syringe 606 and a connector 608 attached thereto. During operation, a vial (not shown) can be attached to the top of the connector 608 and an IV bag (not shown) can be placed in fluid connection with the connector 608 so that fluid can be transferred from the vial to the syringe 606 and then from the syringe 606 into the IV bag, as discussed above. Also, during operation, some or all of the transfer stations 604a-f can be equipped similarly to transfer station 604a. In some embodiments, multiple transfer stations 604a-f can operate simultaneously. In some embodiments, multiple transfer stations 604a-f can be placed in fluid communication with a single IV bag so that fluid from multiple vials can be combined into a single IV bag. In some embodiments, one or more of the transfer stations 604a-f can include a dedicated IV bag so that fluid from only a single transfer stations can be transferred into the dedicated IV bag.

Figure 16A:
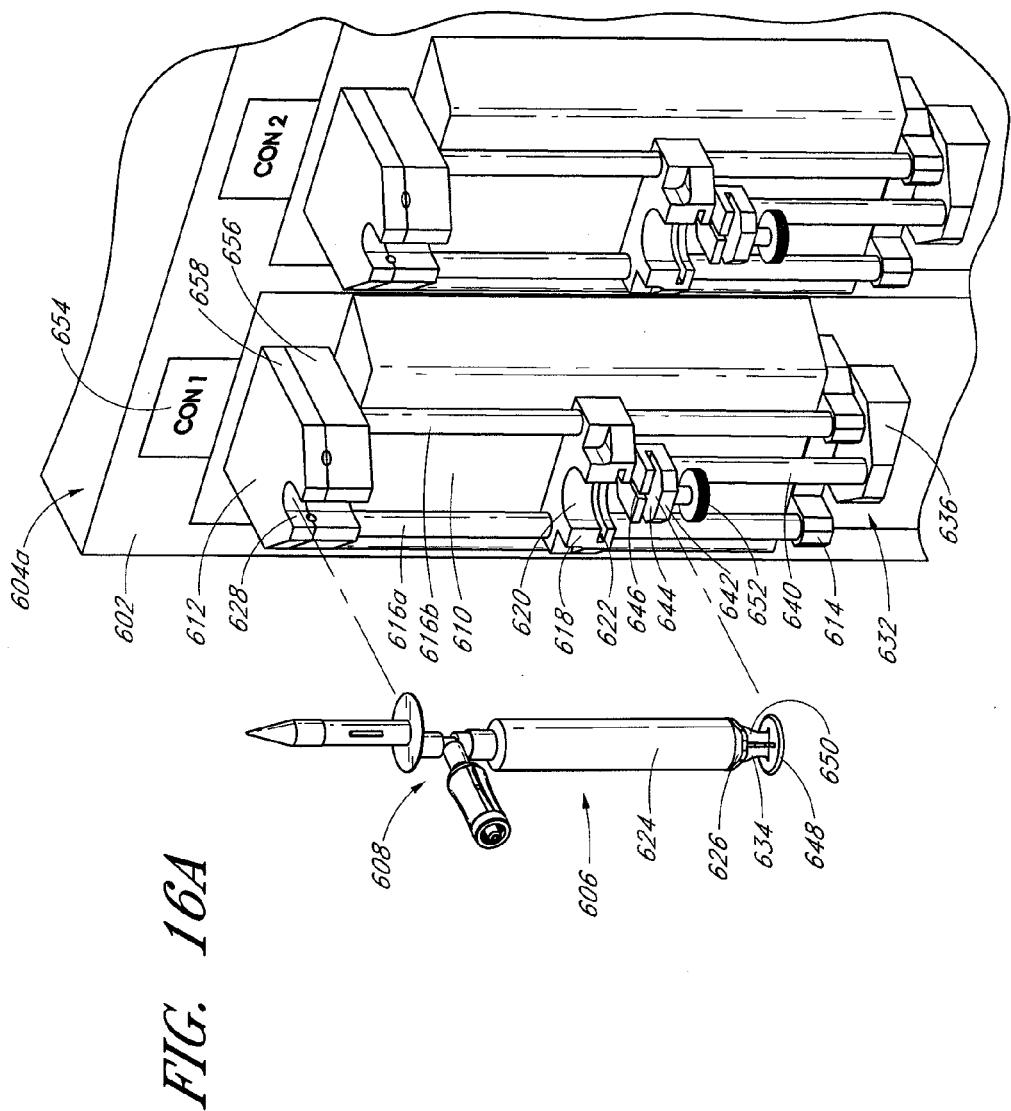
FIG. 16A is perspective view of a transfer station of the system shown in FIG. 15.
Figure 16B:
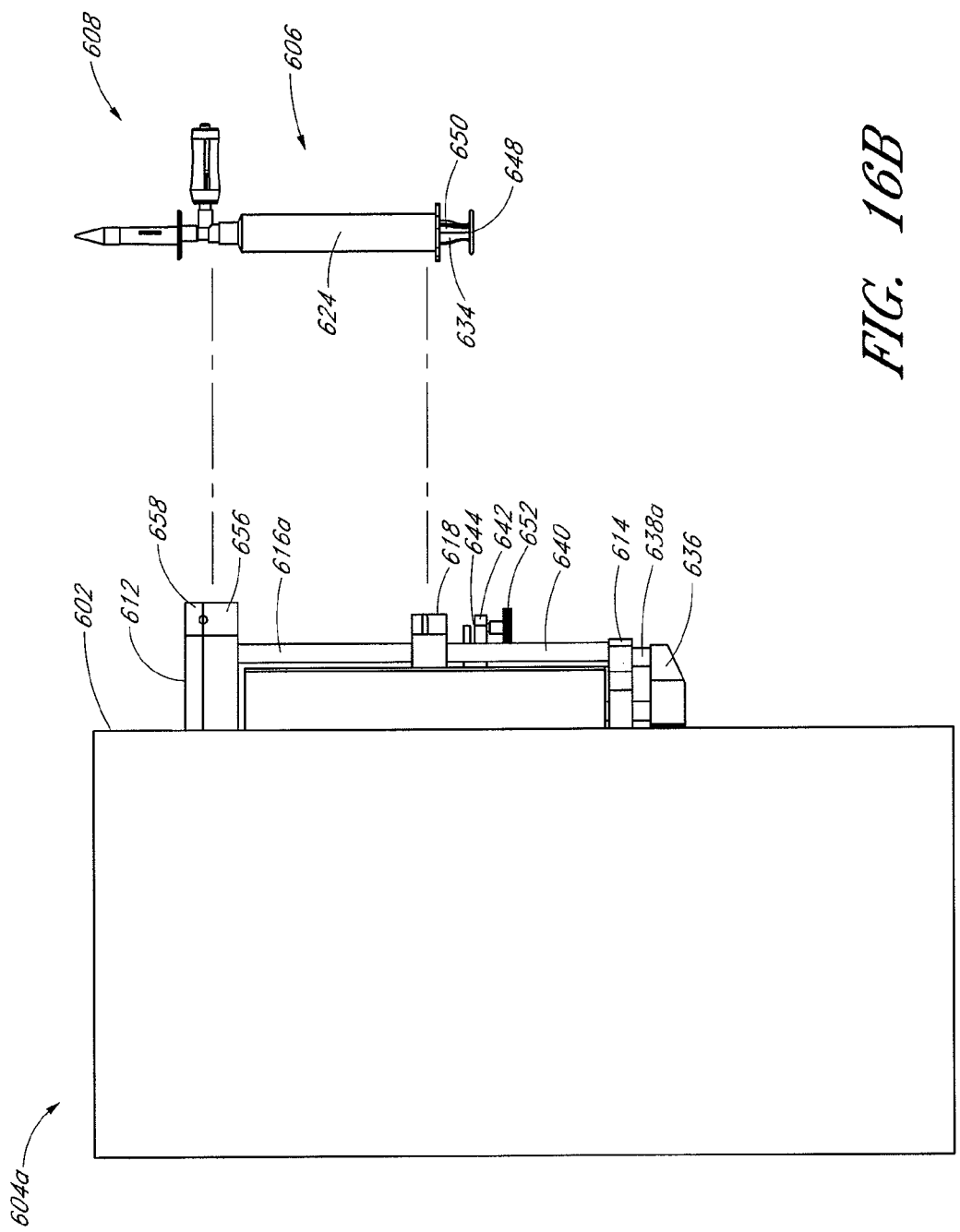
FIG. 16B is a side view of the fluid transfer system shown in FIG. 15.
Figure 16C:
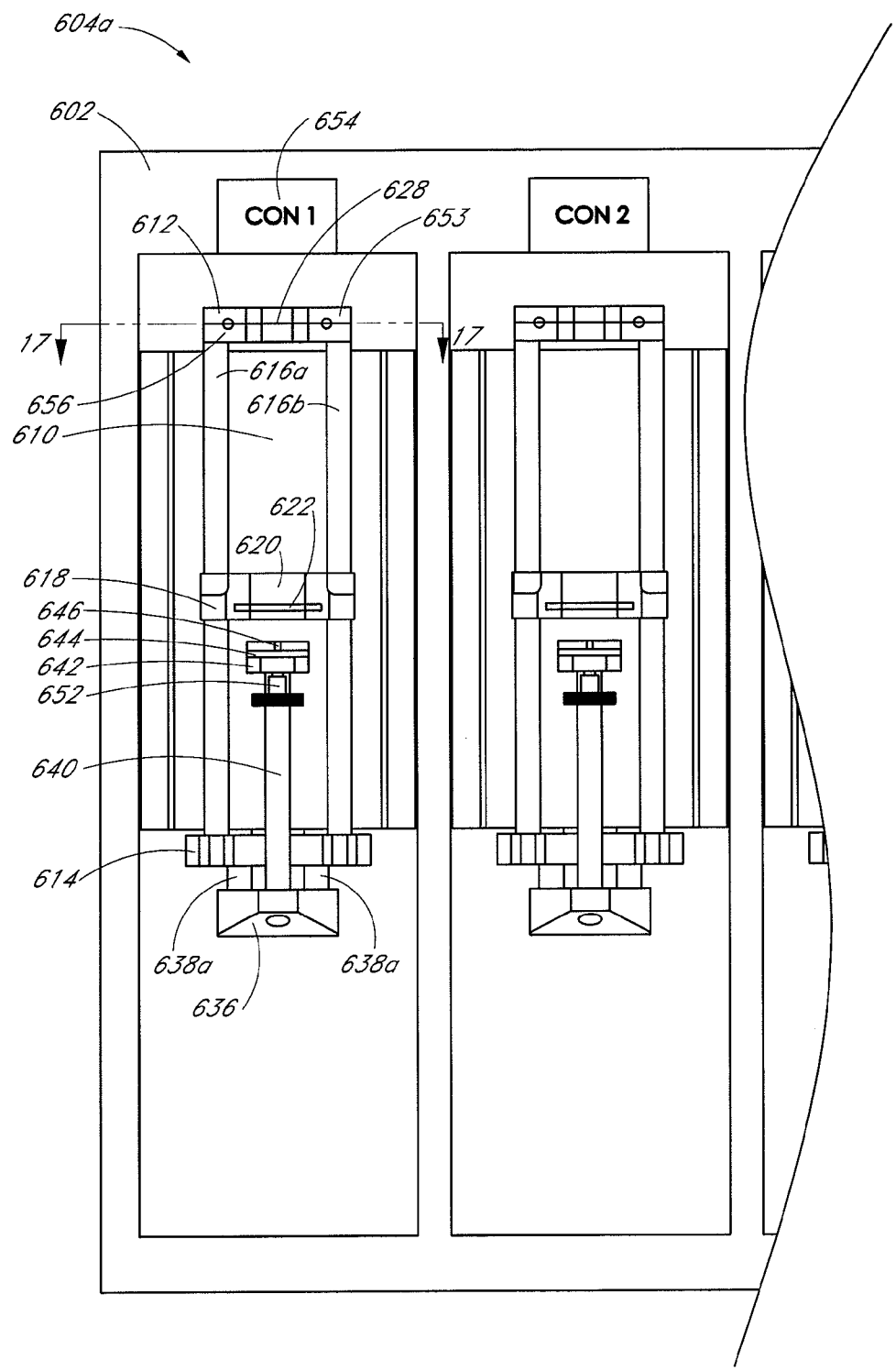
FIG. 16C is a front view of the transfer station shown in FIG. 16A.

Turning now to FIGS. 16A-16C, and 17, a transfer station 604a is shown in greater detail. FIG. 16A shows a partial perspective view of the transfer station 604a, with the syringe 606 and connector 608 in an unengaged configuration. FIG. 16B shows a left-side view of the transfer station 604a, with the syringe 606 and connector 608 in an unengaged configuration. FIG. 16C shows a front-side view of the transfer station 604a, with the syringe 606 and connector 608 omitted from view. The transfer station 604a can include an auxiliary housing 610 connected to the base housing 602. The transfer station 604a can also include a top connector piece 612 attached to the base housing 602 above the auxiliary housing 610, and a bottom connector piece 614 attached to the base housing 602 below the auxiliary housing 610. The top connector piece 612 and the bottom connector piece 614 can extend out a distance past the auxiliary housing 610, and a pair of shafts 616a-b can extend vertically between the top connector piece 612 and the bottom connector piece 614. A middle connector piece 618 can be attached to the shafts 616a-b.

The middle connector piece 618 can have a recess 620 configured to receive the syringe body 624. For example, if the syringe body 624 is generally cylindrical, the recess 620 can in the shape of a half cylinder (as shown). The middle connector piece 618 can also include a slit 622 configured to receive the body flange 626 of the syringe 606. The top connector piece 612 can have a recess 628 configured to receive the shroud 630 of the syringe 606 and a portion of the connector 608. In some embodiments, the middle connector piece 618 can be removable, so that it can be interchanged with additional middle pieces (not shown) to provide compatibility with different sizes and shapes of syringes. Also, in some embodiments, the position of the middle connector piece 618 can be adjustable. For example, the middle connector piece 618 can be slid up and down the shafts 616a-b and secured in a variety of location, providing compatibility with syringes of different lengths. In some embodiments, the position of the middle connector piece 618 can be fixed.

The transfer station 604a can include an actuator 632 configured to retract and advance the plunger 634 of the syringe 606. In the embodiment shown, the actuator 632 includes an actuator base 636. Two shafts 648a-b can be positioned at the back of the actuator base 636 and can extend upward from the actuator base 636 into the auxiliary housing 610. Another shaft 640 can be positioned at the front of the actuator base 636 and can extend upward in front of the auxiliary housing 610. An end piece 642 can be attached to the end of the shaft 640 opposite the actuator base 636. The end piece 642 can include a horizontal slit 644 configured to receive the plunger flange 648 of the syringe 606. The end piece 642 can also be configured to receive a portion of the plunger shaft 650 that is near the plunger flange 648. For example, if the plunger shaft 650 includes four longitudinal ribs (as shown), the end piece 642 can include a vertical slit 646 configured to receive one of the longitudinal ribs. The end piece 642 can also include a thumb screw 652 which can be tightened to apply pressure to the plunger flange 648 and prevent the syringe 606 from accidentally disengaging from the transfer station 604a.

In some embodiments, a motor (not shown) is located inside the auxiliary housing 610. The motor can be an electric motor, a pneumatic motor, a hydraulic motor, or other suitable type of motor capable of moving the actuator 632. In some embodiments, the motor can be a piston type motor. In some embodiments, the motor is contained within the base housing 602 rather than in the auxiliary housing 610. In some embodiments, each transfer station 604a-f has an individual motor dedicated to the individual transfer station 604a-f. In some embodiments, one or more of the transfer stations 604a-f share a motor, and in some embodiments, the system 600 includes a single motor used to drive all the transfer stations 604a-f. The motor can drive the shafts 638a-b downward out of the auxiliary housing 610, which in turn drives the rest of the actuator 632 downward causing the plunger 634 to retract from the syringe body 624 to draw fluid into the syringe. The motor can also draw the shafts 638a-b upward into the auxiliary housing 610, which in turn drives the rest of the actuator 632 upward causing the plunger 632 to advance into the syringe body 624 to expel fluid from the syringe.

In some embodiments, the transfer station 604a can include a label 654 that uniquely identifies the specific transfer station 604a. In some embodiments the label 654 can be prominently displayed at the top of the transfer station 604a. The label 654 can be colored, and each of the transfer stations 604a-f can have a different colored label.

The system 600 can include a controller, for controlling the operations of the transfer stations 604a-f. The controller can start and stop the motor(s) of the system 600 to control the amount of fluid that is transferred from the vial to the IV bag at each transfer station 604a-f. The controller can be one or more microprocessors or other suitable type of controller. The controller can be a general purpose computer processor or a special purpose processor specially designed to control the functions of the system 600. The controller can include, or be in communication with, a memory module that includes a software algorithm for controlling the operations of the system 600. The controller can be contained within the base housing 602. In some embodiments, the controller can be external to the base housing 602, and can be for example the processor of a general purpose computer that is in wired or wireless communication with components of the system 600.

In some embodiments, the transfer station 604a includes a sensor (hidden from view in FIGS. 16A-C) configured to determine when the liquid in the vial (not shown) has run out. If the plunger 634 is retracted to draw fluid into the syringe 606 when the vial contains no more fluid, air is drawn out of the vial and travels into the connector 608 toward the syringe. Air may also be drawn into the connector 608 when the vial still contains a small amount of fluid, but the fluid level is low enough that air is drawn out of the vial along with the fluid (e.g., as an air bubble). In some embodiments, the sensor can detect air in the connector 608. For example, the sensor can be an infrared light source (e.g., an LED) and a photodetector, or other form of electric eye.

Figure 17:
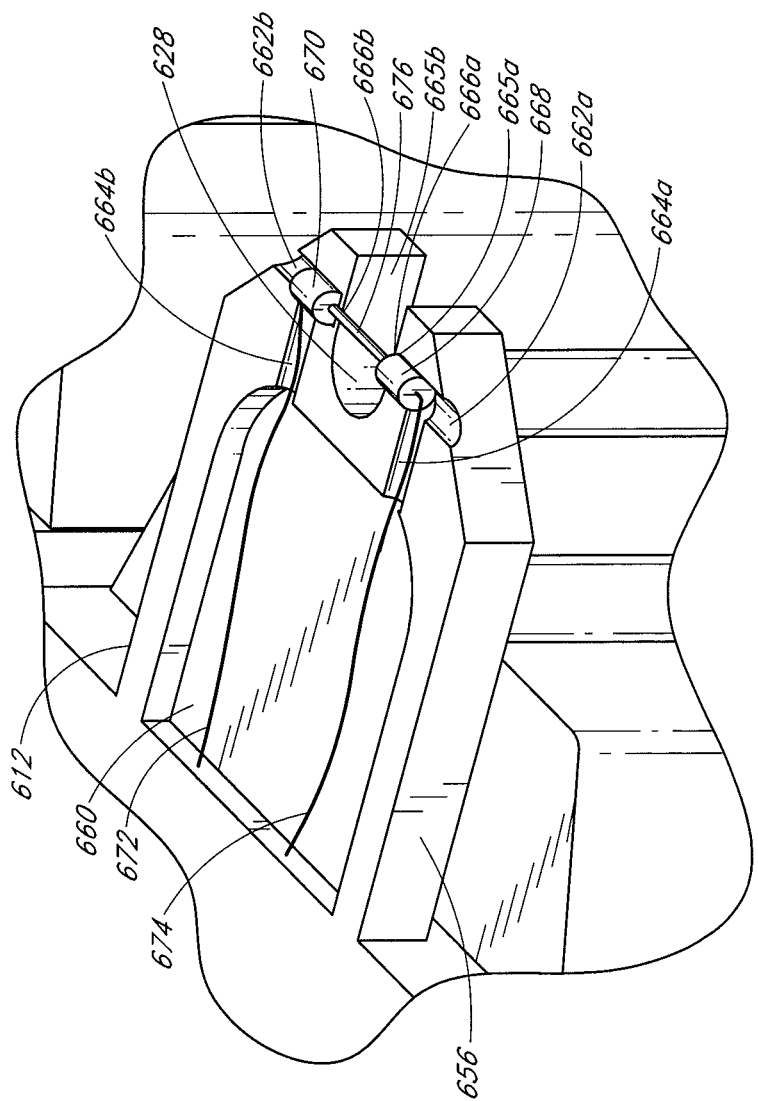
FIG. 17 is a perspective view of the top connector piece of the transfer station shown in FIG. 16A with the top portion thereof removed to show a light source and photodetector disposed therein.

In some embodiments, the sensor can be located inside the top connector piece 612. The top connector piece 612 can be made from a bottom portion 656 and a top portion 658. FIG. 17 shows a perspective view of the bottom portion 656 of the top connector piece 612, with the top portion 658 removed. The bottom portion 656 can include a central cavity 660 and a pair of grooves 662a-b, one on either side of the recess 628. Grooves 664a-b can connect the grooves 662a-b to the central cavity 660. In some embodiments, the grooves 662a-b, 664a-b can have semi-circular cross sections. In other embodiments, the grooves can be V-grooves, or any other suitably shaped grooves. The grooves 662a-b can be open at the ends furthest from the recess 628. In some embodiments, the grooves 662a-b can also be open at the ends closest to the recess 628. In some embodiments, walls 665a-b can separate the grooves 662a-b from the recess 628, except that the walls 665a-b can have holes 666a-b that connect the grooves 662a-b to the recess 628.

A light source 668 can be located in the groove 662a, and a photodetector 670 can be located in the groove 662b. In some embodiments, the light source 668 can be a laser light source that is aligned to direct a laser beam of light through the hole 666a, across the recess 628, into the hole 666b, and onto the photodetector 670. In some embodiments, the light source 668 can be an LED or other type of light source. In some embodiments, the light source 668, can emit light in many directions, so that some of the light passes through the hole 666a, across the recess 628, into the hole 666b, and onto the photodetector 670. A wire 672 can be connected to the light source 668 and can run along the groove 664a and through the central cavity 660. The wire 672 can provide power or other electric signals from the controller to the light source 668. A wire 674 can be connected to the photodetector 670 and can run along the groove 664b and through the central cavity 660. The wire 674 can carry electric signals from the photodetector 670 to the controller.

In some embodiments, the top portion 658 (not shown in FIG. 17) of the top connector piece 612 can have grooves and/or cavities that correspond to the grooves and/or cavities formed in the bottom portion 656. In some embodiments, the top portion 658 can have a generally flat underside so as to act as a lid to the grooves and/or cavities that are formed in the bottom portion 656. The top portion 658 can be attached to the bottom portion 656 by an adhesive, a clamp, snap or friction fit structures, or various other manners known in the art or yet to be devised. In some embodiments, the top portion 658 is removably attached to the bottom portion 656 so that the user can access the light source 668 and photodetector 670 for calibration, repair, replacement, etc.

Figure 18:
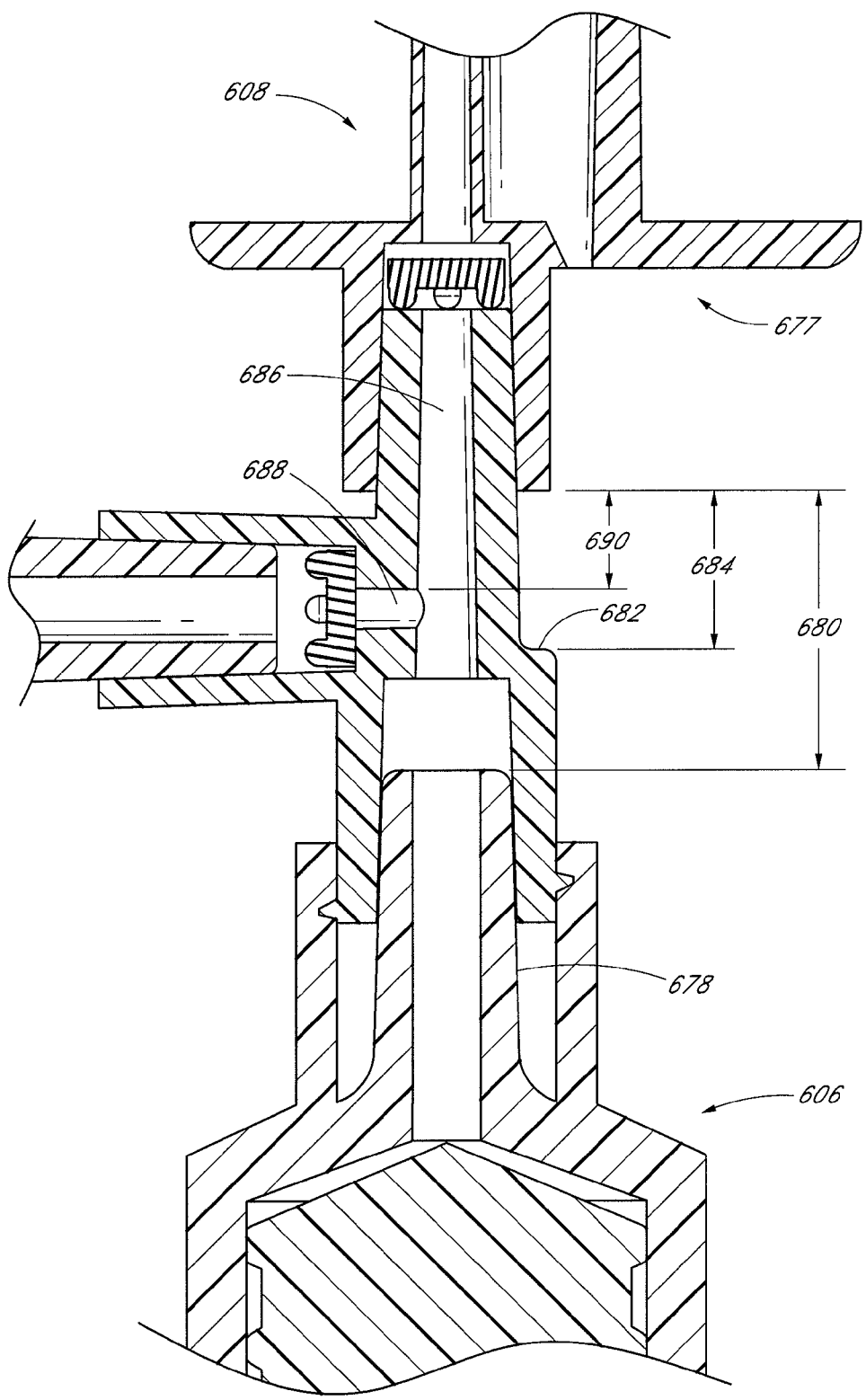
FIG. 18 is a cross sectional view of the syringe and connector of FIG. 15 showing regions where the light from the light source of FIG. 17 can intersect the connector.

When the syringe 606 and connector 608 are attached to the transfer station 604a, the connector 608 (not shown in FIG. 17) can be positioned in the path of light 676 traveling from the light source 668 to the photodetector 670. In some embodiments, the at least a portion of the connector 608 can be made from a substantially transparent plastic or other suitably material that allows the light 676 to pass through the walls of the connector 608. FIG. 18 is a side-view of the syringe 606 and connector 608 and illustrates the location on the connector 608 that intersects the light 676. In some embodiments, the connector 608 can be positioned so that the light 676 passes through the connector 608 at a location that is below the lower end of the source connector portion 677, but above the male luer tip 678 of the syringe 606. This area is marked as region 680 in FIG. 18. In some embodiments, the connector 608 can be positioned so that light 676 passes through the connector 608 above the external shoulder 682 of the connector 608 (shown as region 684). In some embodiments, the connector 608 can be positioned so that light 676 passes through the first fluid passageway 686 at a location above the junction to the second fluid passageway 688 (shown as region 690). In some embodiments, the light 676 passes through the connector 608 near the midpoint between the lower end of the source connector portion 677 and the top of the junction, so that turbulence created as fluid flows in and out of the second fluid passageway 688 does not causes errors in the sensor's readings. In some embodiments, the light 676 passes through the connector 608 at a location that is far enough from the male luer tip 678 of the syringe 606 so that when air is detected as fluid is being drawn into the syringe 606, the flow can be stopped before the air reaches the male luer tip 678.

In some embodiments, the beam of light 676 travelling from the light source 668 to the photodetector 670 is large enough to cover substantially the entire width of the first fluid passageway 686, so that an air bubble cannot travel down into the syringe 606 without crossing the beam of light 676. In some embodiments, the holes 666a-b shown in FIG. 17 can be larger than as shown, or they can be horizontal slits that allow light to intersect substantially the entire width of the first fluid passageway 686.

The light source 668 and photodetector 670 can be configured to detect the presence of air using absorption spectroscopy, emission spectroscopy, scattering spectroscopy, fluorescence spectroscopy, or other suitable manner of distinguishing between the presence of air and the presence of fluid in the path of the beam of light 676.

Figure 19A:
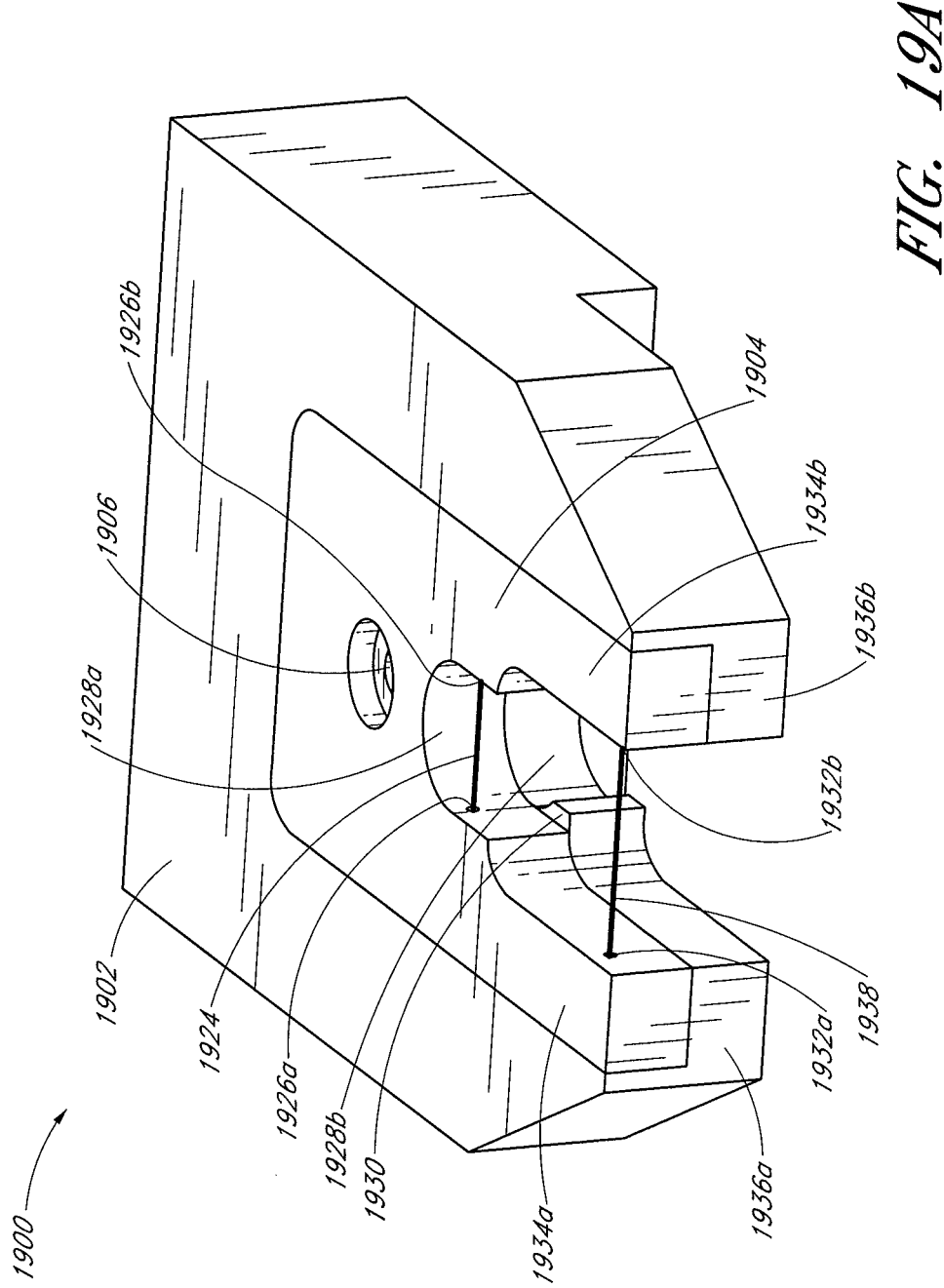
FIG. 19A is a perspective view of another embodiment of a top connector piece.
Figure 19B:
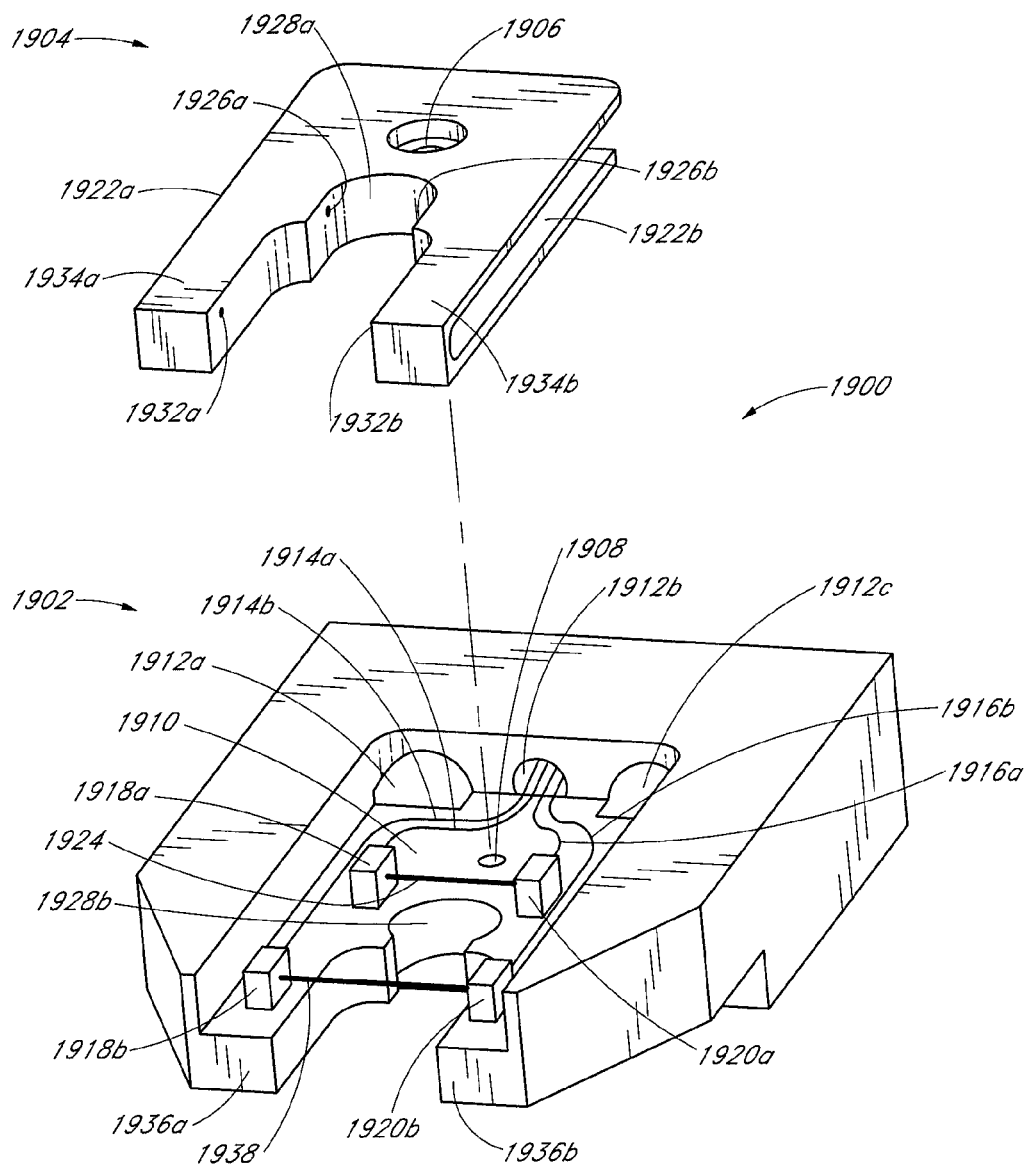
FIG. 19B is an exploded perspective view of the top connector piece of FIG. 19A.

FIG. 19A is a perspective view of another embodiment of a top connector piece 1900 which can be similar in some regards to the top connector piece 612 described above. FIG. 19B is an exploded view of the top connector piece. The top connector piece 1900 can be used in place of the top connector piece 612 in connection with the automated fluid transfer system 600. For example, the top connector piece 1900 can be connected to the base housing 602 and can function to receive a portion of the syringe 606 or a portion of the connector 608.

The top connector piece 1900 can include a base member 1902 and a cassette 1904. In some embodiments, the base member 1902 can be made of metal, such as aluminum, although other materials can be used. The cassette 1904 can be made from plastic, although other materials can be used. The cassette 1904 can include a bore 1906 configured to align with a bore 1908 formed in the base member 1902 such that the cassette 1904 can be secured to the base member 1902 by inserting a bolt, screw, or other fastener through the bores 1906, 1908. In some embodiments, one or both of the bores 1906, 1908 can be threaded to mate with corresponding threads on the bolt or other fastener. The bore 1906 can include a widened upper portion to receive the head of the bolt therein. The cassette 1904 can also be secured to the base member 1902 by a snap-fit, or friction-fit, or in any other suitable manner.

The base member 1902 can include a cutout region 1910 configured to receive the cassette 1904 such that the top surface of the cassette aligns substantially flush with the top surface of the base member 1902. One or more bores 1912a-c can extend from the back surface of the base member 1902 to the cutout region 1910. In the illustrated embodiment three bores 1912a-c are shown, although it will be understood that other numbers of bores can be used. The outer bores 1912a, 1912c can receive pins or other fasteners used to secure the base member 1902 to the housing 602 of the fluid transfer system 600. The inner bore 1912b can provide a channel that allows wires 1914a-b, 1916a-b to pass from the cutout region 1910 through the base member 1902 and to the housing 602. Many other configurations are possible. For example, a single bore can be used for securing the base member 1902 to the housing 602 and for providing a channel for the wires 1914a-b, 1916a-b.

A first light source 1918a and a corresponding first photodetector 1920a can be positioned inside the top connector piece 1900. The first light source 1918a and first photodetector 1920a can be similar to the light source 668 and photodetector 760 discussed above. Although the first light source 1918a and first photodetector 1920a are located in the cutout region 1910 in FIG. 19B, it will be understood that the first light source 1918a and first photodetector 1920a can be positioned inside of the slots 1922a-b formed in the cassette 1904. The first light source 1918a can be configured to direct light 1924 through a hole 1926a formed in the cassette 1902, across a recess 1928a, through a second hole 1926b formed in the cassette 1902 on the other side of the recess 1928a, and to the first photodetector 1920a. The wire 1914a can provide power or other electric signals from the controller to the first light source 1918a. A wire 1916a can carry electric signals from the first photodetector 1920a to the controller.

The first light source 1918a and first photodetector 1920a can be configured to detect air in the connector 608 similar to the light source 668 and photodetector 760 discussed above. The recess 1928a, 1928b can be configured to receive the syringe 606 and/or connector 608 such that a transparent portion of the connector 608 is positioned in the path of the light 1924 such that the light 1924 passes through a portion of the fluid pathway between the vial and the syringe 606 (e.g., as discussed above in connection with FIG. 18). The first light source 1918a and first photodetector 1920a can be configured to detect air in the fluid pathway and provide a signal to the controller indicating that the vial may need to be replaced.

The portion of the recess 1928a formed by the cassette can be substantially semicircular in shape to conform to the portion of the connector 608 configured to assign therewith. The portion of the recess 1928b formed by the base member 1902 can be further enclosed than the portion of the recess 1928a formed by the cassette, such that a step 1930 is formed on either side of the recess 1928b. The steps 1930 can facilitate the proper securing and alignment of the connector 608 with the top connector piece 1900.

A second light source 1918b and a corresponding second photodetector 1920b can be positioned inside the top connector piece 1900. The second light source 1918b and second photodetector 1920b can be similar to the light source 668 and photodetector 760 discussed above. Although the second light source 1918b and second photodetector 1920b are located in the cutout region 1910 in FIG. 19B, it will be understood that the second light source 1918b and second photodetector 1920b can be positioned inside of the slots 1922a-b formed in the cassette 1904. The cassette 1904 can have a pair of arms 1934a-b that extend outwardly, and the slots 1922a-b can extend along the arms 1934a-b. The base member 1902 can have corresponding arms 1936a-b positioned under the arms 1934a-b of the cassette 1904. The second light source 1918b can be configured to direct light 1938 through a hole 1932a formed in a first arm 1934a of the cassette 1902, across a gap formed between the arms 1934a-b, through a second hole 1932b formed in the second arm 1934b of the cassette 1902, and to the second photodetector 1920b. The wire 1914b can provide power or other electric signals from the controller to the second light source 1918b. A wire 1916b can carry electric signals from the second photodetector 1920b to the controller.

In some embodiments, the cassette 1904 can be removable from the base member 1902, providing access to the light sources 1918a-b, photodetectors 1920a-b, and wires 1914a-b, 1916a-b for repair or replacement. In some embodiments, the light sources 1918a-b and/or photodetectors 1920a-b can be secured to the cassette 1904 and the cassette 1904 can be interchanged with a replacement cassette if a light source 1918a-b or photodetector 1920a-b breaks or if different functionality (e.g., a different wavelength of light) is desired.

The second light source 1918b and the second photodetector 1920b can be configured to determine whether an IV bag assembly is connected to the connector 608. In some embodiments, the controller can be configured to abort a command from a user to transfer fluid to an IV bag for a particular transfer station if the controller determines that no IV bag is attached to the particular transfer station, thereby preventing waste of the fluid to be transferred and preventing exposure to potentially hazardous fluids. The controller can also display an error message or alert on the user interface when a command is aborted in this fashion. It should be understood that in some embodiments, a portion of the connector 608 (e.g., target connector portion 338) can be closed when no IV bag assembly is attached thereto, so that the connector can prevent fluid from escaping when no IV bag assembly is attached. However, if the fluid transfer station is permitted to infuse fluid into the closed connector, high pressure can build up in the connector which can compromise the closed seal of the connector allowing fluid to escape, or can cause damage to the system 600. The second light source 1918b and the second photodetector 1920b are one example of a sensor configured to determine whether an IV bag assembly is attached to the connector 608, and it will be understood that other sensor types (e.g., weight sensors) can also be used for detecting the presence of the IV bag assembly.

Figure 19C:
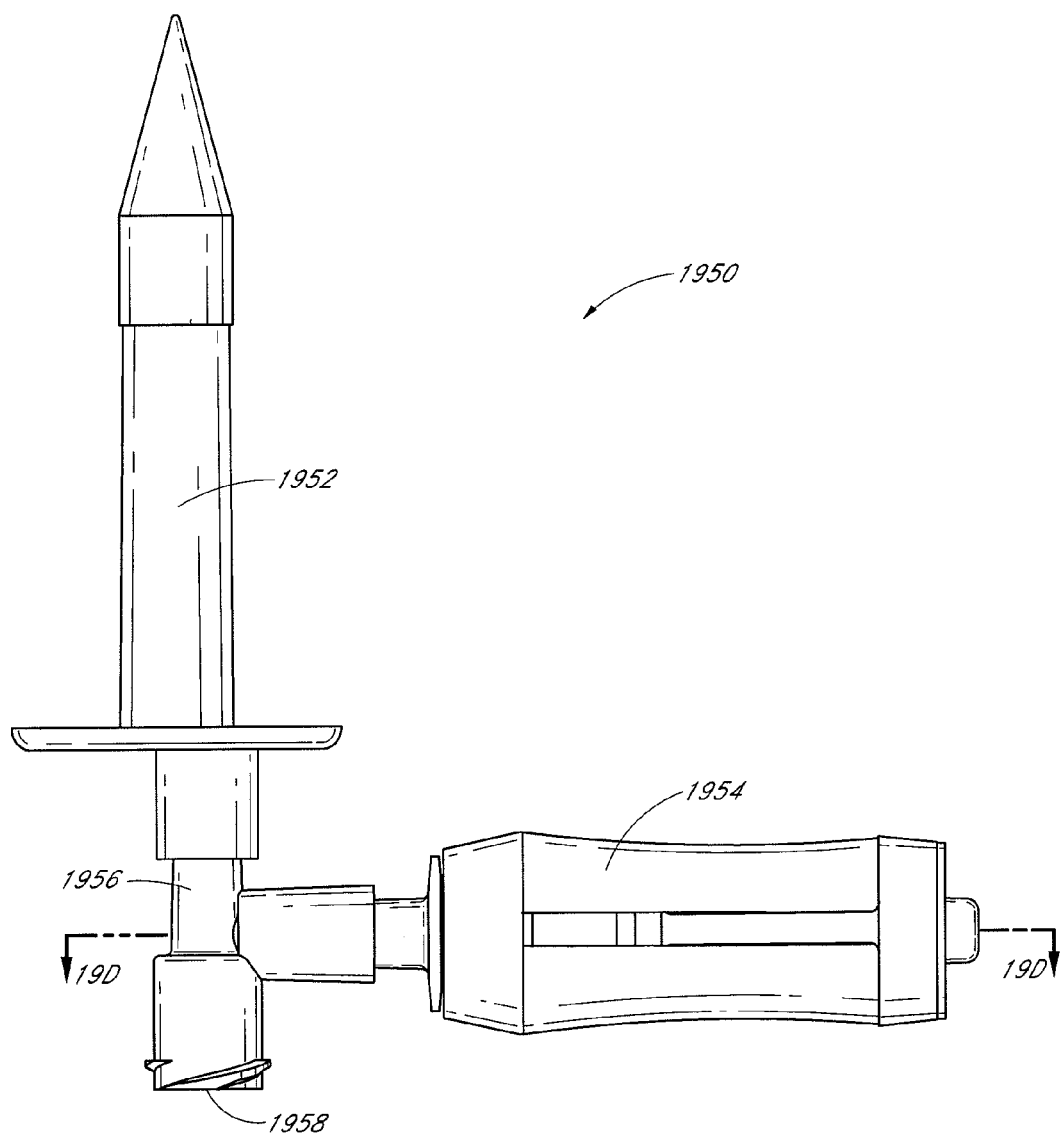
FIG. 19C is a side view of a connector for use in transferring fluid.

The manner in which the second light source 1918b and the second photodetector 1920b detect the presence of an IV bag assembly will be described in connection with FIGS. 19C-E. FIG. 19C is a side view of a connector 1950 which can be similar to the connector 320 or any other connector described herein. The connector 1950 can include a source connector portion 1952 and a target connector portion 1954. In the illustrated embodiment, the source connector portion 1952 and the target connector portion 1954 can be attached to a main body piece 1956 which can have an intermediate connector portion 1958 configured to receive a syringe or other intermediate measuring container.

Figure 19D:
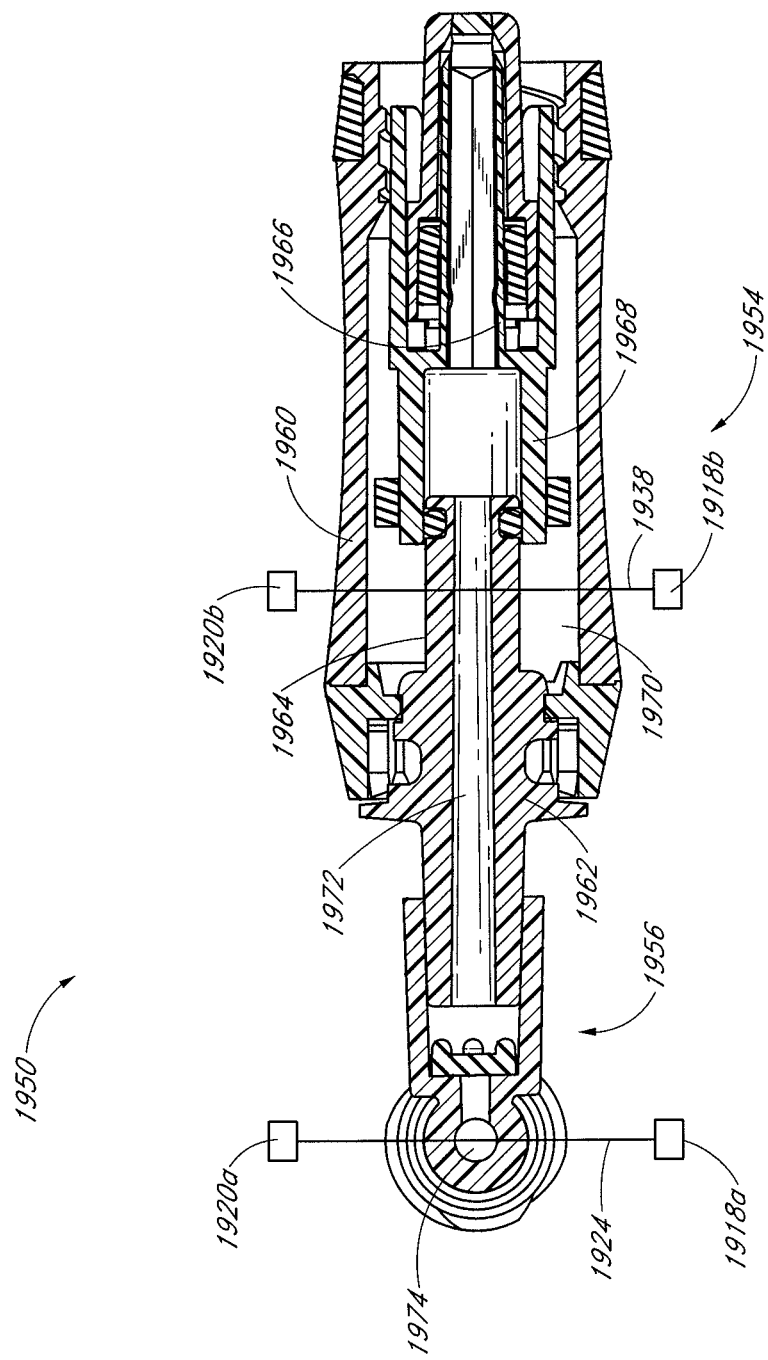
FIG. 19D is a cross sectional view of the connector of FIG. 19C in which the target connector portion is closed.

FIG. 19D is a cross sectional view of the connector 1950 that shows the target connector portion 1954 in a closed state. FIG. 19E is a cross sectional view of the connector 1950 that shows the target connector portion 1954 in an open state. The target connector portion 1954 can be similar to the target connector portion 338 described herein. The target connector portion 1954 can include a housing 1960 and an end cap 1962 that includes an elongate plunger 1964. A valve member 1966 can be slidably engaged with the plunger 1964 such that when the valve is in the closed position, as shown in FIG. 19D, the base 1968 of the valve member 1966 overlaps only the end of the plunger 1964, leaving at least a portion of the plunger 1964 exposed. When the connector 1965 of the IV bag assembly is attached to the target connector portion 1954 (e.g., as described in connection with FIGS. 6D-E), the valve member 1966 is displaced toward the end cap 1962 as shown in FIG. 19E.

Figure 19E:
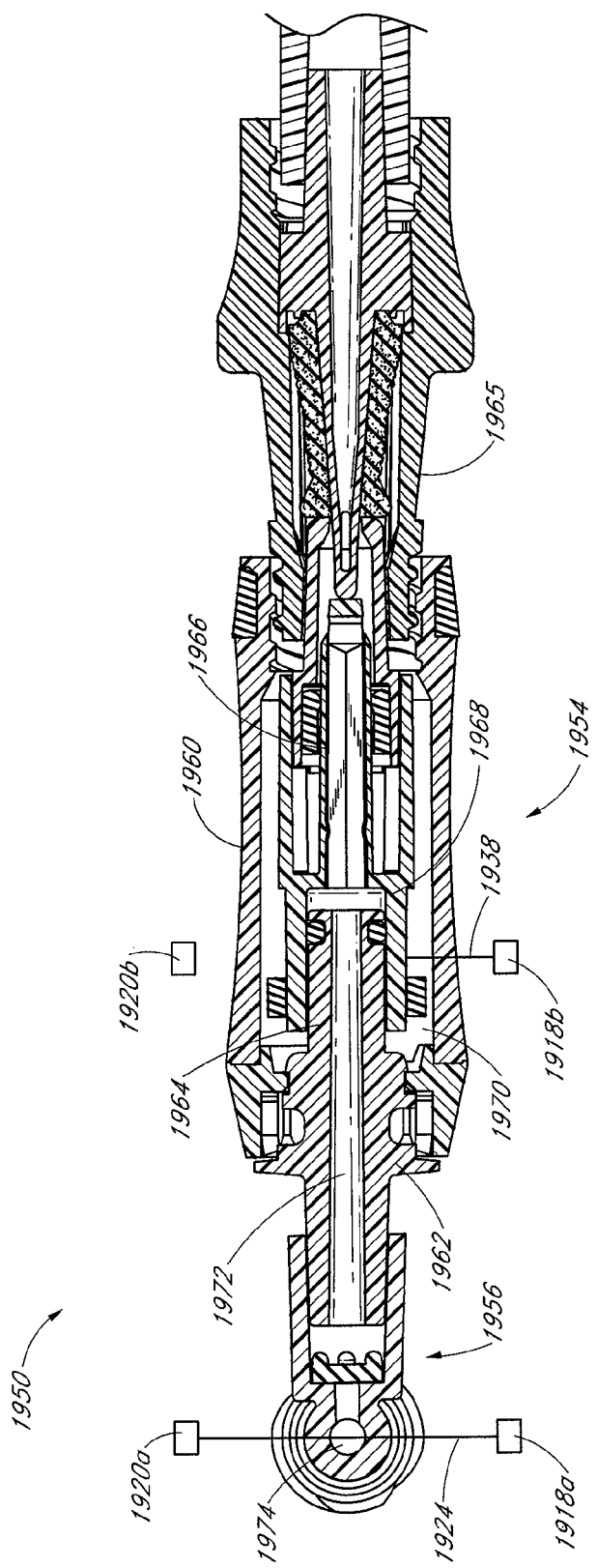
FIG. 19E is a cross sectional view of the connector of FIG. 19C in which the target connector portion is open.

The second light source 1918*b* and the second photodetector 1920*b* are shown schematically in FIGS. 19D-E. In some embodiments, at least a portion of the housing 1960 and at least a portion of the plunger 1964 can be made of a material that is transparent to the light 1938 emitted by the second light source 1918*b*, while the valve member 1966 can be made of a material that is opaque to the light 1938, or otherwise prevents the light 1938 from reaching the second photodetector 1920*b* when placed in the path of the light 1938. Thus, when no IV bag assembly is attached to the connector 1950 and the target connector portion 1954 is in the closed configuration (as shown in FIG. 19D), the light 1938 can pass through the transparent housing 1960, through the transparent plunger 1964, and to the second photodetector 1920*b*. When the second photodetector 1920*b* detects the light 1938 it can send a signal to the system controller indicating that no IV bag assembly is attached to the target connector portion 1954. When the connector of an IV bag assembly is attached to the target connector portion 1954 the base 1958 of the valve member 1966 can intersect the path of the light 1938 and prevent the light 1938 from reaching the second photodetector 1920*b*, as shown in FIG. 19E. When the second photodetector 1920*b* does not detect light 1938, it can send a signal to the system controller indicating that target connector portion 1954 is in the open configuration and an IV bag assembly is attached thereto.

In some embodiments, the connector 1950 can be aligned so that the light 1938 passes through the open space 1970 next to the plunger 1964 without intersecting the plunger 1964. Thus, in some embodiments, the plunger 1964 can be made of a material that not transparent to the light 1938. In the open configuration, as shown in FIG. 19E, the base 1968 of the valve member 1966 fills the space 1970 adjacent to the plunger 1964 to block the light 1938. Thus, in some embodiments, the light 1938 does not pass through the fluid flow path 1972 formed through the target connector portion 1954, which can be advantageous in certain circumstances such as when a fluid is transported through the connector that would prevent the light 1938 from reaching the second photodetector 1920*b*.

FIGS. 19D-E also illustrate the light 1924 emitted by the first light source 1918*a* being transmitted through the fluid flow path 1974 formed between the vial and the syringe to the first photodetector 1920*a*, as described above.

Returning now to FIG. 15, the system 600 can include a user interface 692 for receiving information and commands from the user and for providing information to the user. The user interface 692 can be part of an external unit 694, or it can be integrated into or attached to the base housing 602. The user interface 692 can include, for example, a touch screen display. The user interface 692 can be in wired or wireless communication with the controller. In some embodiments, a cable 696 connects the external unit 694 to the base housing 602 and provides a communication link between the user interface 692 and the controller. In some embodiments, the controller can be contained in the external unit 694 along with the user interface 692 and the controller can send and receive signals to and from components (e.g., the motors) of the system 600 through the cable 696. The user interface 692 can be configured to receive instructions from the user regarding the amounts of fluids to be transferred by the transfer stations 604*a*-604*f*. The user interface 692 can deliver the instructions to the controller to be stored in a memory and/or used to actuate the motor(s) to transfer the desired amount of fluids.

In some embodiments, the system 600 can include a communication interface (shown schematically in FIG. 15 as antenna 691). The communication interface 691 can be configured to provide a communication link between the controller and a remote source, such as a remote terminal or an automated management system. The communication link can be provided by a wireless signal or a cable or combination of the two. The communication link can make use of a network such as a WAN, LAN, or the internet. In some embodiments, the communication interface can be configured to receive input (e.g., fluid transfer commands) from the remote source and can provide information (e.g., results or alerts) from the controller to the remote source. In some embodiments, the remote source can be an automated management system which can coordinate actions between multiple automated fluid transfer systems (e.g., 100, 200, and 600).

The system 600 can also include a bar code scanner 698, in communication with the controller and/or memory. The bar code scanner 698 can be used to provide information about the system 600 to the controller and/or the memory. For example, the syringe 606 can include a bar code that identifies the size and type of the syringe 606. The user can scan the syringe 606 with the bar code scanner 698 and then scan a bar code associated with the transfer station 604*a* to inform the controller of the size of the syringe 606 that is attached to the transfer station 604*a*. Different sizes of syringes can hold different volumes of fluid when their plungers are withdrawn by the same distance. Thus, when the controller is tasked with filling the syringe 606 with a predetermined amount of fluid, the controller can determine how far the plunger is to be withdrawn to fill the particular type of syringe with the predetermined amount of fluid. The vials (not shown) can also include bar codes that indicate the type of fluid contained therein. The user can scan a vial and then scan the bar code associated with the particular transfer station the vial is to be installed onto. Thus, the controller can be aware of what fluids are controlled by which transfer stations to facilitate automated transfer of fluids. Other components of the system 600 can also include bar codes readable by the bar code scanner 698 for providing information about the components to the controller and/or memory. In some embodiments, the user interface 692 can be configured to allow the user to input data relating to the size of the syringe 606, the type of fluid contained in a vial, etc. instead of using the bar code scanner 698.

Figure 20:
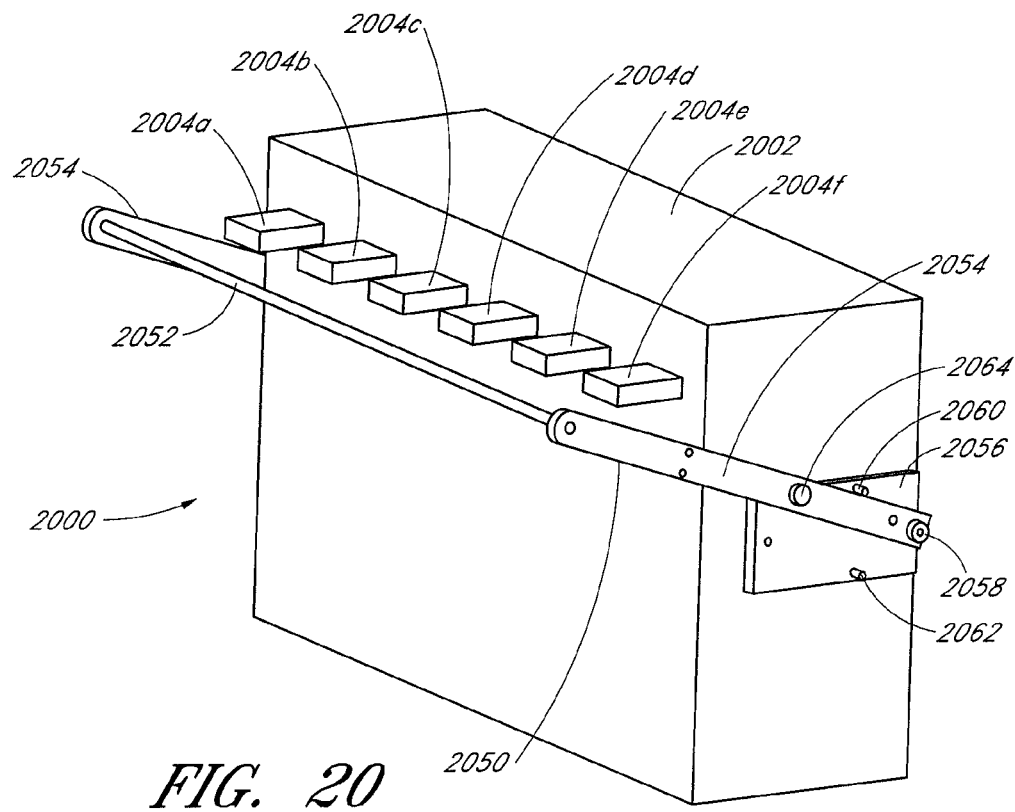
FIG. 20 is a perspective view schematically showing another embodiment of an automated fluid transfer system wherein the system includes a support bar assembly attached to the housing.

FIG. 20 is a perspective view that schematically shows another embodiment of an automated fluid transfer system 2000. Some aspects of the automated fluid transfer system 2000 can be similar to or the same as the other automated fluid transfer systems (e.g., 100, 200, and 600) described above. The automated fluid transfer system 600 can include a base housing 2002, and six transfer stations 2004*a-f* (although the system 600 can have other numbers of transfer stations). In FIG. 20, the transfer stations 2004*a-f* are shown schematically as boxes, but it should be understood that each of the transfer stations 2004*a-f* can include structure similar to or the same as that described above in connection with the transfer station 604*a*. For example, each transfer station can include a fluid transfer subsystem (e.g., subsystem 300 or 1900) including a vial, a syringe, and an IV bag assembly.

Figure 21:
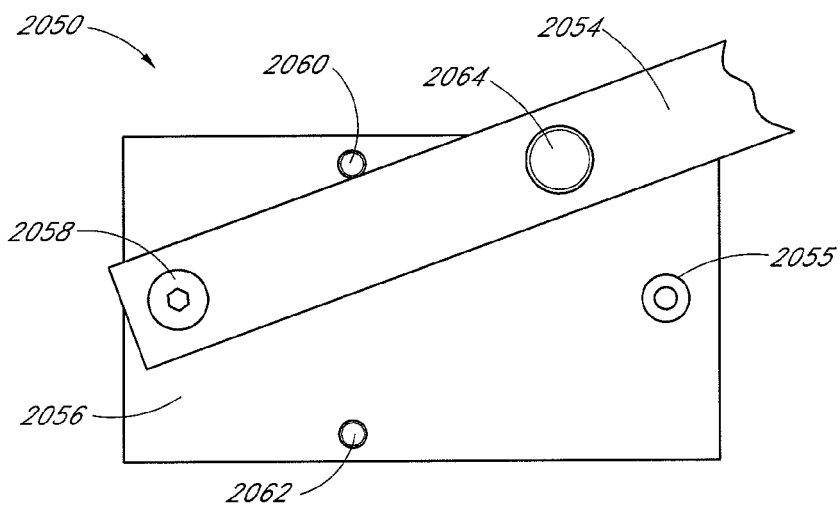
FIG. 21 is a side view of an attachment piece and arm of FIG. 20.

The automated fluid transfer system 2000 can include a support bar assembly 2050. FIG. 21 is a side view schematically showing a portion of the support bar assembly. With reference now to FIGS. 20 and 21, the support bar assembly 2050 can include a substantially horizontal support bar 2052, supported on either side by an arm 2054. Each arm 2054 can be attached to the side of the base housing 2002 by an attachment piece 2056. In some embodiments the attachment piece can be integrally formed with the base housing 2002 or secured thereto, for example, by an adhesive or by one or more screws 2055 or other fasteners. The arm 2054 can be attached to the attachment piece 2056 by a shoulder bolt 2058, so that the arm 2054 can pivot on the shoulder bolt 2058. The rotational range of the arm 2054 can be limited by an upper dowel pin 2060 and a lower dowel pin 2062. A spring plunger 2064 can be positioned on the arm 2054 and can be configured to slide into one or more locking holes (hidden from view in FIGS. 20 and 21) to lock the arm 2054, and the support bar 2052, in position. The spring plunger 1064 can be pulled out of the locking hole to release the arm 2054 from the locked position. In FIGS. 20 and 21, the arms 2054 and support bar 2052 are shown locked in an upward position with the arm 2054 positioned adjacent to the upper dowel 2060. The support bar 2052 can be configured to hold or otherwise support at least a portion of the one or more fluid transfer subsystems of the fluid transfer stations 2004*a*-*f*. For example, when locked in the upward position, the support bar 2052 can be positioned so that the target connector portion, the female connector attached to the target connector portion, the IV bag, or other portion of the IV bag assembly can rest on the support bar 2052 to reduce the amount of stress placed on the connector.

Figure 22:
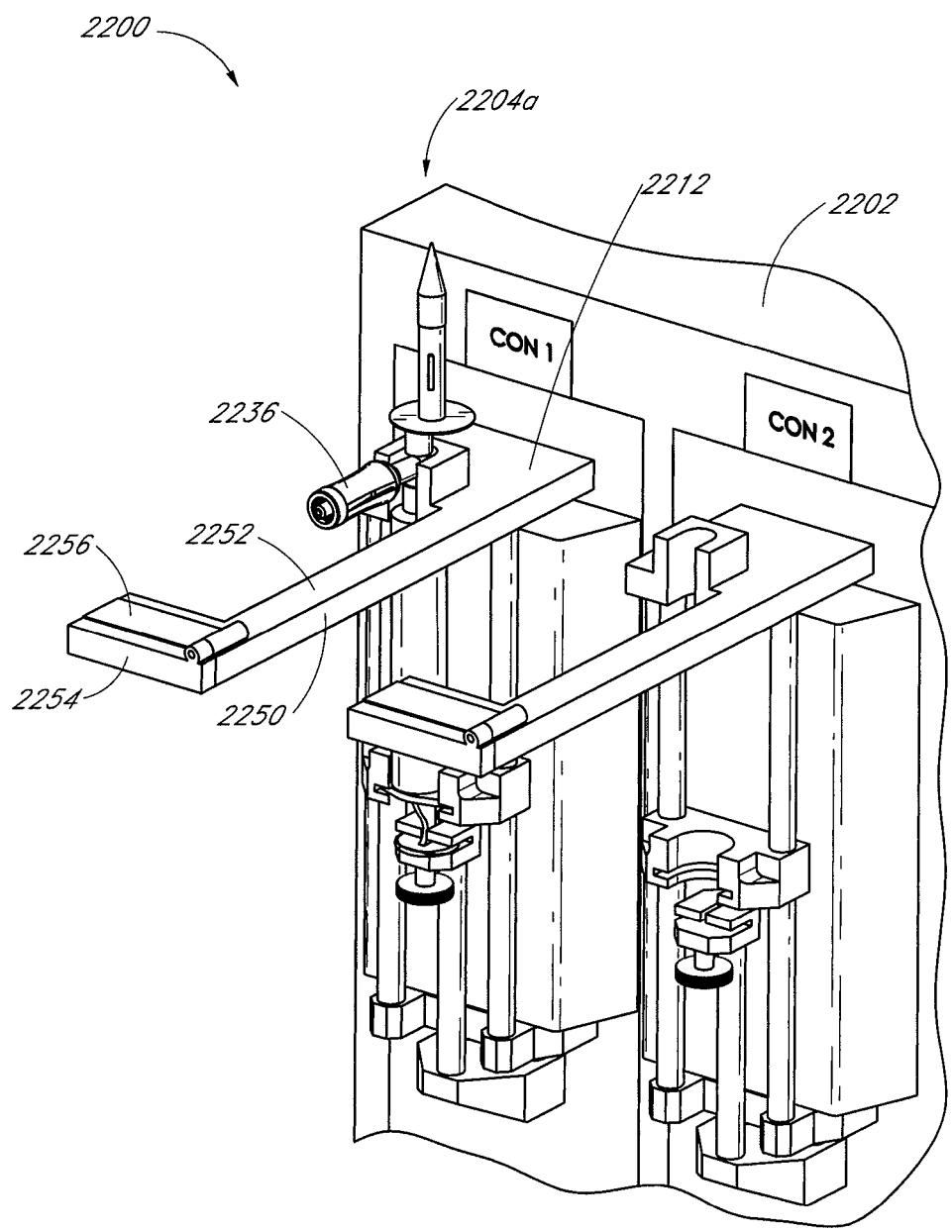
FIG. 22 is a partial perspective view schematically showing another embodiment of an automated fluid transfer system wherein one or more of the transfer stations include a support arm.

FIG. 22 is a partial perspective view that schematically shows another embodiment of an automated fluid transfer system 2200 that, in some regards, can be the same as or similar to the other automated fluid transfer systems (e.g., 100, 200, 600, and 2000) disclosed herein. In some embodiments, one or more of the transfer stations (e.g., 2204*a*) can include a support arm 2250. The support arm 2250 can be integrally formed with or attached to the top connector piece 2212. Alternatively, the support arm 2250 can be separate from the top connector piece 2212 and can be secured, for example, directly to the base housing 2202 by one or more screws or other fasteners. In some embodiments, the support arm 2250 can be substantially "L" shaped, having an elongate extension portion 2252 and a support platform 2254. The support platform 2254 can be configured to hold or otherwise support at least a portion of the fluid transfer subsystems of the fluid transfer station 2204*a*. For example, the support platform 2254 can be positioned so that the target connector portion 2236, the female connector (not shown in FIG. 22) attached to the target connector portion 2236, the IV bag (not shown in FIG. 22), or other portion of the IV bag assembly can rest on the support platform 2254 to reduce the amount of stress placed on the connector.

In some embodiments, the support arm 2250 can include a weight sensor 2256, or other type of sensor, capable of determining whether an IV bag assembly (not shown in FIG. 22) is connected to the target connector portion 2236. For example, the weight sensor 2256 can "feel" the weight of the IV bag as the support arm 2250 provides support thereto. The weight sensor 2256 can be in electronic communication with the controller so that the controller can confirm that an IV bag assembly is attached to the target connector portion 2236 before transferring fluid into the IV bag.

In some embodiments, the weight sensor 2256 can be used to confirm that the correct amount of fluid was transferred to the IV bag. The controller can be configured to calculate an expected weight for the IV bag from the instructions received from the user and from information stored in a memory, e.g., the amount of fluid to be transferred, the density of the fluid to be transferred, the starting weight of the empty IV bag, etc. Once the transfer of fluid is complete the controller can measure the final weight of the IV bag using the weight sensor and can compare the final weight to the expected weight. If the final weight differs from the expected weight by more than an acceptable tolerance amount (e.g., determined by the accuracy of the weight sensor), the controller can send an error message or alert to the user interface informing the user that an error likely occurred in the fluid transfer (e.g., the wrong fluid type was transferred or the wrong amount of fluid was transferred).

FIG. 22A is a partial perspective view of another embodiment of an automated fluid transfer system 2270 that, in some regards, can be the same as or similar to the other automated fluid transfer systems (e.g., 100, 200, 600, 2000, and 2200) disclosed herein. The system 2270 can include a tray 2272 extending out from the housing 2274. The tray 2272 can be configured to support the IV bag 2276. The tray 2272 can have flat base 2278 and sides 2280*a*-*b* that turn up (e.g., by about 30° to about 60°) to prevent the IV bag 2276 from sliding off the side of the tray 2272. The end 2282 of the tray 2272 furthest from the housing 2274 can be open, having no turned up side, so that the IV bag can hang over the edge of the tray 2272. A support foot 2279 can extend from the base of the housing 2274 to prevent the system 2270 from tipping forward under the weight of the IV bag 2276.

The tray 2272 can include a hole or cutout 2284 configured to align with the target connector portion 2286 of the connector (which can be similar to the connector 320 or any other connector disclosed herein). In some embodiments, the outer housing 2288 of the target connector portion 2286 can rotate relative to the connector 2290 (which can be similar to the female connector 322) of the IV bag assembly. Because at least a portion of the target connector portion 2286 is rotatable, the connector 2290 is not required to rotate when it is attached or detached to the target connector portion 2286, so that the tubing 2292 is not twisted or kinked and the IV bag 2276 need not be twisted. In some embodiments, the target connector portion 2286 can rotate to engage the connector 2290 in a manner similar to that described above in connection with FIGS. 6D-E, although it will be understood that any rotating connector can be used. The hole or cutout 2284 formed in the tray 2272 can be configured to allow a user's hand to pass though therethrough when rotating the housing 2288 of the target connector portion 2286.

The tray 2272 can be removably secured to the housing 2274. In some embodiments, the tray 2272 can be bolted, screwed, or otherwise fastened to the housing 2274. A snap fit connection or a friction-fit connection can also be used. In some embodiments, the end of the tray can fit between the top connector piece 2294 and the auxiliary housing 2296 of the transfer station with which the tray 2272 is associated. The embodiment illustrated in FIG. 22A shows a single tray 2272 attached to a transfer station of the system 2270, but it will be understood that a plurality of individual trays can be used, each tray being associated with one of the transfer stations. In some embodiments, a single tray can be used for more than one or all the transfer stations.

Figure 23:
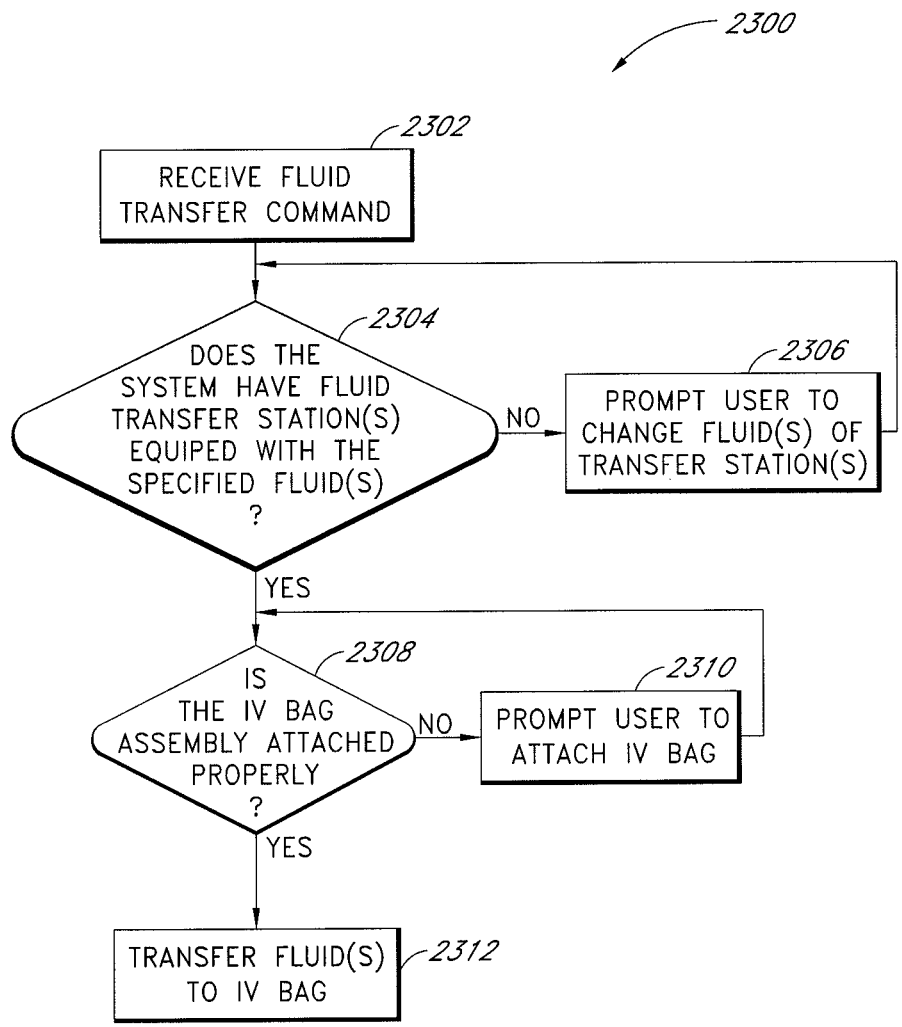
FIG. 23 is a flowchart that shows an embodiment of a method of operation for an automated fluid transfer system.

FIG. 23 is a flowchart that schematically shows a method 2300 of operation for an automated fluid transfer system (e.g., 100, 200, 600, 2000, and 2200). At block 2302, the system receives a fluid transfer command. The fluid transfer command can be received, for example, via a user interface from inputs provided by a user, or via a communication interface from a remote terminal or an automated management system. The fluid transfer command can include information such as a fluid type to be transferred, an amount of the fluid to be transferred, and a desired concentration of the fluid. In some embodiments, a fluid transfer command can include information for multiple fluids to be combined into a compounded mixture.

At block 2304, the controller determines whether the fluid transfer stations of the system are currently equipped to transfer the requested fluids. In some embodiments, the system includes a memory that includes, for example, a database or lookup table so that the controller can determine the type of fluids associated with each transfer station. If the fluid transfer stations do not have the specified fluid, the method can proceed to block 2306 wherein the user interface can prompt the user to change the fluid(s) of the fluid transfer station(s). In some embodiments, the controller can determine a recommended fluid to replace (e.g., using a history of usage stored in the memory) and provide the recommendation to the user via the user interface. After the user makes the changes to the fluid transfer station(s), the method 2300 can return to block 2304 to confirm that the transfer station(s) are properly equipped.

In some embodiments, the user can specify one or more transfer stations to use for the fluid transfer, rather than specifying the types of fluids desired. Thus in some embodiments, blocks 2304 and 2306 can be omitted. In some embodiments, the user interface can display to the user the types of fluids associated with the different transfer stations to aid the user in selecting the transfer stations to use for the fluid transfer.

In some embodiments, the system can contain concentrated fluids in the source containers and in some circumstances the fluids are to be diluted with a diluent prior to delivery to the patient. Therefore, in some instances, the controller can determine a desired amount of diluent based upon the concentration of the fluid in the source container, the desired concentration, and the amount of fluid to be transferred. The user interface can prompt the user to fill the target IV bag with the desired amount diluent. Alternatively one or more of the transfer stations of the system can include diluents. Thus, in some embodiments, the controller will determine whether transfer stations are equipped with the desired medication and the desired diluent.

If the fluid transfer stations are properly equipped, the method 2300 can proceed to block 2308 where the controller determines whether the IV bag assembly is properly attached. In some embodiments, the system can include, for example, a weight sensor or IR sensor capable of determining whether the target connector portion for a transfer station is connected to an IV bag assembly. In some embodiments, the weight sensor and controller can determine whether the IV has been filled with a desired amount of diluent. In some embodiments, the memory can include a database or lookup table indicating which transfer stations are associated with which IV bags (which can be especially useful when multiple transfer stations are associated with a single IV bag). The information can be input by the user via the user interface or by scanning bar codes on the IV bags and transfer stations. If the controller determines that the IV bag assembly is not properly attached (e.g., no IV bag attached, or incorrect IV bag weight for desired diluent, or a wrong combination of transfer stations associated with the IV bag), the user interface can prompt the user to attach an IV bag or otherwise change the IV bag configuration. After the user makes the changes, the process 2300 can return to block 2308 to confirm that the IV bag assembly is properly attached and configured.

If the IV bag assembly is properly attached, the process 2300 proceeds to block 2312 where the system transfers fluid(s) from the transfer station(s) to the IV bag, as will be described in greater detail below.

Figure 24:
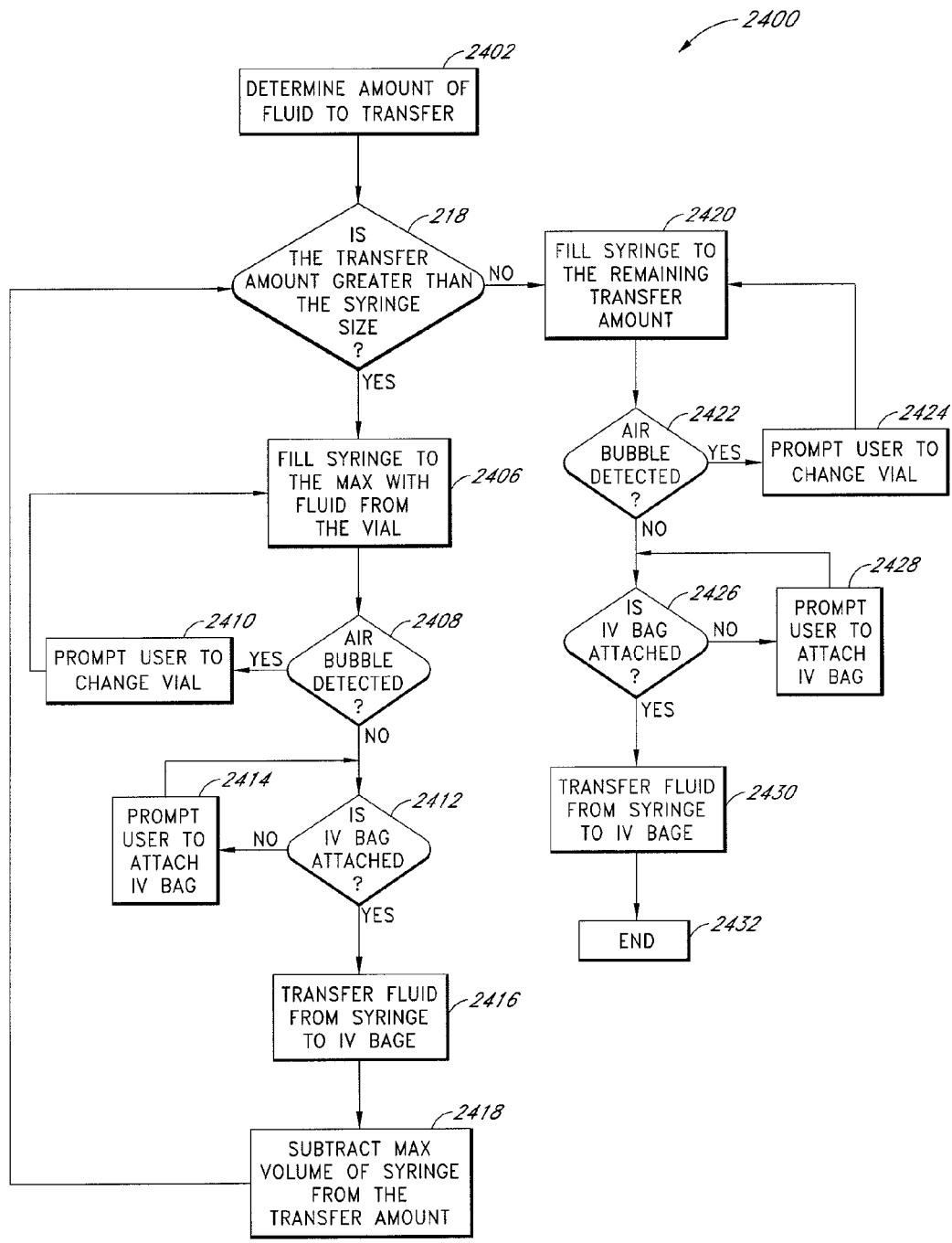
FIG. 24 is a flowchart that shows an embodiment of a method for transferring fluid.

FIG. 24 is a flowchart that schematically shows an embodiment of a method 2400 for transferring an amount of fluid from a vial to an IV bag. At block 2402, the controller determines an amount of fluid to be transferred. In some embodiments, the amount can be specified directly by the fluid transfer command. In some embodiments, the amount of fluid (e.g., medication or diluent) can be affected by the desired concentration and the concentration of the fluid contained in the vial.

At block 2404, the controller determines whether the transfer amount is greater than the effective maximum volume of the syringe associated with the transfer station. In some embodiments, the memory can include a database or lookup table that stores the sizes of the syringes associated with the different transfer stations. The information can be input by the user via the user interface or by scanning bar codes on the syringes and transfer stations. In some embodiments, the effective maximum volume of a syringe is the volume of the syringe when the plunger is substantially fully retracted. In some embodiments, the effective maximum volume of the syringe is the volume of the syringe when the plunger is retracted by the maximum amount that the actuator is able to retract.

If the amount to be transferred is greater than the effective maximum volume of the syringe, the method 2400 proceeds to block 2406 where the controller causes the plunger of the syringe to be withdrawn so as to draw the effective maximum volume of fluid from the vial into the syringe. As the fluid is transferred to the syringe in block 2406, the system can monitor for air bubbles, in block 2408, which can indicate that the fluid in the vial has run out. If a bubble is detected at block 2408, the method 2400 can interrupt block 2406 and prompt the user to replace the empty vial at block 2410. Once the vial has been replaced, the method 2400 can return to block 2406 and finish filling the syringe.

Once the syringe has been filled the method can proceed to block 2412 where the system determines whether an IV bag is attached to the target connector portion of the relevant transfer station. In some embodiments, a weight or IR sensor can be used to detect the presence of an IV bag or a connector attached to the target connector portion. Because an IV bag can be disconnected by mistake during a fluid transfer, in some embodiments the system can be configured to check for a connected IV bag each time the plunger of the syringe is to be advanced to drive fluid out of the syringe. In some embodiments, the system checks for an attached IV bag only at the start of the fluid transfer, so blocks 2412 and 2414 can be omitted. If the IV bag is not attached, the method 2400 can proceed to block 2414 where the user interface can prompt the user to reattach the IV bag. In some embodiments, the UI can provide an alert message to the user indicating that an error has likely occurred (e.g., an IV bag was removed prematurely). Once the changes have been made, the method 2400 can return to block 2412 to confirm that the IV bag is properly attached. In some embodiments, if the IV bag is not properly attached, the method 2400 can abort the fluid transfer, rather than proceeding to block 2414, and display an error message or alert to the user.

Once the system determines that the IV bag is attached, the method 2400 can advance to block 2416 where the controller can cause the actuator to advance the plunger of the syringe to drive the fluid out of the syringe and into the IV bag. At block 2418, the method can subtract the effective max volume of the syringe (i.e., the amount added to the IV bag at block 2416) from the amount of fluid to be transferred. Then the method 2400 can return to block 2404.

If, at block 2404, the controller determines that the amount to be transferred is less than the effective maximum volume of the syringe, the method 2400 can advance to block 2420 where the controller causes the actuator to withdraw the plunger of the syringe by a distance to draw the remaining transfer amount of fluid into the syringe. The controller can be configured to determine the distance to draw back the plunger based on the amount fluid remaining to be transferred and by the size of the syringe, which can be stored in a database or lookup table in the memory.

At block 2422, the system can monitor for air bubbles similarly to block 2408. If an air bubble is detected, the process 2400 can interrupt block 2420 and proceed to block 2424 where the user interface can prompt the user to replace the empty vial. Once the vial has been replace the method 2400 can return to block 2420 and finish filling the syringe with the desired amount of fluid.

Once the syringe contains the remaining fluid to be transferred, the process can advance to block 2426, where the system determines whether an IV bad is attached similar to block 2412. If no IV bag is properly attached, the method 2400 can advance to block 2428, where the user interface can prompt the user to reattach the IV bag. Once the changes have been made the method 2400 can return to block 2426 to confirm that an IV bag is properly attached. Then the method 2400 can advance to block 2430 where the controller can cause the actuator to advance the plunger of the syringe to drive the fluid from the syringe into the IV bag.

The method 2400 can end at block 2432. In some embodiments, the method 2400 can repeat for one or more additional fluids (e.g., a diluent or additional medication for a compounding procedure) transferred from one or more additional transfer stations. In addition, the blocks and order illustrated are exemplary methods. Modification is also possible. For example, the system can detect whether a bag is attached (e.g., blocks 2412, 2426) prior to drawing fluid into the syringe (e.g., blocks 2406, 2420).

Figure 25:
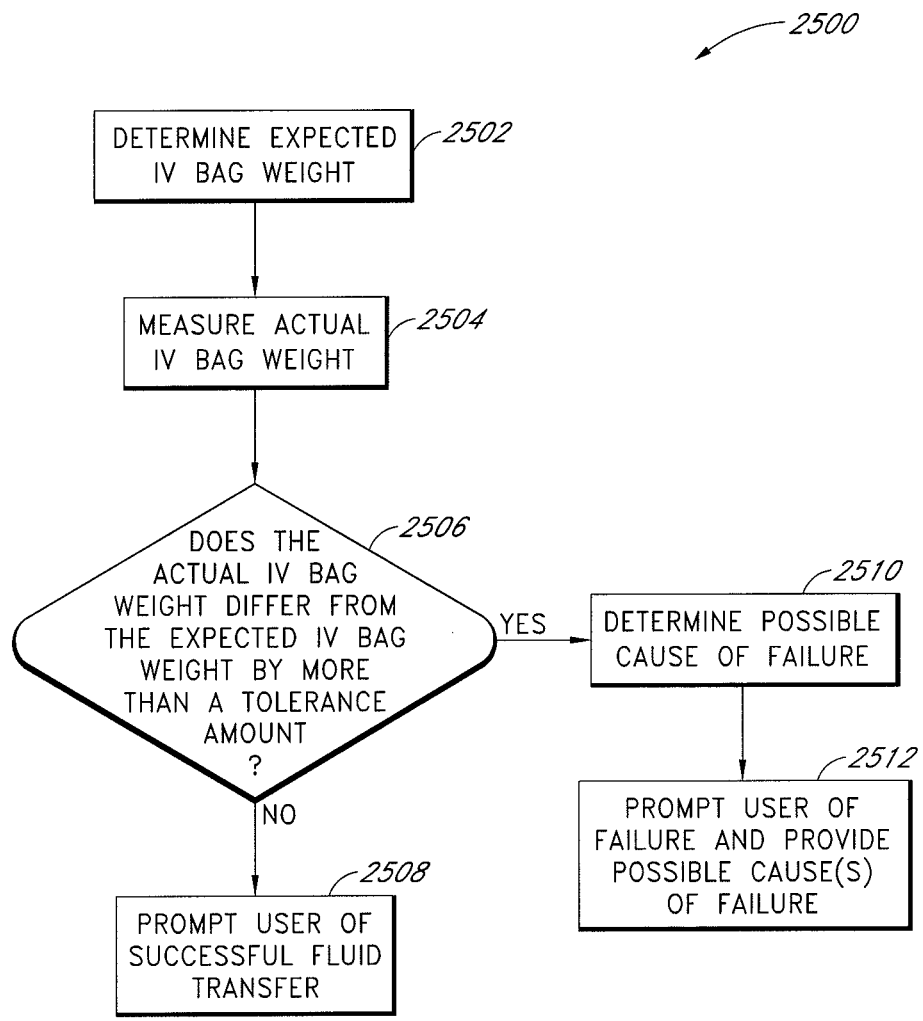
FIG. 25 is a flowchart that shows an embodiment of a method for confirming the successful transfer of fluid by checking the IV bag weight.

FIG. 25 is a flowchart that schematically shows an embodiment of a method 2500 for confirming the successful transfer of fluid by checking the weight of the final IV bag. At block 2502, the controller can determine an expected IV bag weight for the final IV bag filled with the transferred fluid. The expected weight can be determined by the starting weight of the empty IV bag (or the starting weight of the IV bag with diluent), and the amount and density of fluid to be transferred into the IV bag.

At block 2504, the system can measure the actual IV bag weight. In some embodiments, the system can include a weight sensor and can automatically measure the weight of the IV bag once the fluid transfer is complete. In some embodiments, the user interface can prompt the user to weigh the IV bag and enter the weight. In some embodiments, the user interface can prompt the user that the transfer is complete and display the expected weight for the IV bag. The user can then weigh the IV bag and compare the actual weight against the displayed expected weight.

At block 2506, the controller can compare the actual IV bag weight to the expected IV bag weight. If the actual IV bag weight differs from the expected IV bag weight by more than a threshold tolerance amount, the method 2500 can determine that an error occurred during the fluid transfer and advance to block 2510. At block 2510, the controller can attempt to determine possible causes of the fluid transfer failure. Many circumstances can lead to a fluid transfer failure. For example, if the user changes the type of fluid for a fluid transfer station without properly updating the database, the IV bag can contain the correct amount of fluid but since the fluid can have a different density the final weight of the IV bag can be different from the expected amount. If the user changes the syringe size for the transfer station without properly updating the database the actuation of the plunger can transfer an amount of fluid different than intended and the final weight of the IV bag can differ from the expected weight. The controller can be configured determine possible causes for the failure based at least in part on the amount by which the actual IV bag weight differs from the expected weight. At block 2512, the user interface can inform the user of the failure and can display one or more possible causes for the failure to aid the user in trouble shooting the problem.

If the actual IV bag weight is within the threshold tolerance amount of the expected weight, the system can conclude that the fluid was transferred successfully, and the method can advance to block 2508. At block 2508, the user interface can inform the user that the fluid was transferred successfully. The threshold tolerance amount can be determined by several factors, including the precision of the weight sensors, the amount of fluid transferred, and the accuracy provided by the syringe(s) used. It should be noted that some fluid transfer errors can go undetected by checking the weight of the IV bag. For example, if an incorrect fluid is used that has the same density as the correct fluid, the final IV bag will weigh the correct amount. However, by checking the weight of the IV bag, many errors can be detected.

Figure 26:
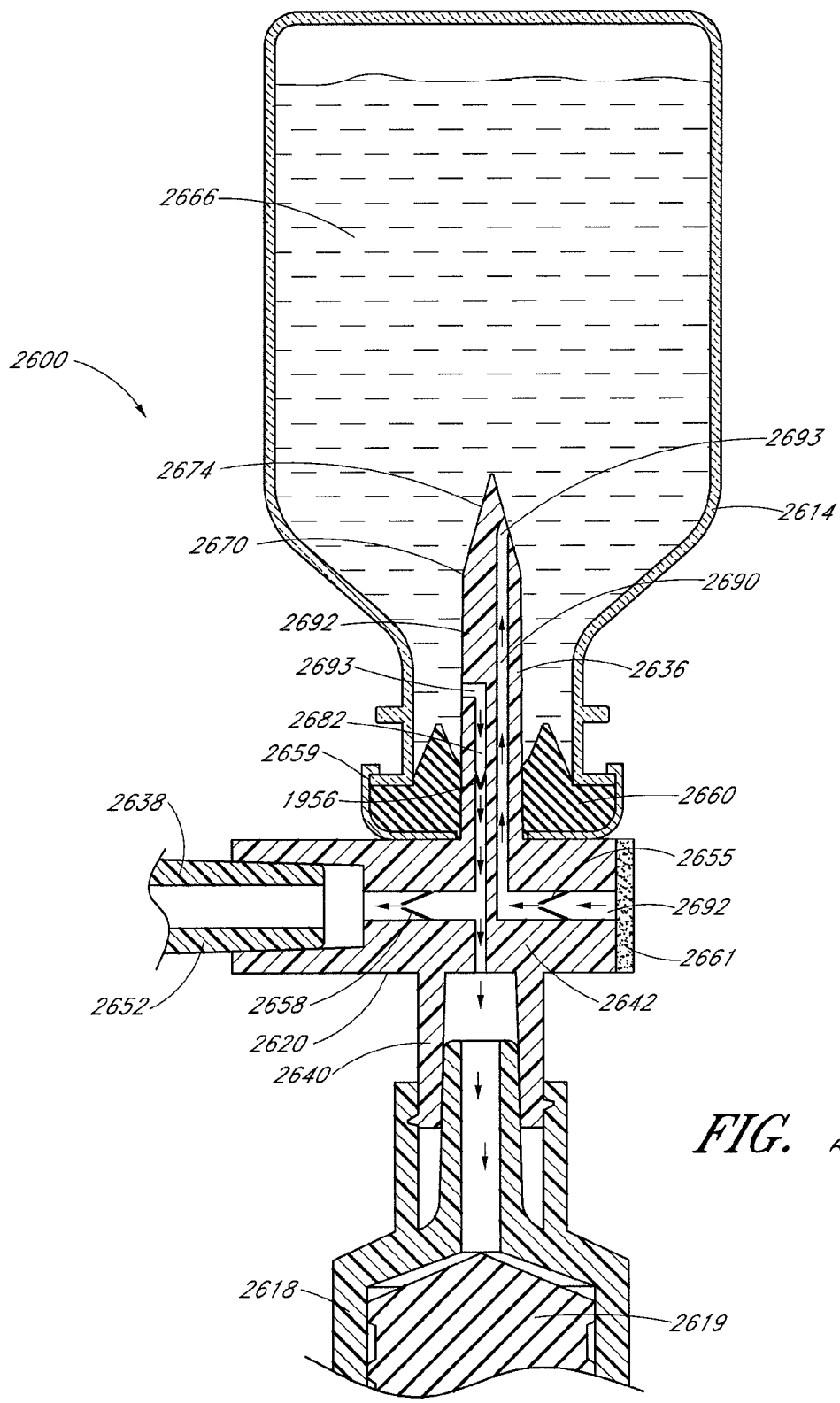
FIG. 26 is a cross sectional view of another embodiment of a connector for transferring fluid.

FIG. 26 is a partial sectional view that schematically shows another embodiment of a fluid transfer subsystem 2600 that can includes a vial 2614, a syringe 2618, and a connector 2620. In some embodiments, the vial 2614, syringe 2618, and connector 2620 shown in FIG. 26 can be the same as or similar to, for example, to the vial 314, syringe 318, and connector 320 described above. In some embodiments, the connector 2620 can include a main body portion 2642, a source connector portion 2636 configured to connect to the vial 2614, a target connector portion 2638 (partially shown in FIG. 26) configured to connect to an IV bag assembly (not shown in FIG. 26), and an intermediate connector portion 2640 configured to connect to the syringe 2618.

In some embodiments, the source connector portion 2636 can similar to the source connector portion 336 described above. The source connector portion 2636 can be integrally formed with the main body portion 2642 of the connector 2620, or the source connector portion 2636 can be separately formed and secured to the main body portion 2642, for example, by a plastic welding adhesive or other manner as described above. In some embodiments, the source connector portion 2636 includes a piercing member 2670 which can include an elongate shaft 2672 and pointed tip 2674. The piercing member 2670 can be configured to puncture a septum 2660 formed in a cap 2659 of the vial 2614 when the vial 2614 is pressed onto the connector 2620.

In some embodiments, the source connector portion can include a fluid extraction channel 2682 extending from an extraction aperture 2683 formed in a portion of the piercing member 2670 to the main body portion 2642 of the connector 2620. The fluid extraction channel 2682 can be configured to allow fluid 2666 to flow out of the vial 2614 and into the connector 2620, e.g., when the plunger 2619 of the syringe 2618 is withdrawn. In some embodiments, the connector 2620 can include a source check valve 2656 formed therein and configured to allow fluid to flow from the vial into the connector 2620 and prevent fluid from flowing from the connector 2620 into the vial 2614. In some embodiments, the source check valve 2656 can be similar to the check valve 356 described above or it can be a duckbill valve formed in the fluid extraction channel 2682, as schematically shown in FIG. 26. Many other variations are possible.

The source connector portion 2636 can also include a regulator channel 2690 extending from a regulator aperture 2692 up through a portion of the elongate shaft 2672 to an opening 2693 formed in the piercing member 2670. The regulator channel 2690 can allow air to enter the connector 2620 and flow into the vial 2614 as the fluid 2666 is withdrawn, thereby maintaining a substantially constant pressure inside the vial 2614. In some embodiments, a regulator check valve 2655 can be formed in the regulator channel 2690 to prevent fluid 2666 from escaping from the vial 2614 via the regulator channel 2690. The connector 2620 can also include a filter 2661 formed over the regulator aperture 2692 to prevent contaminants or other foreign particles from entering the regulator channel 2690 and contacting the fluid 2666. In some embodiments, the filter 2661 can be permeable to air so that air is permitted to enter the vial 2614 via the regulator channel 2690. In some embodiments, the filter 2661 can be impermeable to the fluid 2666 and can be used in conjunction with, or in place of, the regulator check valve 2655 to prevent fluid 2666 from exiting the vial 2614 via the regulator channel 2690.

In some embodiments, the source connector portion 2636 can differ from the source connector portion 336 by not including a bag to hold the air that enters the vial 2614. Thus, the air that enters the vial 2614 can directly contact the fluid 2666 contained therein. In some embodiments, the connector portion 2636 is only used for vials 2614 containing fluid 2666 that will not react with, or otherwise be adversely affected by, the air. In some embodiments, the filter 2661 and/or regulator check valve 2655 can be configured to allow only certain gases, which will not adversely affect the fluid 2666, to enter the vial 2614.

The target connector portion 2638 can be similar to the target connector portion 338 described above, the disclosure of which applies to the embodiment shown in FIG. 26. Only the mail connector portion 2652 of the target connector portion 2638 is shown in FIG. 26. The target connector portion can be configured to provide fluid communication between the connector 2620 and an IV bag assembly (not shown in FIG. 26) similar or the same as the IV bag assembly 330 described above. The connector 2620 can include a target check valve 2658 configured to allow fluid to flow from the connector into the IV bag assembly, e.g., when the plunger 2619 of the syringe 2618 is advanced, and prevent fluid from flowing from the VI bag assembly into the connector 2620. The target check valve 2658 can be similar or the same as the target check valve 358 described above, or it can be a duckbill valve as shown schematically in FIG. 26.

The intermediate connector portion 2640 can be configured to removably receive the syringe 2618 and provide a sealed fluid pathway between the connector 2620 and the syringe 2618. In some embodiments, the intermediate connector portion 2640 can be the same as or similar to the intermediate connector portion 340 described above.

The fluid transfer subsystem 2600 can be used as a fluid transfer station on an automated fluid transfer system, which can be, for example, similar to the automated fluid transfer system 600 described above.

Figure 27A:
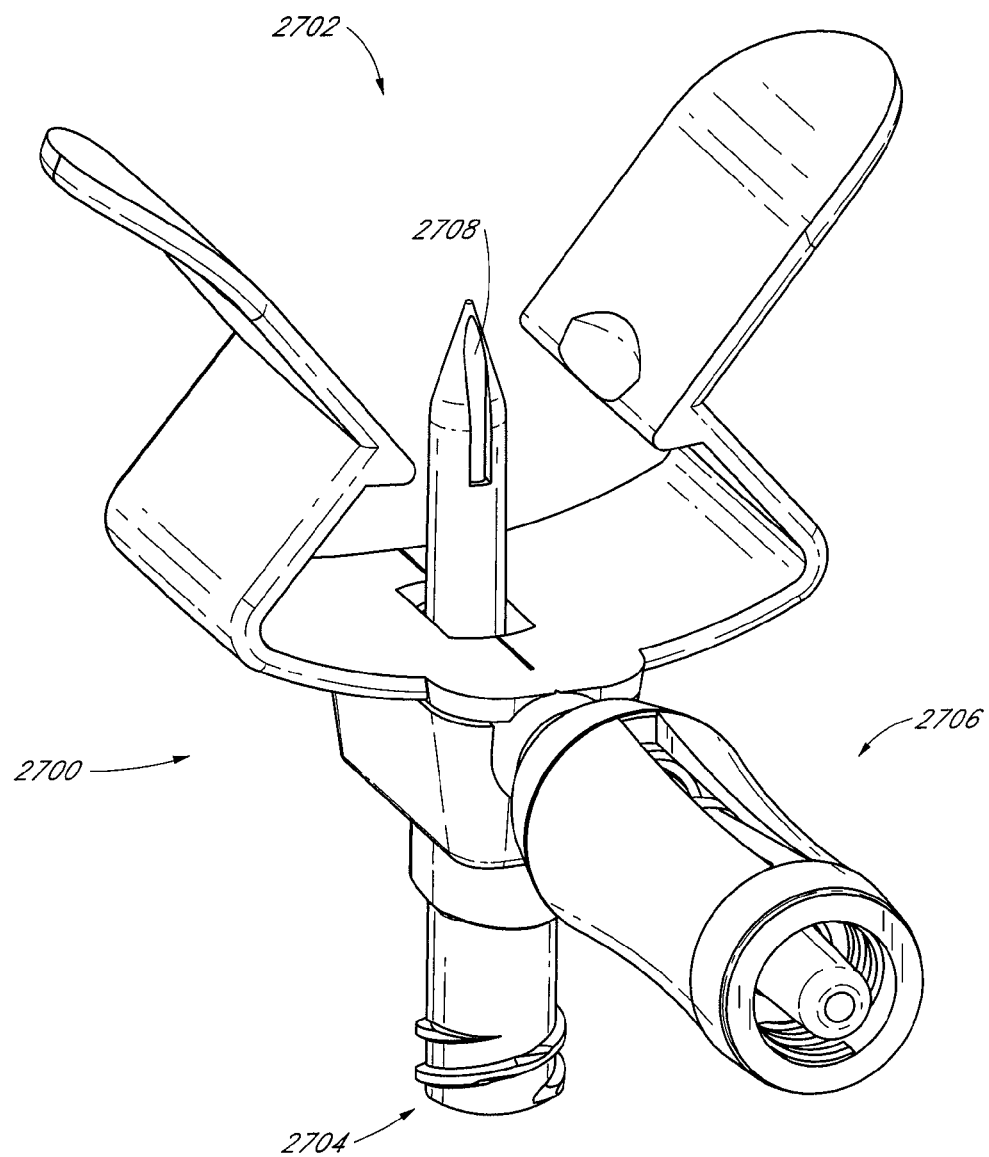
FIG. 27A is a perspective view of another embodiment of a connector for transferring fluid.
Figure 27B:
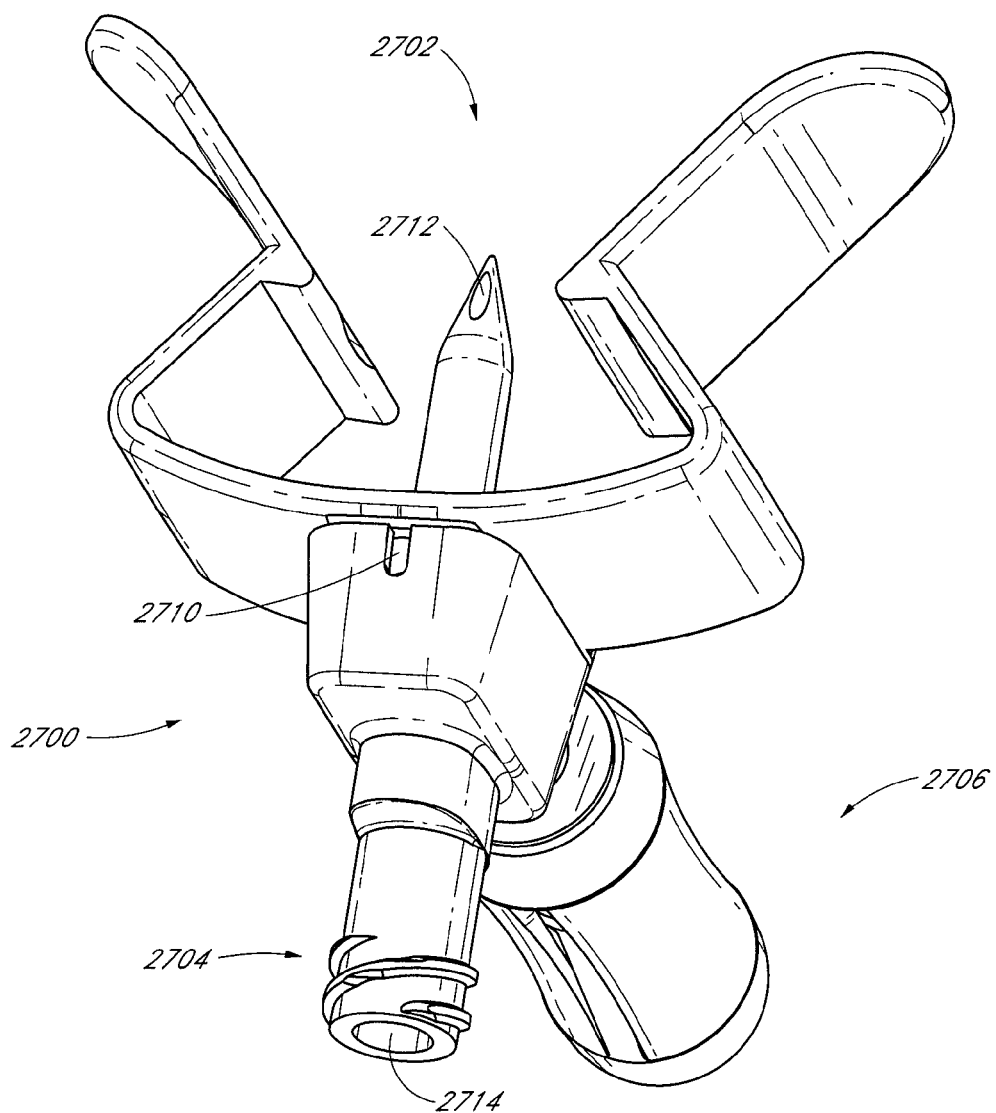
FIG. 27B is another perspective view of the connector of FIG. 27A.

FIG. 27A is a perspective view of an embodiment of a fluid transfer module in the form of a connector 2700, which can be similar in many regards to the connector 320 or any other connector disclosed herein. FIG. 27B is another perspective view of the connector 2700. The connector 2700 can be used to transfer fluid from a source container (e.g., a vial) to an intermediate measuring container (e.g., a syringe) and then to a target container (e.g., an IV bag). The connector 2700 can include a source connector portion 2702 configured to interface with the source container (e.g., a vial), an intermediate connector portion 2704 configured to interface with the intermediate measuring container (e.g., a syringe), and a target connector portion 2706 configured to interface with the target container (e.g., an IV bag assembly).

The connector 2700 can function to transfer fluid from the source container to the target container similarly to the connector 320 or the connector 2600 or any other connector disclosed herein. Fluid can be extracted from a vial (not shown) through the fluid extraction aperture 2708, and air can enter the vial via the air inlet 2710 and air outlet 2712 to replace the volume of extracted fluid. The fluid extracted from the vial can be drawn through the connector 2700 and into the syringe (not shown) via the opening 2714 formed in the intermediate connector portion 2704. A source check valve (hidden from view in FIGS. 27A-B) can be configured to allow fluid to flow from the fluid extraction aperture 2708 to the opening 2714 in the intermediate connector portion 2704 while preventing fluid from flowing in the reverse direction back into the vial. The fluid can be driven from the syringe into the connector 2700 via the opening 2714, and the fluid can be directed into the target connector portion 2706 and into an IV bag assembly (not shown) attached to the target connector portion 2706. A target check valve (hidden from view in FIGS. 27A-B) can be configured to allow the fluid to flow from the opening 2714 in the intermediate connector portion 2704 to the target connector portion 2706 while preventing fluid from flowing in the reverse direction.

Figure 28A:
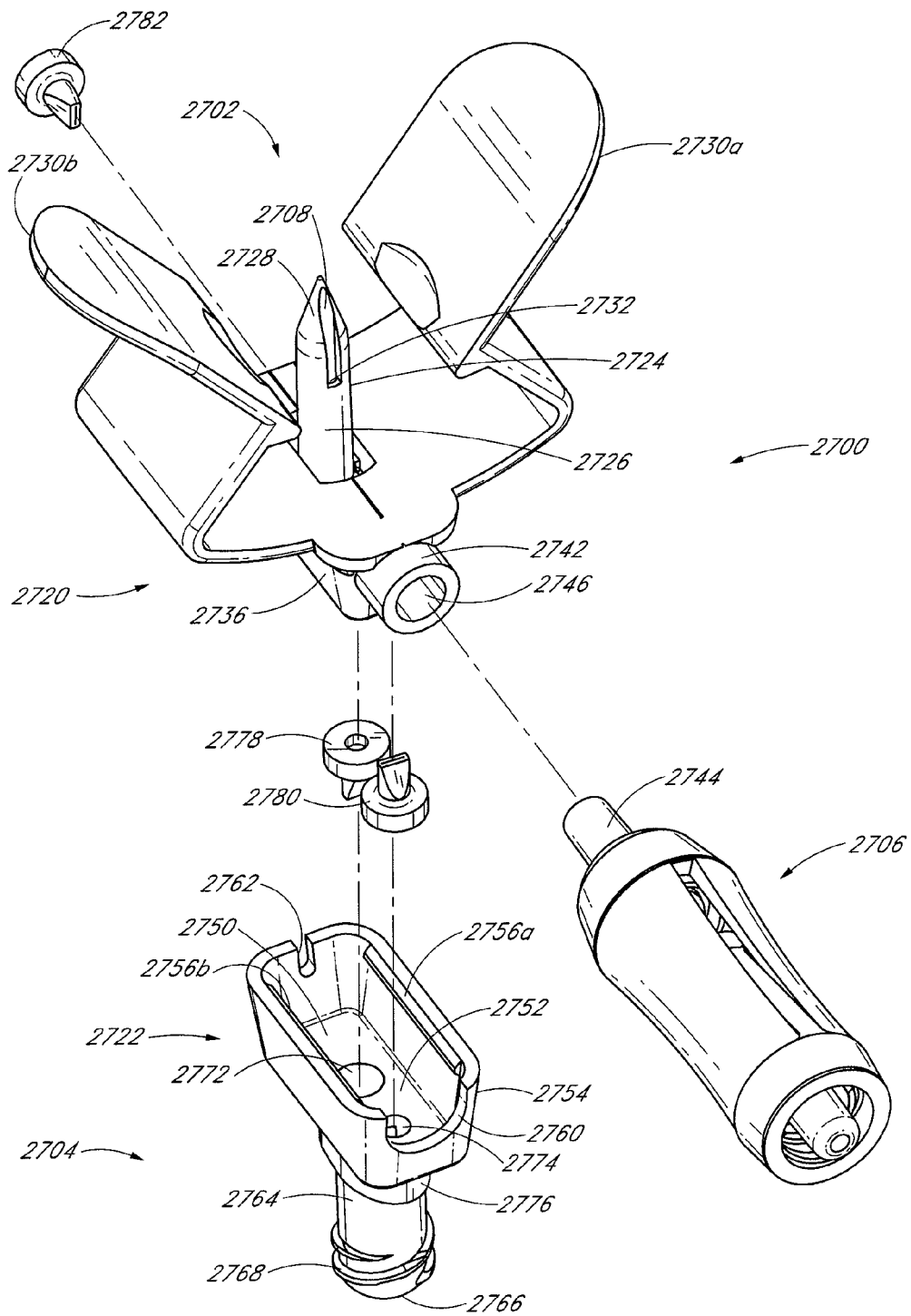
FIG. 28A is an exploded perspective view of the connector of FIG. 27A.
Figure 28B:
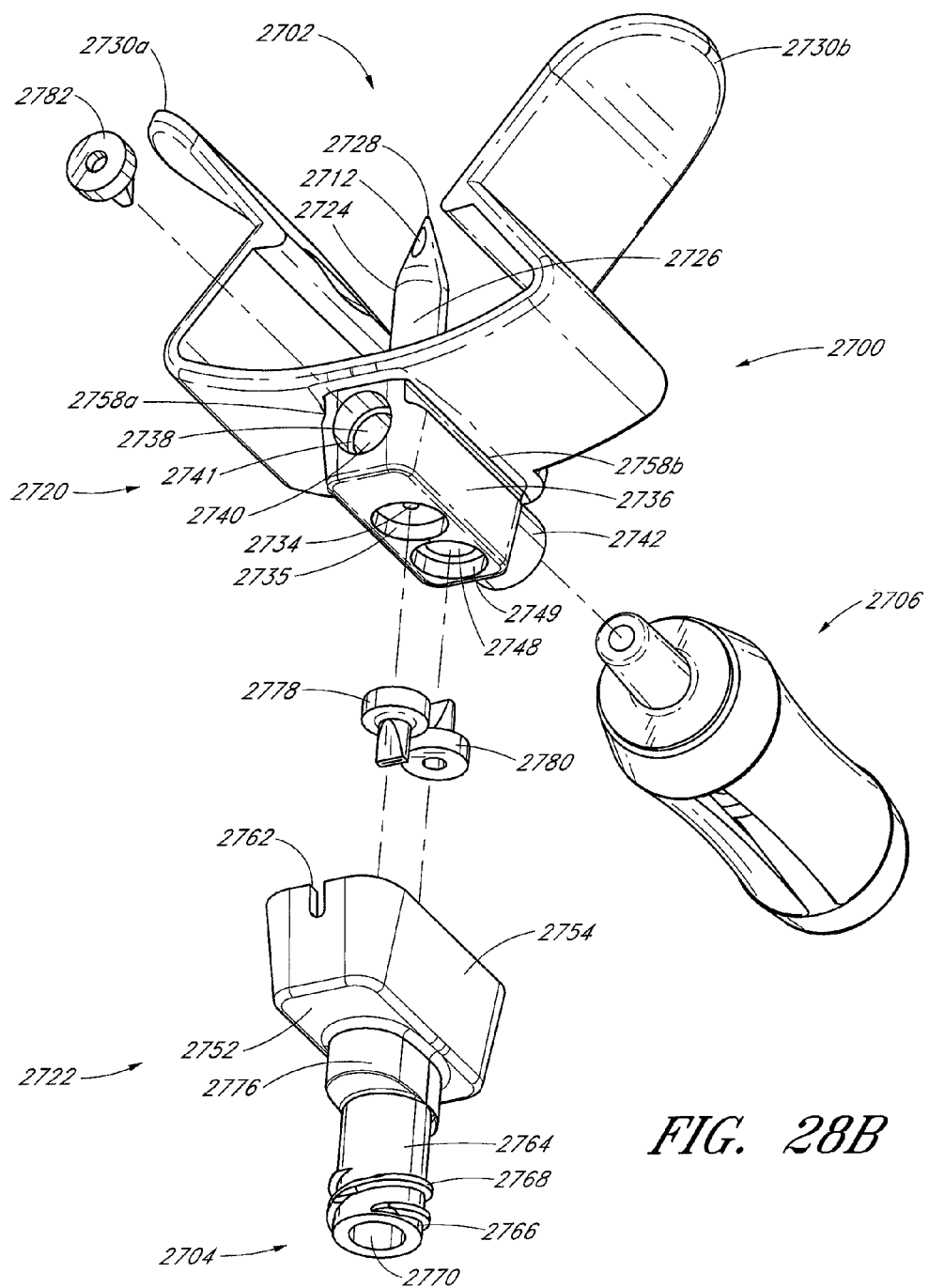
FIG. 28B is another exploded perspective view of the connector of FIG. 27A.

FIG. 28A is an exploded perspective view of the connector 2700. FIG. 28B is another exploded perspective view of the connector 2700. The connector 2700 can include an upper housing member 2720 and a lower housing member 2722. The upper housing member 2720 can include the source connector portion 2702 of the connector 2700, and the lower housing member 2722 can include the intermediate connector portion 2704 of the connector 2700.

The upper housing member 2720 can include a piercing member 2724 made up of an elongate substantially cylindrical shaft 2726 and a pointed tip 2728. The piercing member 2724 can be configured to pierce the septum of a vial (not shown) when the vial is attached thereto. The upper housing member 2720 can include retaining arms 2730*a-b* configured to secure the vial to the connector 2700, as described herein. The piercing member 2724 can include a fluid extraction aperture 2708 formed on one side thereof. The fluid extraction aperture can be a slit that extends from near the end of the pointed tip 2728 down onto the shaft 2726, although openings of other shapes can also be used. In some embodiments, the slit shape can facilitate the full extraction of fluid from the vial. A fluid pathway 2732 can extend from the fluid extraction aperture 2708 to a fluid outlet opening 2734 formed in the bottom surface of the base 2736 of the upper housing member 2720. The piercing member 2724 can also included an air outlet 2712 that allows air to enter the vial as fluid is extracted therefrom to equalize the pressure differential caused by the extraction of fluid. The air outlet 2712 can receive air from an air pathway 2738 that extends through the shaft 2726 and through the base 2736 and to an air inlet opening 2740 formed in the base 2736 of the upper housing 2720.

The upper housing member 2720 can include a female end 2742 configured to receive a male end 2744 of the target connector portion 2706. The target connector portion 2706 can be similar to the other target connector portions described herein (e.g., 338), the disclosure of which applies also to the target connector portion 2706. The male end 2744 can be secured to the female end 2742 by applying a plastic welding adhesive (such as Dichloromethane) to the outer surface of the male end 2744 and/or to the inner surface of the female end 2742 before insertion. The Dichloromethane can chemically weld the outer surface of the male end 2744 to the inner surface of the female end 2742. Other methods can be used to connect the male end 2744 to the female end 2742, such as sonic welding, threading, adhesives, etc. It will also be understood that the target connector portion can include the female end of the interface while the top housing member can include the male end thereof. Indeed, any suitable interface for securing the target connector portion 2706 to the upper housing member 2702 can be used. In some embodiments, the connection between the male end 2744 and the female end 2742 is hermetically sealed, and in some embodiments includes a sealing member (not shown), such as an O-ring, to provide the hermetic seal. A fluid pathway 2746 can extend from the opening in the female end 2742 to a fluid inlet opening 2748 formed in the bottom surface of the base 2736 of the upper housing member 2720.

The lower housing member 2722 can include a chamber 2750 enclosed by a base wall 2752 and by side walls 2754 having an open top. The chamber 2750 can be configured to receive the base 2736 of the upper housing member 2720 when the top housing member 2720 is secured to the bottom housing member 2722. The side walls 2754 can include projections 2756a-b formed near the top thereof, which can be configured to mate with corresponding slots 2758a-b formed in the upper portion of the base 2736 for provide a snap-fit connection between the top housing member 2720 and the bottom housing member 2722. It will be understood that the top housing member 2720 can be secured to the bottom housing member 2722 using various other techniques including an adhesive, sonic welding, a friction-fit, or any other suitable manner. The side walls 2754 of the lower housing member 2722 can include a front cutout 2760 configured to receive a portion of the female end 2742 therein. The side walls 2754 can also include a back cutout 2762 which can be align with the air inlet opening 2740 so that air is allowed to flow enter the air pathway 2738 by passing through the back cutout 2762 and through the air inlet opening 2740.

A shaft 2764 can extend downward from the base wall 2752 of the lower housing member 2722, and the shaft 2764 can have a female end 2766 configured to receive the male end of a syringe (not shown). The female end 2766 can include external threads 2768 configured to mate with internal threads of the syringe for securing the syringe thereto. A fluid pathway 2770 can extend from the opening formed in the female end 2766 up through the shaft 2764. The fluid pathway 2770 can include a fork or branch that divides the fluid pathway 2770 so that a fluid inlet opening 2772 and a fluid outlet opening 2774 are both in fluid communication with the fluid pathway 2770. The shaft 2764 can include an enlarged portion 2776 that is wider than the female end 2766 to accommodate the fork or branch in the fluid pathway 2770.

When the top housing member 2720 is attached to the bottom housing member 2722, the fluid outlet opening 2734 of the upper housing member 2720 can align with the fluid inlet opening 2772 of the lower housing member 2722 such that fluid can flow from the vial, through the fluid pathway 2732, out the fluid outlet opening 2734, in the fluid inlet opening 2772, through the fluid pathway 2770, and into the syringe. Also, the fluid inlet opening 2748 of the upper housing member 2720 can align with the fluid outlet opening 2774 of the lower housing member 2722 such that fluid can flow from the syringe, through the fluid pathway 2770, out the fluid outlet opening 2774, in the fluid inlet opening 2748, through the fluid pathway 2746, and to the target connector portion 2706.

A source check valve 2778 can be disposed between the top housing member 2720 and the lower housing member 2722, and can be configured to allow fluid to flow from the fluid outlet opening 2734 to the fluid inlet opening 2772 while preventing fluid from flowing in the reverse direction. The source check valve 2778 can be a duckbill check valve as shown in the illustrated embodiment, or any other form of check valve capable of allowing fluid to flow in one direction while preventing fluid flow in the opposite direction.

A target check valve 2780 can also be disposed between the top housing member 2720 and the lower housing member 2722, and can be configured to allow fluid to flow from the fluid outlet opening 2774 to the fluid inlet opening 2748 while preventing fluid from flowing in the reverse direction. The target check valve 2780 can be a duckbill check valve as shown in the illustrated embodiment, or any other form of check valve capable of allowing fluid to flow in one direction while preventing fluid flow in the opposite direction.

An air check valve 2782 can be disposed between the base 2736 of the upper housing member 2720 and a side wall 2754 of the lower housing member 2722. The check valve 2782 can be positioned between the back cutout 2762 and the air inlet opening 2740 such that air is permitted to flow from the back cutout 2762 to the air inlet opening 2740, but air and fluid are not allowed to flow out of the air inlet opening 2740. The air check valve 2782 can be a duckbill check valve as shown in the illustrated embodiment, or any other form of check valve capable of allowing fluid to flow in one direction while preventing fluid flow in the opposite direction. In some embodiments, a filter (not shown) can be used in conjunction with or in place of the air check valve 2782. The filter can be placed between, or within one of, the back cutout 2762 and the air inlet opening 2740. The filter can be permeable to air so that air is permitted to enter the air passageway 2738. In some embodiments, the filter can be impermeable to the fluid to prevent fluid from exiting the vial via the air pathway 2738. In some embodiments, a bag (not shown) at least partially disposed within the air passageway 2738 can be used to prevent the air that enters the vial from mixing with the fluid. For example, the piercing member 2724 can include a bag and can be similar to the piercing member 370 discussed above in connection with FIGS. 5A-D.

Figure 29A:
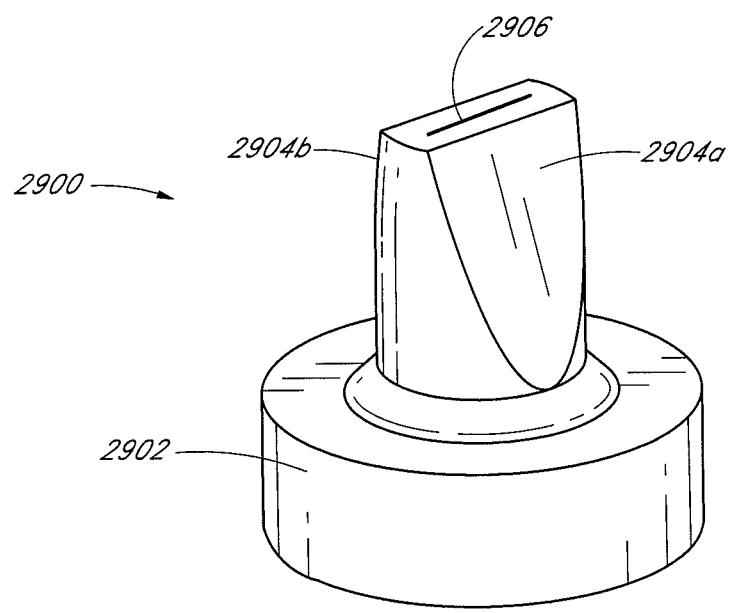
FIG. 29A is a perspective view of a duckbill check valve.
Figure 29B:
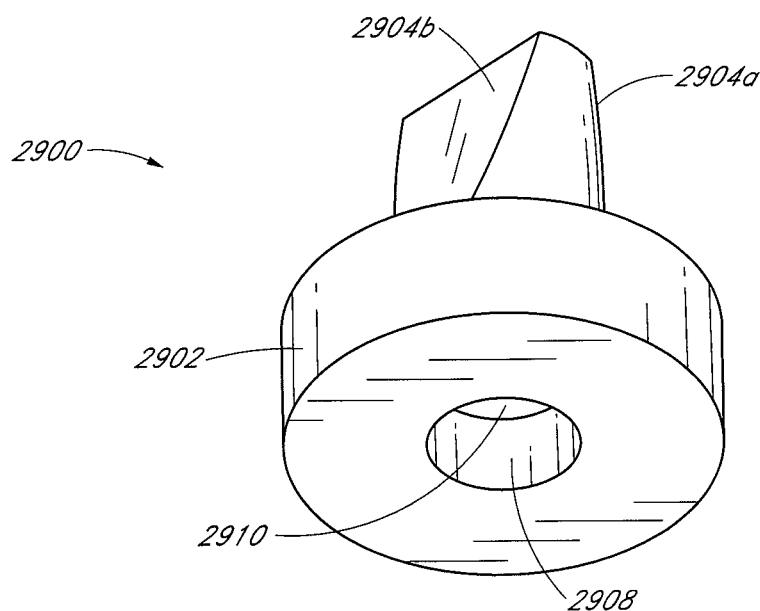
FIG. 29B is another perspective view of the duckbill check valve of FIG. 29A.

FIG. 29A is a perspective view of a check valve 2900 which can be used as the source check valve 2778, the target check valve 2780, and/or the air check valve 2782. In some embodiments, the source check valve 2778, the target check valve 2780, and the air check valve 2782 can each have the same shape and size so that they are interchangeable, thereby reducing the cost (e.g., mold creation) that would be required to produce two or three distinct check valve designs. The check valve 2900 can include a base 2902, which can by cylindrical in shape, although other shapes can also be used. A pair of generally opposing bill members 2904a-b can extend upward from the base 2902. The bill members 2904a-b can abut against one another at their ends furthest from the base 2902 forming a slit 2906 therebetween. In the check valve's 2900 relaxed state, the slit 2906 can be closed as shown in FIGS. 29A-B. The base 2902 can include an opening 2908 in fluid communication with a chamber 2910 formed between portions of the bill members 2904a-b.

Figure 29C:
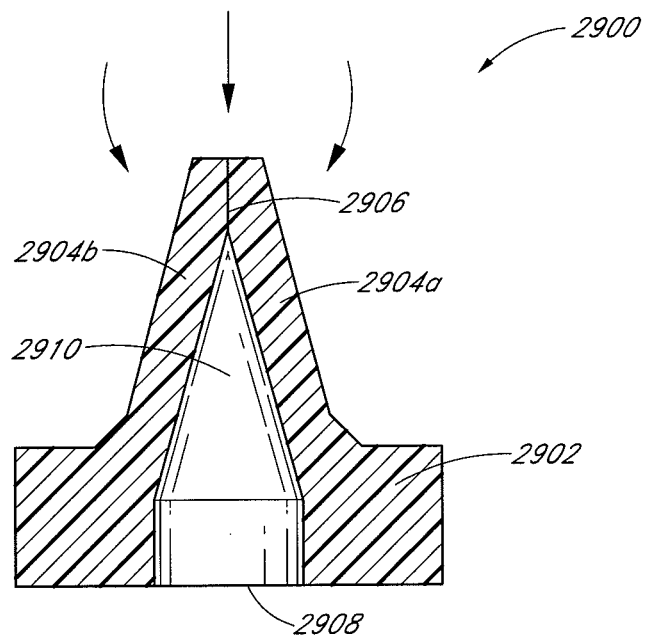
FIG. 29C is a cross sectional view of the duckbill check valve of FIG. 29A in a closed configuration.
Figure 29D:
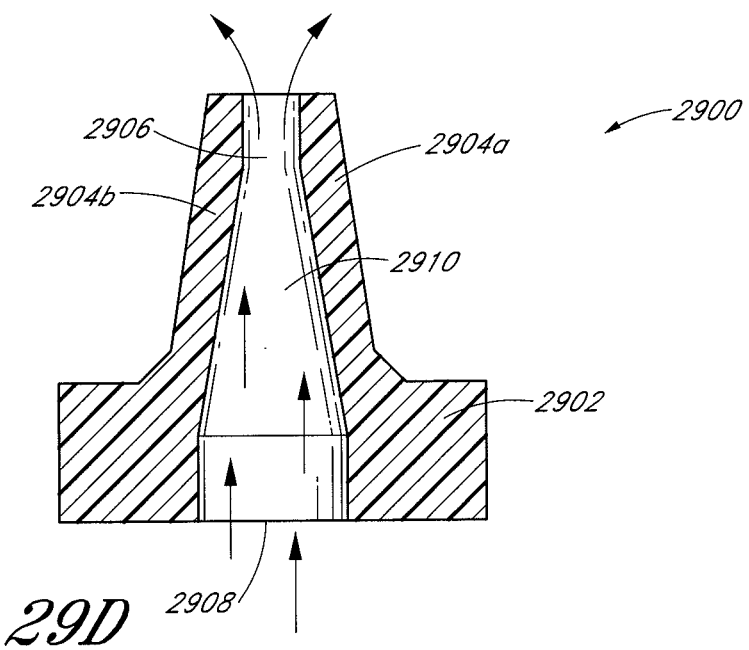
FIG. 29D is a cross sectional view of the duckbill check valve of FIG. 29A in an open configuration.

FIG. 29C is a cross sectional view of the check valve 2900 in the closed configuration. When the slit 2906 is closed and fluid is directed to the check valve 2900 in the direction that the check valve 2900 is configured to block, as shown in FIG. 29C by fluid flow lines, the resulting pressure applied to the outside surfaces of the bill members forces the slit closed. Thus, as greater pressure is applied, the slit 2906 closes more strongly to prevent fluid flow in the undesired direction. Likewise, when fluid is withdrawn from the fluid chamber 2910, the bill members 2904a-b are also drawn together causing the slit 2906 to seal more tightly. FIG. 29D shows the check valve 2900 in the open configuration as fluid is directed through the check valve 2900 in the desired direction, as shown by fluid lines. When fluid is directed through the opening 2908 and into the chamber 2910, the resulting pressure applied to the inside surfaces of the bill members 2904a-b causes the bill members 2904a-b to move away from one another forcing the slit 2906 to open. Likewise, when fluid is drawn away from the outside surfaces of the bill members 2904a-b (with flow in the opposite direction of the flow lines shown in FIG. 29C), the resulting pressure can pull the bill members 2904a-b apart to open the slit 2906. The check valve 2900 can be formed from silicone or any other suitable resilient material.

Returning now to FIGS. 28A-B, the fluid inlet opening 2772 can be wide enough to receive the duckbill portion of the source check valve 2778, and the fluid inlet opening 2748 can be wide enough to receive the duckbill portion of the target check valve 2780. Thus, in some embodiments, the fluid inlet opening 2772 can be wider than the fluid outlet opening 2774, and the fluid inlet opening 2748 can be wider than the fluid outlet opening 2734. The fluid outlet opening 2734 can include a widened end portion that produces a step 2735. The widened portion and the step 2735 can be configured to receive the base of the source check valve 2778. The step 2735 can have a height that is less than the height of the base of the source check valve 2778 so that the base of the check valve 2778 can be compressed between the top housing member 2720 and the lower housing member 2722 when they are attached. Thus, the compressed base of the check valve 2778 can function to seal off the interface between the fluid outlet opening 2734 and the fluid inlet opening 2772 so that fluid can flow through the check valve 2778 without escaping. This can be particularly advantageous when a chemotherapy drug or other hazardous fluid is transported through the connector 2700. The fluid inlet opening 2748 can also have a widened end portion that creates a step 2749 to receive and compress the base of the target check valve 2780 to seal the interface between the fluid outlet opening 2774 and the fluid inlet opening 2748. The air inlet opening 2740 can also include a widened end portion that forms a step 2741 and receives the base of the air check valve 2782 to seal the interface between the back cutout 2762 and the air inlet opening 2740. In some embodiments, all fluid flow paths through the connector are sealed (e.g., hermetically sealed) such that no fluid (e.g., chemotherapy drugs or other hazardous materials) can escape during operation.

Figure 30A:
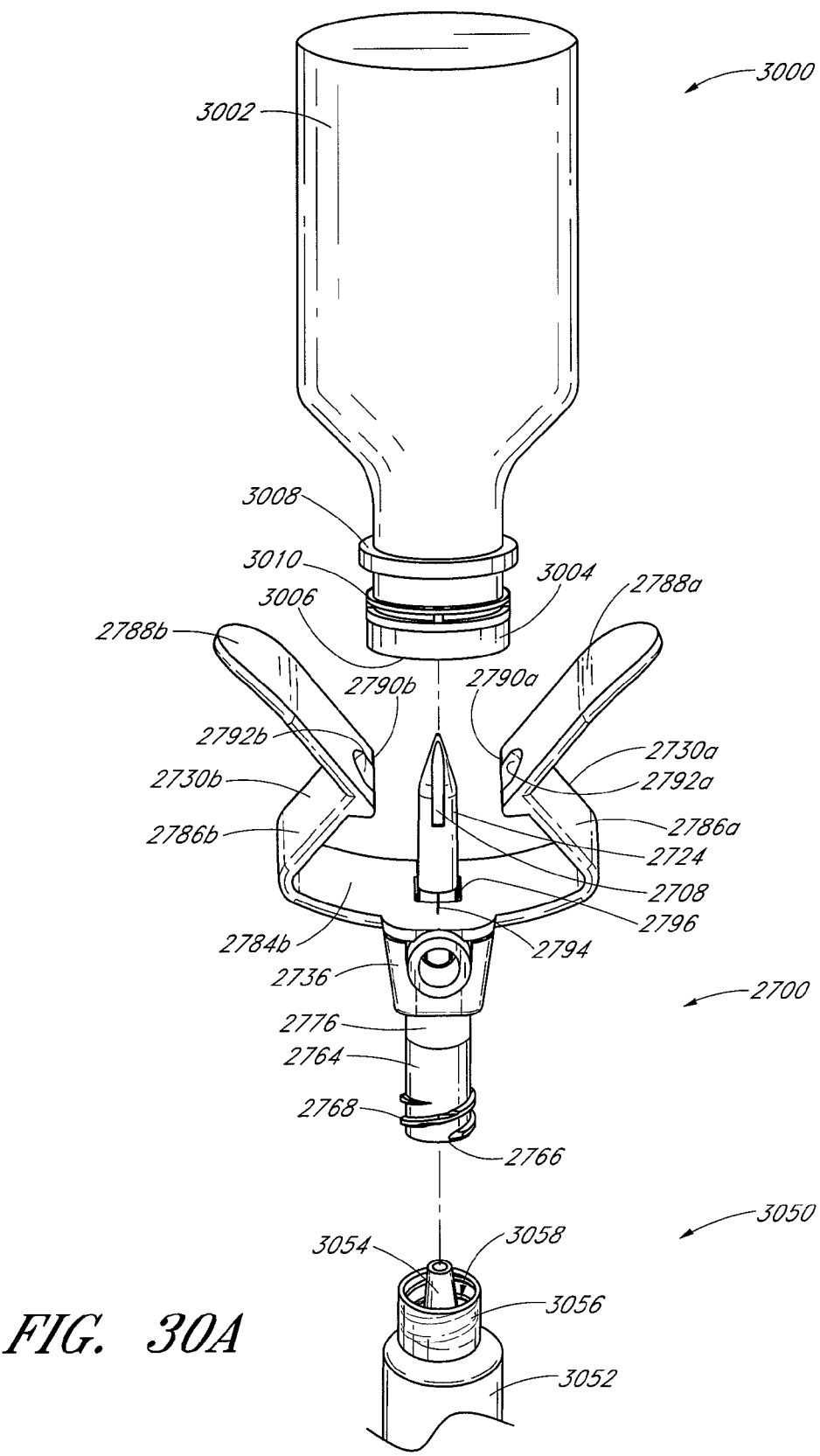
FIG. 30A is a perspective view of the connector of FIG. 27A, and a syringe, and a vial in an unassembled configuration.
Figure 30B:
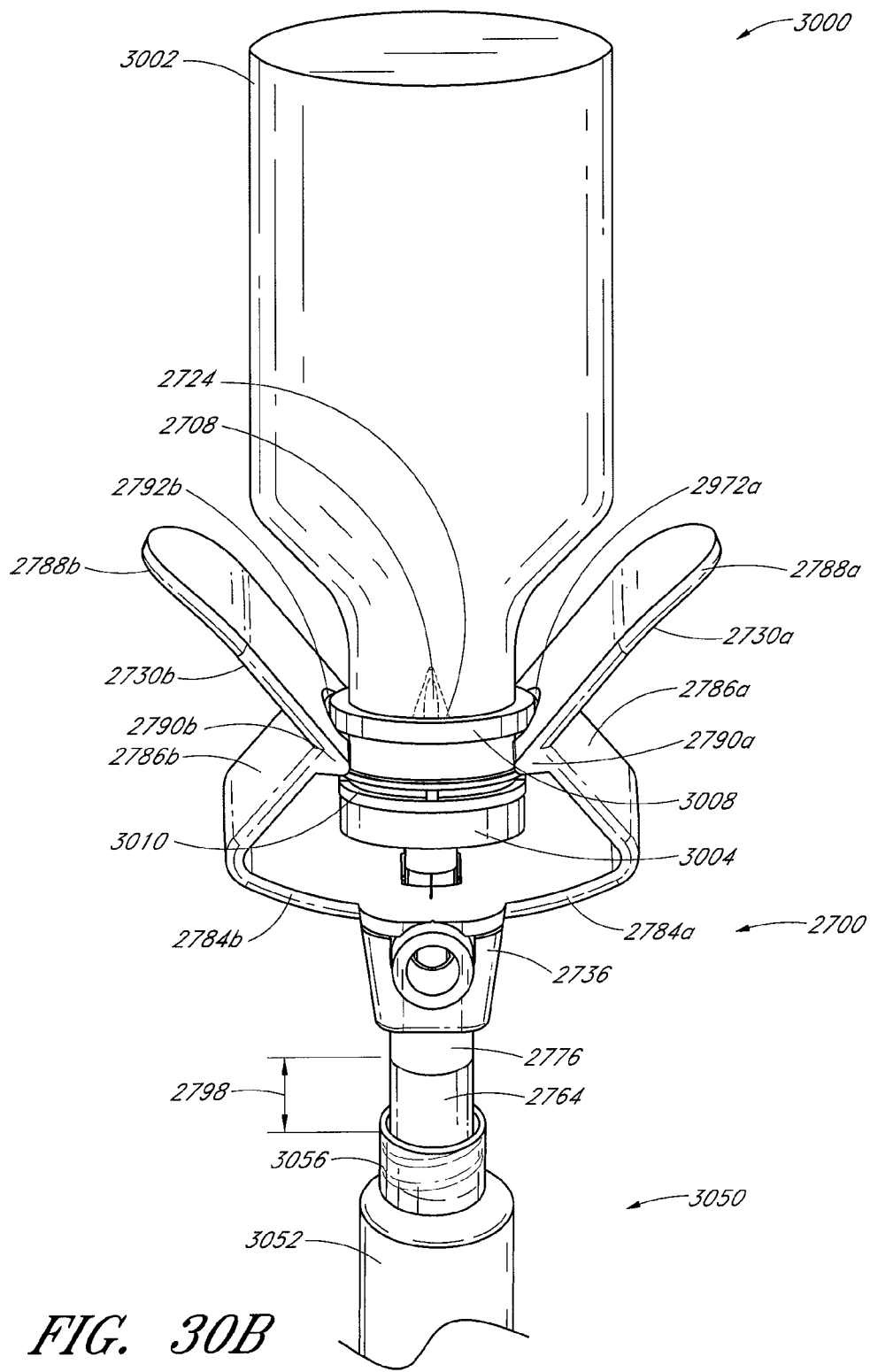
FIG. 30B is a perspective view of the connector of FIG. 27A, and a syringe, and a vial in an assembled configuration.
Figure 30C:
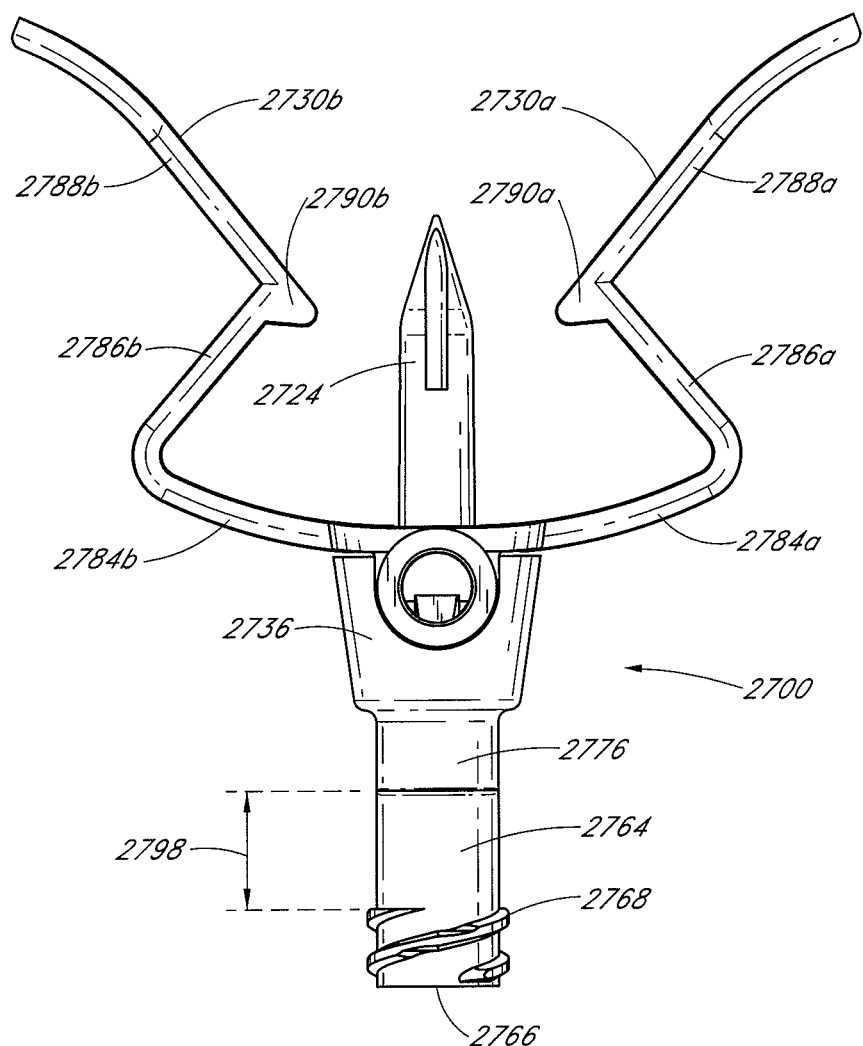
FIG. 30C is a front view of the connector of FIG. 27A.

FIG. 30A shows the connector 2700, a vial 3000, and a syringe 3050 in an unattached configuration. FIG. 30B shows the connector 2700, the vial 3000, and the syringe 3050 in an attached configuration. FIG. 30C shows a front view of the connector 2700. In FIGS. 30A-C, the connector 2700 is illustrated without the target connector portion 2706. The vial 3000 can include a body 3002, and a cap 3004, with a septum 3006 (hidden from view in FIGS. 30A-B) disposed within the cap 3004. The vial can include a securing ring 3008 formed on the neck of the body 3002, and/or the cap 3004 can overhang over the edge of the body 3002 forming a securing step 3010. The vial 3000 can be similar to the vial 314 described herein or any other medical vial or any other suitable container of fluid. It will be understood that various vial shapes and sizes can be used other than the vials shown herein. For example, the vial 3000 can be much larger than the vials (e.g., 314 or 3000) shown. Also, in some embodiments, other fluid containers can be used in place the vials shown.

As mentioned above, the connector 2700 can include retaining arms 2730a-b for securing the vial 3000 to the connector 2700. The manner of securing the vial 3000 to the connector 2700 will be discussed in greater detail with reference to FIGS. 30A-C. The retainer arms 2730a-b can be general z-shaped, having a lower portion 2784a-b, a middle portion 2786a-b, and an upper portion 2788a-b. The lower portions 2784a-b can extend outward from the base 2736 of the upper housing member 2720. As can best be seen in FIG. 30C, the lower portions 2784a-b can be slightly curved and can angle upward slightly (e.g., at an angle of at least about 10° and/or no more than about 20°, and in some embodiments at an angle of about 15°, from the horizontal plane). The middle portions 2786a-b can extend inwardly from the ends of the lower portions 2784a-b and can angle upward at an angle of at least about 30° and/or no more than about 60°, and in some embodiments by an angle of about 45°, from the horizontal plane. The upper portions 2788a-b can extend outwardly from the ends of the middle portions and can angle upward at an angle of at least about 30° and/or no more than about 60°, and in some embodiments by an angle of about 45°, from the horizontal plane. In some embodiments, the ends of the upward portions 2788a-b can be curved as best seen in FIG. 30C. Securing projections 2790a-b can be located at the junctions between the middle portions 2786a-b and the upper portions 2788a-b.

The retaining arms 2730a-b can be formed of a material and thickness such that the retaining arms can resiliently bend outwardly, causing the distance between the securing projections 2790a-b to increase. To attach the vial 3000 to the connector 2700, the vial 3000 can be positioned as shown in FIG. 30A, and the vial 3000 can be pushed toward the connector 2700 such that the piercing member 2724 punctures through the septum 3006 of the vial 3000. As the cap 3004 of the vial 3000 contacts presses against the top/inner surfaces of the upper portions 2788a-b of the retainer arms 2730a-b, the retainer arms 2730a-b can be flexed away from one another until the cap 3004 slips past the securing projections 2790a-b, at which point the retaining arms 2730a-b snap back. When the retaining arms 2730a-b snap back, the securing projections 2790a-b can engage the securing step 3010 on the side of the cap 3004 facing the body 3002 of the vial 3000. In some embodiments, the vial can be advanced until the securing projections 2790a-b engages with the securing step 3010 on the cap 3004 (as shown in FIG. 30B) or with the securing ring 3008. In some embodiments, the retaining arms 2730a-b can include indentations 2792a-b that can be configured to receive a portion of the vial body 3002 prevent the vial 3000 from shifting once secured to the connector 2700. If the securing step 3010 on the cap 3004 engages the securing projections 2790a-b, the securing ring 3008 can engage the indentations 2792a-b (as shown in FIG. 30B). If the securing ring 3008 engages the securing projections 2790a-b, the portion of the vial 3000 where the neck widens to the body 3002 can be received by the indentations 2792a-b.

As shown in FIG. 30B, the piercing member 2724 can extend into the body 3002 of the vial 3000 such that the fluid extraction aperture 2708 is place into contact with the fluid inside the vial 3000. In some embodiments, the slit shape of the fluid extraction aperture 2708 can allow the fluid to remain in contact with the fluid extraction aperture 2708 as the fluid is emptied from the vial 3000. For example, in some embodiments, a portion of the fluid extraction aperture 2708 does not fully pass through the septum so that when the vial 3000 is nearly empty, the little remaining fluid can still be withdrawn through the fluid extraction aperture 2708. In some embodiments, at least a portion of the septum of the vial can be thicker than the length of the fluid extraction aperture 2708 so that when the piercing member 2724 is inserted through the septum the fluid extraction aperture 2708 is not in simultaneous communication with both the interior and exterior of the vial.

In some embodiments, the connector can include a slit 2894 that extends through a portion of the base 2736 along a midline between the retainer arms 2730a-b. The slit 2794 can facilitate the flexing of the retainer arms 2730a-b so that the slit can widen as the arms 2730a-b are separated from each other. In some embodiments, the piercing member 2724 can connect to the base 2736 of the upper housing member 2720 within an indentation 2796 formed in the upper surface of the base 2736. The indentation 2796 can also facilitate the flexing of the retainer arms 2730a-b because the arms 2730 can flex without directly applying pressure to the piercing member 2708. In some embodiments, the slit 2794 can extend out from the front and back sides of the indentation 2796.

With further reference to FIGS. 30A-C, the syringe 3050 can be similar to the syringe 318 discussed above, or any other syringe discussed herein. The syringe 3050 can include a body 3052, a male luer tip 3054, and a shroud 3056 surrounding the male luer tip 3054. Internal threads 3058 can be formed on the inside surface of the shroud 3056 to mate with the external threads 2768 formed on the outside surface of the female end 2766.

It will be understood that the connector 2700 can be used in connection with an automated fluid transfer system (e.g., system 600). When attached to a fluid transfer station, the connector 2700 can align with sensors for optically detecting the presence of air in the fluid pathway between the vial 3000 and the syringe 3050 as discussed above in connection with FIGS. 17-19D. With further reference now to FIGS. 30B-C, in some embodiments the connector 2700 can be aligned such that the light (e.g., light 676 or 1924) passes through the fluid pathway 2770 (hidden from view in FIG. 30C) formed in the shaft 2764 within the region 2798 between the enlarged portion 2776 of the shaft 2764 and the location where the upper end of the syringe shroud 3056 ends when the syringe is attached (e.g., as shown in FIG. 30B). In some embodiments, all or a portion of the lower housing member 2722 can be made from a material that is transparent to the light transmitted through the region 2798. In some embodiments, the entire shaft 2764 or the entire portion of the shaft below the enlarged portion 2776 thereof can be transparent. In some embodiments, the shaft 2764 includes a transparent window portion that covers all or a portion of the region 2798, with the remainder of the lower housing member 2722 being made from a material that is opaque to the light.

Figure 31A:
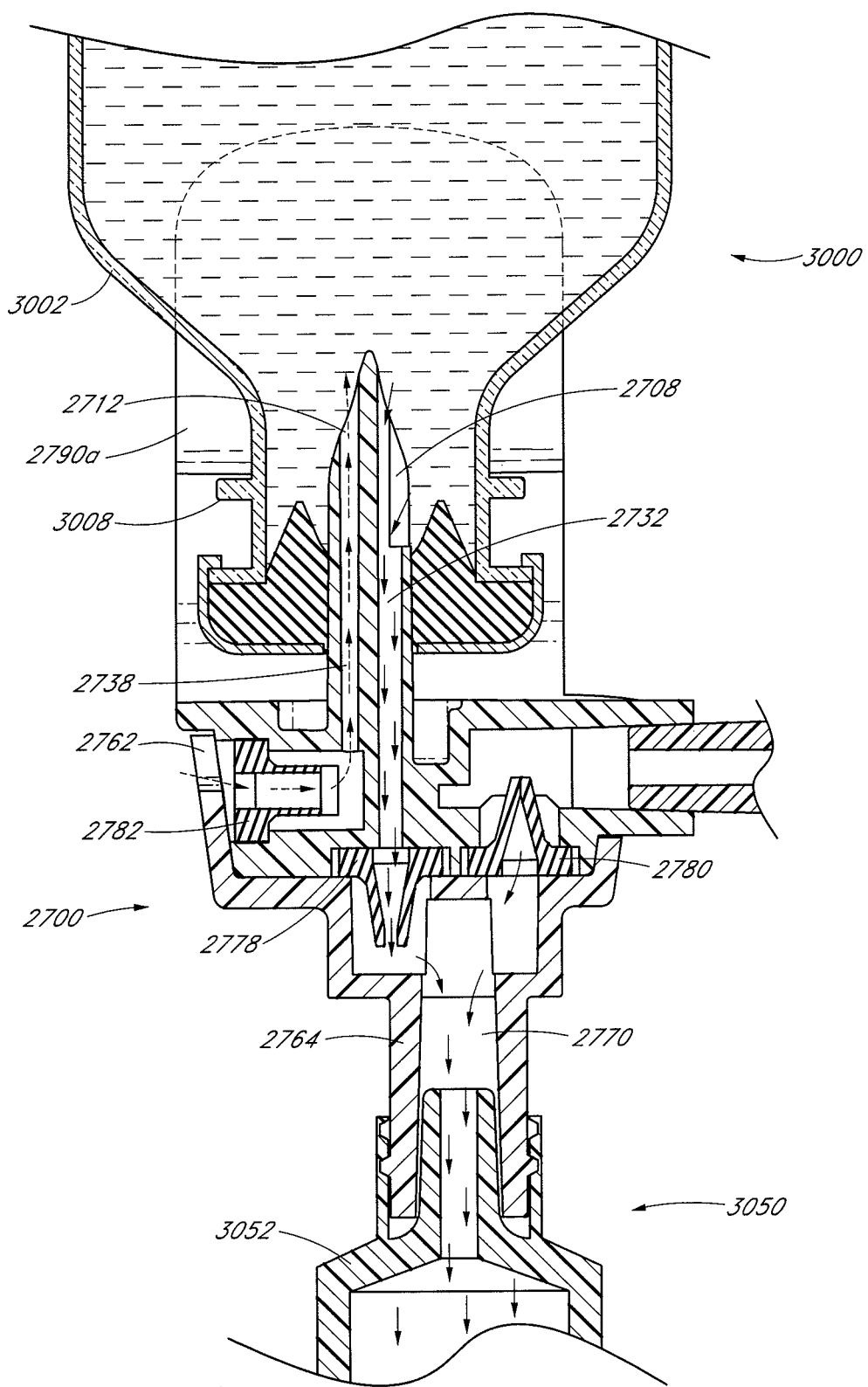
FIG. 31A is a cross sectional view of the connector of FIG. 27A, a vial, and a syringe as fluid is drawn from the vial, through the connector, and into the syringe.

FIG. 31A shows a cross sectional view of the connector 2700, the vial 3000, and the syringe 3050 as fluid is drawn through the connector 2700 from the vial 3000 to the syringe 3050. As the plunger (not shown) of the syringe 3050 is withdrawn, fluid can be drawn into the body 3052 of the syringe 3050 from the fluid pathway 2770 formed in the shaft 2764. The fluid pathway 2770 can fork or branch so that both the source check valve 2778 and the target check valve 2780 are exposed to the pressure differential caused by the fluid being withdrawn from the fluid pathway 2770. The slit of the target check valve 2780 closes more tightly as fluid is drawn away from it and towards the syringe 3050. The slit of the source check valve 2778 opens as the fluid is drawn toward the syringe. When the source check valve 2778 opens, fluid can be drawn from the source container (e.g., vial 3000) toward the syringe 3050 to compensate for the pressure differential. Fluid can enter the fluid pathway 2732 via the fluid extraction aperture 2708, and flow through the source check valve 2778, into the fluid pathway 2770, and down into the syringe 3050. As fluid is extracted from the vial 3000, air can be drawn into the vial to compensate for the loss of fluid volume. The air can pass through the back cutout 2762, through the air check valve 2782, through the air pathway 2738, and through the air outlet 2712 into the body 3002 of the vial 3000.

Figure 31B:
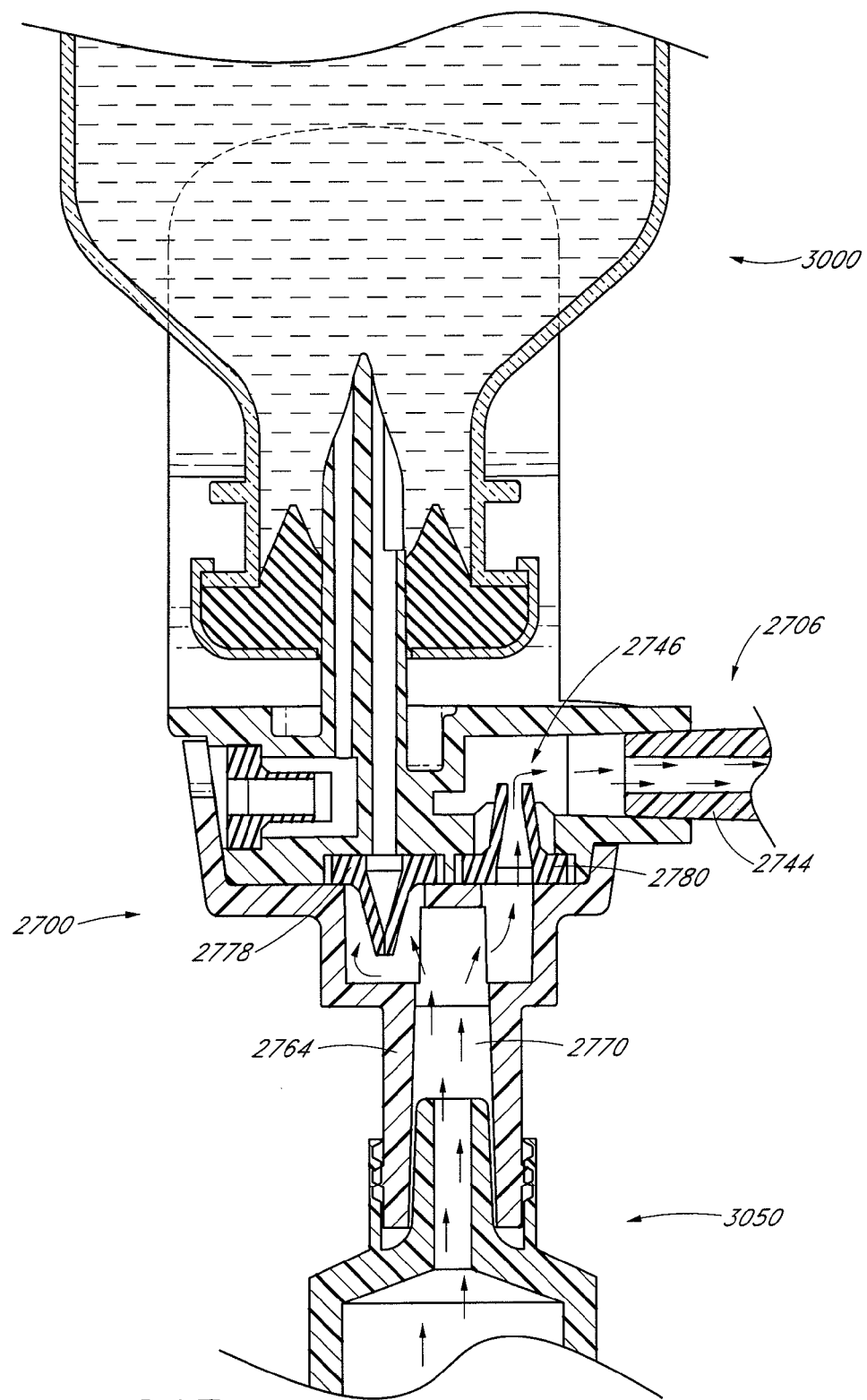
FIG. 31B is a cross sectional view of the connector of FIG. 27A, a vial, and a syringe as fluid is driven from the syringe, through the connector, and into an IV bag.

FIG. 31B shows a cross sectional view of the connector 2700, the vial 3000, and the syringe 3050 as fluid is driven through the connector 2700 from the syringe 3050 to the target connector portion 2706 which leads to the IV bad assembly (not shown). As the plunger (not shown) of the syringe 3050 is advanced, fluid can be driven from the body 3052 of the syringe 3050 into the fluid pathway 2770 formed in the shaft 2764. The fluid pathway 2770 can fork or branch so that both the source check valve 2778 and the target check valve 2780 are exposed to the pressure differential caused by the fluid being driven into the fluid pathway 2770. The slit of the source check valve 2778 closes more tightly as fluid is pressed against the outside surfaces of its bill members. The slit of the target check valve 2780 opens as the fluid pushed into its chamber and its bill members are pushed away from each other. When the target check valve 2780 opens, fluid can pass through the target check valve 2780, through the fluid pathway 2746, and into the male end 2744 of the target connector portion 2706. Although not shown in FIG. 31B, it will be understood that the fluid can be driven through the target connector portion 2706 and into an IV bag that is attached thereto.

It will be understood that many variations and modifications can be made to the connector 2700. For example, although the illustrated embodiment is shown having an upper housing member 2720 and a lower housing member 2722, it will be understood that the main housing can be made up of a different number of housing members. Some features that are shown as integrated components can be separately formed, and vice versa. For example, in some embodiments, the retaining arms 2730a-b can be separately formed and attachable to the upper housing member 2720. Also, features and elements that are shown as part of the upper housing member 2720 may, in some embodiments, be formed as part of the lower housing member 2722 and vice versa. For example, female end 2742 that is configured to receive the target connector portion 2706 can be formed as part of the lower housing member 2702. Many other variations are also possible.

Figure 32B:
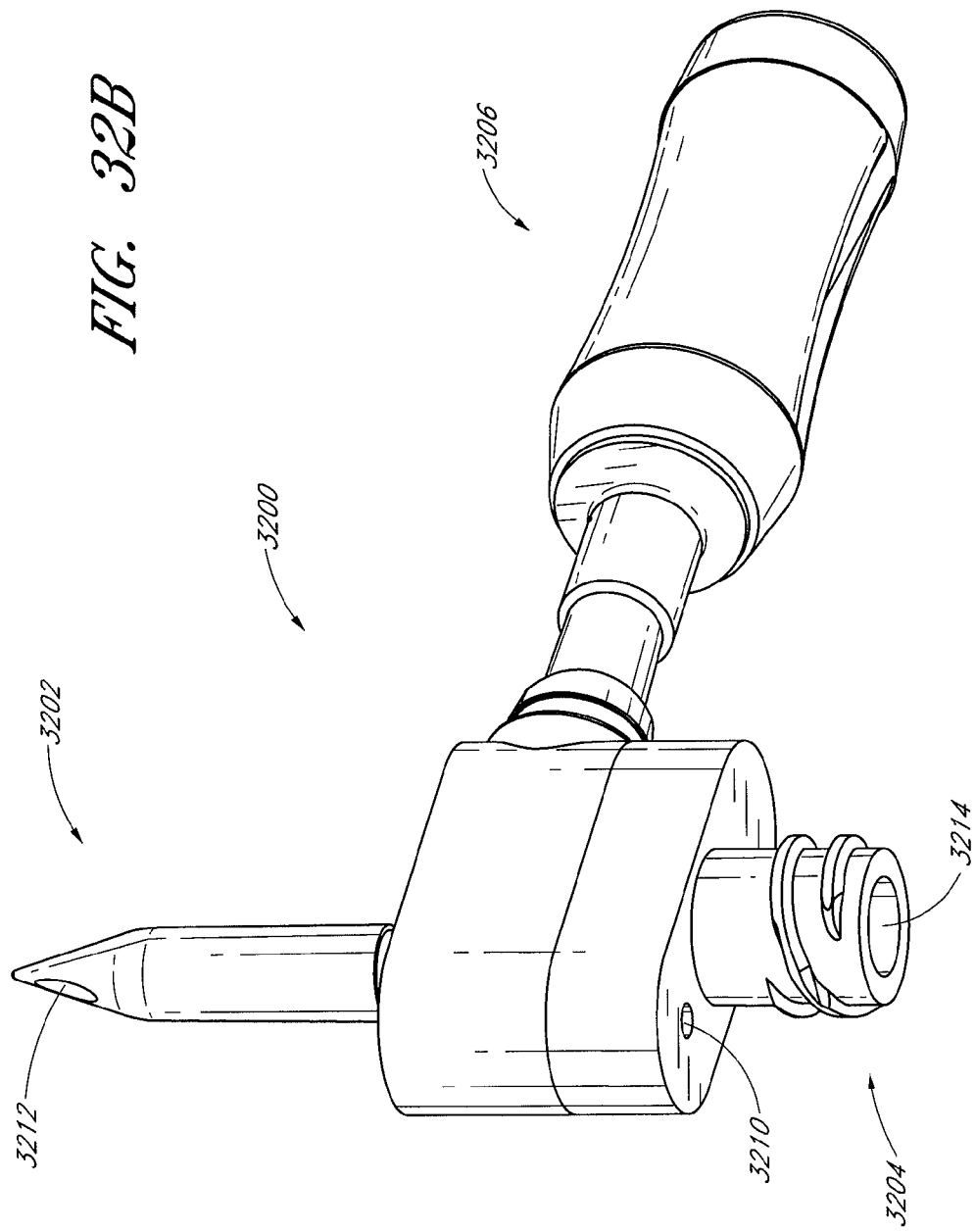
FIG. 32B is another perspective view of the connector of FIG. 32A.

FIG. 32A is a perspective view of an embodiment of a fluid transfer module in the form of a connector 3200, which can be similar in many regards to the connector 320 or any other connector disclosed herein. FIG. 32B is another perspective view of the connector 3200. The connector 3200 can be used to transfer fluid from a source container (e.g., a vial) to an intermediate measuring container (e.g., a syringe) and then to a target container (e.g., an IV bag). The connector 3200 can include a source connector portion 3202 configured to interface with the source container (e.g., a vial), an intermediate connector portion 3204 configured to interface with the intermediate measuring container (e.g., a syringe), and a target connector portion 3206 configured to interface with the target container (e.g., an IV bag assembly).

The connector 3200 can function to transfer fluid from the source container to the target container similarly to the connector 320 or the connector 2700 or any other connector disclosed herein. Fluid can be extracted from a vial (not shown) through the fluid extraction aperture 3208, and air can enter the vial via the air inlet 3210 and air outlet 3212 to replace the volume of extracted fluid. The fluid extracted from the vial can be drawn through the connector 3200 and into the syringe (not shown) via the opening 3214 formed in the intermediate connector portion 3204. A source check valve (hidden from view in FIGS. 32A-B) can be configured to allow fluid to flow from the fluid extraction aperture 3208 to the opening 3214 in the intermediate connector portion 3204 while preventing fluid from flowing in the reverse direction back into the vial. The fluid can be driven from the syringe into the connector 3200 via the opening 3214, and the fluid can be directed into the target connector portion 3206 and into an IV bag assembly (not shown) attached to the target connector portion 3206. A target check valve (hidden from view in FIGS. 32A-B) can be configured to allow the fluid to flow from the opening 3214 in the intermediate connector portion 3204 to the target connector portion 3206 while preventing fluid from flowing in the reverse direction.

Figure 33A:
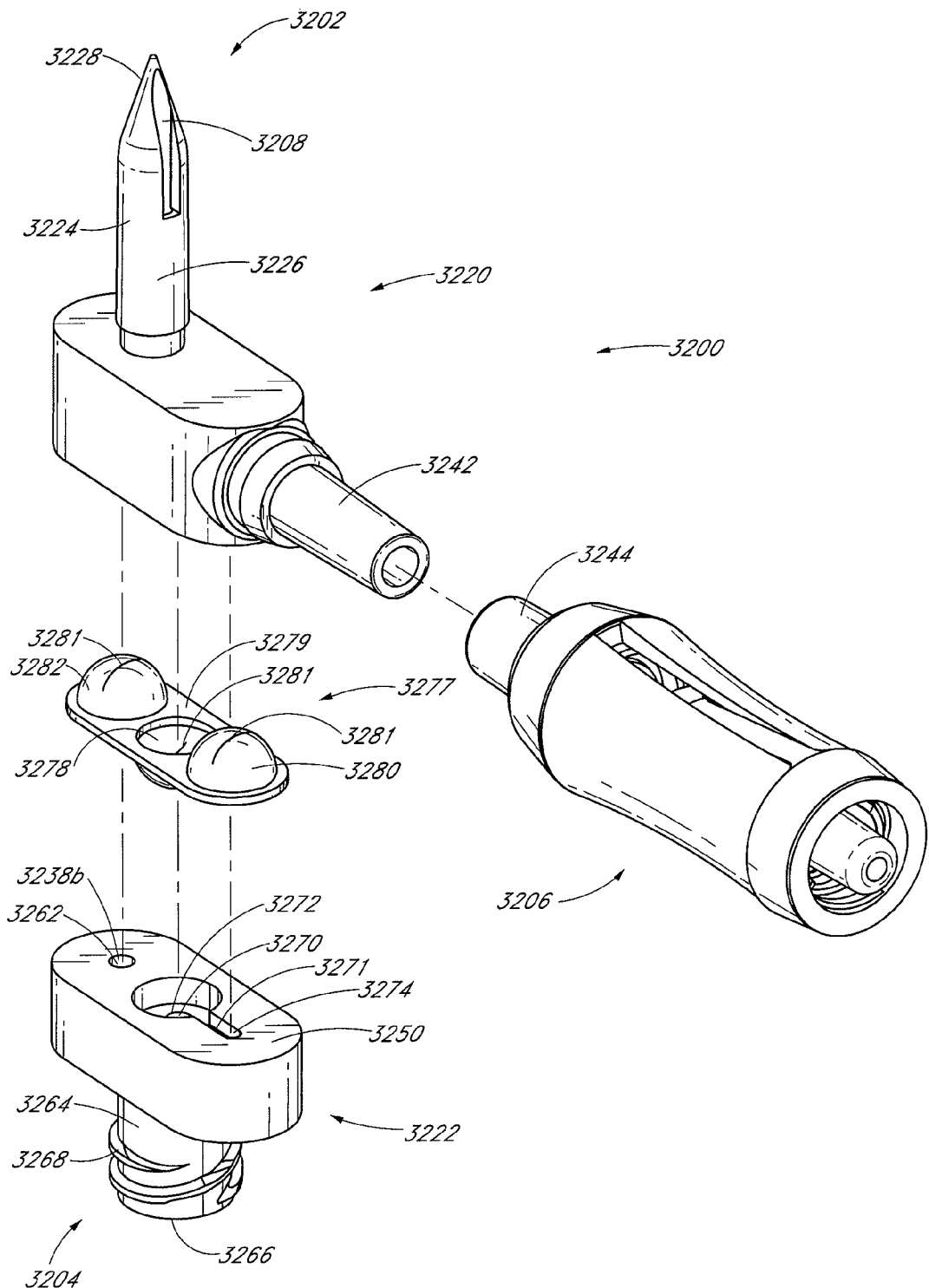
FIG. 33A is an exploded perspective view of the connector of FIG. 32A.
Figure 33B:
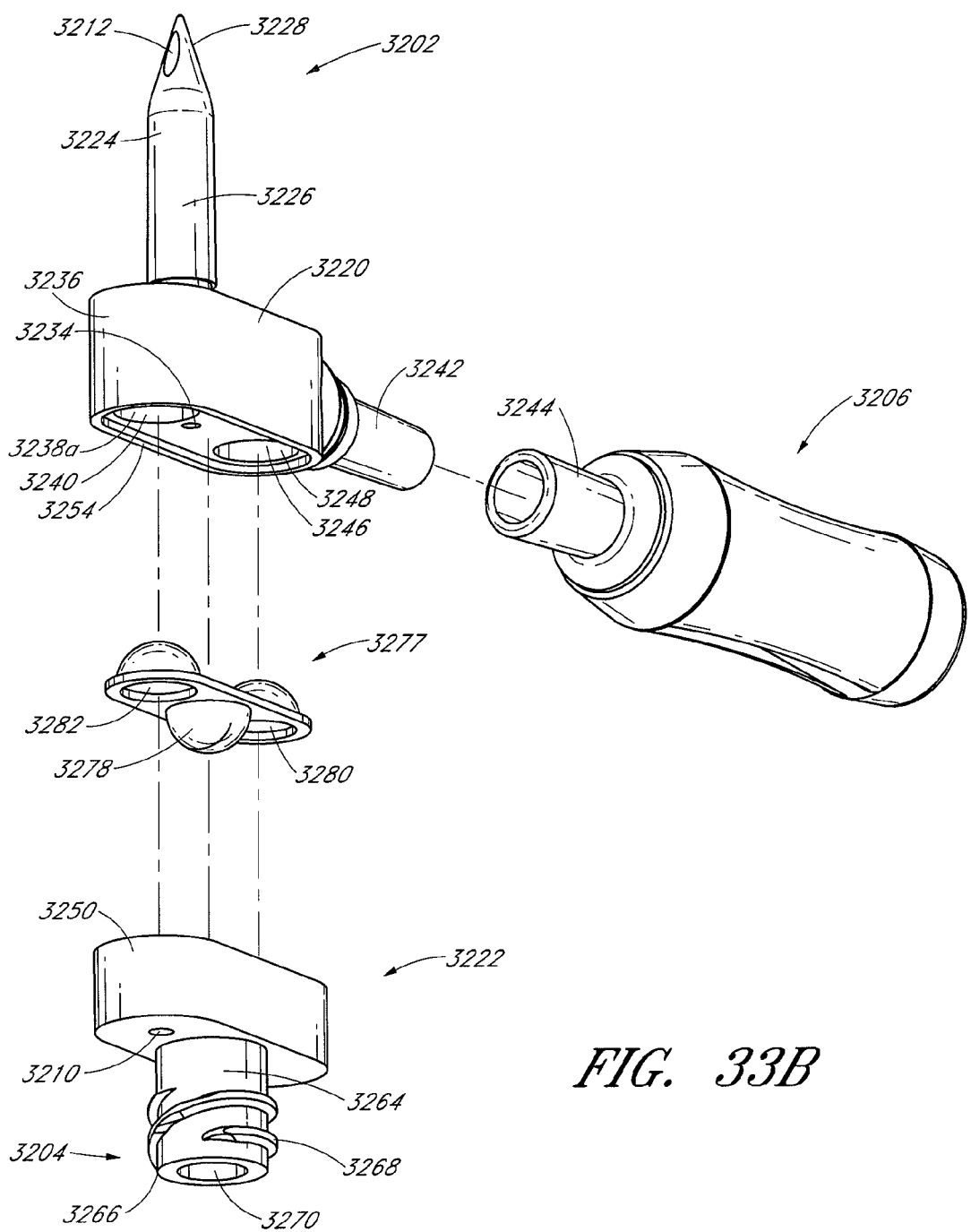
FIG. 33B is another exploded perspective view of the connector of FIG. 32A.

FIG. 33A is an exploded perspective view of the connector 3200. FIG. 33B is another exploded perspective view of the connector 3200. The connector 3200 can include an upper housing member 3220 and a lower housing member 3222. The upper housing member 3220 can include the source connector portion 3202 of the connector 3200, and the lower housing member 3222 can include the intermediate connector portion 3204 of the connector 3200.

The upper housing member 3220 can include a piercing member 3224 made up of an elongate substantially cylindrical shaft 3226 and a pointed tip 3228. The piercing member 3224 can be configured to pierce the septum of a vial (not shown) when the vial is attached thereto. The piercing member 3224 can include a fluid extraction aperture 3208 formed on one side thereof. The fluid extraction aperture can be a slit that extends from near the end of the pointed tip 3228 down onto the shaft 3226, although openings of other shapes can also be used. The piercing member 3224 can also included an air outlet 3212 that allows air to enter the vial as fluid is extracted therefrom to equalize the pressure differential caused by the extraction of fluid. The air outlet 3212 can receive air from an air pathway 3238a that extends through the shaft 3226 and through the base 3236 and to an air inlet opening 3240 formed in the base 3236 of the upper housing 3220.

The upper housing member 3220 can include a male end 3242 configured to receive a female end 3244 of the target connector portion 3206. The target connector portion 3206 can be similar to the other target connector portions described herein (e.g., 338), the disclosure of which applies also to the target connector portion 3206. In the illustrated embodiment, the target connector portion can include the female end 3244 of the interface while the top housing member can include the male end 3242 thereof. Indeed, any suitable interface for securing the target connector portion 3206 to the upper housing member 3202 can be used. The male end 3242 can be secured to the female end 3244 by applying a plastic welding adhesive (such as Dichloromethane) to the outer surface of the male end 3242 and/or to the inner surface of the female end 3244 before insertion. The Dichloromethane can chemically weld the outer surface of the male end 3242 to the inner surface of the female end 3244. Other methods can be used to connect the male end 3242 to the female end 3244, such as sonic welding, threading, adhesives, etc. In some embodiments, the connection between the male end 3242 and the female end 3244 is hermetically sealed, and in some embodiments includes a sealing member (not shown), such as an O-ring, to provide the hermetic seal. A fluid pathway 3246 can extend from the opening in the male end 3242 to a fluid inlet opening 3248 formed in the bottom surface of the base 3236 of the upper housing member 3220.

The lower housing member 3222 can include a base 3250 configured to mate with the base 3236 of the upper housing member 3220. The base 3236 of the upper housing member 3220 can include a lip 3254 on the bottom surface thereof, forming an indentation. The periphery of the top surface of the base 3250 of the lower housing member 3222 can be configured to contact the bottom surface of the lip 3254 when attached. The upper housing member 3220 can be secured to the lower housing member 3222 using an adhesive, or plastic welding material, or sonic welding, or a snap-fit, or any other suitable technique.

The lower housing member 3222 can include an air inlet 3210 and an air outlet opening 3262 with a fluid pathway 3238b extending therebetween. A shaft 3264 can extend downward from the base 3250 of the lower housing member 3222, and the shaft 3264 can have a female end 3266 configured to receive the male end of a syringe (not shown). The female end 3266 can include external threads 3268 configured to mate with internal threads of the syringe for securing the syringe thereto. A fluid pathway 3270 can extend from the opening formed in the female end 3266 up through the shaft 3264. The fluid pathway 3270 can include a channel 3271 that diverts from the main flow path. Thus the fluid pathway 3270 can provide a fluid inlet opening 3272 and a fluid outlet opening 3274.

When the top housing member 3220 is attached to the bottom housing member 3222, the fluid outlet opening 3234 of the upper housing member 3220 can align with the fluid inlet opening 3272 of the lower housing member 3222 such that fluid can flow from the vial, through the fluid pathway 3232, out the fluid outlet opening 3234, in the fluid inlet opening 3272, through the fluid pathway 3270, and into the syringe. Also, the fluid inlet opening 3248 of the upper housing member 3220 can align with the fluid outlet opening 3274 of the lower housing member 3222 such that fluid can flow from the syringe, through the fluid pathway 3270, out the fluid outlet opening 3274, in the fluid inlet opening 3248, through the fluid pathway 3246, and to the target connector portion 3206. Also, the air outlet opening 3262 can align with the air inlet opening 3240 so that air is allowed to enter through the air inlet 3210, flow through the air pathway 3238*b*, out the air outlet opening 3262, in the air inlet opening 3240, through the air pathway 3238*a*, through the air outlet 3212 and into the vial.

A check valve assembly 3277 can be disposed between the top housing member 3220 and the lower housing member 3222. The check valve assembly 3277 can include a base which can be shaped to fit into the indentation formed by the lip 3254. The check valve assembly 3277 can include a source check valve 3278 configured to allow fluid to flow from the fluid outlet opening 3234 to the fluid inlet opening 3272 while preventing fluid from flowing in the reverse direction. The source check valve 3278 can be a dome valve as shown in the illustrated embodiment, or any other form of check valve capable of allowing fluid to flow in one direction while preventing fluid flow in the opposite direction.

The check valve assembly 3277 can include a target check valve 3280 configured to allow fluid to flow from the fluid outlet opening 3274 to the fluid inlet opening 3248 while preventing fluid from flowing in the reverse direction. The target check valve 3280 can be a domed check valve as shown in the illustrated embodiment, or any other form of check valve capable of allowing fluid to flow in one direction while preventing fluid flow in the opposite direction.

The check valve assembly 3277 can include an air check valve 3282 configured such that air is permitted to flow from the air outlet 3262 to the air inlet opening 3240, but air and fluid are not allowed to flow out of the air inlet opening 3240. The air check valve 3282 can be a domed check valve as shown in the illustrated embodiment, or any other form of check valve capable of allowing fluid to flow in one direction while preventing fluid flow in the opposite direction. In some embodiments, a filter (not shown) can be used in conjunction with or in place of the air check valve 3282. The filter can be placed in or near the air inlet, or within the air pathways 3238*a-b*. The filter can be permeable to air so that air is permitted to enter the air passageway 3238*a-b*. In some embodiments, the filter can be impermeable to the fluid to prevent fluid from exiting the vial via the air pathway 3238*a-b*. In some embodiments, a bag (not shown) at least partially disposed within the air passageway 3238*a* can be used to prevent the air that enters the vial from mixing with the fluid. For example, the piercing member 3224 can include a bag and can be similar to the piercing member 370 discussed above in connection with FIGS. 5A-D.

Although the domed check valves 3278, 3280, 3282 are shown as being interconnected by the base 3279, it will be understood that the domed check valves 3278, 3280, 3282 can be separately formed. A domed check valve can include a dome having a convex side and a concave side. One or more slits 3281 can be formed in the dome. Although a single slit is shown in the illustrated embodiment, it will be understood that two crossing slits, or various other slit configurations can be used. In the domed check valve's relaxed state, the slit can be closed.

When the slit 3281 is closed and fluid is directed to the check valve 3278, 3280, 3282 in the direction that the check valve 3278, 3280, 3282 is configured to block, the resulting pressure that pushes on the convex side forces the slit 3281 closed. Thus, as greater pressure is applied, the slit 3281 closes more strongly to prevent fluid flow in the undesired direction. Likewise, when fluid is withdrawn from the concave side, the slit 3281 is sealed more tightly. When fluid is pushed toward the concave side, the resulting pressure causes the dome to flex outwardly such that the slit 3281 opens. Likewise, when fluid is drawn away from the convex side, the resulting pressure can pull the dome members such that they flex outwardly and the slit 3281 opens. The check valve assembly 3277 can be formed from silicone or any other suitable resilient material.

With further reference to FIGS. 33A-B, the fluid inlet opening 3272 can be wide enough to receive the dome portion of the source check valve 3278, and the fluid inlet opening 3248 can be wide enough to receive the dome portion of the target check valve 3280. Thus, in some embodiments, the fluid inlet opening 3272 can be wider than the channel 3271 that functions as the fluid outlet opening 3274, and the fluid inlet opening 3248 can be wider than the fluid outlet opening 3234. The indentation formed by the lip 3254 can have a height that is less than the height of the base 3279 of the check valve assembly 3277 so that the base 3279 can be compressed between the top housing member 3220 and the lower housing member 3222 when they are attached. Thus, the compressed base 3279 of the check valve assembly 3277 can function to seal off the interfaces between the upper housing member 3220 and the lower housing member 3222 so that fluid can flow therethrough without escaping. This can be particularly advantageous when a chemotherapy drug or other hazardous fluid is transported through the connector 3200. In some embodiments, all fluid flow paths through the connector 3200 are sealed (e.g., hermetically sealed) such that no fluid (e.g., chemotherapy drugs or other hazardous materials) can escape during operation.

Figure 34A:
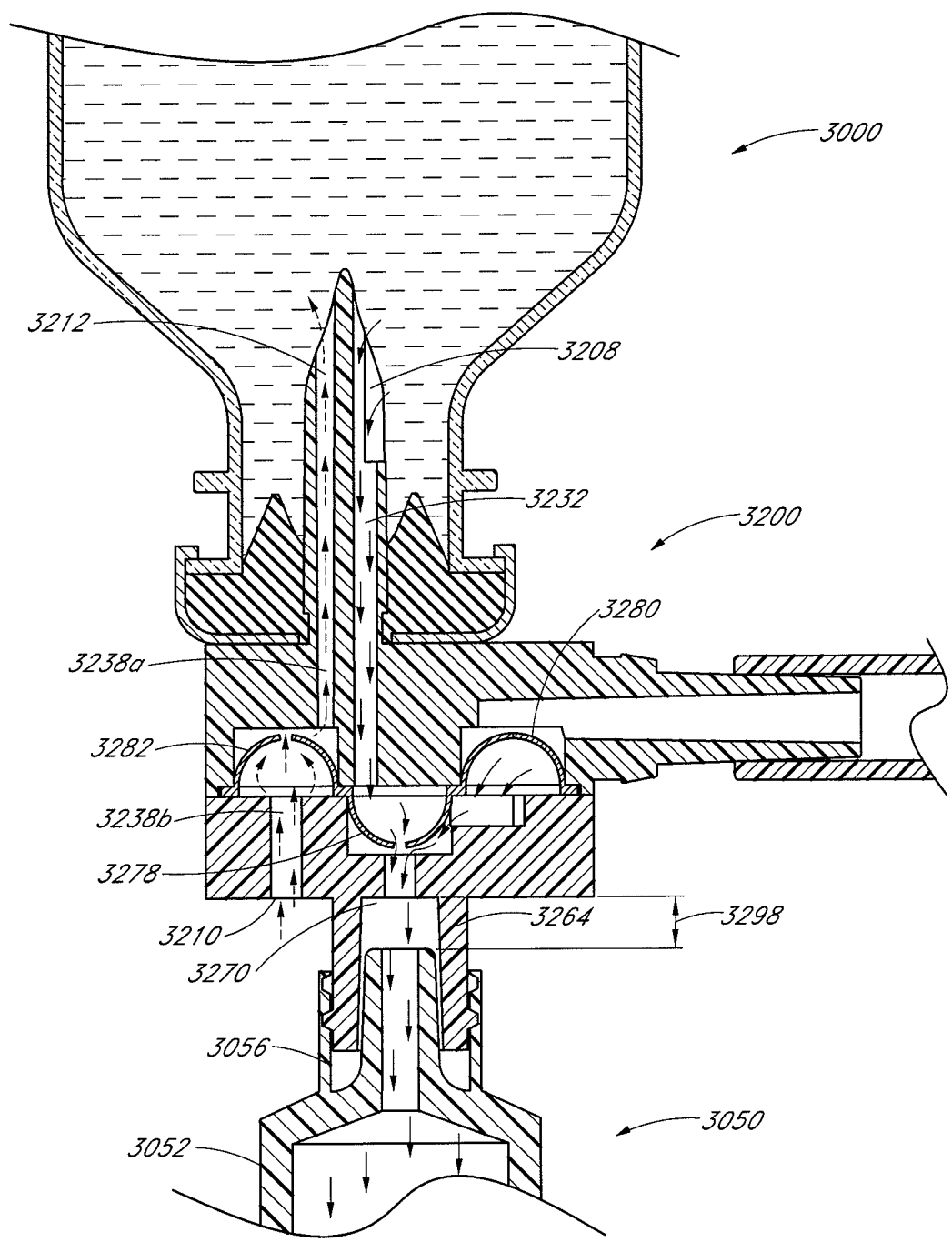
FIG. 34A is a cross sectional view of the connector of FIG. 32A, a vial, and a syringe as fluid is drawn from the vial, through the connector, and into the syringe.

FIG. 34A shows a cross sectional view of the connector 3200, the vial 3000, and the syringe 3050 as fluid is drawn through the connector 3200 from the vial 3000 to the syringe 3050. As the plunger (not shown) of the syringe 3050 is withdrawn, fluid can be drawn into the body 3052 of the syringe 3050 from the fluid pathway 3270 formed in the shaft 3264. The fluid can be drawn in from the pathway 3270 including the channel 3271 so that both the source check valve 3278 and the target check valve 3280 are exposed to the pressure differential caused by the fluid being withdrawn from the fluid pathway 3270. The slit of the target check valve 3280 closes more tightly as fluid is drawn away from it and towards the syringe 3050. The slit of the source check valve 3278 opens as the fluid is drawn toward the syringe. When the source check valve 3278 opens, fluid can be drawn from the source container (e.g., vial 3000) toward the syringe 3050 to compensate for the pressure differential. Fluid can enter the fluid pathway 3232 via the fluid extraction aperture 3208, and flow through the source check valve 3278, into the fluid pathway 3270, and down into the syringe 3050. As fluid is extracted from the vial 3000, air can be drawn into the vial 3000 to compensate for the loss of fluid volume. The air can pass through the air inlet 3210, through the air pathway 3238*b*, through the air check valve 3282, through the air pathway 3238*a*, and through the air outlet 3212 into the body 3002 of the vial 3000.

Figure 34B:
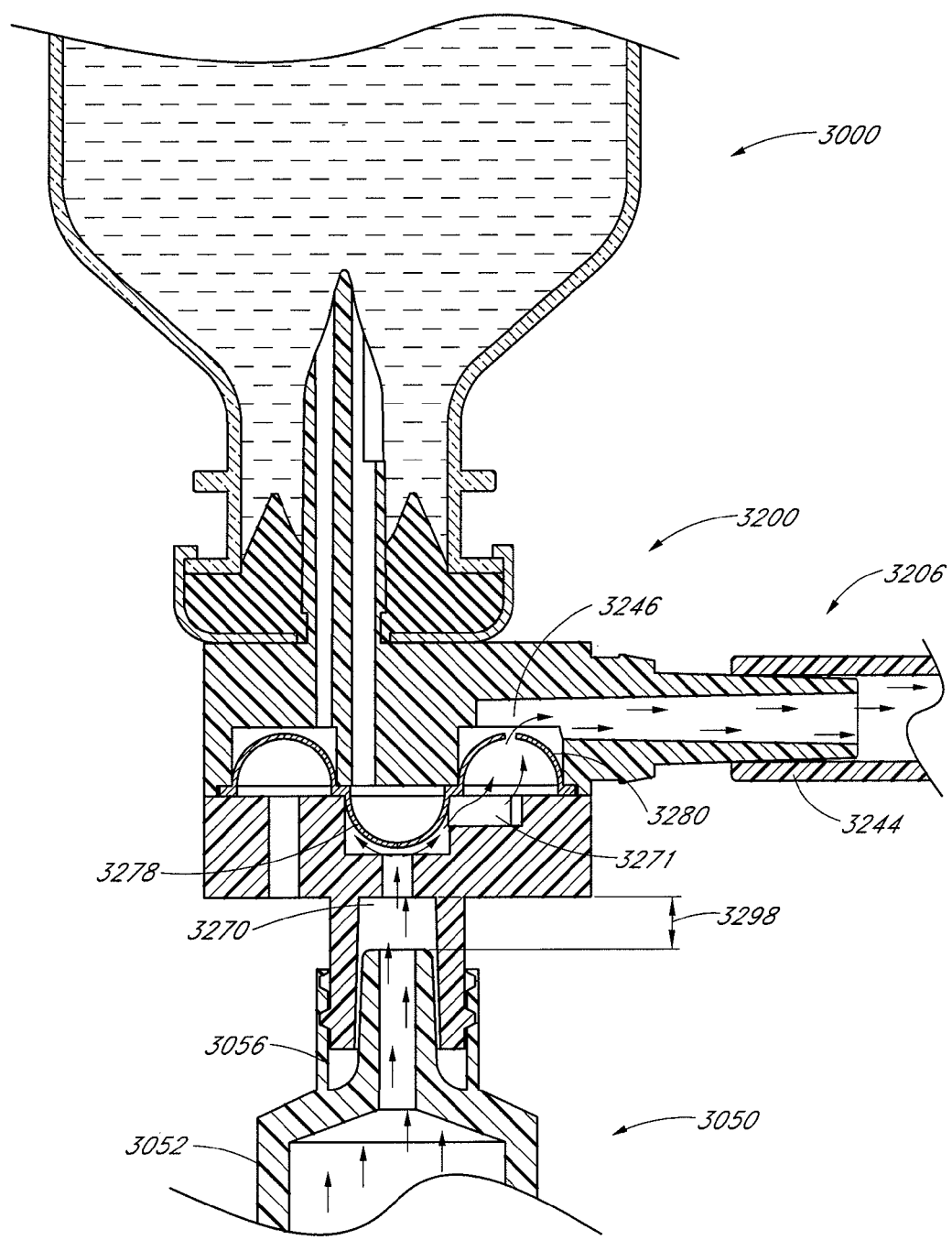
FIG. 34B is a cross sectional view of the connector of FIG. 32A, a vial, and a syringe as fluid is driven from the syringe, through the connector, and into an IV bag.

FIG. 34B shows a cross sectional view of the connector 3200, the vial 3000, and the syringe 3050 as fluid is driven through the connector 3200 from the syringe 3050 to the target connector portion 3206 which leads to the IV bad assembly (not shown). As the plunger (not shown) of the syringe 3050 is advanced, fluid can be driven from the body 3052 of the syringe 3050 into the fluid pathway 3270 formed in the shaft 3264. The fluid can enter the channel 3271 so that both the source check valve 3278 and the target check valve 3280 are exposed to the pressure differential caused by the fluid being driven into the fluid pathway 3270. The slit of the source check valve 3278 closes more tightly as fluid is pressed against the convex surface of its dome. The slit of the target check valve 3280 opens as the fluid pushed against the concave surface of its dome. When the target check valve 3280 opens, fluid can pass through the target check valve 3280, through the fluid pathway 3246, and into the female end 3244 of the target connector portion 3206. Although not shown in FIG. 34B, it will be understood that the fluid can be driven through the target connector portion 3206 and into an IV bag that is attached thereto.

It will be understood that the connector 3200 can be used in connection with an automated fluid transfer system (e.g., system 600). When attached to a fluid transfer station, the connector 3200 can align with sensors for optically detecting the presence of air in the fluid pathway between the vial 3000 and the syringe 3050 as discussed above in connection with FIGS. 17-19D. With further reference now to FIGS. 34A-B, in some embodiments the connector 3200 can be aligned such that the light (e.g., light 676 or 1924) passes through the fluid pathway 3270 formed in the shaft 3264 within the region 3298 above the location where the upper end of the syringe shroud 3056 ends when the syringe 3050 is attached. In some embodiments, all or a portion of the lower housing member 3222 can be made from a material that is transparent to the light transmitted through the region 3298. In some embodiments, the entire shaft 3264 can be transparent. In some embodiments, the shaft 3264 includes a transparent window portion that covers all or a portion of the region 3298, with the remainder of the lower housing member 3222 being made from a material that is opaque to the light.

It will be understood that many variations and modifications can be made to the connector 3200. For example, although the illustrated embodiment is shown having an upper housing member 3220 and a lower housing member 3222, it will be understood that the main housing can be made up of a different number of housing members. Also, features and elements that are shown as part of the upper housing member 3220 may, in some embodiments, be formed as part of the lower housing member 3222 and vice versa.

Figure 35A:
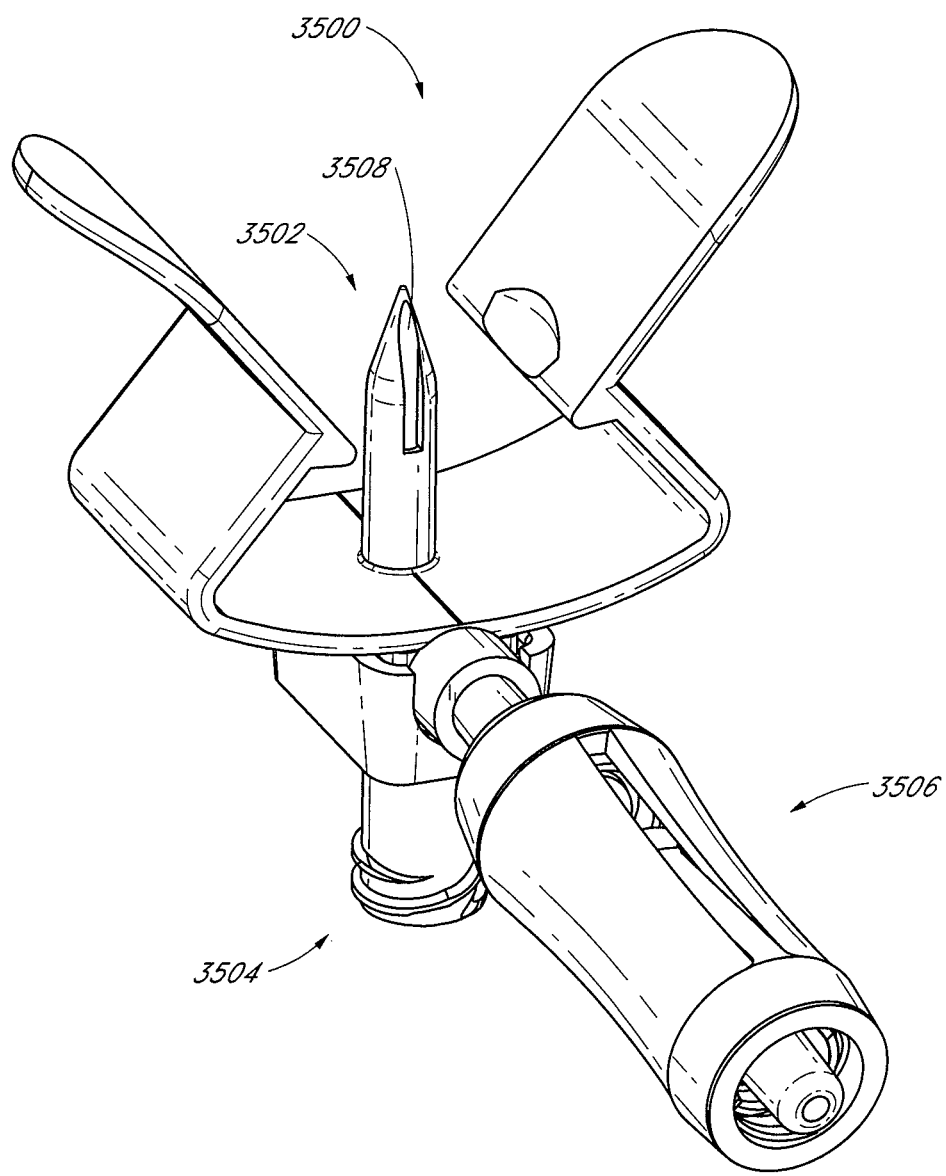
FIG. 35A is a perspective view of another embodiment of a connector for transferring fluid.
Figure 35B:
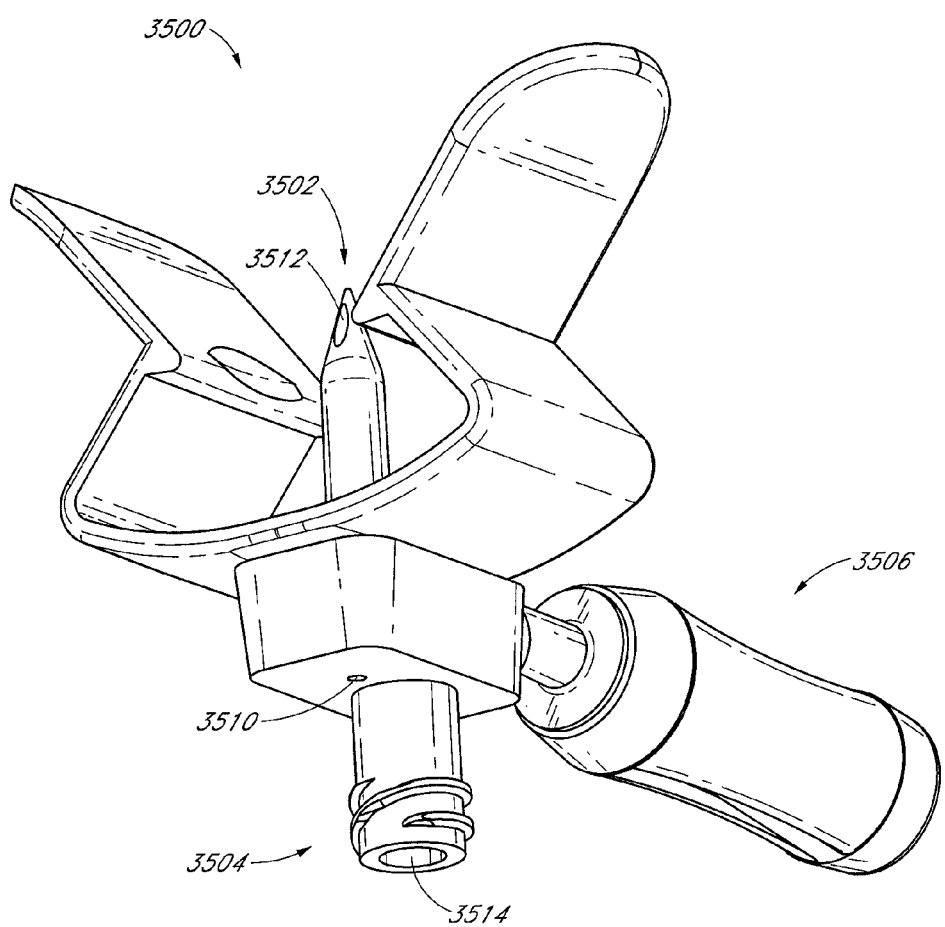
FIG. 35B is another perspective view of the connector of FIG. 35A.

FIG. 35A is a perspective view of an embodiment of a connector 3500, which can be similar in many regards to the connector 350 or any other connector disclosed herein. FIG. 35B is another perspective view of the connector 3500. The connector 3500 can be used to transfer fluid from a source container (e.g., a vial) to an intermediate measuring container (e.g., a syringe) and then to a target container (e.g., an IV bag). The connector 3500 can include a source connector portion 3502 configured to interface with the source container (e.g., a vial), an intermediate connector portion 3504 configured to interface with the intermediate measuring container (e.g., a syringe), and a target connector portion 3506 configured to interface with the target container (e.g., an IV bag assembly).

The connector 3500 can function to transfer fluid from the source container to the target container similarly to the connector 350 or the connector 2700 or any other connector disclosed herein. Fluid can be extracted from a vial (not shown) through the fluid extraction aperture 3508, and air can enter the vial via the air inlet 3510 and air outlet 3512 to replace the volume of extracted fluid. The fluid extracted from the vial can be drawn through the connector 3500 and into the syringe (not shown) via the opening 3514 formed in the intermediate connector portion 3504. A source check valve (hidden from view in FIGS. 35A-B) can be configured to allow fluid to flow from the fluid extraction aperture 3508 to the opening 3514 in the intermediate connector portion 3504 while preventing fluid from flowing in the reverse direction back into the vial. The fluid can be driven from the syringe into the connector 3500 via the opening 3514, and the fluid can be directed into the target connector portion 3506 and into an IV bag assembly (not shown) attached to the target connector portion 3506. A target check valve (hidden from view in FIGS. 35A-B) can be configured to allow the fluid to flow from the opening 3514 in the intermediate connector portion 3504 to the target connector portion 3506 while preventing fluid from flowing in the reverse direction.

Figure 36A:
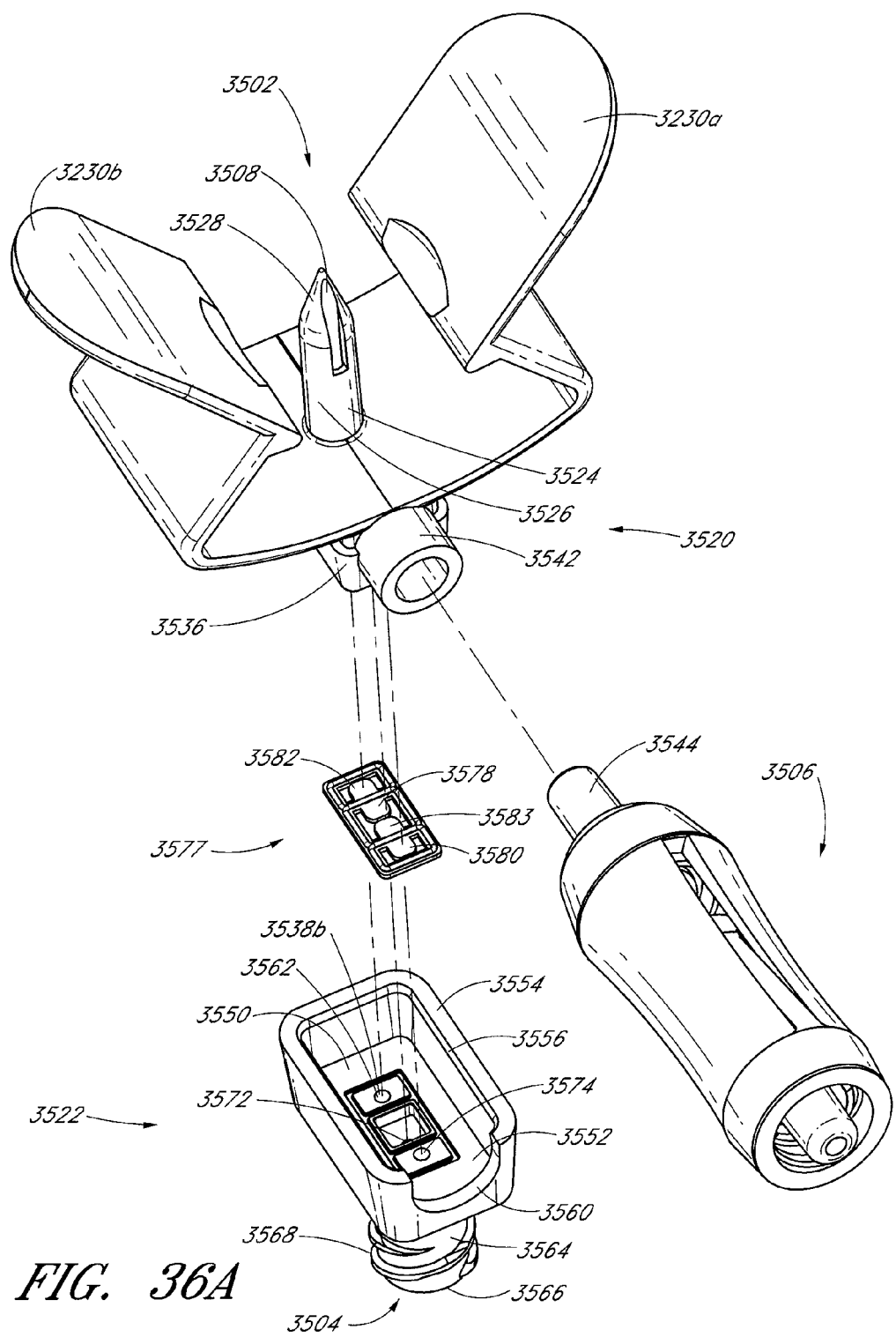
FIG. 36A is an exploded perspective view of the connector of FIG. 35A.
Figure 36B:
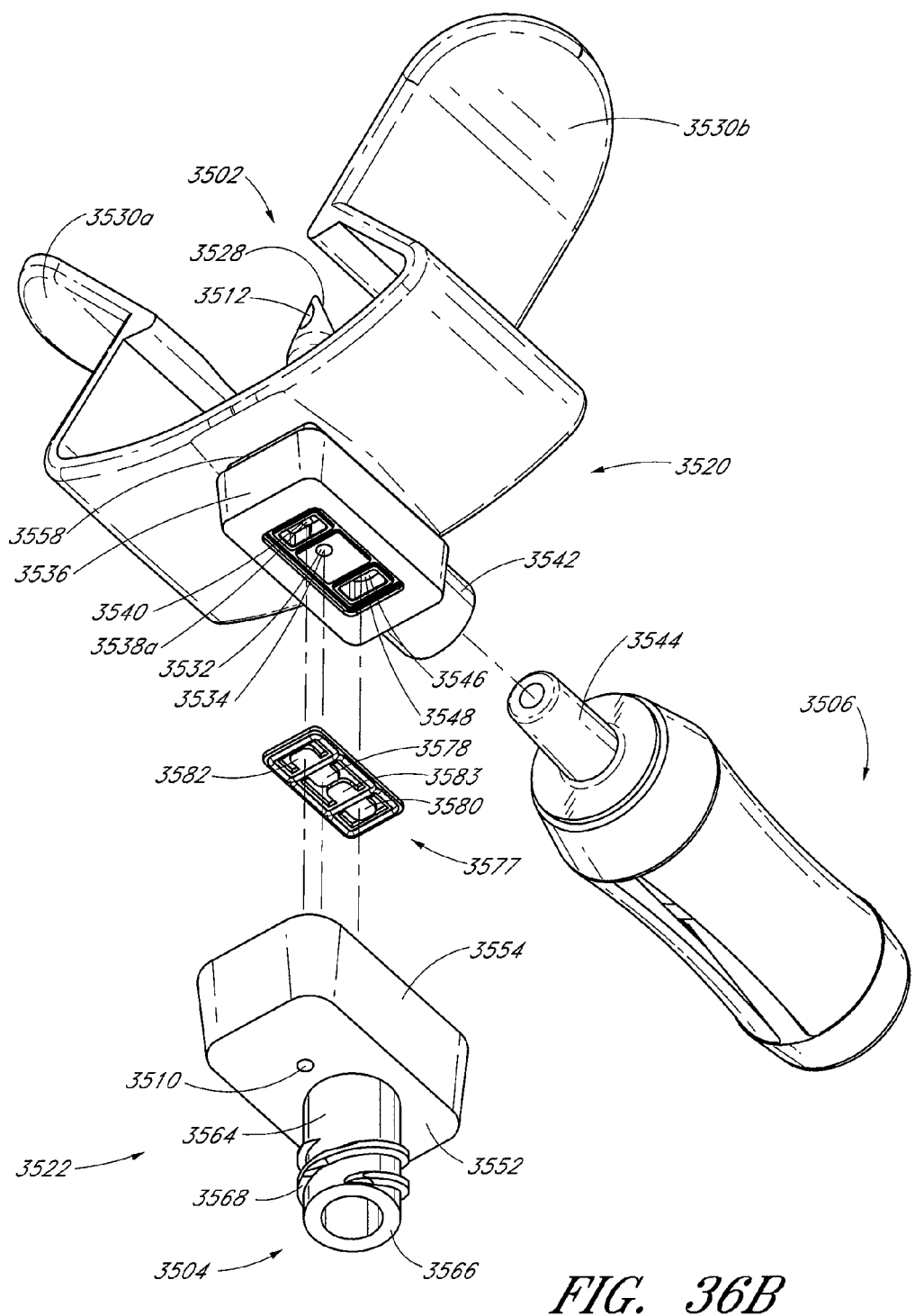
FIG. 36B is another exploded perspective view of the connector of FIG. 35A.

FIG. 36A is an exploded perspective view of the connector 3500. FIG. 36B is another exploded perspective view of the connector 3500. The connector 3500 can include an upper housing member 3520 and a lower housing member 3522. The upper housing member 3520 can include the source connector portion 3502 of the connector 3500, and the lower housing member 3522 can include the intermediate connector portion 3504 of the connector 3500.

The upper housing member 3520 can include a piercing member 3524 made up of an elongate substantially cylindrical shaft 3526 and a pointed tip 3528. The piercing member 3524 can be configured to pierce the septum of a vial (not shown) when the vial is attached thereto. The upper housing member 3220 can include retaining arms 3230a-b configured to secure the vial to the connector 2700 in a manner similar to that described in connection with the retaining arms 2730a-b. The piercing member 3524 can include a fluid extraction aperture 3508 formed on one side thereof. The fluid extraction aperture can be a slit that extends from near the end of the pointed tip 3528 down onto the shaft 3526, although openings of other shapes can also be used. The piercing member 3524 can also included an air outlet 3512 that allows air to enter the vial as fluid is extracted therefrom to equalize the pressure differential caused by the extraction of fluid. The air outlet 3512 can receive air from an air pathway 3538a that extends through the shaft 3526 and through the base 3536 and to an air inlet opening 3540 formed in the base 3536 of the upper housing 3520.

The upper housing member 3520 can include a female end 3542 configured to receive a male end 3544 of the target connector portion 3506. The target connector portion 3506 can be similar to the other target connector portions described herein (e.g., 338), the disclosure of which applies also to the target connector portion 3506. Any suitable interface for securing the target connector portion 3506 to the upper housing member 3502 can be used. The female end 3542 can be secured to the male end 3544 by applying a plastic welding adhesive (such as Dichloromethane) to the outer surface of the male end 3544 and/or to the inner surface of the female end 3542 before insertion. The Dichloromethane can chemically weld the outer surface of the male end 3544 to the inner surface of the female end 3542. Other methods can be used to connect the male end 3544 to the female end 3542, such as sonic welding, threading, adhesives, etc. In some embodiments, the connection between the male end 3544 and the female end 3542 is hermetically sealed, and in some embodiments includes a sealing member (not shown), such as an O-ring, to provide the hermetic seal. A fluid pathway 3546 can extend from the opening in the female end 3542 to a fluid inlet opening 3548 formed in the bottom surface of the base 3536 of the upper housing member 3520.

The lower housing member 3522 can include a chamber 3550 enclosed by a base wall 3252 and by side walls 3254 and can have an open top. The chamber 3250 can be configured to receive the base 3536 of the upper housing member 2720 when the top housing member 3520 is secured to the bottom housing member 3522. The side walls 3554 can include a lip 3556 near the top thereof which can be configured to mate with corresponding slots 3558 formed in the upper portion of the base 3536 for provide a snap-fit connection between the top housing member 3520 and the bottom housing member 3522. It will be understood that the top housing member 3520 can be secured to the bottom housing member 3522 using various other techniques including an adhesive, sonic welding, a friction-fit, or any other suitable manner. The side walls 3554 of the lower housing member 3522 can include a front cutout 3560 configured to receive a portion of the female end 3542 therein.

The lower housing member 3522 can include an air inlet 3510 and an air outlet opening 3562 with a fluid pathway 3538b extending therebetween. A shaft 3564 can extend downward from the base wall 3552 of the lower housing member 3522, and the shaft 3564 can have a female end 3566 configured to receive the male end of a syringe (not shown). The female end 3566 can include external threads 3568 configured to mate with internal threads of the syringe for securing the syringe thereto. A fluid pathway 3570 can extend from the opening formed in the female end 3566 up through the shaft 3564. The fluid pathway 3570 can include a fork or branch that divides the fluid pathway 3570 so that a fluid inlet opening 3572 and a fluid outlet opening 3574 are both in fluid communication with the fluid pathway 3570.

When the top housing member 3520 is attached to the bottom housing member 3522, the fluid outlet opening 3534 of the upper housing member 3520 can align with the fluid inlet opening 3572 of the lower housing member 3522 such that fluid can flow from the vial, through the fluid pathway 3532, out the fluid outlet opening 3534, in the fluid inlet opening 3572, through the fluid pathway 3570, and into the syringe. Also, the fluid inlet opening 3548 of the upper housing member 3520 can align with the fluid outlet opening 3574 of the lower housing member 3522 such that fluid can flow from the syringe, through the fluid pathway 3570, out the fluid outlet opening 3574, in the fluid inlet opening 3548, through the fluid pathway 3546, and to the target connector portion 3506. Also, the air outlet opening 3562 can align with the air inlet opening 3540 so that air is allowed to enter through the air inlet 3510, flow through the air pathway 3538b, out the air outlet opening 3562, in the air inlet opening 3540, through the air pathway 3538a, through the air outlet 3512 and into the vial.

A check valve assembly 3577 can be disposed between the top housing member 3520 and the lower housing member 3522. The check valve assembly 3577 can include a source check valve 3578 configured to allow fluid to flow from the fluid outlet opening 3534 to the fluid inlet opening 3572 while preventing fluid from flowing in the reverse direction. The source check valve 3578 can be a flap check valve as shown in the illustrated embodiment, or any other form of check valve capable of allowing fluid to flow in one direction while preventing fluid flow in the opposite direction.

The check valve assembly 3577 can include a target check valve 3580 configured to allow fluid to flow from the fluid outlet opening 3574 to the fluid inlet opening 3548 while preventing fluid from flowing in the reverse direction. The target check valve 3580 can be a flap check valve as shown in the illustrated embodiment, or any other form of check valve capable of allowing fluid to flow in one direction while preventing fluid flow in the opposite direction.

The check valve assembly 3577 can include an air check valve 3582 configured such that air is permitted to flow from the air outlet 3562 to the air inlet opening 3540, but air and fluid are not allowed to flow out of the air inlet opening 3540. The air check valve 3582 can be a flap check valve as shown in the illustrated embodiment, or any other form of check valve capable of allowing fluid to flow in one direction while preventing fluid flow in the opposite direction. In some embodiments, a filter (not shown) can be used in conjunction with or in place of the air check valve 3582. The filter can be placed in or near the air inlet 3510, or within the air pathway 3538a-b. The filter can be permeable to air so that air is permitted to enter the air pathway 3538a-b. In some embodiments, the filter can be impermeable to the fluid to prevent fluid from exiting the vial via the air pathway 3538a-b. In some embodiments, a bag (not shown) at least partially disposed within the air pathway 3538a can be used to prevent the air that enters the vial from mixing with the fluid. For example, the piercing member 3524 can include a bag and can be similar to the piercing member 370 discussed above in connection with FIGS. 5A-D.

Figure 37:
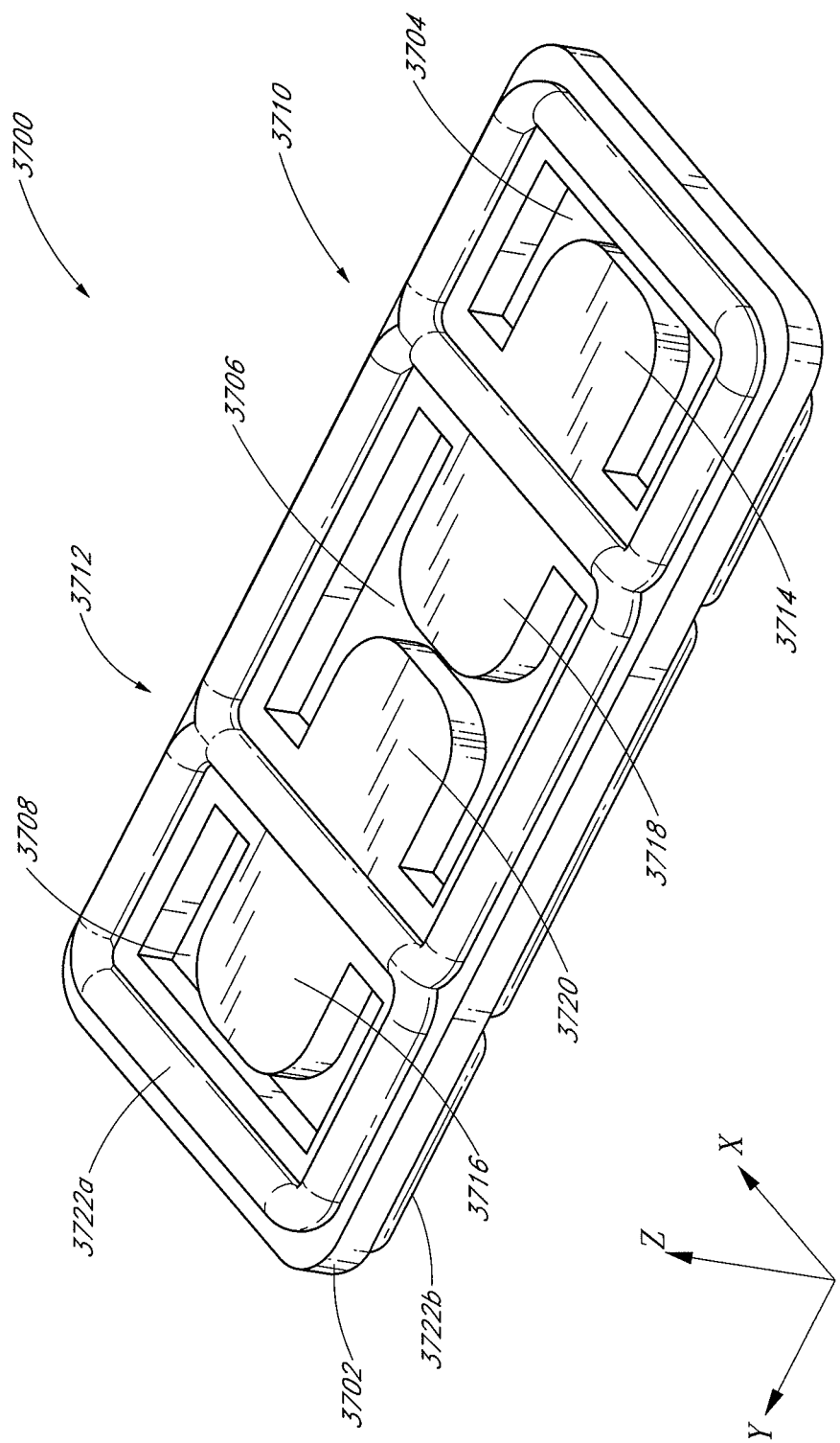
FIG. 37 is a perspective view of a check valve assembly that can be used with the connector of FIG. 35A.

FIG. 37 is a perspective view of a check valve assembly 3700 which can be used as the check valve assembly 3577 discussed herein. The check valve assembly 3577 can include a base 3702 with a right opening 3704, a central opening 3706, and a left opening 3708 formed therethrough. A series of raised ridges 3722a can outline the openings 3704, 3706, 3708 on the top side of the base 3702, and a series of raised ridges 3722b can outline the openings 3704, 3706, 3708 on the bottom side of the base 3702. A right divider 3710 can divide the right opening 3704 from the central opening 3706. A left divider 3712 can divide the left opening 3708 from the central opening 3706.

A right flap 3714 can extend from the right divider 3710 into the right opening 3704. The right flap 3714 can be sized so as to cover a substantial portion of the right opening 3704 but leaving a narrow open area surrounding the right flap 3714. A left flap 3716 can extend from the left divider 3712 into the left opening 3708. The left flap 3716 can be sized so as to cover a substantial portion of the left opening 3708 but leaving a narrow open area surrounding the left flap 3716. A first central flap 3718 can extend from the right divider 3710 into the central opening 3706. A second central flap 3720 can extend from the left divider 3712 into the central opening 3706. The first and second central flaps 3718, 3720 can be configured to fill a substantial portion of the central opening 3706 but leaving a narrow open area surrounding the first and second central flaps 3718, 3720.

The flaps 3714, 3716, 3718, 3720 can resiliently deform to open a fluid pathway. The flaps 3714, 3716, 3718, 3720 are shown in FIG. 37 in relaxed positions. However, if a force (e.g., fluid pressure) is applied to one side of a flap 3714, 3716, 3718, 3720, the flap 3714, 3716, 3718, 3720 can be displaced in the direction of the applied force. In some embodiments, the flaps 3714, 3716, 3718, 3720 can pivot or hinge on the dividers 3710, 3712 and/or the flaps 3714, 3716, 3718, 3720 themselves can bend to assume a curved shape. The manner in which the flaps 3714, 3716, 3718, 3720 operation as check valves will be described in greater detail below.

In some embodiments, the check valve assembly 3700 can by symmetrical across the x-y plane, the x-z plane, and/or the y-z plane. This symmetry can facilitate assembly of the connector because the check valve assembly 3700 cannot be inserted backwards or upside-down.

Returning now to FIGS. 36A-B, the check valve assembly 3577 can include a source check valve 3578 (e.g., second central flap 3720), and a target check valve 3580 (e.g., right flap 3714), and an air check valve 3582 (e.g., left flap 3716). In some embodiments, the check valve assembly 3577 can include an extra flap 3583 (e.g., first central flap 3718) that does not function as a check valve. The extra flap 3581 can be included to maintain the symmetry of the check valve assembly 3577 to simplify assembly of the connector 2500.

With further reference to FIGS. 33A-B, the fluid inlet opening 3572 can be wide enough to allow the source check valve 3578 to swing open, but the fluid outlet opening 3534 can fit flush against the flap of the source check valve 3578, thereby allowing the flap of the source check valve 3578 to open only in the direction toward the fluid pathway 2770. The fluid inlet opening 3548 can be wide enough to allow the target check 3580 valve to swing open, but the fluid outlet opening 3574 can fit flush against the flap of the target check valve 3580, thereby allowing the flap of the target check valve 3580 to open only in the direction toward the fluid pathway 3546. The air inlet opening 3540 can be wide enough to allow the air check valve 3582 to swing open, but the air outlet opening 3562 can fit flush against the flap of the air check valve 3582, thereby allowing the flap of the air check valve 3582 to open only in the direction toward the fluid pathway 3538*a*. The functionality of the check valves 3578, 3580, and 3582 can also be seen in FIGS. 38A-B which will be discussed below.

The height of the base 3702 and/or ridges 3722*a-b* of the check valve assembly 2577 can be configured such that the base 3702 and/or ridges 3722*a-b* are compressed between the top housing member 3520 and the lower housing member 3522 when they are attached. Thus, the compressed base 3702 and/or ridges 3722*a-b* of the check valve assembly 2577 can function to seal off the interfaces between the upper housing member 3520 and the lower housing member 3522 so that fluid can flow therethrough without escaping. This can be particularly advantageous when a chemotherapy drug or other hazardous fluid is transported through the connector 3500. In some embodiments, all fluid flow paths through the connector 3500 are sealed (e.g., hermetically sealed) such that no fluid (e.g., chemotherapy drugs or other hazardous materials) can escape during operation.

Figure 38A:
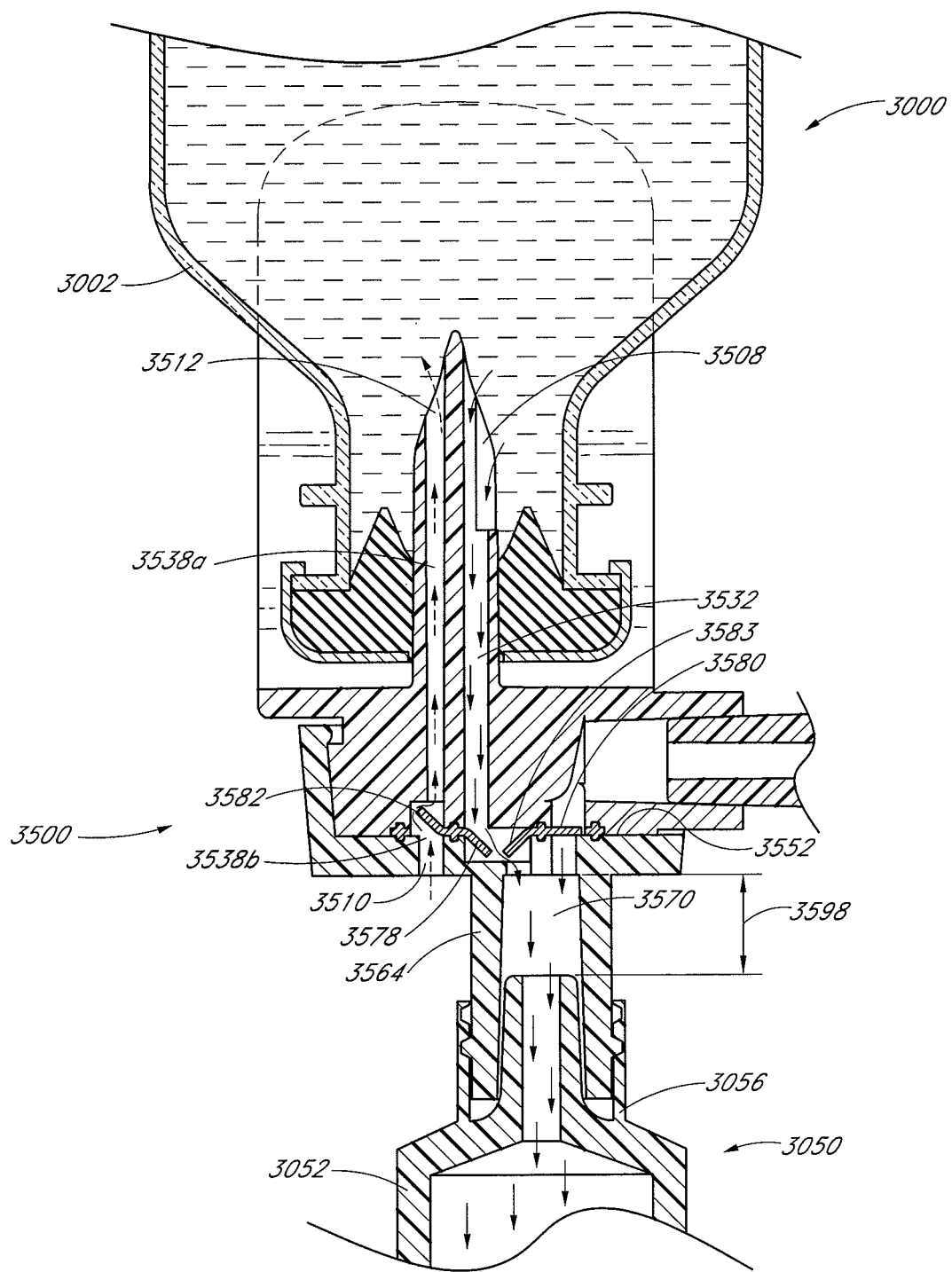
FIG. 38A is a cross sectional view of the connector of FIG. 35A, a vial, and a syringe as fluid is drawn from the vial, through the connector, and into the syringe.

FIG. 38A shows a cross sectional view of the connector 3500, the vial 3000, and the syringe 3050 as fluid is drawn through the connector 3500 from the vial 3000 to the syringe 3050. As the plunger (not shown) of the syringe 3050 is withdrawn, fluid can be drawn into the body 3052 of the syringe 3050 from the fluid pathway 3570 formed in the shaft 3564. Because the fluid pathway 3570 forks or branches, both the source check valve 3578 and the target check valve 3580 are exposed to the pressure differential caused by the fluid being withdrawn from the fluid pathway 3570. The pressure differential caused by the fluid being withdrawn from the fluid pathway 3570 pulls the flap of the target check valve 3580 more firmly closed against the base wall 3552 because the fluid outlet opening 3574 is not wide enough to accommodate the flap. The pressure differential can pull the flap of the source check valve 3578 open. When the source check valve 3578 opens, fluid can be drawn from the source container (e.g., vial 3000) toward the syringe 3050 to compensate for the pressure differential. Fluid can enter the fluid pathway 3532 via the fluid extraction aperture 3508, and flow past the source check valve 3578, into the fluid pathway 3570, and down into the syringe 3050. The extra flap 3583 can also be pulled down into the fluid inlet opening 3572 toward the fluid pathway 3570. In some embodiments, the extra flap 3583 does not function as a check valve and does not substantially affect the flow of fluid in either the relaxed or deformed configuration. In some embodiments, the extra flap 3583 can be omitted. As fluid is extracted from the vial 3000, air can be drawn into the vial 3000 to compensate for the loss of fluid volume. The air can pass through the air inlet 3510, through the air pathway 3538*b*, past the air check valve 3582, through the air pathway 3538*a*, and through the air outlet 3512 into the body 3002 of the vial 3000.

Figure 38B:
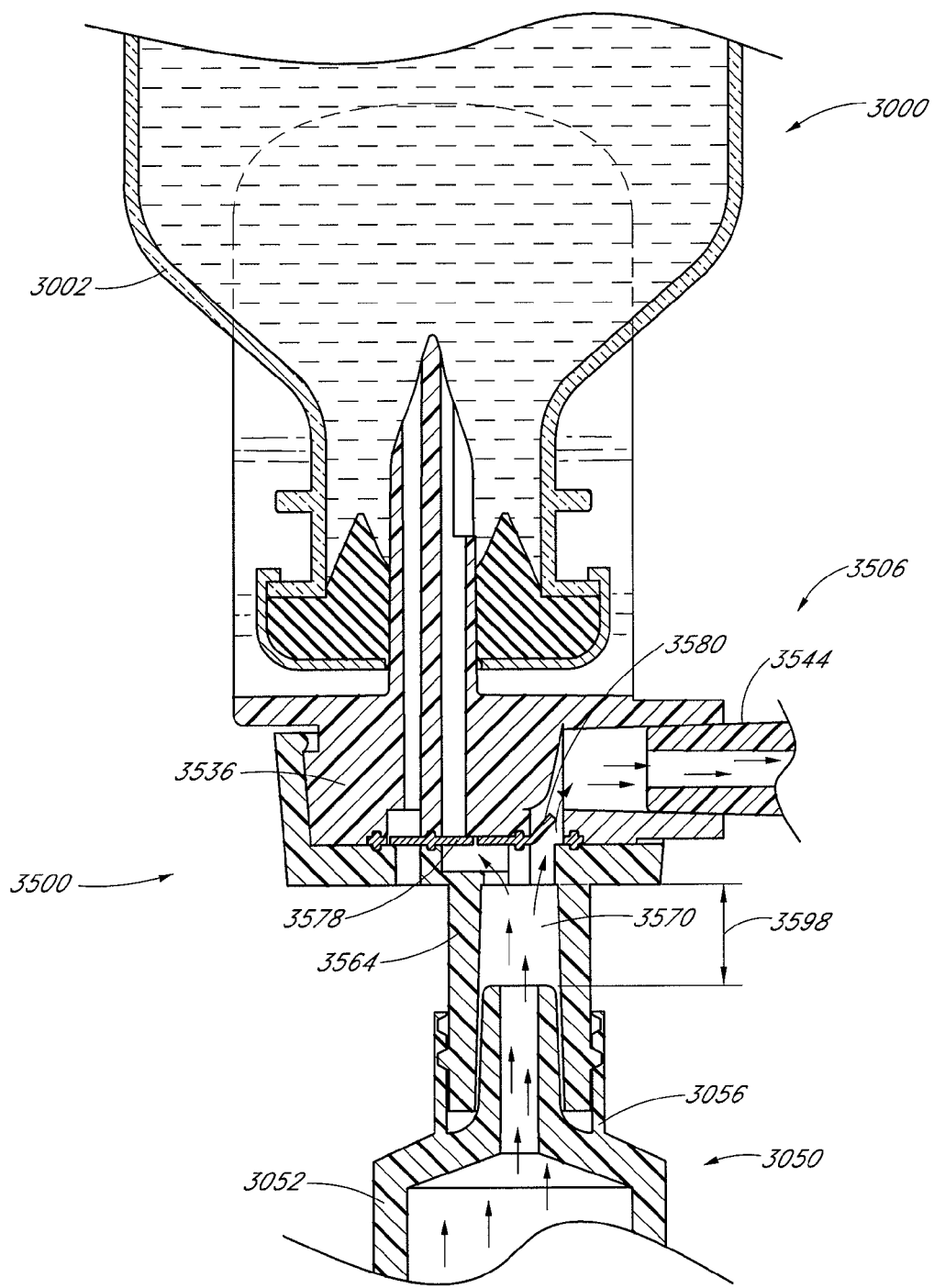
FIG. 38B is a cross sectional view of the connector of FIG. 35A, a vial, and a syringe as fluid is driven from the syringe, through the connector, and into an IV bag.

FIG. 38B shows a cross sectional view of the connector 3500, the vial 3000, and the syringe 3050 as fluid is driven through the connector 3500 from the syringe 3050 to the target connector portion 3506 which leads to the IV bad assembly (not shown). As the plunger (not shown) of the syringe 3050 is advanced, fluid can be driven from the body 3052 of the syringe 3050 into the fluid pathway 3570 formed in the shaft 3564. The fluid pathway 3570 can fork or branch so that both the source check valve 3578 and the target check valve 3580 are exposed to the pressure differential caused by the fluid being driven into the fluid pathway 3570. The pressure differential caused by the fluid being driven into the fluid pathway 3570 can push the flap of the source check valve 3578 more firmly closed against the bottom surface of the base 2536 because the fluid outlet opening 3534 is not wide enough to accommodate the flap. The flap of the target check valve 3580 can swing open as the fluid pushed against the flap. When the target check valve 3580 opens, fluid can flow past the target check valve 3580, through the fluid pathway 3546, and into the male end 3544 of the target connector portion 3506. Although not shown in FIG. 38B, it will be understood that the fluid can be driven through the target connector portion 3506 and into an IV bag that is attached thereto.

It will be understood that the connector 3500 can be used in connection with an automated fluid transfer system (e.g., system 600). When attached to a fluid transfer station, the connector 3500 can align with sensors for optically detecting the presence of air in the fluid pathway between the vial 3000 and the syringe 3050 as discussed above in connection with FIGS. 17-19D. With further reference now to FIGS. 38A-B, in some embodiments the connector 3500 can be aligned such that the light (e.g., light 676 or 1924) passes through the fluid pathway 3570 formed in the shaft 3564 within the region 3598 above the location where the upper end of the syringe shroud 3056 ends when the syringe 3050 is attached. In some embodiments, all or a portion of the lower housing member 3522 can be made from a material that is transparent to the light transmitted through the region 3598. In some embodiments, the entire shaft 3564 can be transparent. In some embodiments, the shaft 3564 includes a transparent window portion that covers all or a portion of the region 3598, with the remainder of the lower housing member 3522 being made from a material that is opaque to the light.

It will be understood that many variations and modifications can be made to the connector 3500. For example, although the illustrated embodiment is shown having an upper housing member 3520 and a lower housing member 3522, it will be understood that the main housing can be made up of a different number of housing members. Also, features and elements that are shown as part of the upper housing member 3520 may, in some embodiments, be formed as part of the lower housing member 3522 and vice versa.

Several connectors for transferring fluid are described herein (e.g., connectors 320, 2600, 2700, 3200, 3500, 3910). It will be understood that many of the features described in connection with one connector can also be applied to the other connectors disclosed herein. Many components of the connectors can be interchangeable with corresponding components of the other connectors. For example, The connectors 2700 and 3500 are shown as having retaining arms for securing a vial thereto, and the retaining arms can similarly be incorporated into the other connectors (e.g., 320 or 3200). Indeed, in some embodiments, the retaining arms can be removably attachable and can slide over the piercing member and snap into place into a groove formed in the base of the shaft of the piercing member (see FIG. 32A). Each of the connectors can be modified to incorporate the check valve types disclosed in connection with each of the other connectors. In some embodiments, a single connector can use different check valve types for different check valves. One possible configuration is to use a series of three duckbill check valves (e.g., as shown in connector 2700) but integrated into a single check valve assembly and oriented similar to the check valve assembly of the connector 3200. Many other modifications are possible.

Figure 39:
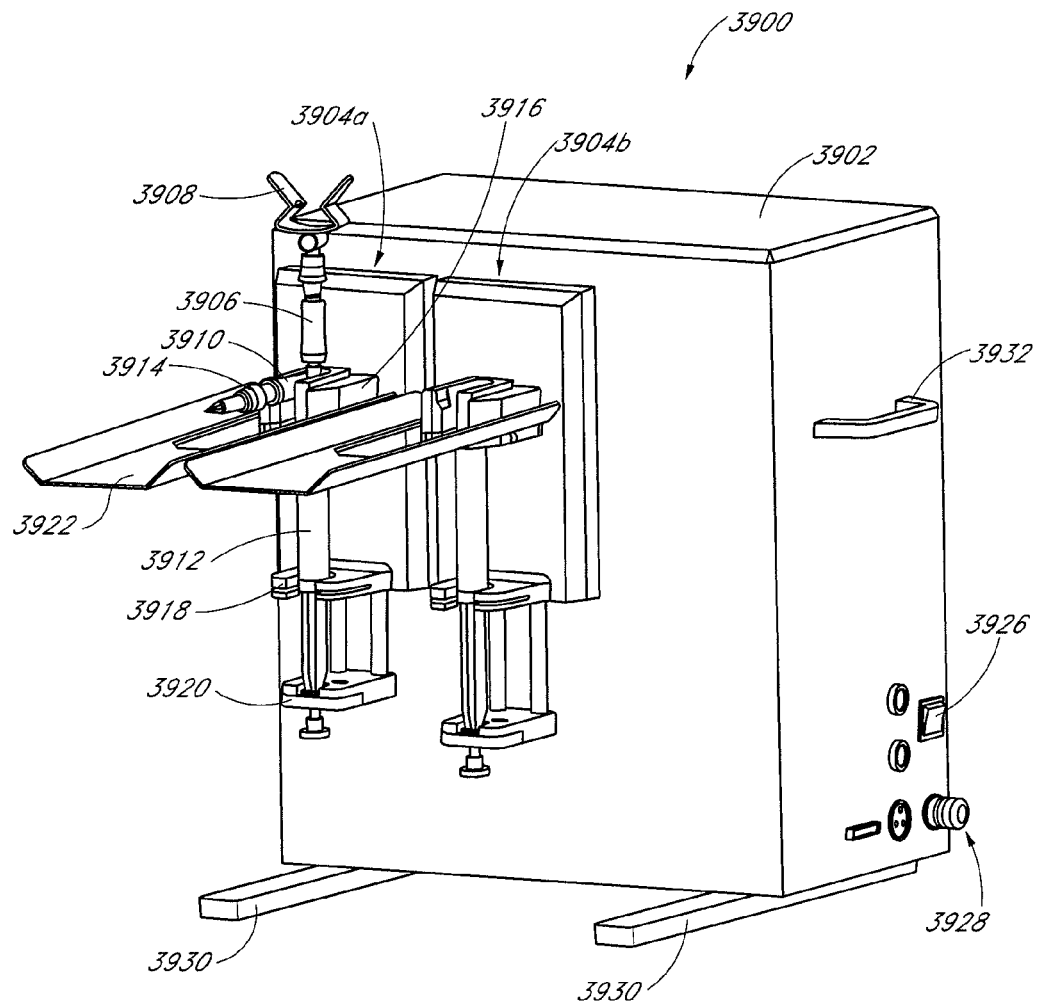
FIG. 39 is a perspective view of a system for transferring precise amounts of fluid.

FIG. 39 is a perspective view of another example embodiment of a fluid transfer system 3900. The fluid transfer station 3900 can be similar to, or the same as, fluid transfer systems 100 or 600 or any other fluid transfer system discussed herein. Thus, the discussion associated with many features of other fluid transfer systems described herein is also applicable to the fluid transfer system 3900, even when not specifically identified.

The fluid transfer system can include a main housing 3902 that supports two transfer stations 3904a-b, although any other suitable number of transfer stations can be used (e.g. one, three, four, five, or more transfer stations). The transfer stations 3904a-b can be similar to, or the same as, the transfer stations 604a-f discussed above. Although only transfer station 604a is discussed in further detail below, it should be understood that the transfer station 604b can be the same as transfer station 604a, or the transfer stations 604a-b can vary (e.g., having different sized syringes).

The transfer station 3904a can be configured to receive a fluidics assembly 3906 in a manner similar to that described in connection with transfer station 604a. The fluidics assembly 3906 can include a vial (not shown in FIG. 39), a vial adapter 3908, a fluid transfer module or connector 3910, a syringe 3912, and an IV bag assembly 3914 (partially shown in FIG. 39). The transfer station can be configured to secure the syringe 3912 and/or connector 3910 using, for example, a top connector 3916, a middle connector 3918, and an end piece 3920. The transfer station 3904a can include a motor (inside the housing 3902) to cause the end piece 3920 to move with respect to the middle connector 3918, thus withdrawing or advancing the plunger of the syringe 3912. In some embodiments, the motor can be a high precision stepping motor able to withdraw the plunger of the syringe 3912 by a precise distance, thereby facilitating precision fluid transfer. In some embodiments, the system 3900 can transfer amounts of fluid in increments within the range of approximately 0.05 milliliters to approximately 0.3 milliliters. In some embodiments, the system 3900 can transfer amounts of fluid in increments of about 0.1 milliliters. In some embodiments, the system 3900 can transfer fluid at a rate in the range of about 10 to 70 milliliters per minute for each transfer station. In some embodiments, the rate can be about 30 milliliters per minute for each fluid transfer station. In some embodiments, the system 3900 can transfer fluid with an error rate in the range of about 0% to about 8% when transferring a volume of more than 1 milliliter. In some embodiments, the error rate can be about 3%.

In some embodiments fluid transfer station 3904a can include a compatibility mechanism configured to ensure that an approved connector is used, to provide reliable accurate fluid transfer. The compatibility mechanism can be a mounting feature (e.g., of the top connector 3916) that is configured specifically to fit with a portion of the connector 3910. In some embodiments, the fluid transfer module or connector 3910 can be a single-use, disposable portion. The fluid transfer module 3910 can be provided with instructions to the user for inserting the fluid transfer module 3910 into the electronically controlled fluid dispensing system to properly position and align the various components to allow for fluid transfer and safety features. The fluid transfer module 3910 also can be provided with instructions to the user for disconnecting the fluid transfer module 3910 after fluid transfer is completed. In some embodiments, the user instructions can include information indicating that the fluid transfer module should be disposed of in a biohazard receptacle after a single use.

The fluid transfer station 3904a can include a tray 3922 to support the IV bag assembly 3914. The tray 3922 can be similar to, or the same as the tray 2272 described above. In some embodiments, the tray 3922 can be secured to the top connector 3916 or other portion of the housing 3902 using screws or the tray 3922 can be inserted into a slot. Other supports can be used. In some embodiments, the tray 3922 can pivot down when not in use, as will be discussed in greater detail below.

An electronically controlled fluid dispensing system, such as the fluid transfer system 3900 can include a power switch 3926, and various input and/or output ports 3928 for connecting external devices (e.g., a keypad, touchscreen, controller, printer, barcode scanner, monitor, or computer). In some embodiments a foot pedal can connect to one of the ports 3928. The foot pedal can include a button or switch to start and stop the fluid transfer process. The housing 3902 can have support feet 3930 extending therefrom, and handles 3932.

Figure 40:
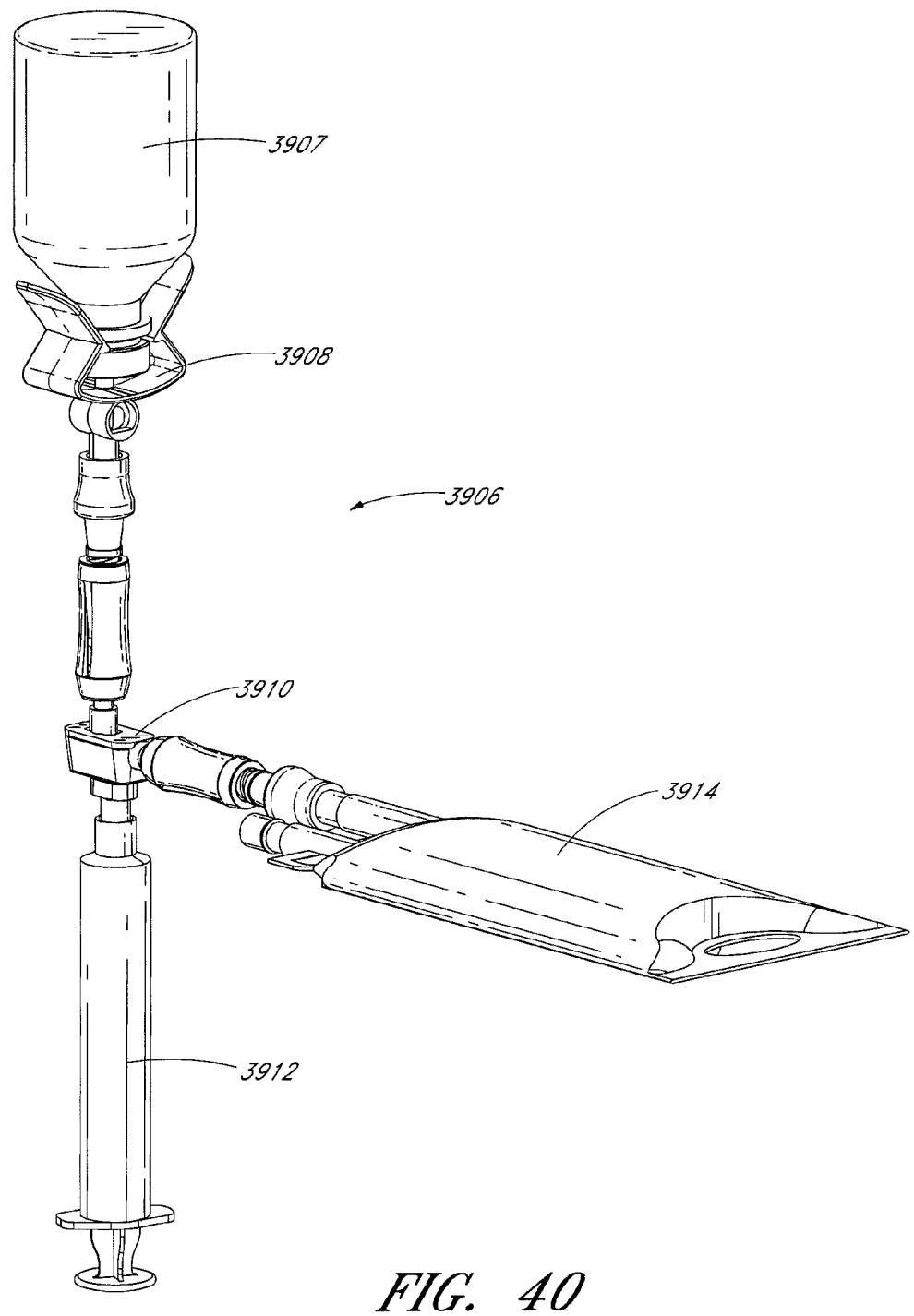
FIG. 40 is a perspective view of a fluidics assembly for use with the system of FIG. 39.
Figure 41:
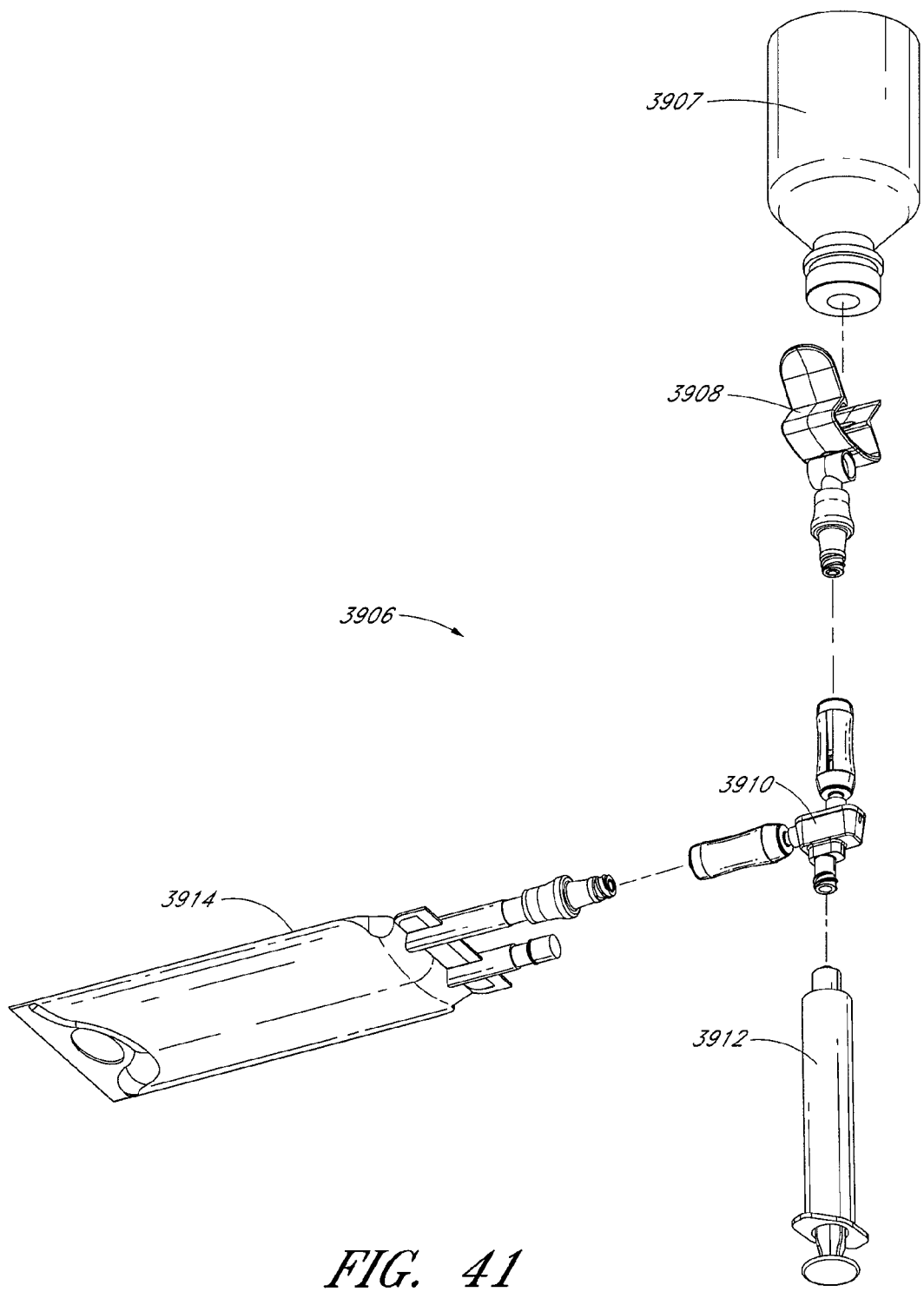
FIG. 41 is an exploded perspective view of the fluidics assembly of FIG. 40.

FIG. 40 is a perspective view of the fluidics assembly 3906 in an assembled configuration. FIG. 41 is a perspective exploded view of the fluidics assembly 3906 from a different angle than that shown in FIG. 40. The fluid assembly 3906 can be used to transfer precise amounts of fluid from the vial 3907 to the IV bag 3914. The fluidics assembly 3906 includes a vial 3907, a vial adapter 3908 configured to provide fluid communication with the fluid (e.g., chemotherapy drug or other medication) contained within the vial, a syringe 3912, an IV bag assembly 3914, and a connector 3910 for directing fluid from the vial adapter 3908 into the syringe 3912 and from the syringe toward the IV bag assembly. In some embodiments, the fluidics assembly 3906 can have features similar to, or the same as, those of the other fluidics systems disclosed. In some embodiments, the fluidics assembly 3096 can be configured to allow the vial 3907 and vial adapter 3908 to be replaced (e.g., when the vial runs out of fluid) without replacing the connector 3910 or syringe 3912. Unlike many of the connectors disclosed herein, in the fluidics assembly 3906, air enters the vial 3907 via the vial adapter 3908 rather than through the connector 3910.

Figure 42:
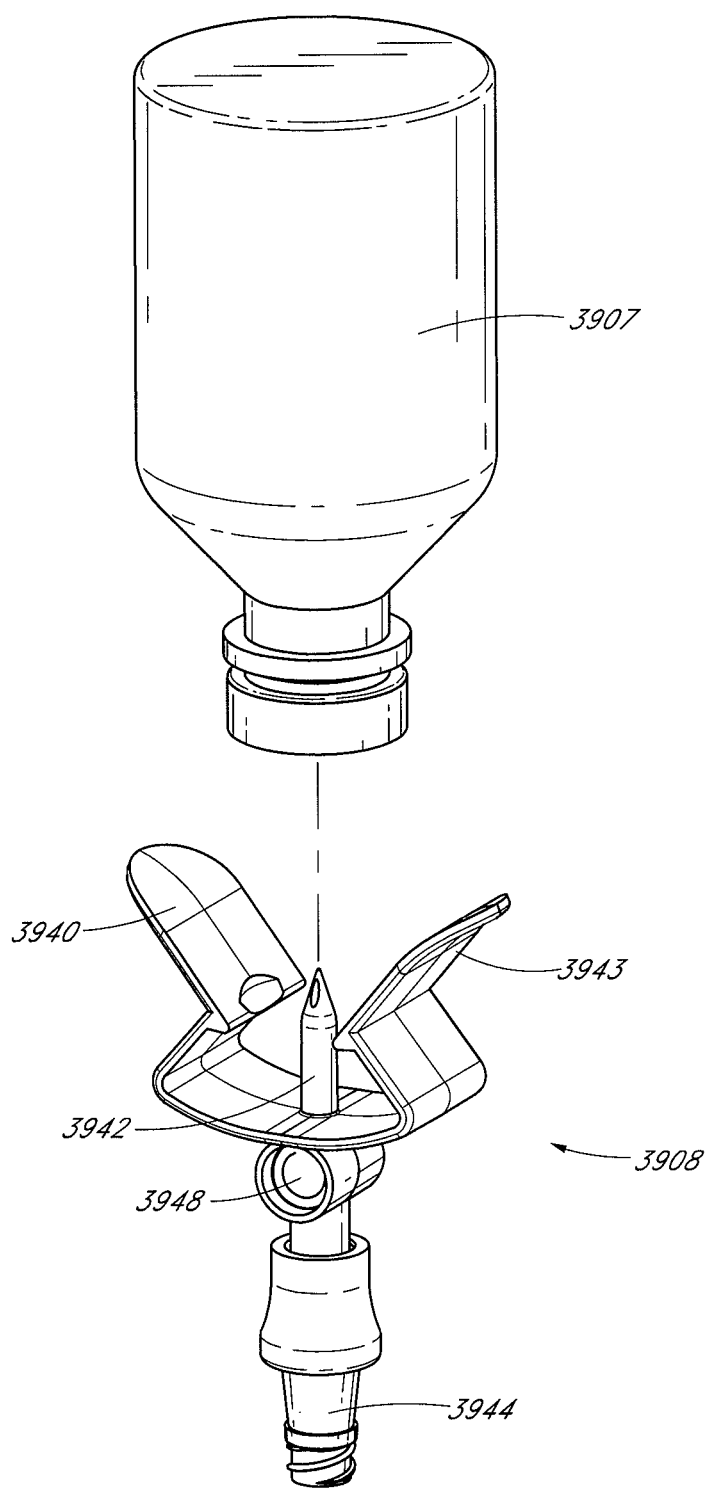
FIG. 42 is an exploded perspective view of a vial adapter.

FIG. 42 is a perspective view showing the vial adapter 3908 and the vial 3907 in a separated configuration, such as before the vial 3907 is attached to the vial adapter 3908. The vial adapter can have a top portion 3940 that is similar to, or the same as, the top of the connector 2700, the connector 3500, or any of the other connectors described as being able to access fluid in a vial (or bag or other fluid source container). For example, the top portion 3940 can include a spike 3942 configured to piece the septum on the cap of the vial 3907 and arms 3942 to retain the vial 3907 onto the vial adapter 3908.

Opposite the upper portion 3940, the vial adapter can include a connector, which can be, for example, a female connector 3944. The connector 3944 can be, for example, a version of the Clave® connector manufactured by ICU Medical, Inc., of San Clemente, Calif. Various embodiments of a connector of this type are described in the '866 patent. The female connector 3944 can seal the end of the vial adapter 3908 such that no fluid is allowed to escape from the vial adapter 3908 until a male connector is attached to the female connector 3944. It should be understood that in many embodiments discussed herein, the male and female connectors can be switched. For example, the vial adapter 3908 can include a male connector which is configured to mate with a female connector on the connector 3910.

The vial adapter 3908 can include an air intake channel 3946 configured to direct air into the vial 3907 to compensate for fluid removed from the vial 3907 to reduce the pressure differential. The air intake channel 3946 can include a filter 3948 configured to allow air to pass through the filter 3948 and toward the vial 3907 while also preventing fluid from passing through the filter. For example, the filter 3948 can include an air permeable but fluid impermeable membrane. The filter 3948 can be a hydrophobic filter. In some embodiments, the vial adapter 3908 can include a check valve in place of or in addition to the filter 3948. The vial adapter 3908 can also have a bag that is configured to increase in volume while preventing the input air to contact the fluid inside the vial 3907, similar to the bag 394 discussed above. Thus, the vial 3907 can be vented by a mechanism independent of the connector 3910.

Figure 43:
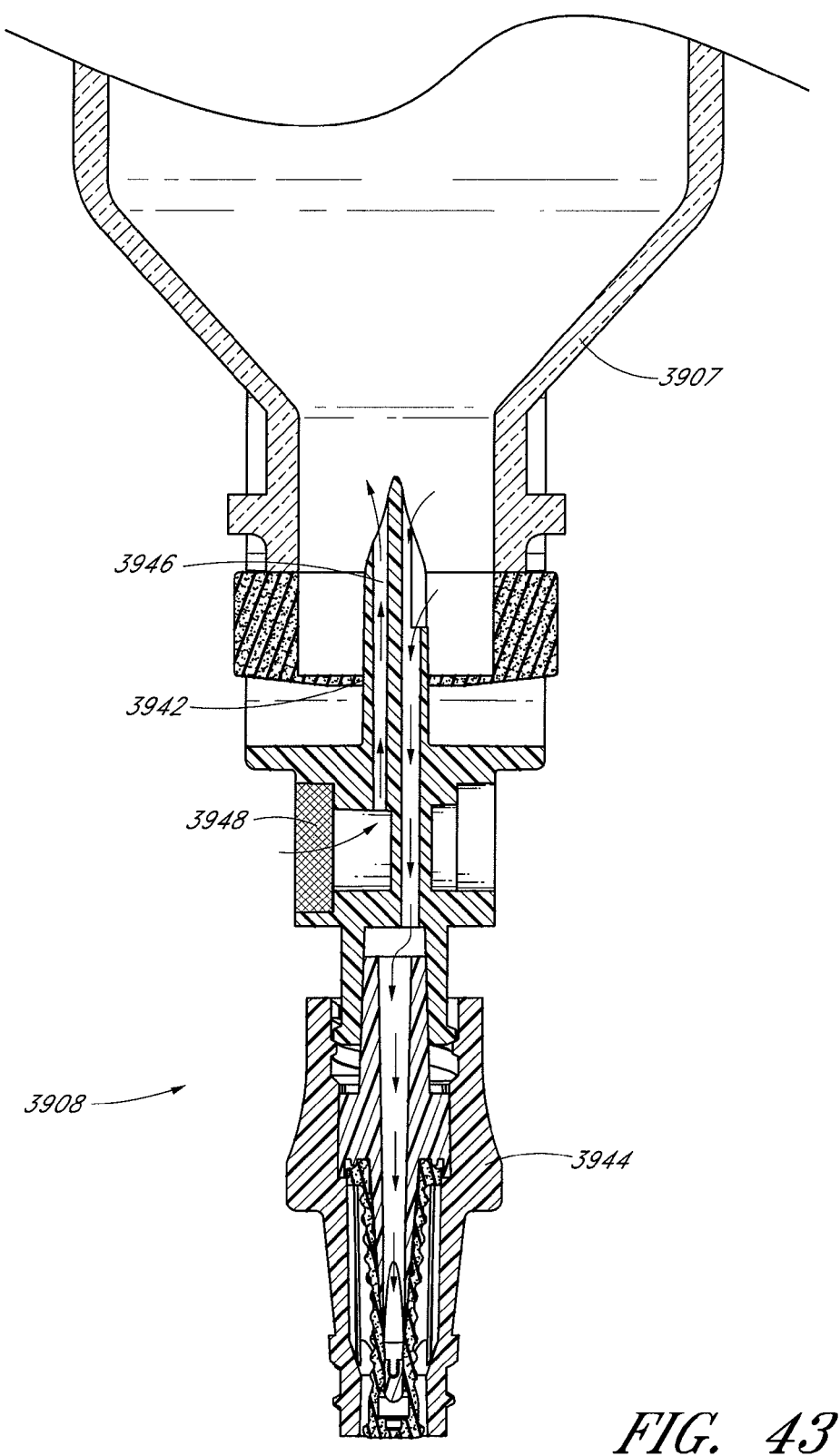
FIG. 43 is a cross sectional view of the vial adapter of FIG. 42.

FIG. 43 is a cross sectional view of the vial 3907 and vial adapter 3908 in an assembled configuration. As shown by the flow lines in FIG. 43. Air can pass through the filter 3948, through the air inlet channel 3946, and into the vial 3907 to compensate for the fluid that is drawn out of the vial 3907 through a fluid channel 3950. The fluid channel 3950 can pass through the spike 3942, and down through the female connector 3944 as shown. Although the female connector 3944 is shown in a closed configuration in FIG. 43, it will be understood that the female connector 3944 can be opened by the first male connector 3964 of the connector 3910 to allow fluid to pass from the vial adapter 3908 to the connector 3910.

Figure 44:
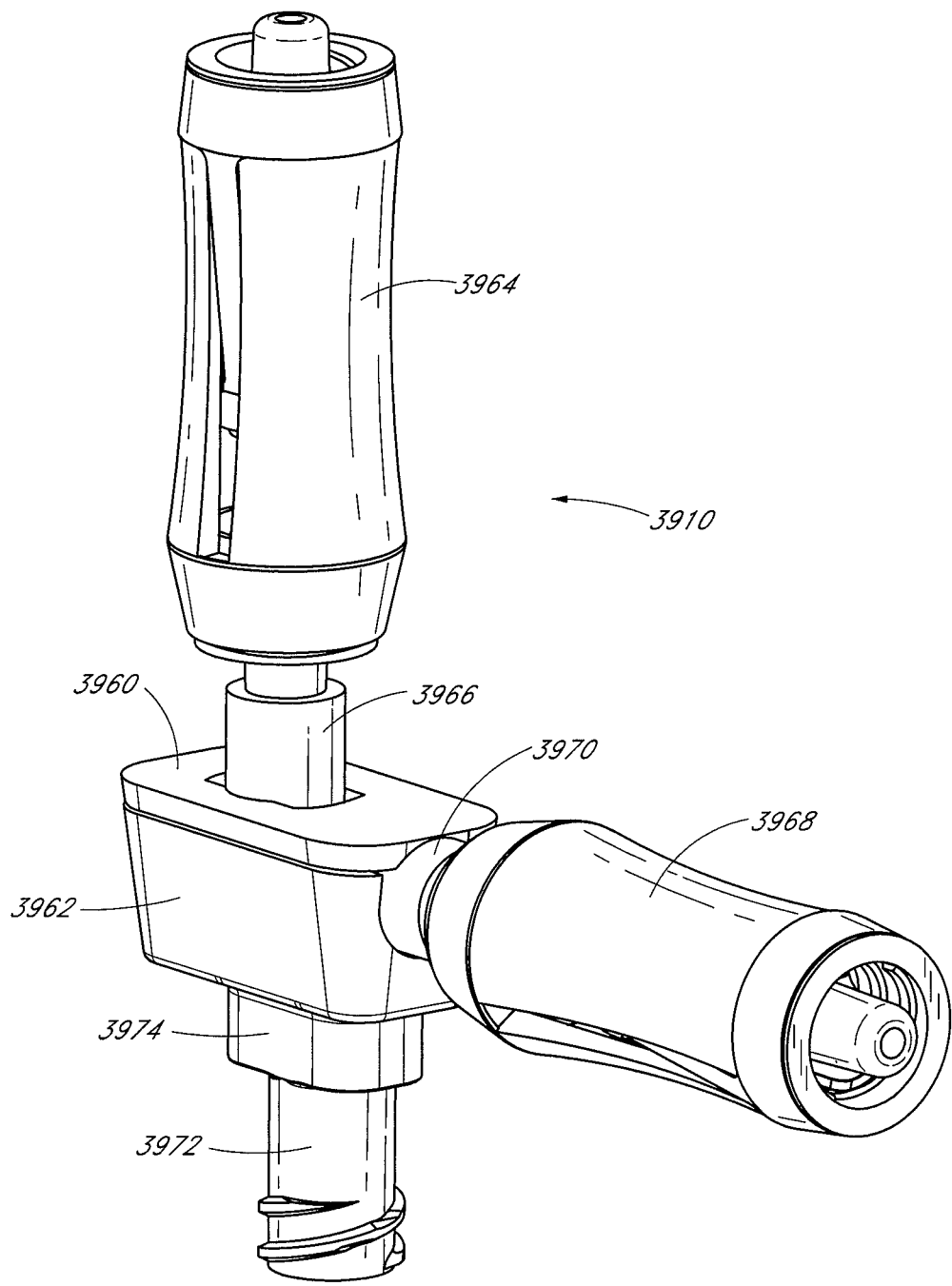
FIG. 44 is a perspective view of a connector of the fluidics assembly of FIG. 40.
Figure 45:
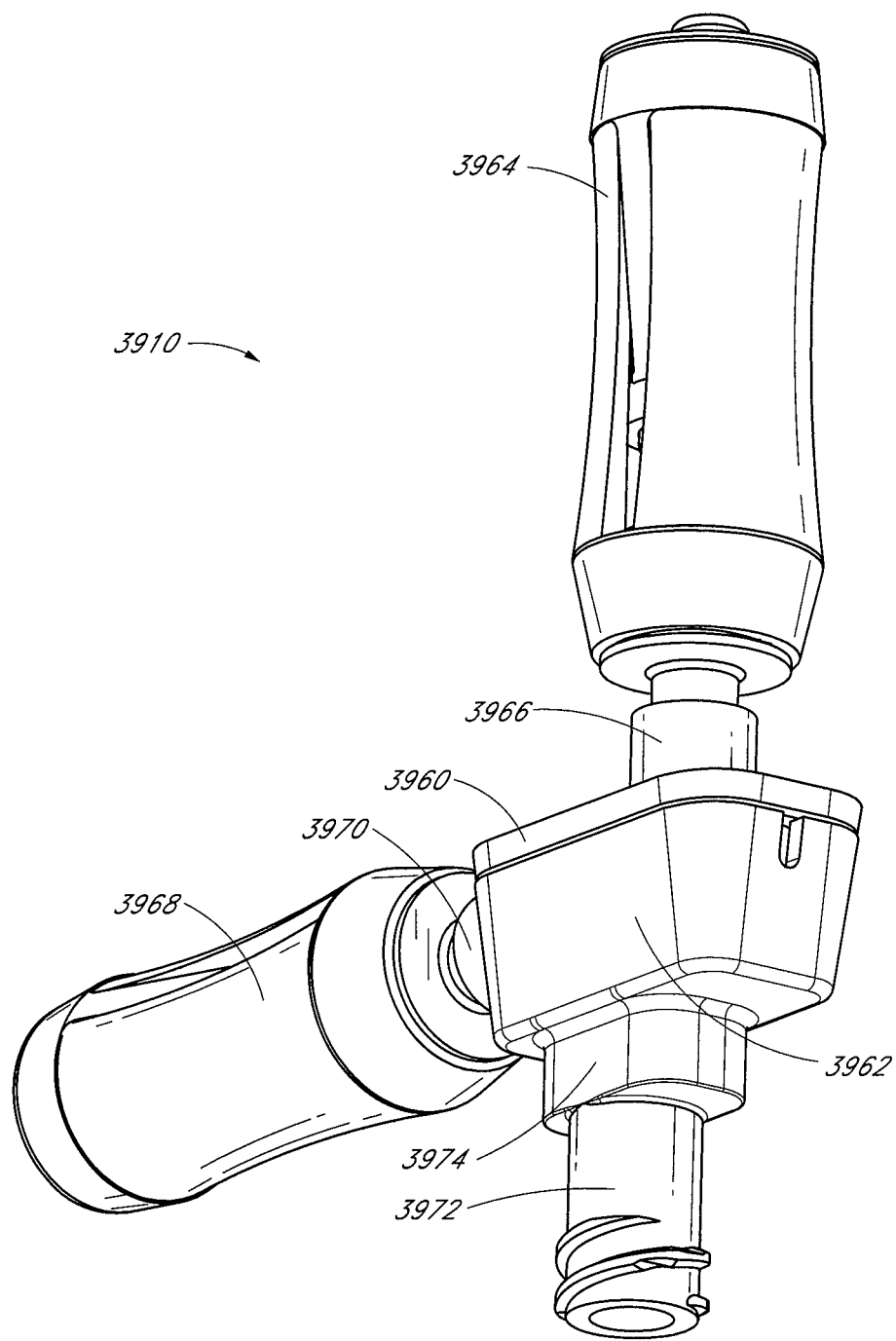
FIG. 45 is another perspective view of the connector of FIG. 44.
Figure 46:
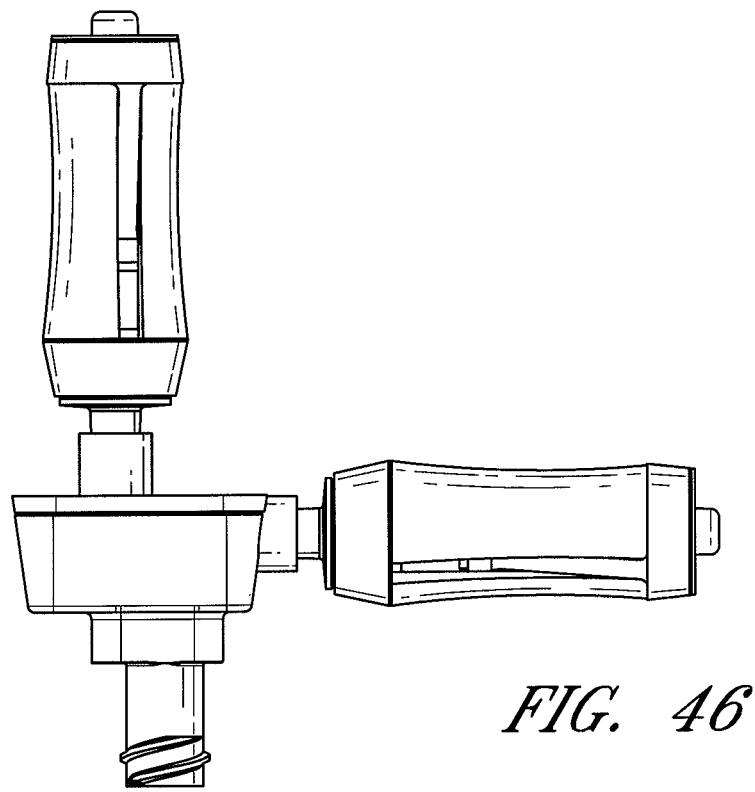
FIGS. 46-51 show various views of the connector of FIG. 44.
Figure 51:
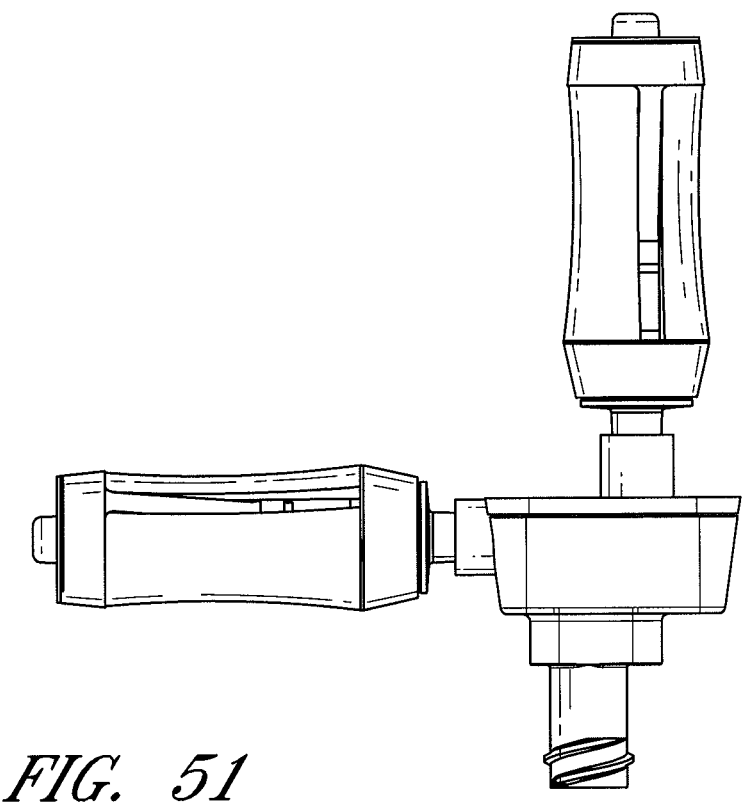
Figure 47:
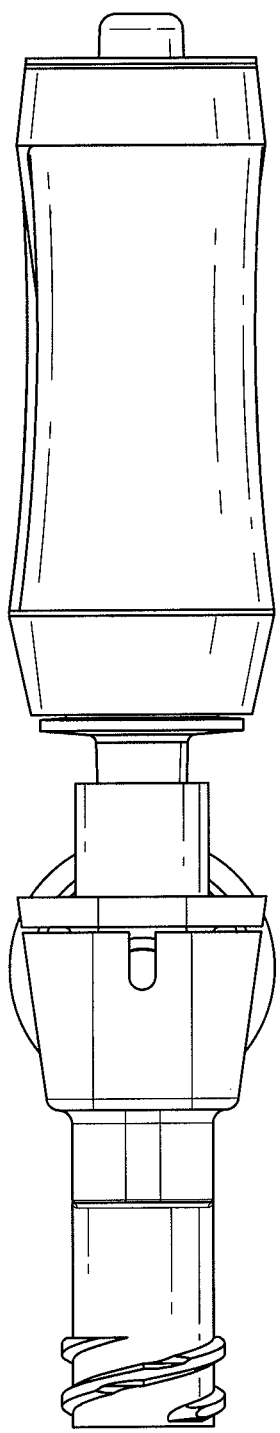
Figure 48:
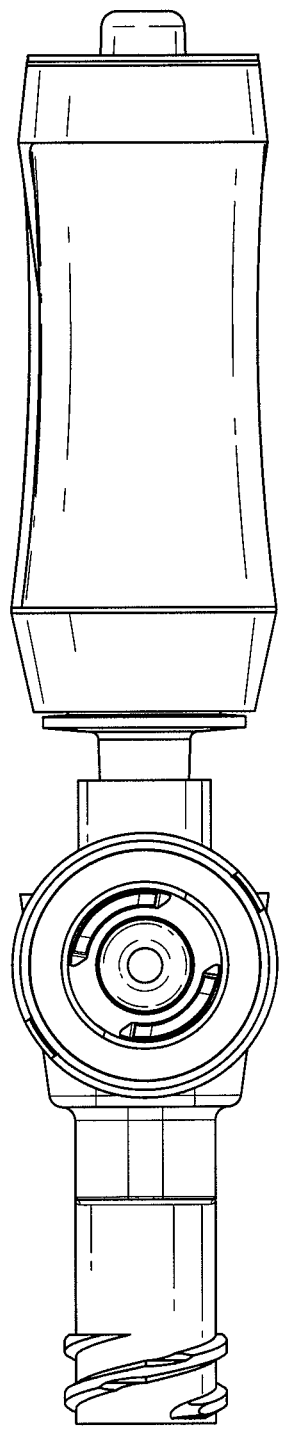
Figure 49:
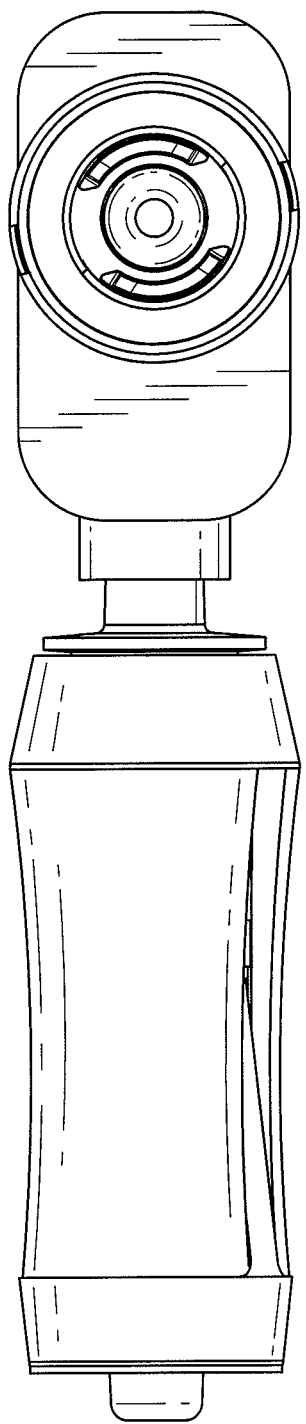
Figure 50:
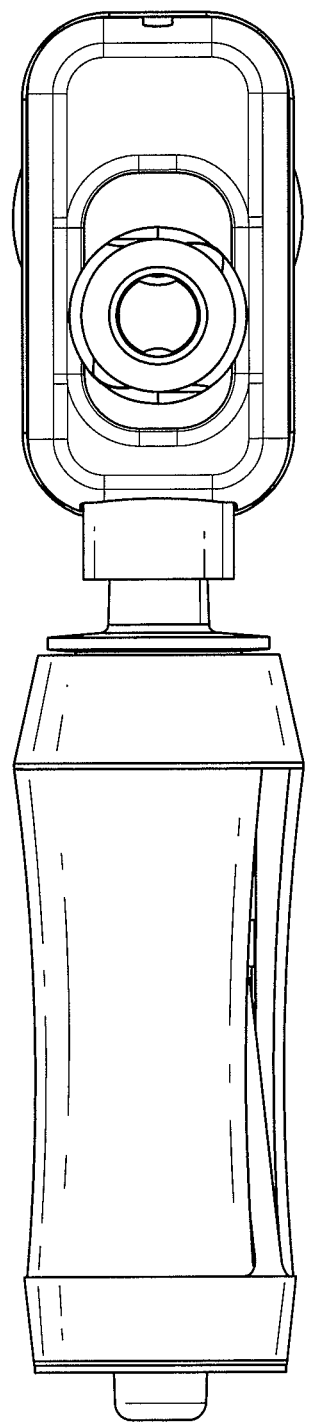

FIG. 44 is a perspective view of the connector 3910. FIG. 45 is a perspective view of the connector taken from a different angle than the view of FIG. 44. FIG. 46 is a right-side view of the connector 3910. FIG. 47 is a back view of the connector 3910. FIG. 48 is a view of the connector 3910. FIG. 49 is a top-down view of the connector 3910. FIG. 50 is a bottom-up view of the connector 3910. FIG. 51 is a left-side view of the connector 3910.

The connector 3910 can have features similar to, or the same as, those of the connector 2700 or any other connector disclosed here. The connector 3910 can include an upper housing portion 3960 and a lower housing portion 3962. A first male connector 3964 can be attached to a female end 3966 of the upper housing portion. A second male connector 3964 can be attached to a female end 3968 of the lower housing portions 3962. The male connectors 3964, 3968 can be a version of the Spiros® closeable male connector manufactured by ICU Medical, Inc., of San Clemente, Calif. Various embodiments of connectors of this type are described in the '920 Publication. A syringe interface 3972 can extend down from the bottom of the lower housing portion 3962 to receive the syringe 3912. A sensor region 3974 can also be positioned at the base of the lower housing portion 3962 and can be configured to allow light to pass through the fluid pathway in the connector 3910 to detect the presence of bubbles, which can indicate that the vial 3907 has run out of fluid. In some embodiments, the surface of the sensor region can be flat to allow light to pass through the wall of the sensor region 3974 at an angle that is perpendicular to the surface, thereby allowing the light to more reliably strike the corresponding sensor.

Figure 52:
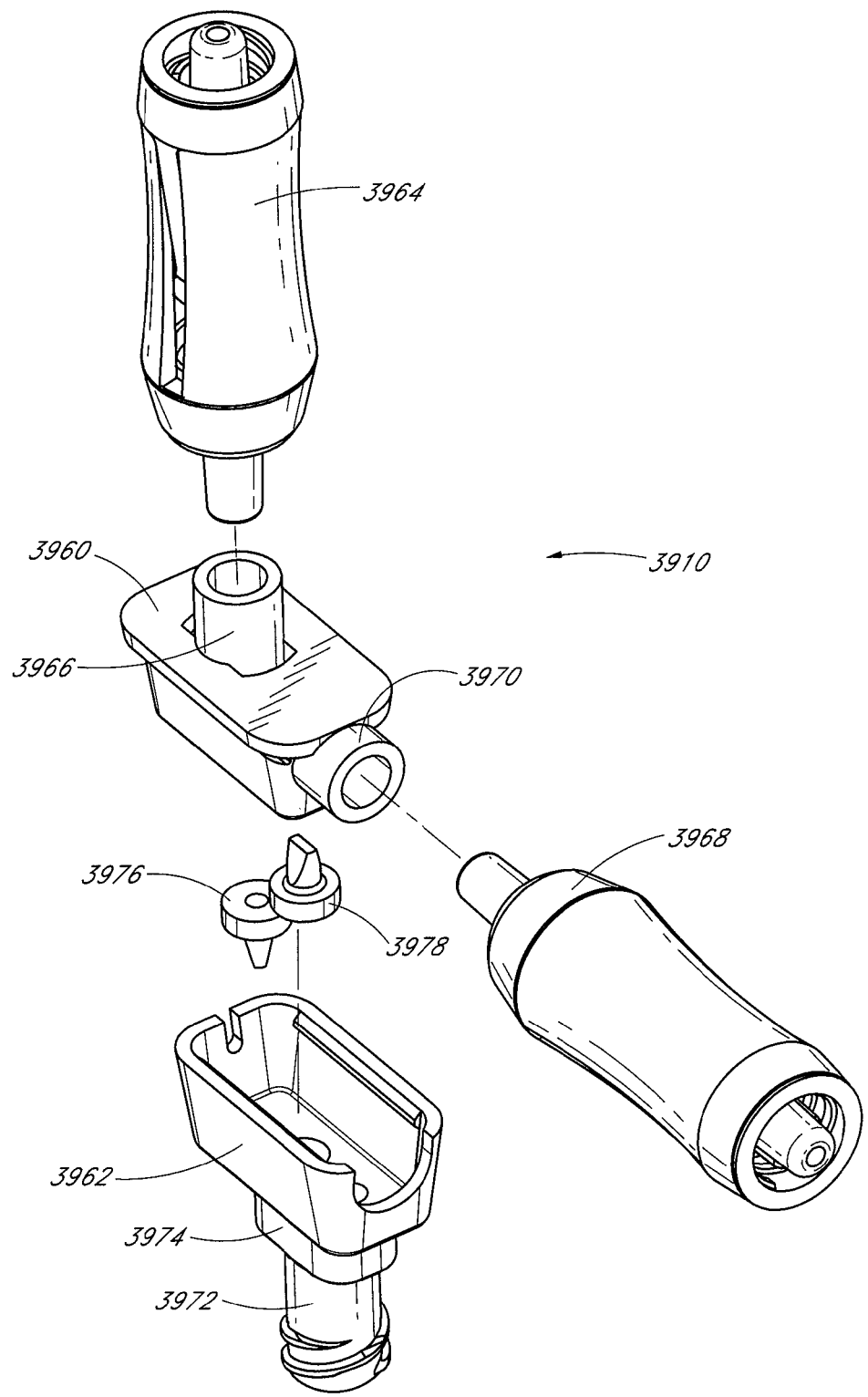
FIGS. 52-53 are exploded perspective views of the connector of FIG. 44.
Figure 53:
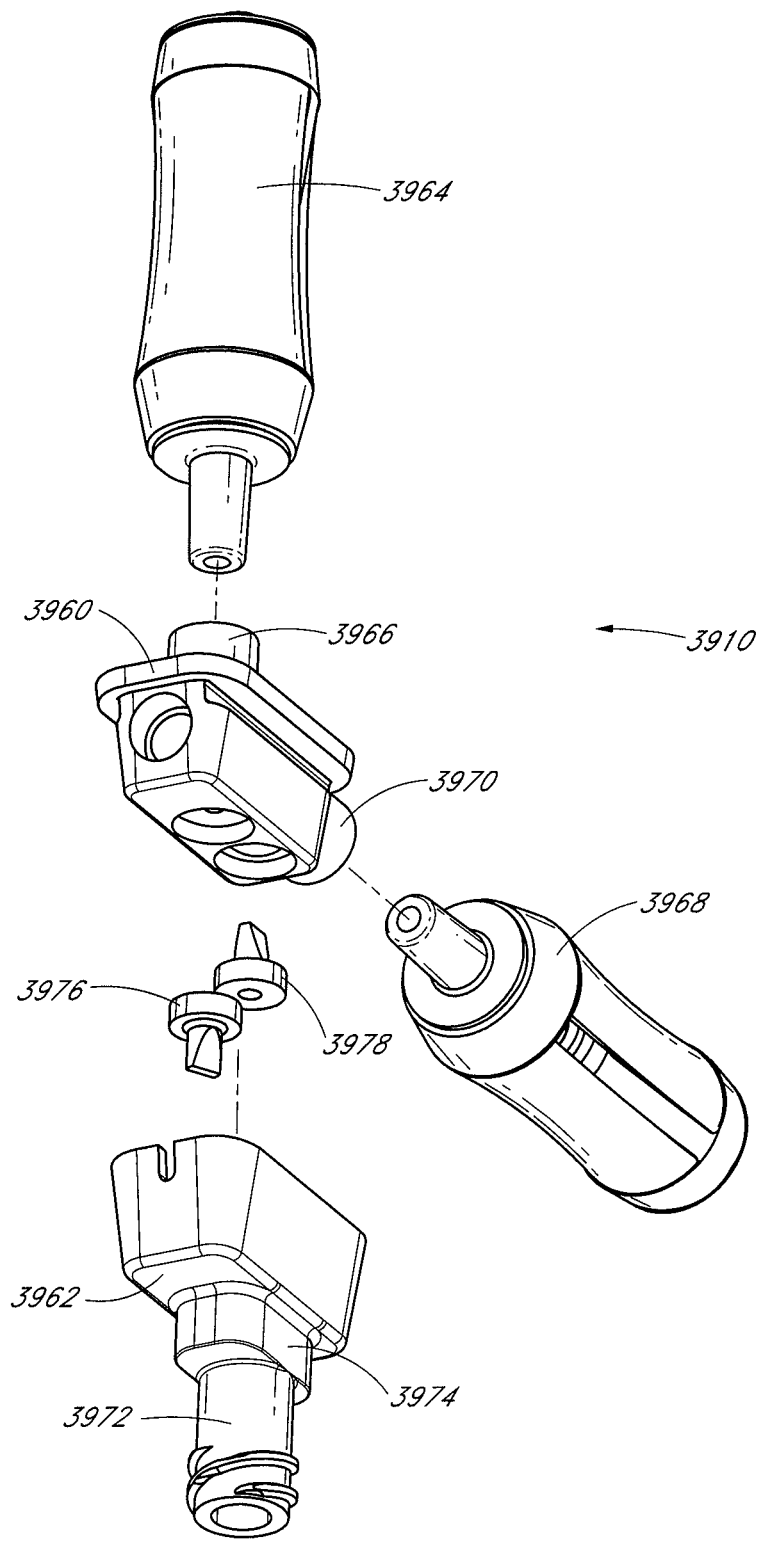

FIG. 52 is an exploded perspective view of the connector 3910. FIG. 53 is an exploded perspective view of the connector 3910 taken from a different view than FIG. 52. The connector 3910 can be similar to the connector 2700 in many respects. However, instead of including a vial adapter built into the upper housing portion, as is the case for the connector 2700, the connector 3910 includes the first male connector 3964 which is configured to removably interface with the female connector 3944 of the separate vial adapter 3908. Thus, when the vial 3907 runs out of fluid, the vial 3907 and vial adapter 3908 can be replaced without replacing the connector 3910, syringe 3912, or any other part of the fluidics assembly 3906. This can provide the benefit of reducing the amount of disposable pieces and fluid sent to waste during a vial replacement. Because the vial adapter is not part of the connector 3910, the connector 3910 also differs from the connector 2700 in that the connector 3910 does not include an air inlet channel or an air check valve. Other connectors which are described herein as having an integrated vial adapter (e.g., the connectors 320, 3200, 3500) can be similarly modified to be compatible with a separate vial adapter.

When the vial 3907, vial adapter 3908, connector 3910, syringe 3912, and IV bag assembly 3914 are connected, a source fluid pathway can be formed between the vial 3907 and the syringe 3912, and a target fluid pathway can be formed between the syringe 3912 and the IV bag. The connector 3910 can include a source check valve 3976 positioned in the source fluid pathway to allow fluid to flow from the vial 3907 into the syringe and prevent fluid from flowing back into the vial 3907. The connector 3910 can also include a target check valve 3978 positioned in the target fluid pathway to allow fluid to flow from the syringe 3912 to the IV bag and prevent fluid from flowing from the IV bag back toward the syringe 3912. The source and target check valves 3976, 3978 can be duck bill check valves similar to the check valve 2900 discussed herein, although dome check valves or disc check valves or any other suitable check valve can be used.

Figure 54:
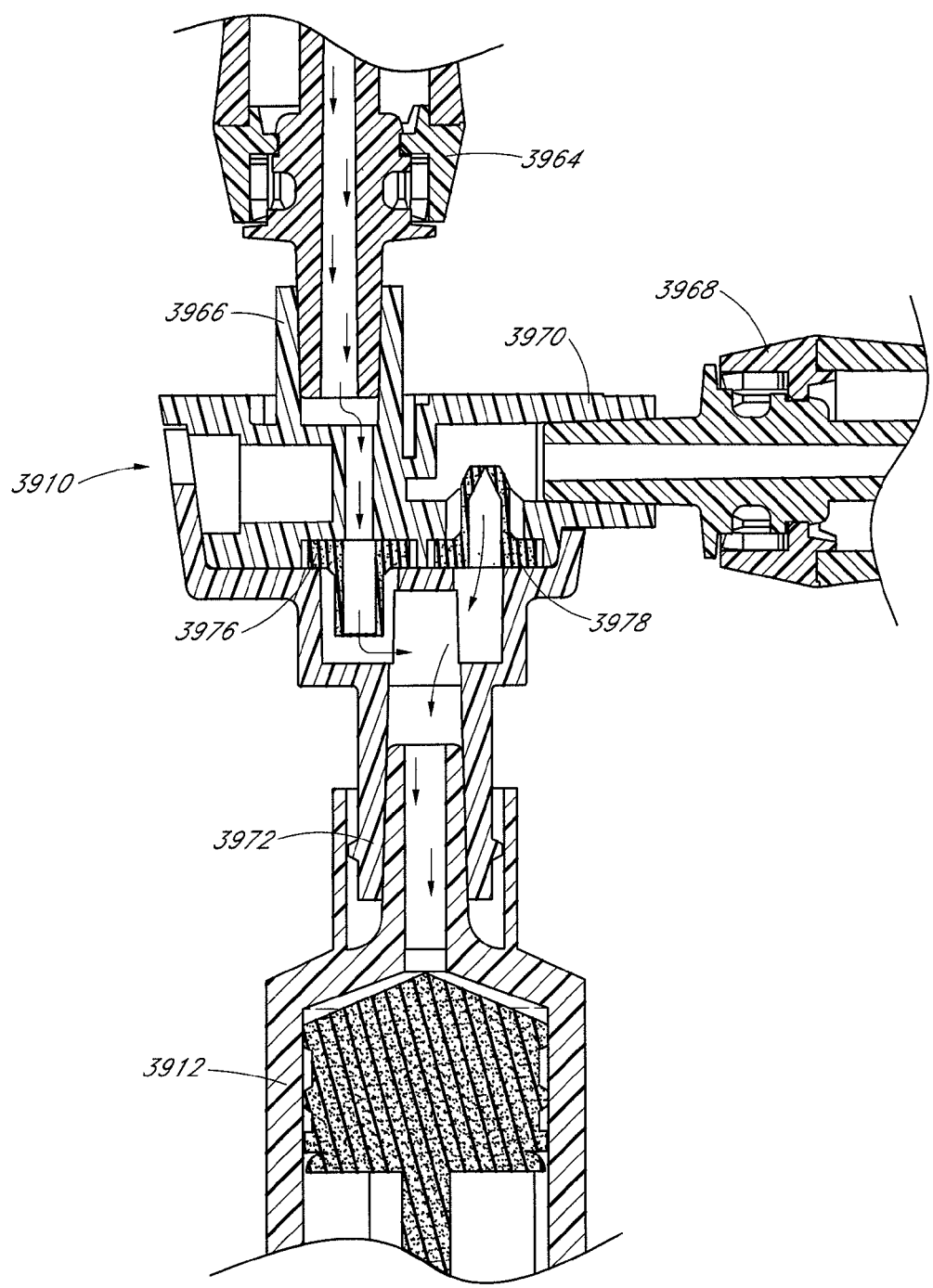
FIGS. 54-55 are cross sectional views of the connector and syringe of the fluidics assembly of FIG. 40.

FIG. 54 is a cross sectional view of the connector 3910 and syringe 3912 showing fluid flowing through the connector 3910 from the vial 3907 to the syringe 3912. As the plunger of the syringe 3912 is withdrawn, fluid is drawn into the syringe. The pressure causes the source check valve 3976 to open so that fluid is allowed to flow from the vial 3907 to the syringe 3912. The pressure also causes the sides of the target check valve 3978 to bear against each other to maintain the target check valve 3978 closed. Thus, fluid drawn into the syringe 3912 will be drawn from the vial 3907 and not the IV bag. As fluid is drawn out of the vial 3907, air can enter the vial 3907 through the air inlet channel 3946 as described above in connection with FIG. 43.

Figure 55:
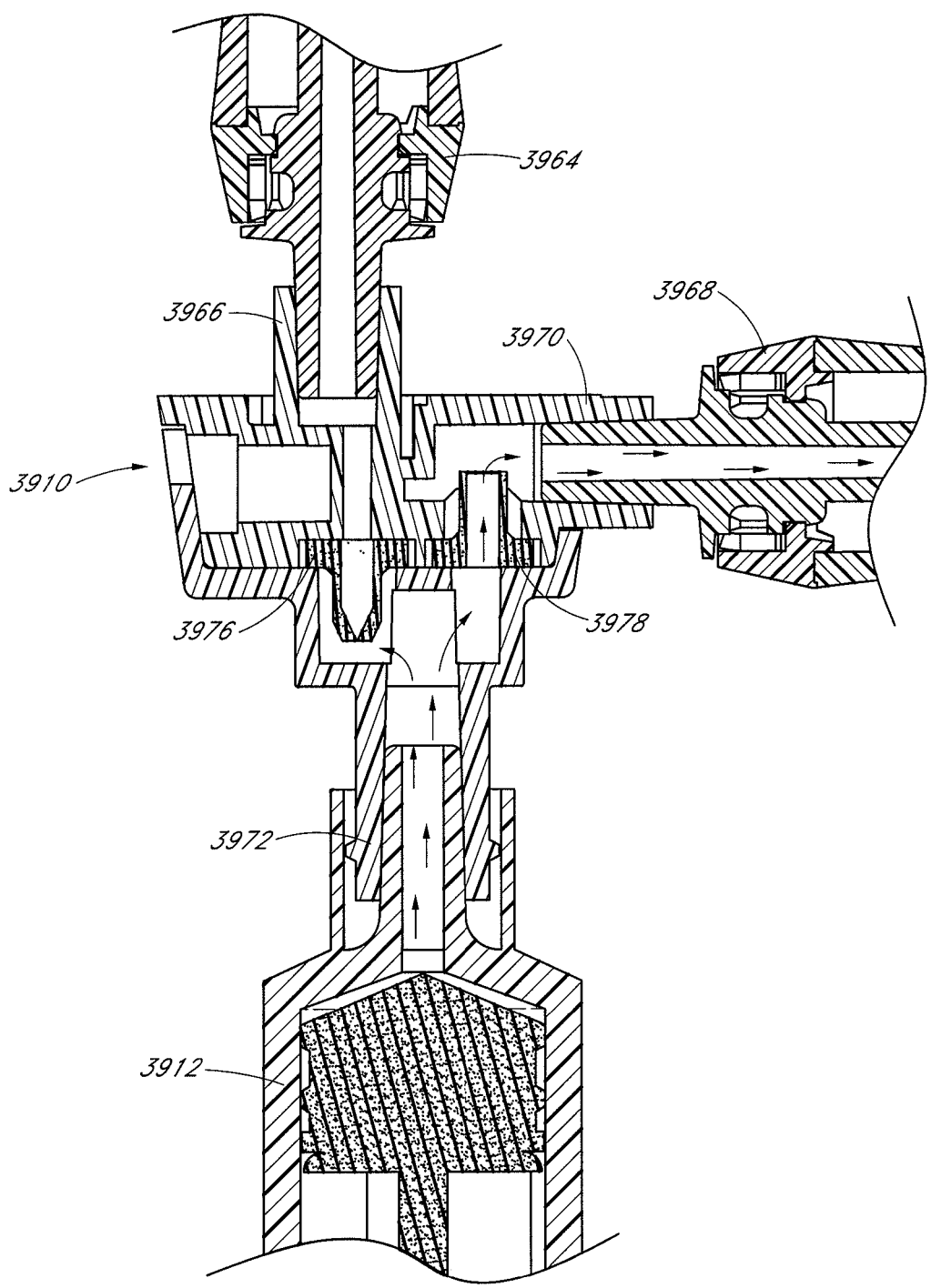

FIG. 55 is a cross sectional view of the connector 3910 and syringe 3912 showing fluid flowing through the connector 3910 from the syringe 3912 toward the IV bag assembly 3914. As the plunger of the syringe 3912 is advanced, fluid is driven out of the syringe. The pressure causes the target check valve 3978 to open so that fluid is allowed to flow from the syringe 3912 toward the IV bag assembly 3914. The pressure also causes the sides of the source check valve 3976 to bear against each other to maintain the source check valve 3976 closed. Thus, fluid driven out the syringe 3912 will be directed to the IV bag and not back into the vial 3907.

Figure 56:
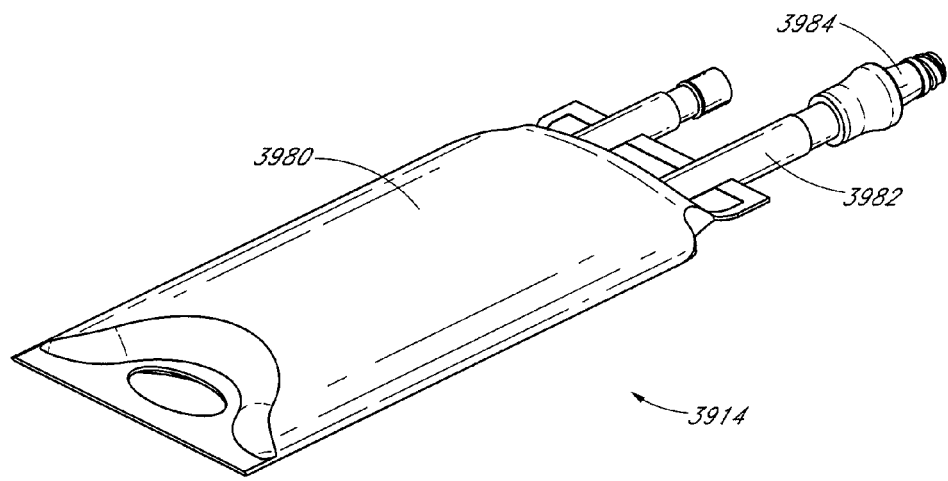
FIG. 56 is a perspective view of the IV bag assembly of the fluidics system of FIG. 40.

FIG. 56 is a perspective view of the IV bag assembly 3914. The IV bag assembly 3914 can include an IV bag 3980, a length of tubing 3982, and a female connector 3984. The female connector 3984 can be removably or irremovably attached to the tubing 3982. The female connector 3984 can function to seal off the IV bag assembly 3914 so that no fluid can escape from the IV bag 3980 except when a male connector is attached thereto.

Figure 57:
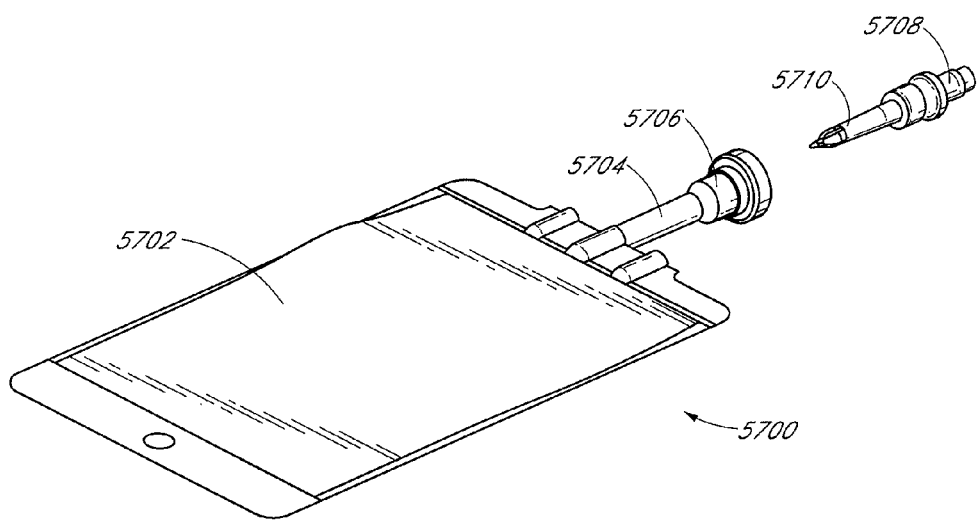
FIG. 57 is an exploded perspective view of an another sample embodiment of an IV bag assembly.

FIG. 57 is an alternative IV bag assembly 5700 which may be used with the fluidics assembly 3906 or with various other embodiments discussed herein. The IV bag assembly 5700 can include an IV bag 5702 and a length of tubing attached thereto 5704. A spike port 5706 can be positioned at the end of the tubing 5704, and the spike port 5706 can include a piercing membrane or barrier that when closed prevents fluid from entering or exiting the IV bag 5702. The female connector 5708 can have a spike 5710 attached thereto. The spike 5710 can be inserted into the spike port 5706 until it pierces the membrane or barrier thereby providing access to the interior of the IV bag.

Figure 62:
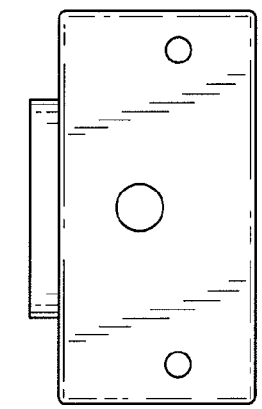
FIGS. 60-65 show various views of the top connector of FIG. 58.
Figure 65:
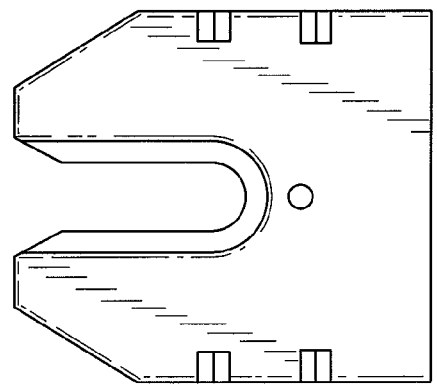
Figure 61:
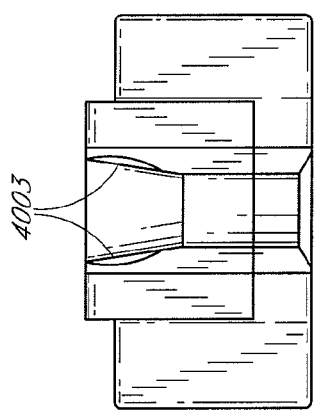
Figure 64:
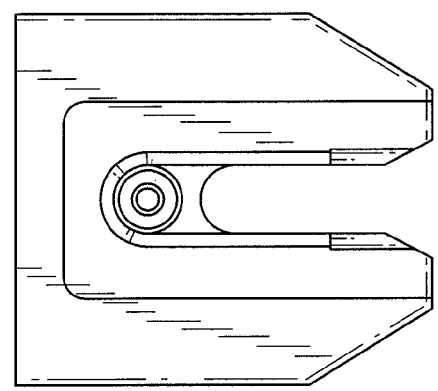
Figure 60:
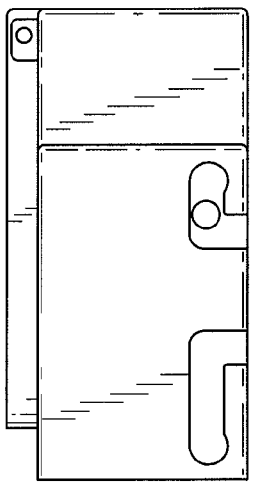
Figure 63:
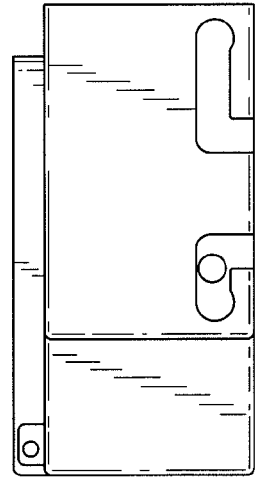

FIG. 58 is a perspective view of the top connector 3916 which includes a base member 4002 and a cassette 4004 in an engaged configuration. FIG. 59 is an exploded perspective view of the top connector 3916 with the base member and cassette 4004 in a disengaged configuration. FIG. 60 is a right-side view of the top connector 3916. FIG. 61 is a front view of the top connector 3916. FIG. 62 is a back view of the top connector 3916. FIG. 63 is a left-side view of the top connector 3916. FIG. 64 is a top-down view of the top connector 3916. FIG. 65 is a bottom-up view of the top connector 3916. FIG. 60 is a right-side view of the top connector 3916. FIG. 60 is a right-side view of the top connector 3916. FIG. 61 is a front view of the top connector 3916. FIG. 62 is a back view of the top connector 3916. FIG. 63 is a left-side view of the top connector 3916. FIG. 64 is a top-down view of the top connector 3916. FIG. 65 is a bottom-up view of the top connector 3916.

Figure 68:
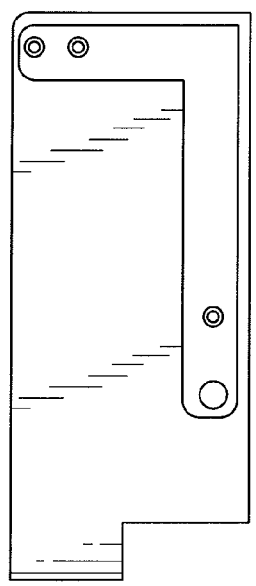
FIGS. 66-71 show various views of the cassette of the top connector of FIG. 58.
Figure 71:
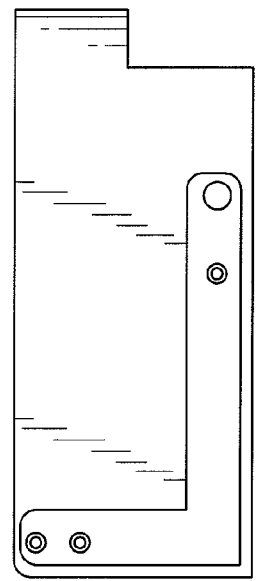
Figure 67:
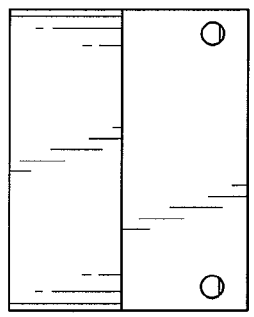
Figure 70:
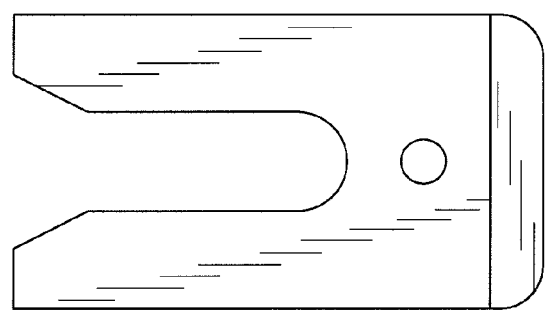
Figure 66:
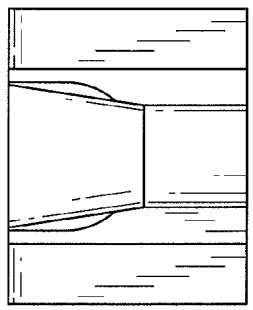
Figure 69:
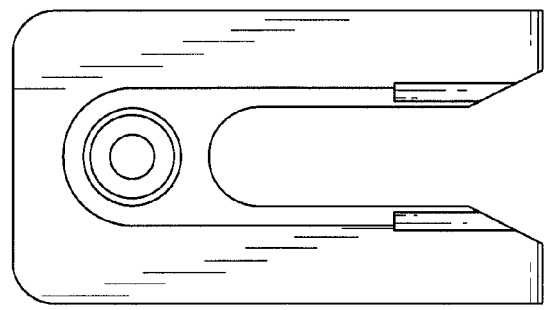

FIG. 66 is a front view of the cassette 4004. FIG. 67 is a back view of the cassette 4004. FIG. 68 is a right-side view of the cassette 4004. FIG. 69 is a top-down view of the cassette 4004. FIG. 70 is a bottom-up view of the cassette 4004. FIG. 71 is a left-side view of the cassette 4004.

Figure 74:
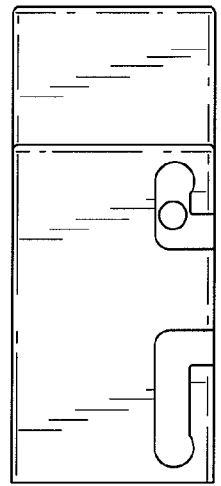
FIGS. 72-77 show various views of the base member of the top connector of FIG. 58.
Figure 73:
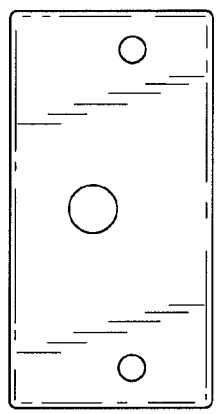
Figure 72:
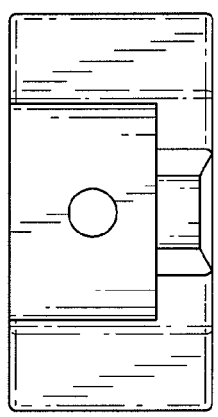
Figure 77:
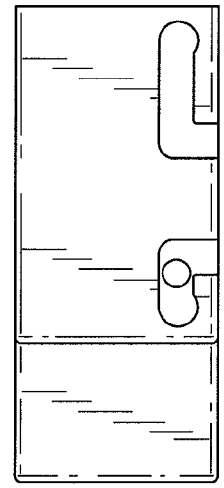
Figure 76:
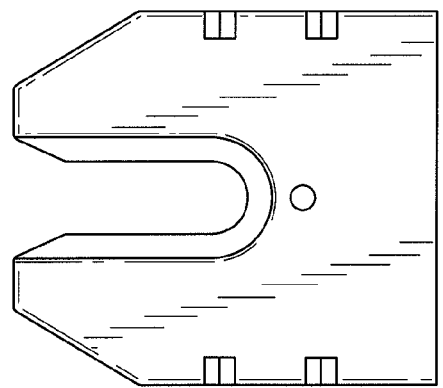
Figure 75:
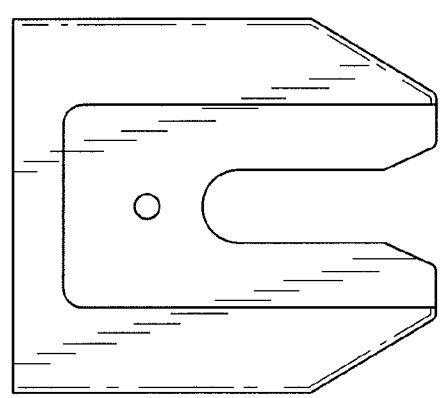

FIG. 72 is a front view of the base member 4002. FIG. 73 is a back view of the base member 4002. FIG. 74 is a right-side view of the base member 4002. FIG. 75 is a top-down view of the base member 4002. FIG. 76 is a bottom-up view of the base member 4002. FIG. 77 is a left-view of the base member 4002.

The top connector 3916 can have features that are similar to, or the same as, the top connector 1900, or any other suitable top connector discussed herein. For example, the top connector can include a light source and sensor to detect an air bubble in the connector 3910, which can be an indication that the vial 3907 is empty. In some instances, infrared light can be used to detect the presence of air in the connector 3910. For example, in some embodiments, light having a wavelength of at least about 980 nanometers and/or no more than about 1180 nanometers, or of at least about 1050 nanometers and/or no more than about 1110 nanometers, or of approximately 1080 nanometers can be effective for detecting air in the connector 3910. Other wavelengths of light can also be used, such as light having a wavelength of at least about 850 nanometers and/or no more than about 1050 nanometers, or of at least about 920 nanometers and/or no more than about 980 nanometers, or of approximately 950 nanometers. Light can be used that has a wavelength of at least about 1380 nanometers and/or no more than about 1580 nanometers, at least about 1450 nanometers and/or no more than about 1510 nanometers, or about 1480 nanometers. One suitable optical sensor that can be used is the DL20JJ 1480 nm sensor available from STM Sensor Technologie Munchen GmbH of Germany. Light can be directed between hole 4006*a* and hole 4006*b* (hidden from view). The sensor region 3974 of the connector 3910 can be positioned between hole 4006*a* and hole 4006*b* when it is properly attached to the top connector 3916.

In various embodiments disclosed herein which use a light source and a light sensor (e.g., to detect air or to detect the presence of an IV bag), the light source can pulse or flash at a predetermined frequency, and the light sensor can be configured to synchronize with the pulsing light source. In some embodiments, the light sensor can be configured to ignore light that is not pulsed at the predetermined frequency. Thus, the light sensor can differentiate between light emitted by the corresponding light sensor (which is pulsed at the predetermined frequency) and light emitted from other sources (e.g., light from a different sensor that is pulsed at a different frequency, or ambient light). In some embodiments, light sources can used that provide a constant beam of light.

Figure 78:
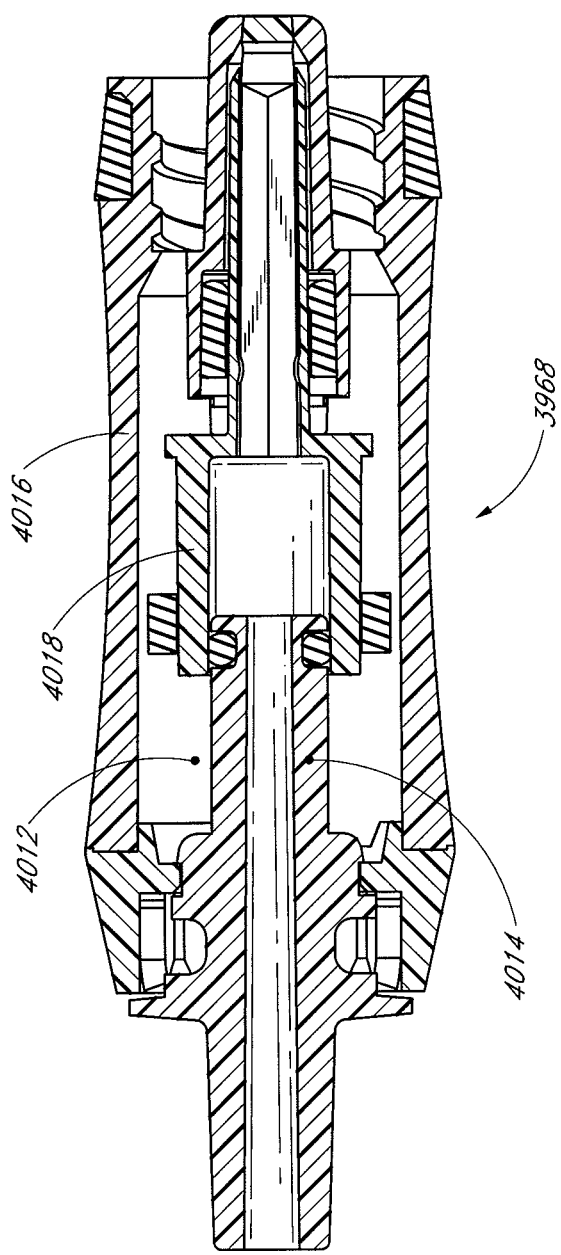
FIG. 78 is a cross sectional view of the second male connector of the connector of FIG. 44.

The top connector 3916 can also include a light source and sensor configured to detect whether an IV bag assembly 3914 is attached to the connector 3910. Light can be directed from hole 4008*a* to hole 4008*b* (hidden from view) and can intersect the second male connector 3968 at a location that is not obstructed when the second male connector 3968 is closed (when no IV bag is attached) and is obstructed when the second male connector 3968 is open (when an IV bag is attached). For example the location where the light intersects the second male connector 3968 can be the location 4012 shown in FIG. 78. FIG. 78 is a cross sectional view of the second male connector 3968 in the closed configuration, with no IV bag assembly attached thereto. The light can pass through the clear housing 4016 unobstructed when the second male connector 3968 is in the open configuration. When the light reaches the corresponding detector, a signal can be generated that indicates that no IV bag is attached to the second male connector 3968. When the valve member 4018 of the second male connector 3968 is pushed back to the open configuration (when the IV bag is attached), the opaque valve member 4018 is positioned to occupy the location 4012 and obstruct the light from reaching the corresponding detector. When no light reaches the detector, a signal can be generated that indicates that the second male connector 3968 is in the open configuration and the IV bag assembly 3914 is attached.

One suitable optical sensor that can be used with some embodiments for detecting the presence of IV bag or other target container is the DL20RM 645 nm sensor available from STM Sensor Technologie Munchen GmbH of Germany. In some embodiments, an amplifier can be used to amplify the signal of the light detector so that a relatively small amount of light can trigger the sensor. Thus, the amplifier can allow the sensor to accurately identify a closed valve member 4018 in the second male connector 3968 even when a portion of the light is reflected or refracted or otherwise redirected away from the light detector. One suitable amplifier that can be used is the V8-C or V8-D amplifier available from STM Sensor Technolgie Munchen GmbH of Germany.

The top connector 3916 can also include a light source and detector configured to detect the presence of the second male connector 3968 regardless of whether it is open or closed. Light can be directed between hole 4010a to hole 4010b which is aligned with an opaque portion of the second male connector 3968, e.g., at location 4014 as shown in FIG. 78. When light passes unobstructed between hole 4010a and hole 4010b (hidden from view) the detector can generate a signal indicating that the connector 3910 (of which the second male connector 3968 is a part) is not present. When the light is obstructed by the plunger at location 4014 and does not reach the detector, a signal can be generated that indicates that the second male connector 3968, and the rest of the connector 3910 is present.

In some embodiments, the two optical sensors can both function to detect whether an IV bag is attached. As further described below, if the light from one of the optical sensors is unintentionally blocked from reaching the corresponding light detector when the valve member is closed and no IV bag is present, the light from the other optical sensor can reach the corresponding light detector to provide an indication that the valve member is closed.

FIG. 79 is a perspective view showing the top connector 3916 cut to reveal the inner channels used to route wires for the light sources and detectors described above. FIG. 80 is a perspective view showing the top connector 3916 cut along a different axis to further reveal the channels used to route wires. Wires can pass from the main housing 3902 to the top connector 3916 via the hole 4020. The wires can then enter the channel 4016 which leads to the holes 4006a-b. As seen in FIG. 80, the channels 4016 turn upward and lead to the holes 4008a-b and the holes 4010a-b.

In some embodiments, the cassette 4004 can be shaped or otherwise configured to be compatible with only authorized connectors 3910. For example, as can best be seen in FIG. 61 (front view of the top connector 3916), the side walls 4003 of the cassette 4004 are slanted. The slanted side walls can correspond to the slanted side walls of the lower housing portion 3962 of the connector 3910. When an authorized connector 3910 specifically designed for use with the fluid transfer system 3900 is attached to the top connector 3916, the tapered walls can fit snuggly to properly position the connector 3910. If an unauthorized connector of different size or shape were to be connected to the top connector, it would not fit properly with the top connector 3016. The tapered walls can reliably position the connector 3910 with little or no freedom of movement in the vertical direction when the connector 3910 is attached to the top connector 3916. The side walls can also restrict the freedom of movement of the connector along a horizontal direction that intersects the side walls.

It can be beneficial to limit the connectors that can be used with the system 3900 to ensure accurate and reliable transfer of fluid. For example, as discussed below, in some embodiments, the proper priming of the connector 3910 relies in part on the internal volume of the connector 3910. Thus, if a different connector 3910 having a different internal volume were used, the system 3900 may improperly prime the connector 3910.

Figure 82:
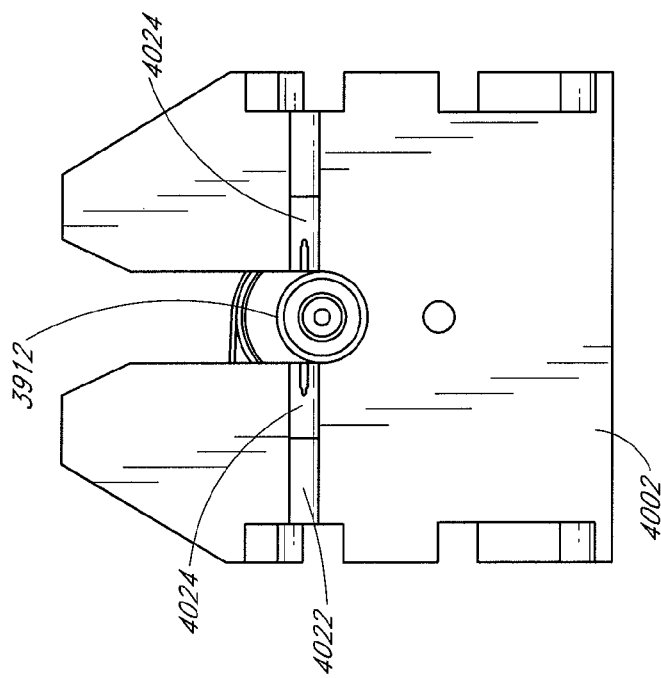
FIG. 82 is a top-down view of the top connector and syringe of FIG. 81.
Figure 81:
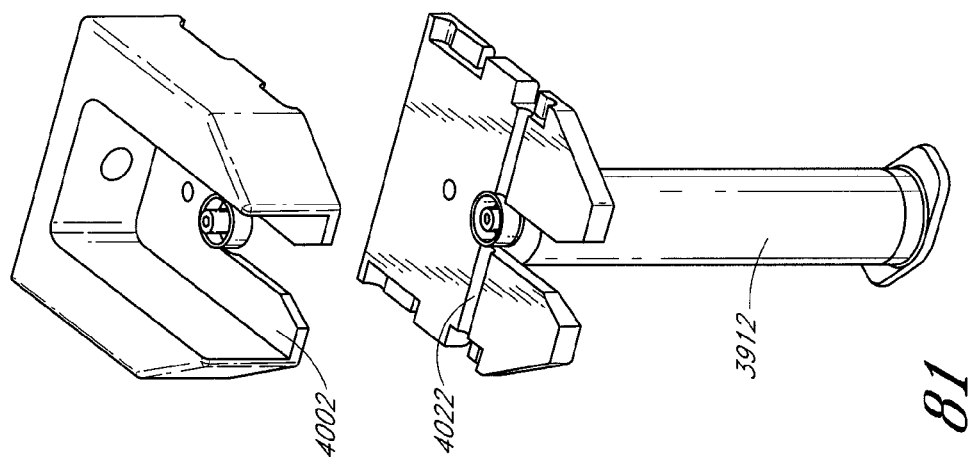

In some embodiments, the top connector 3916 can be configured to hold the fluidics assembly 3906 in place using a securing mechanism. FIG. 81 is a perspective view of the base member 4002 of the top connector 3916 and the syringe 3912 cut and separated to reveal a channel 4022. FIG. 82 is a top-down view taken at the cutting plane of FIG. 81. The channel 4022 can be positioned such that when the syringe 3912 is fully attached to the top connector 3916, the central axis of the syringe 3912 is positioned slightly past the central axis through the channel 4022. As shown in FIG. 82, one or more securing mechanisms 4024 can be positioned in the channel 4022. In their relaxed position, the securing mechanisms 4024 can protrude partially past the channel 4022 and into the space shown occupied by the syringe 3912. The securing mechanisms 4024 can be resiliently movable along the axis down the channel 4022. As the syringe 3912 is slid into the top connector 3916, the outer walls of the syringe 3912 contact the securing mechanisms 4024 and displace them into the channel 4022. Once the widest portion of the syringe 3912 clears the securing mechanisms 4024, the securing mechanisms 4024 return at least partially to their previous position, thereby securing the syringe 3912, and the rest of the fluidics assembly 3906 in place. The securing mechanisms 4024 can attach the fluidics assembly 3906 to the top connector 3916 with little or no freedom of movement in the horizontal direction that is substantially perpendicular to the channel 4022. By restricting the freedom of movement of the connector 3910, the connector 3910 can reliably be aligned with respect to the optical sensors when it is attached to the top connector 3916.

Figure 83:
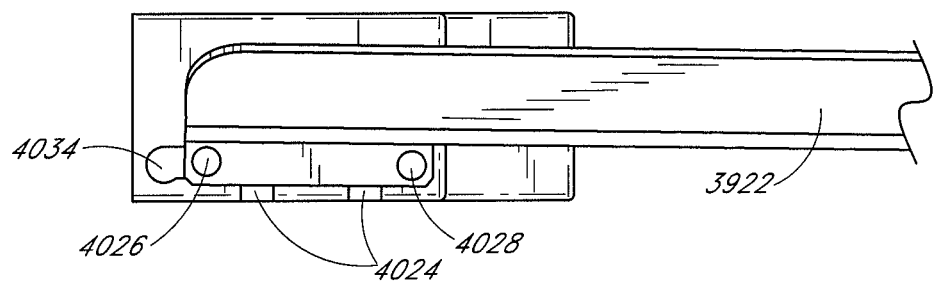
FIG. 83 is a side view of a tray attached to the top connector.
Figure 84:
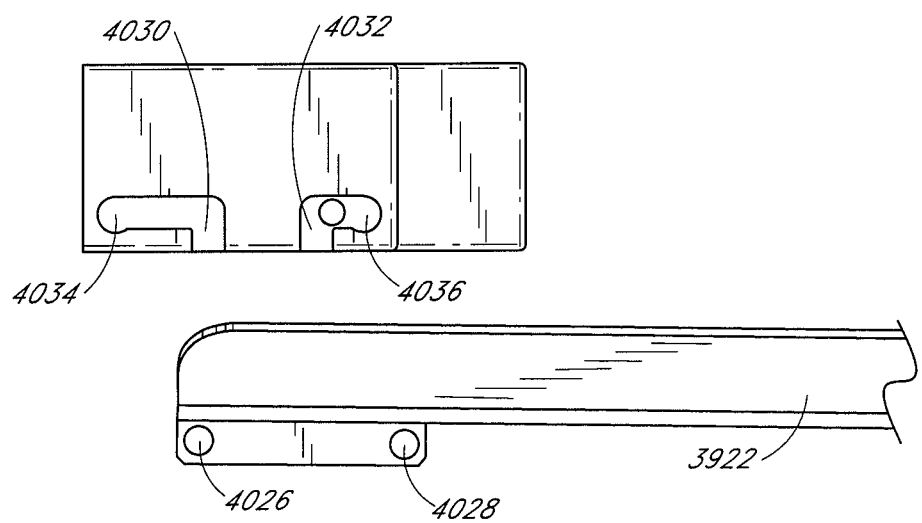
FIG. 84 is a side view of the tray and top connector in a disengaged configuration.

In some embodiments, the tray 3922 can be positioned as shown in FIG. 39 when in use and can be pivoted downward when not in use. The base member 4002 can be configured to facilitate the pivoting of the tray 3922. FIG. 83 is a right-side view of the base member 4002 with the tray 3922 attached thereto. FIG. 84 is a right-side view of the base member 4002 and the tray 3922 in a disengaged configuration. The tray 3922 can have a rear connector 4026 and a front connector 4028. The base member 4002 can include a rear connection slot 4030 that turns rearward and a front connection slot 4032 that turn forward. It will be understood that the other side of the tray 3922 and base member 4002 can be symmetrical or similarly configured. To attach the tray 3922 to the base member 4002, the rear connector 4026 can be inserted into the read connection slot 4030 until the rear connector 4026 reaches the rear depression 4034. At this point the tray 3922 can hand from the top connector base member 4002 in the pivoted-down, unused position. The tray 3922 can be pivoted up until the forward connector 4028 enters the forward connection slot 4032, and the tray can be shifted forward to the in-use position shown in FIG. 83 where the forward connector 4028 engages the forward depression 4036.

Figure 85:
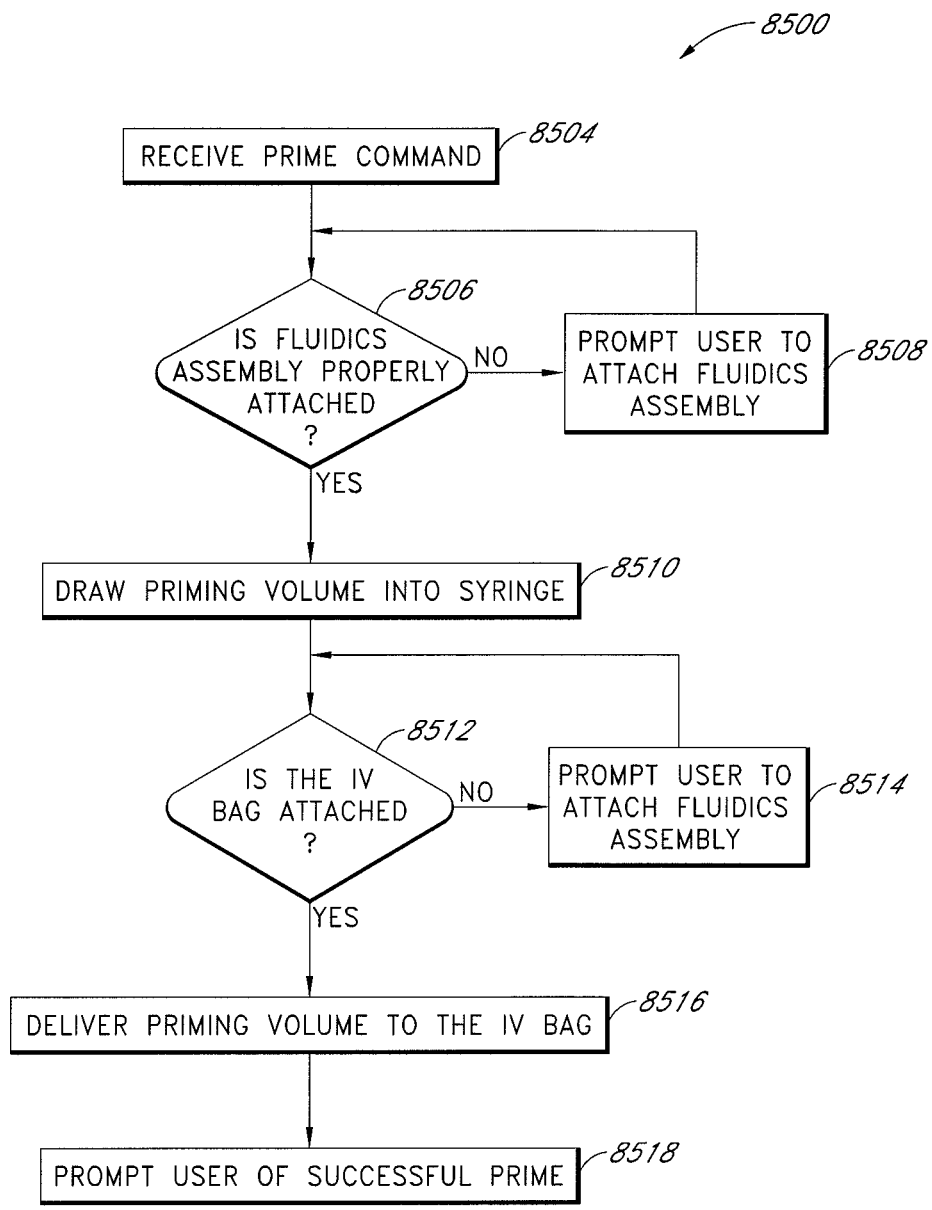
FIG. 85 is a flowchart showing an embodiment for priming the fluidics assembly of FIG. 40.

In some embodiments, the system 3900 (or other systems described herein) can prime the fluidics assembly 3906 before the desired volume of fluid is transferred from the vial 3907 to the IV bag 3980. When the user first assemblies the fluidics assembly, the internal volumes contain air. FIG. 85 is flowchart that schematically shows an example embodiment of a method 8500 for priming a fluidics assembly.

At block 8504 a prime command is received. In some embodiments, the user can initiate the prime by providing an instruction to the system 3900 to prime the fluidics assembly. In some embodiments, the system 3900 can ask the user (via a user interface) whether the fluidics assembly should be primed. In some embodiments, the system can recognize when a new fluidics assembly has been attached to the system. For example the sensor that detects the presence of the second male connector can indicate when a fluids assembly was added to the system. Also, in some embodiments, other sensors can be used. The sensor for detecting air in the connector can also be configured to recognize whether the connector itself is present in the light path. Other sensor types are also possible. For example the securing mechanisms discussed above can include a sensor for detecting whether they are displaced, indicate that the connector is present. In some embodiments, the sensor that is used to detect air for determining whether vial has run empty can also be used to indicate whether the connector has already been primed by determining whether air is present in the connector. Thus, the system can be configured to determine when to automatically prime the fluidics assembly and when to prompt the user to decide whether to prime.

At block 8506 the method determines whether the fluidics assembly is properly attached. For example, the sensors discussed above can be used to determine whether the fluidics assembly is present and whether a prime is needed. In some embodiments, this step is performed before block 8504, as discussed above. If the fluidics assembly is not properly attached, block 8508 can inform the user to attach or correct the fluidics assembly. If the fluidics assembly is properly attached, the method 8500 advances to block 8510.

At block 8510, the syringe plunger is withdrawn by the distance necessary to draw the priming volume into the syringe. The system can ignore the signal from the air detector when priming the fluidics assembly. Normally, the air detector can be used to prevent air from being drawn into the syringe. However, during the priming process, air can be drawn into the syringe before the fluid reaches the syringe.

In some embodiments, the priming volume is the volume of the fluidics assembly between (and excluding) the vial and the IV bag assembly when the syringe plunger is fully advanced. The priming volume can be the volume of air in the fluidics assembly that needs to be pushed into the IV bag in order to bring the leading edge of fluid up to the entrance to the IV bag, which may be the end of a connector attached to the bag via a length of tubing. Thus, using the system 3900 as an example, the priming volume can, for example, be equal to the internal volume of the vial adapter 3908, plus the internal volume of the connector 3910 (which includes the internal volume of the both male connectors 3964, 3968, the internal volume in the internal chamber with the check valves, and the internal volume of the syringe interface that is not occupied by the syringe). In some embodiments, the internal volume of the IV bag assembly is excluded from the priming volume. However, in some embodiments the internal volume of the female connector 3984 and the tubing 3982 and any other portions of the IV bag assembly other than the IV bag itself are included. This can be useful if the parts of the IV bag assembly need to be replaced or removed prior to patient delivery. In some embodiments, the priming volume can include a portion of the syringe's internal volume, such as the internal volume of the syringe tip above the plunger's end. In some embodiments, the vial adapter can be self priming, in which case, the internal volume of the vial adapter can be excluded from the priming volume. For example, in some embodiments, the air in the fluid pathway of the vial can rise up into the vial such that the fluid from the vial advances to the end of the female connector of the vial adapter.

In some embodiments, the system 3900 can calculate the priming volume based on information acquired from the user or from sensors or otherwise. For example, the priming volume may vary depending on the model of vial adapter that is used or the model of syringe being used. The system 3900 can prompt the user for information to be used for calculating the priming volume. In some embodiments, the priming volume can be a predetermined amount. For example, the priming volume can about 0.7 milliliters.

At 8512 the system determines whether the IV bag is attached, for example. If the IV bag is not attached properly, the system prompts the user to properly attached the IV bag at 8514. If the IV bag is attached, the method 8500 advances to Block 8516. At 8516, the syringe drive the priming volume into the connector, through the second male connector, and into the IV bag assembly. In some embodiments, the priming volume that is drawn into and expelled from the syringe contains both air and fluid. If calculated and executed properly, in some embodiments, the leading edge of the fluid from the vial will be positioned at the entrance to the IV bag assembly, or in some cases at the entrance to the IV bag itself. At block 8518 the method can optionally prompt the user that the fluidics assembly was successfully primed.

The method 8500 can be varied in many ways. For example, the checks at blocks 8506 and 8512 can be omitted or performed together or performed before block 8504. In some embodiments, the system does not perform a separate priming procedure. Instead the system can merely add the priming volume to the first volume of fluid that is transferred through the fluidics assembly.

Figure 86:
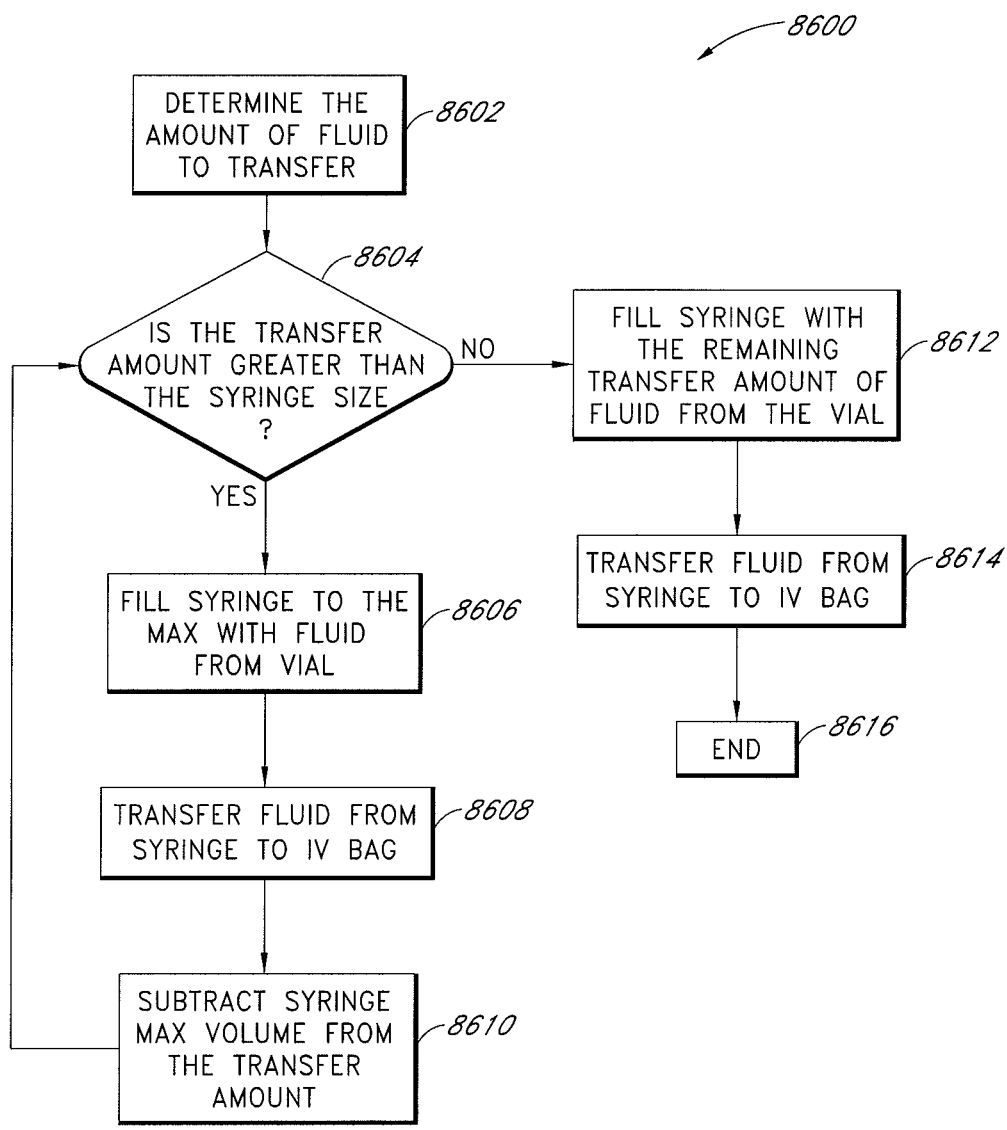
FIG. 86 is a flowchart showing an embodiment for transfer fluid.

FIG. 86 is a flowchart schematically showing a sample embodiment of a method 8600 for transferring fluid from a vial to an IV bag. This method can be similar in some ways to the method 2400 discussed above. At block 8602, the amount of fluid to be transferred is determined. At block 8604, the system determines whether the amount remaining to be transferred is greater than the maximum volume that can be transferred by the syringe. If that remaining volume to be transferred is larger than the maximum volume of the syringe, the method proceeds to block 8606 where the system fills the syringe with the maximum syringe fluid volume. As fluid is drawn into the syringe, the air detector monitors for the presence of air in the connector, as will be discussed in greater detail in connection with FIG. 87.

At block 8608, the fluid is transferred from the syringe into the IV bag. In some embodiments the system can first perform a check to ensure that the IV bag is properly attached before advancing the plunger of the syringe. At block 8610, the maximum volume of the syringe is subtracted from the volume to be transferred, and the process returns to Block 8604.

Once the amount of volume to be transferred is less than the maximum volume of the syringe, the process advances to block 8612 where the system fills the syringe with the remaining amount of volume to be transferred. Again, while the fluid is drawn into the syringe, the air detector monitors for the presence of air in the connector, as will be discussed in greater detail in connection with FIG. 87. At block 8614 the fluid is driven from the syringe into the IV bag. In some embodiments, the system can perform a check to ensure that the IV bag is properly attached before pushing fluid into the IV bag. The process then ends at block 8616.

Figure 87:
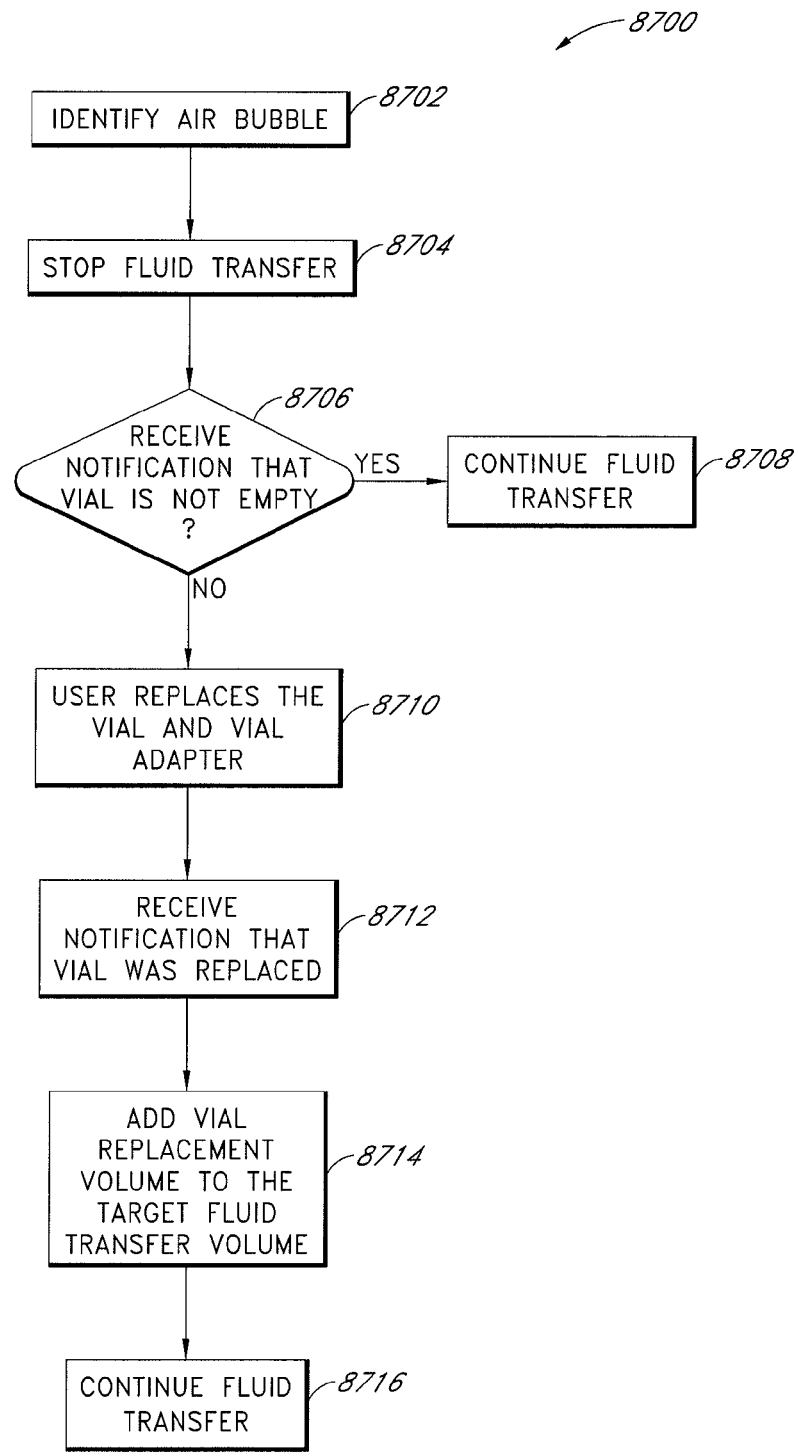
FIG. 87 is a flowchart showing an example embodiment for replacing a vial during the transfer of fluid.

FIG. 87 is a flowchart that schematically illustrates an example embodiment of a method for replacing a vial of fluid to be transferred. At block 8702, the air detector identifies air in the connector, and at block 8704 the system stops the transfer of fluid. In some embodiments, the system can prompt the user that air was detected and ask the user to check the vial. In some embodiments, the user interface can allow the user to indicate that the vial is not yet empty, in which case, the detected air was likely merely a small bubble. If the system receives notification that the vial is not empty at block 8706, the process will then continue transferring the fluid at block 8708.

If the vial was indeed empty, the user can replace the vial and the corresponding vial adapter. In some embodiments, the user can press a button or otherwise indicate that the vial has been replaced. Once notification is received that the vial has been replaced at block 8712, the system then adds a replacement volume amount to the target fluid transfer amount to compensate for the volume of air that was drawn from the vial before the air was detected. In some embodiments, the vial replacement volume can be substantially equal to the internal volume of the flow path through the vial adapter, through the first male connector, and through the portion of the connector that is on the syringe side of the target check valve and before the sensing location where the air was detected. In some embodiments, the volume of the flow path through the new vial adapter should also be added to the vial replacement volume since the air in the new vial adapter will also be drawn into the syringe and then pushed to the IV bag. As discussed above, variations are possible. For example, for a self priming vial adapter, the volume for the replacement vial adapter does not need to be included. In some embodiments, the vial replacement volume can be 0.3 milliliters.

At block 8716 the method continues with the fluid transfer process. In some embodiments, the system can ignore air detected in the connector for a short time after the vial is replaced. In some embodiments, after the vial replacement volume has been added to the total transfer volume, the system can reevaluate whether an additional syringe draw will be needed to reach the desired total fluid transfer amount.

Figure 88:
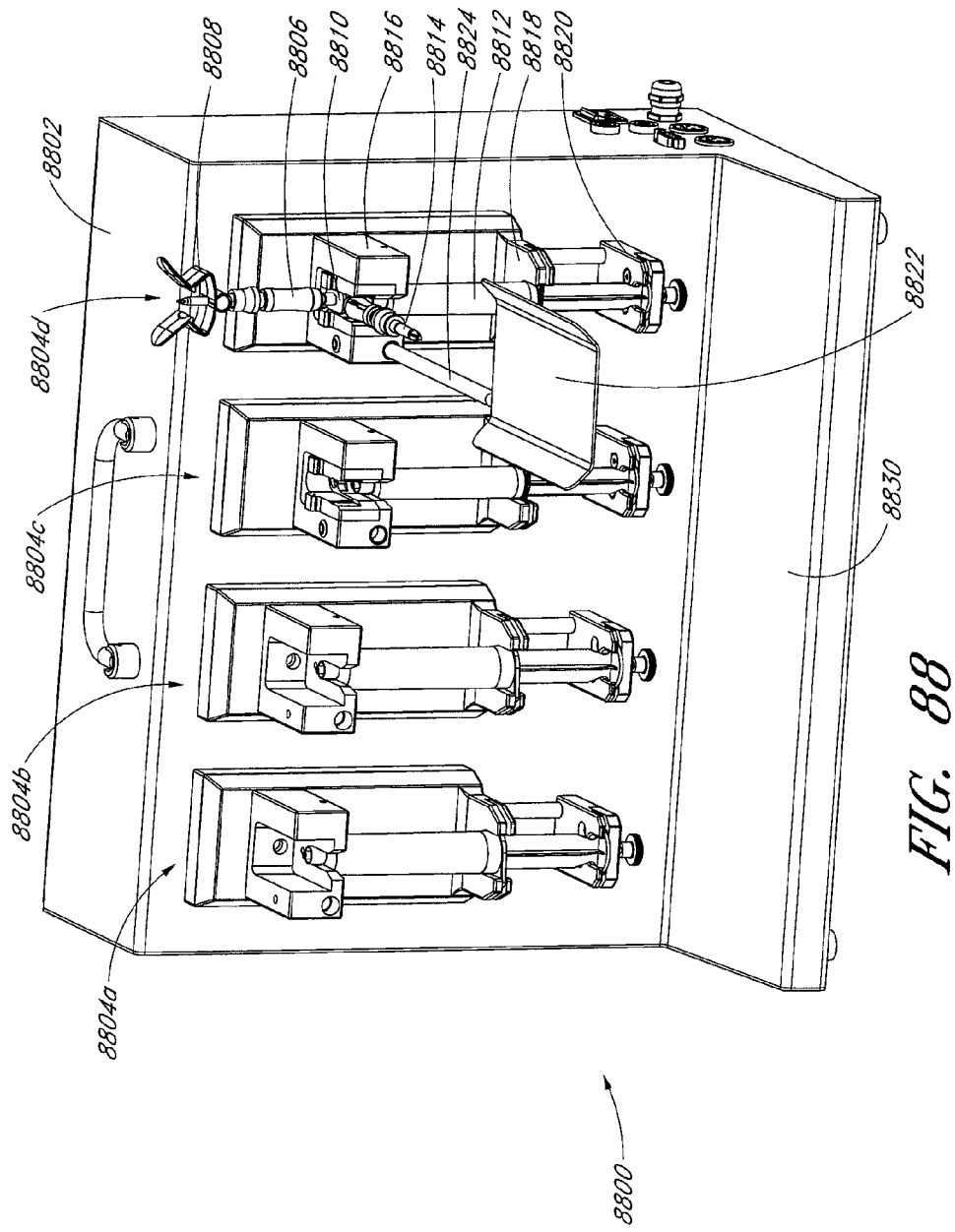
FIG. 88 is a perspective view of another example embodiment of a system for transferring fluid.

FIG. 88 is a perspective view of another example embodiment of a fluid transfer system 8800. The fluid transfer station 8800 can be similar to, or the same as, fluid transfer systems 3900, 100, or 600 or any other fluid transfer system discussed herein. Thus, the discussion associated with many features of other fluid transfer systems described herein is also applicable to the fluid transfer system 8800, even when not specifically identified.

The fluid transfer system 8800 can include a main housing 8802 that supports four fluid transfer stations 8804*a-d*, although any other suitable number of fluid transfer stations can be used. In the illustrated embodiment, the fluid transfer stations 8804*a-b* are configured to receive larger syringes than the fluid transfer stations 8804*c-d*. For example, fluid transfer stations 8804*a-b* can be configured to use 20 milliliter syringes and fluid transfer stations 8804*c-d* can be configured to use 10 milliliter syringes, although other sizes of syringes can also be used. In some embodiments, a larger syringe (e.g., 20 milliliters) can allow fluid to be transferred from the source container to the target container at a faster rate, while a smaller syringe (e.g., 10 milliliters) can allow fluid to be transferred from the source container to the target container with greater precision. It will be understood that the fluid transfer stations 8804*a-d* can be configured to use various other syringe sizes, such as syringes of sizes between about 1 milliliter and about 100 milliliters or even syringes outside these ranges.

The fluid transfer station 8804*d* is shown as having a fluidics assembly 8806 attached thereto. The fluidics assembly can include a vial (not shown in FIG. 88), a vial adapter 8808, a connector 8810, a syringe 8812, and an IV bag assembly 8814 (partially shown in FIG. 88), which can be similar to, or the same as, the corresponding components discussed in connection with the embodiment shown in FIG. 39, or any other embodiments disclosed herein. The transfer station 8804*d* can be configured to receive the syringe 8812 and/or the connector 8810 using, for example, a top connector 8816, a middle connector 8818, and a lower connector end piece 8820. A motor (hidden from view in FIG. 88) can cause the lower connector 8820 to move to withdraw and advance the plunger of the syringe 8812. As discussed above, the motor can be a high precision stepping motor.

The fluid transfer station 8804*d* can include a tray 8822 to support the IV bag (not shown in FIG. 88). The tray 8822 can be attached to the top connector 8816 by a tray arm 8824 as will be discussed in greater detail below. The housing 8802 can include a step or foot 8830 positioned at the base thereof to provide increased stability to the housing 8802, for example to prevent the weight of the IV bags from tipping the housing 8802 forward.

Figure 89:
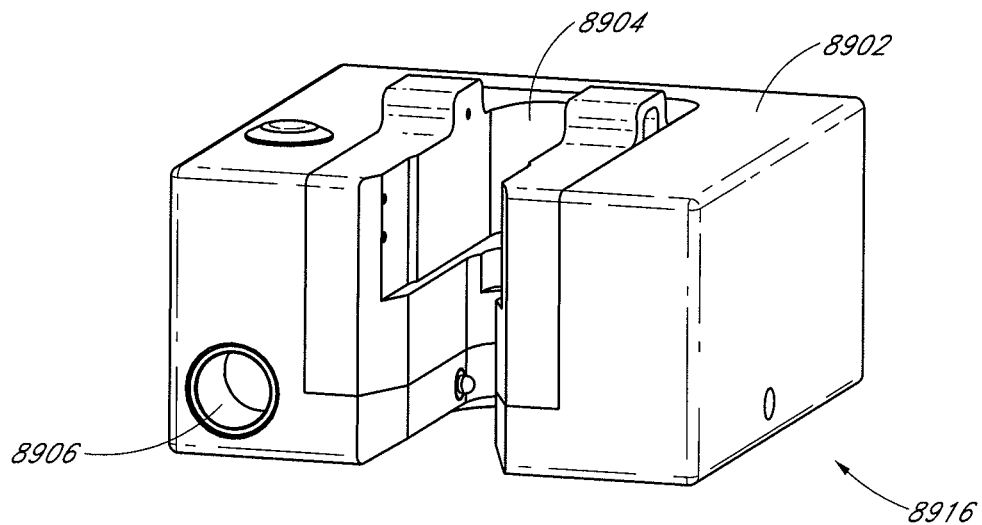
FIG. 89 is a perspective view of a top connector from a fluid transfer station of the system of FIG. 88.
Figure 90:
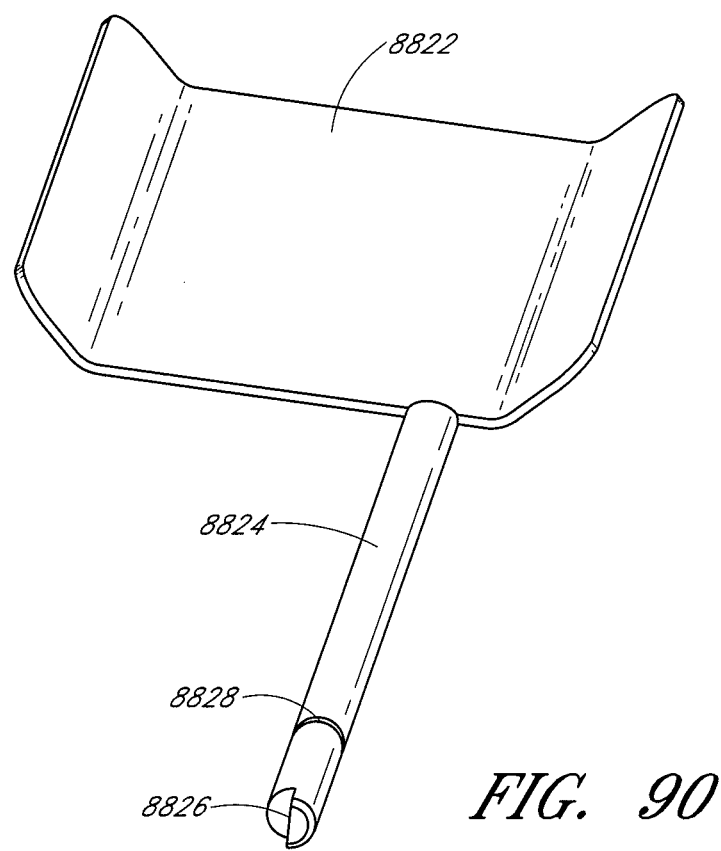
FIG. 90 is a perspective view of the tray associated with the top connector of FIG. 89.

FIG. 89 is a perspective view of the top connector piece 8816. The top connector piece can be similar to, or the same as the top connector pieces 3916 or 1900 or any other top connector piece described herein. The top connector 8816 can include a base member 8902 and a removable cassette 8904. The base member 8902 can include a tray hole 8906 that is configured to receive the tray arm 8824 therein. The tray hole 8906 can be positioned near a side edge of the base member 8902 and the tray arm 8824 can similarly be attached near a side edge of the tray 8822 (as seen in FIG. 90). Thus, the tray 8822 can be positioned substantially centered in front of the top connector 8816 while the tray arm 8824 is offset to the side so that the tray arm 8824 does not interfere with the attaching and detaching of the IV bag assembly.

With further reference to FIG. 90, the tray arm can have a substantially circular cross-sectional shape, or can otherwise be configured to allow the tray arm 8824 to rotate within the tray hole 8906. The tray arm 8824 can include a notch 8826 formed in the end opposite the tray 8822. The tray arm 8824 can also include a groove 8828 that extends around all or part of the circumference of the tray arm 8824.

Figure 91:
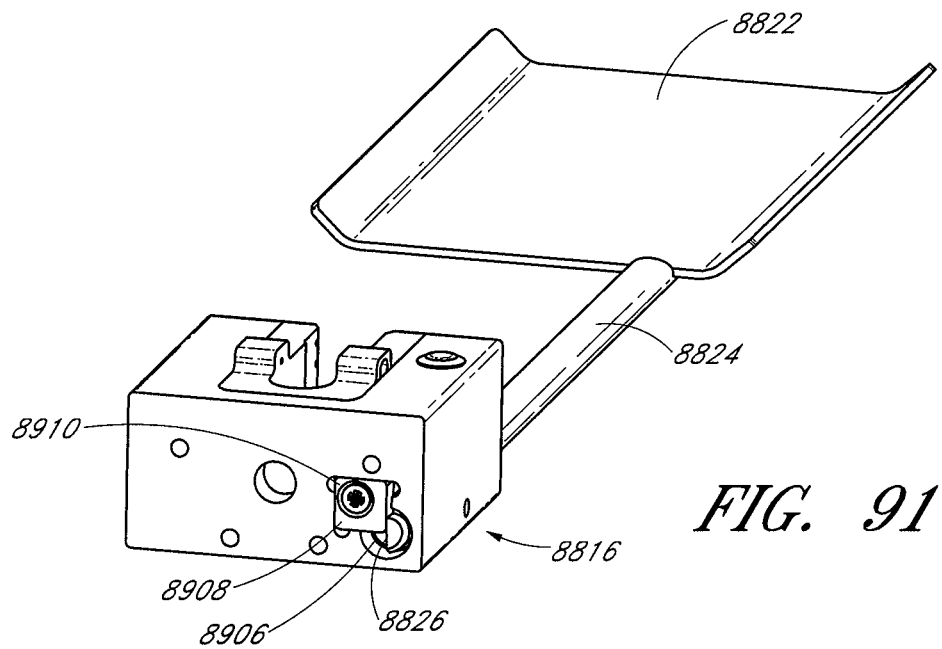
FIG. 91 is a perspective view of the top connector of FIG. 89 with the tray attached thereto in a first configuration.
Figure 92:
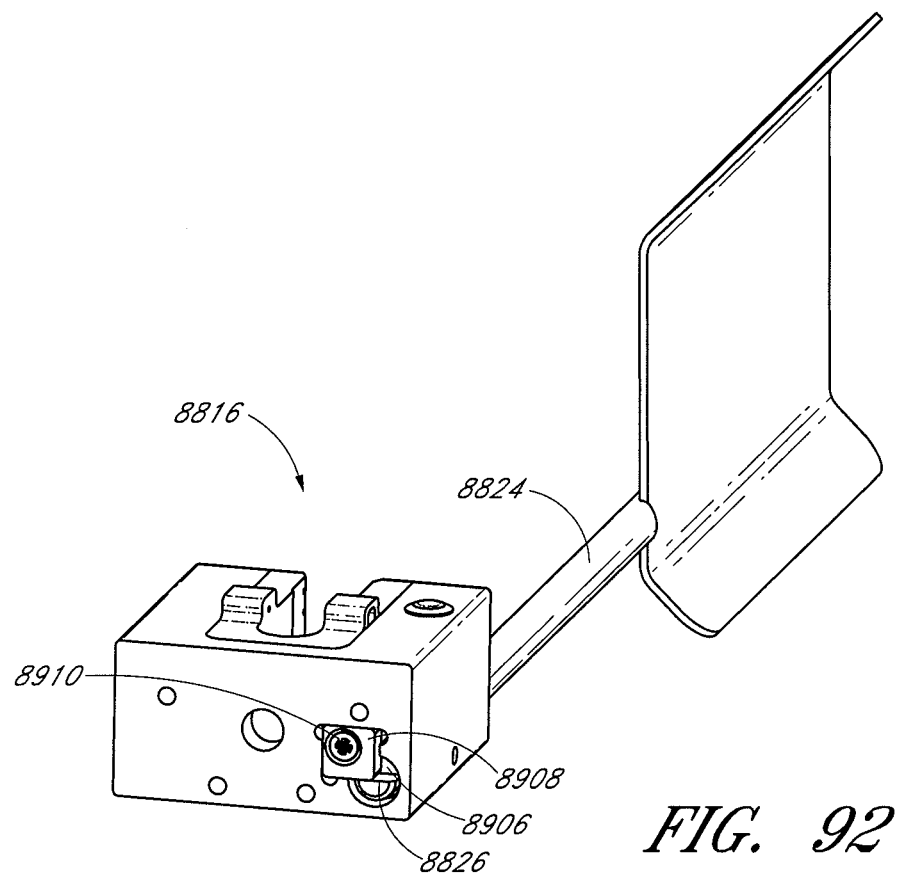
FIG. 92 is a perspective view of the top connector of FIG. 89 with the tray attached thereto in a second configuration.

FIG. 91 shows a rear perspective view of the top connector 8816 with the tray 8822 attached thereto in a first configuration wherein the tray 8822 is positioned to support an IV bag. FIG. 92 shows another rear perspective view of the top connector 8816 with the tray 8822 attached thereto in a second configuration wherein the tray 8822 is pivoted by about 90° to provide unobstructed access to the cassette 8904. The user can, for example, pivot the tray 8822 out of the way to the second configuration (shown in FIG. 92) when attaching the syringe 8812 and/or the connector 8810 to the fluid transfer station 8804*d*. Then the user can pivot the tray 8822 back to the first configuration (shown in FIG. 91) and place the IV bag onto the tray 8822.

The top connector 8816 can include a stop plate 8908, which can be positioned to occupy a portion of the tray hole 8906. The stop plate 8908 can be secured to the back surface of the base member 8902 using, for example, a screw 8910, and the back surface of the base member 8902 can have a recess shaped to receive the stop plate 8908 therein. The stop plate 8908 can have a thickness that is configured to fit into the notch 8826. When the tray 8822 is in the first configuration (shown in FIG. 91), the wall of the notch 8826 abuts against the side surface of the stop plate 8908 to prevent the tray 8822 from rotating past the first configuration. When the tray 8822 is rotated to the second configuration (shown in FIG. 92), the wall of the notch 8826 abuts against the bottom surface of the stop plate 8908 to prevent the tray 8822 from pivoting past the second configuration. In the illustrated embodiment, the stop plate 8908 is generally square shaped, such that the tray 8822 pivots by at least about 75° and/or no more than about 105°, or in some cases about 90° between the first configuration and the second configuration. The shape of the stop plate 8908 and/or the shape of the notch 8826 can be modified to change the rotational distance between the first and second tray configurations. For example, in some embodiments, the tray can pivot by about 180°, or by any angular distance, between the first and second configurations. Also, the notch and/or the stop 8826 plate 8908 can be moved or modified so that the tray 8822 rotates in the opposite direction of that shown in FIGS. 91-92.

Figure 93:
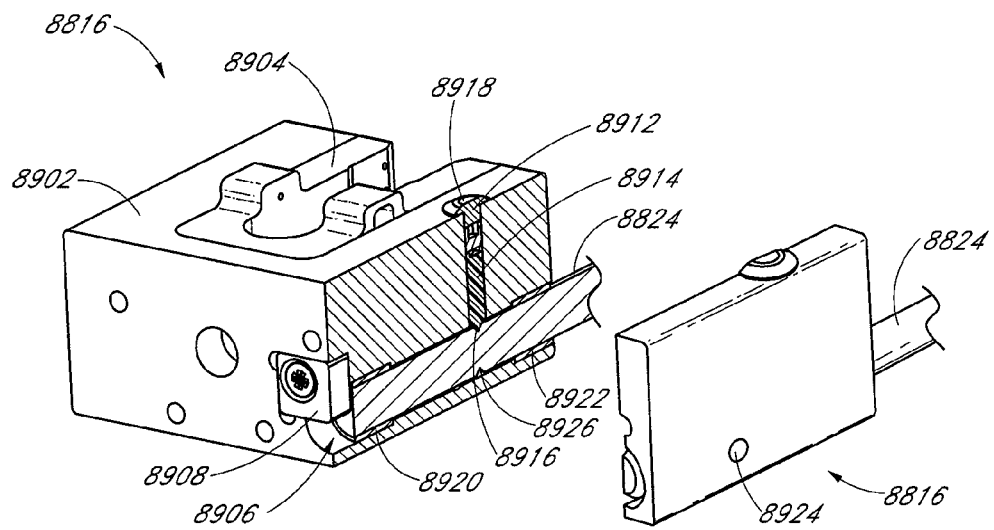
FIG. 93 is a split perspective view of the top connector of FIG. 89 and the tray.

FIG. 93 is a perspective view of the top connector 8816 and the tray arm 8824 cut along a vertical plane that intersects the axis of the tray hole 8906. A top hole 8912 can be formed in the base member 8902 and can intersect the tray hole 8906. When the tray arm 8824 is inserted into the tray hole 8906, the groove 8826 can align with the top hole 8912. A securing mechanism 8914 can be positioned in the top hole 8912 so that the securing mechanism 8914 can interface with the groove 8826 to secure the tray arm 8824 into the tray hole 8906. The securing mechanism 8914 can have a tip 8916 that is attached to a spring such that the tip 8916 can be axially displaced along the top hole 8912 in a direction away from the tray hole 8906 to compress the spring. When the tray arm 8824 is inserted into the tray hole 8906, the tray arm 8824 displaces the tip 8916 of the securing mechanism 8914 and compresses the spring. Once the tray arm 8824 is inserted far enough for the groove 8826 to align with the securing mechanism 8914, the tip 8916 can snap down into the groove 8826. Thus, the securing mechanism 8914 can prevent the tray arm 8824 from being accidentally removed from the tray hole 8806. To remove the tray arm 8824 from the tray hole 8906, the user can pull the tray arm 8824 with enough force to compress the spring the drive the tip 8916 out of the groove 8826. The groove 8826 can be V-shaped to facilitate the removal of the tray arm 8824.

Although not shown in the illustrated embodiment, the groove 8826 can include deepened portions that are configured to receive the tip 8916 when the tray 8822 is in the first configuration and in the second configuration, so that the tray 8822 can be "locked" into the first configuration or into the second configuration. To break the "lock" and allow the tray 8822 to pivot, the user can apply a rotational force that is sufficient to compress the spring and drive the tip 8916 out of the deepened portion of the groove 8826. In some embodiments, the groove 8826 can be omitted, and the tray arm 8824 can include two holes configured to receive the tip 8916 when in one of the first and second configurations.

With further reference to FIG. 93, a cap 8918 can be placed over the top opening of the top hole 8912 to prevent debris from entering the hole 8912. Two bushings 8920, 8922 can be positioned in the arm hole 8906, one near the stop plate 8908, and the other near the opening of the arm hole 8906. Other numbers of bushings can be used, or the bushings can be omitted. The bushings 8920, 8922 can be made from a compressible material and can have openings that are slightly smaller than the diameter of the tray arm 8824. Thus, the tray arm 8824 can compress the bushings 8920, 8922 as the tray arm 8824 is inserted into the tray hole 8906. The pressure applied to the tray arm 8824 by the bushings 8920, 8922 can provide additional stability to the tray 8824 to prevent rattling or accidental rotation.

Figure 94:
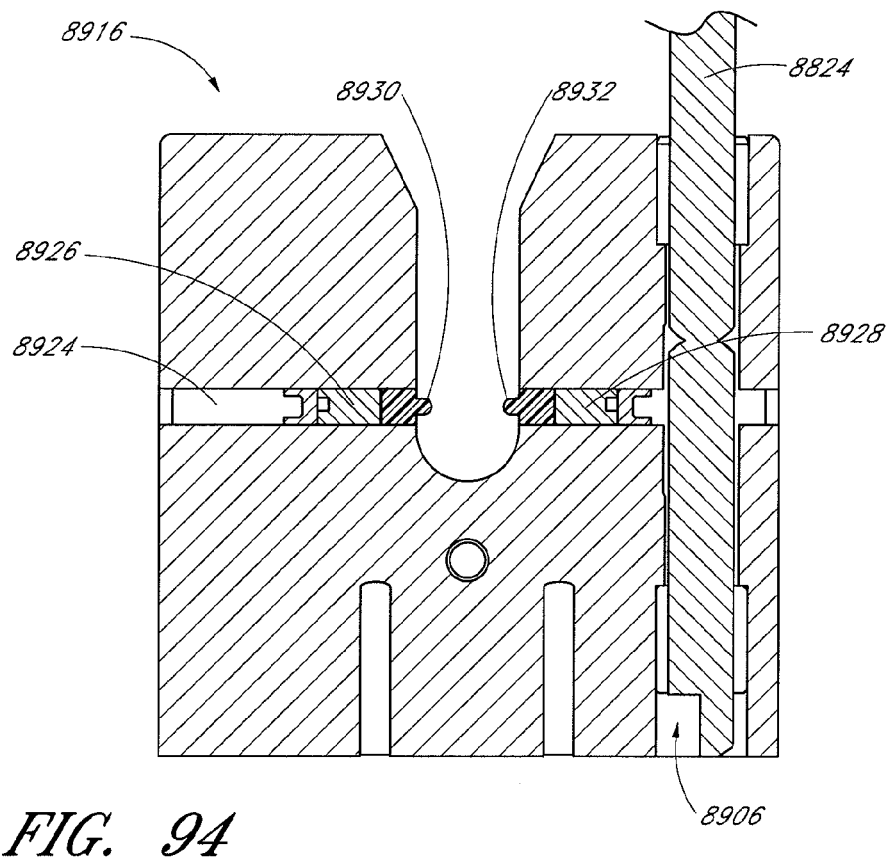
FIG. 94 is a cross sectional view of the top connector of FIG. 89 and the tray.

FIG. 94 is a cross sectional view of the top connector 8816 and tray arm 8824 taken along a horizontal plane that intersects the axis of the tray hole 8906. A channel 8824 can extend through the base member 8902, and securing mechanisms 8926, 8928 can be positioned in the channel 8924 so that the tips 8930, 8932 thereof extend out from the channel 8824. In the illustrated embodiment, the channel 8924 can intersect the tray hole 8906. As similarly discussed in connection with FIG. 82, when a syringe is attached to the top connector 8816, the syringe can displace the tips 8930, 8932 into the channel 8824 to compress the springs of the securing mechanisms 8826, 8828. Once the widest portion of the syringe passes the tips 8930, 8932, the springs can drive the tips 8930, 8932 toward each other to secure the syringe to the top connector 8816. Securing mechanisms can similarly be used to secure other portions of the fluidics assembly 8806 (e.g., the connector 8810, or vial adapter 8808) to the transfer station 8804*d*.

Figure 95:
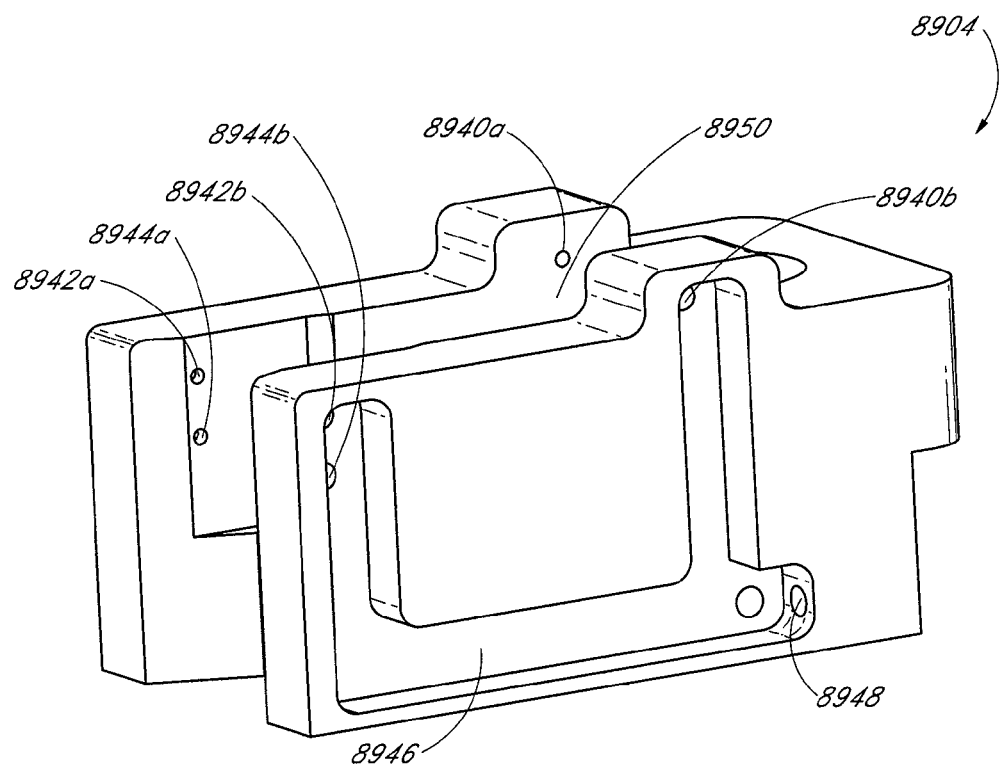
FIG. 95 is a perspective view of the cassette from the top connector of FIG. 89.

FIG. 95 is a perspective view of the cassette 8904, which can be similar to, or the same as, the cassette 4004, 1904, or any other suitable cassette described herein. The cassette 8904 can include holes 8940*a-b* that are configured to provide light path between a light source and a light sensor configured to detect air in the connector 8810. The cassette 8904 can also provide holes 8942*a-b* and holes 8944*a-b* to provide light paths between corresponding light sources and light detectors for detecting the presence of an IV bag assembly. The cassette 8904 can include channels 8946 configured to provide a path for wires to reach the light sources and light detectors. The wires can pass through a hole in the base member 8902 (not shown in FIG. 95) and through a hole 8948 that leads to the channels 8946. One channel can lead to the holes 8942*b* and 8944*b* used in detecting the presence of the IV bag, and another channel can branch off and lead to the hole 8940*b* used for detecting air. The other side of the cassette 8904 can have similar channels leading to the holes 8904*a*, 8942*a*, and 8944*a*. As discussed herein, the cassette 8904 can be removably attachable (e.g., using a screw) to the base member 8902, so that the cassette 8904 can be detached to provide access to the channels 8946 and to the light sources and light detector, if, for example, a component needs to be repaired or replaced.

Figure 96:
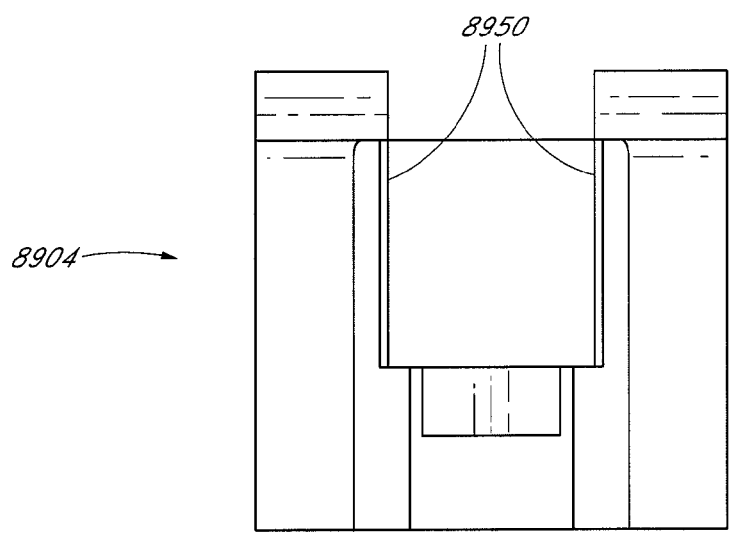
FIG. 96 is a front view of the cassette of FIG. 95.

The cassette 8904 can have side walls 8950 that are tapered similar to the cassette 4004 disclosed above. In the illustrated embodiment, the cassette 8904 has vertical side walls 8950 that are not tapered (as can be seen in FIG. 96).

Figure 97:
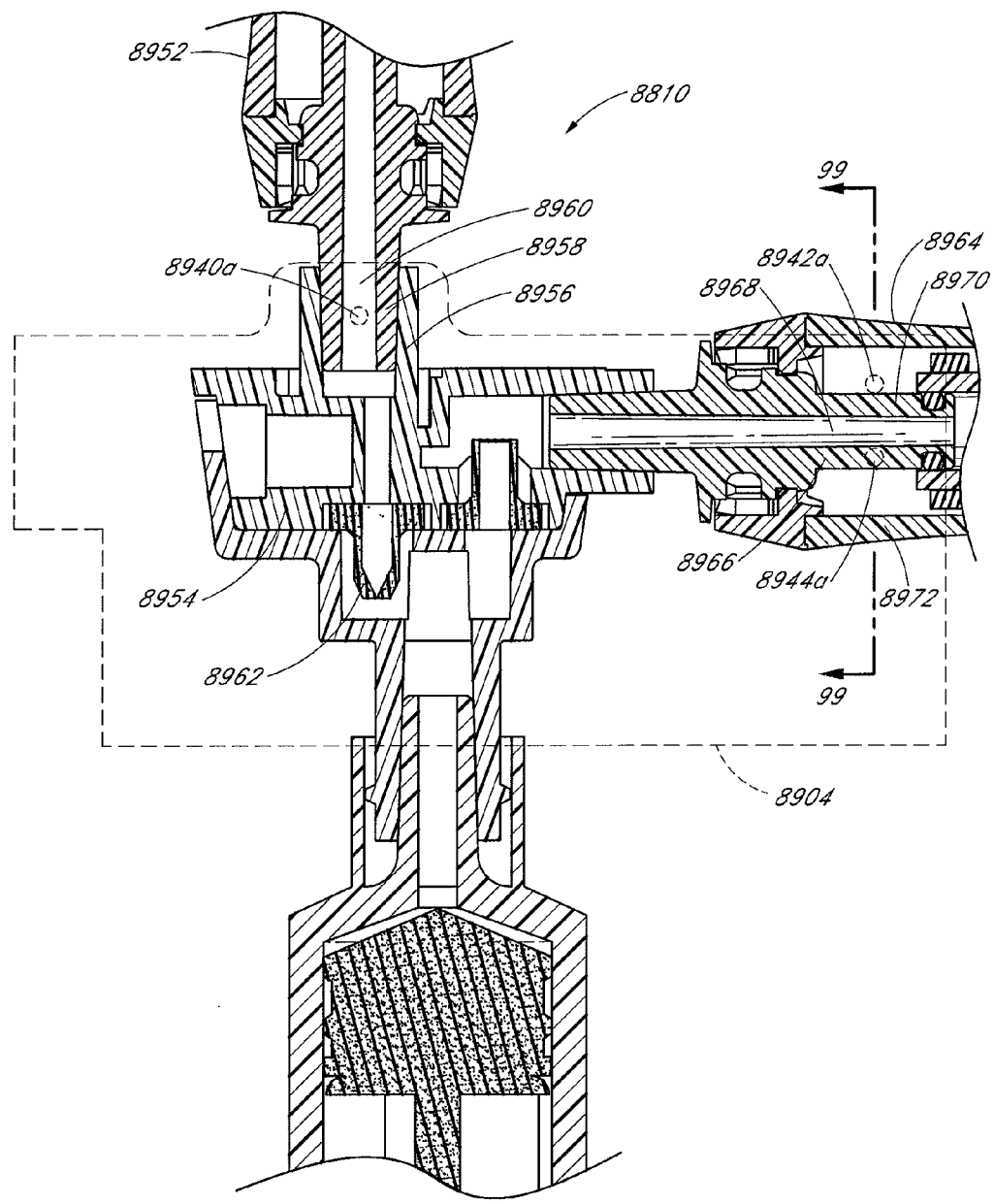
FIG. 97 is a cross sectional view of the connector shown in FIG. 88 with an outline of the cassette from FIG. 95.

FIG. 97 is a cross sectional view of the connector 8810 with an outline of the cassette 8904 shown in dotted lines. In the illustrated embodiment, the hole 8940*a* for the air sensor aligns with the fluid pathway through the transition between the source connector piece 8952 and the main connector body 8954. Thus, the light used to detect air passes through a wall of the female end 8956, through a wall of the male end 8958, through the fluid pathway 8960, then through an opposite wall of the male end 8958, and through an opposite wall of the female end 8956. At least a portion of the female end 8956 and at least a portion of the male end 8958 can be substantially transparent to the light used for the air sensor. In some cases, at least the entire pieces that are integrally formed with the female end 8956 and the male end 8958 can be substantially transparent to the light of the air sensor.

The air detection light can intersect the fluid pathway at a location of the fluid pathway between the source check valve 8962 and the source container (not visible in FIG. 97). In some cases, detecting air bubbles at a location upstream from the source check valve 8962 can reduce the occurrence of false air bubble reads which can result from the turbulent flow of fluid through the source check valve 8962 even when the source container has not run dry. In some embodiments, the light for the air sensor can pass through a fluid passageway that is less than about 4 millimeters wide, or less than about 2 millimeters wide; and the fluid passageway can be less than about quadruple the size, less than about triple the size, less than about double the size, or no larger than the hole 8940a associated with the light for the air sensor. By causing the light from the air sensor to cover a large portion of the fluid pathway, the sensor can more reliably identify the leading edge of air when the source container has run dry.

Figure 98:
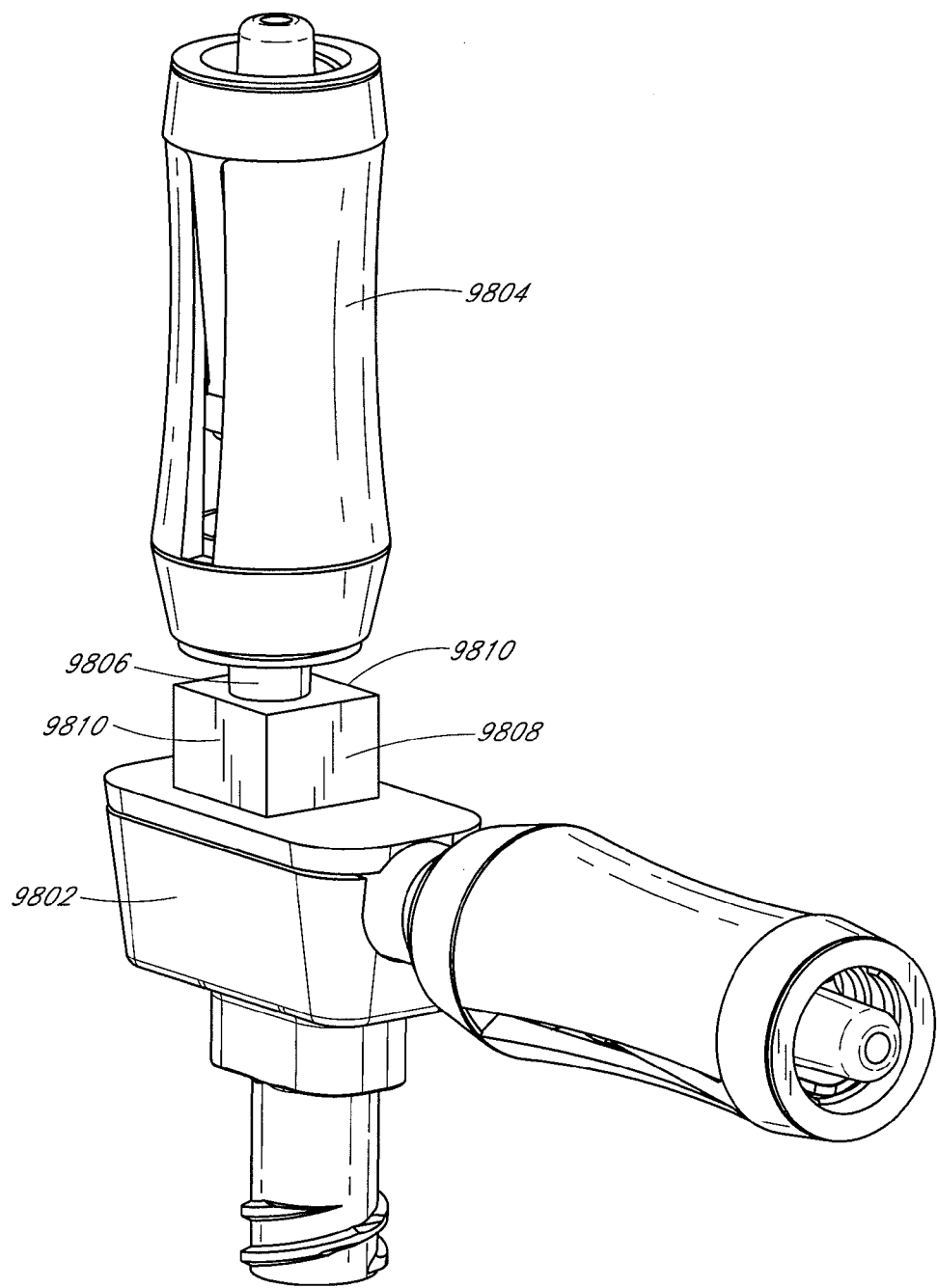
FIG. 98 is a perspective view of another example embodiment of a connector for transferring fluid.

FIG. 98 is a perspective view of a connector 9800 which can be similar to the connector 8810, or any other connector disclosed herein. A male end 9806 of the source connector piece 9804 can connect to a female end 9808 of the main body portion 9802 of the connector 9800. The female end 9808 can have substantially flat outer surfaces 9810 where the light from the air sensor intersects the female end 9808 to enter the connector 9800, so that the light enters the connector at a direction that is substantially normal to the surface 9810 (e.g., within about 10° or 5° or less of a direction normal to the surface 9810), thereby reducing the likelihood that the light will be refracted, or otherwise misdirected, away from the light sensor.

In the embodiment illustrated in FIG. 98, the inner surface of the female end 9808 is curved and tapered so as to receive the curved and tapered outer surface of the male end 9806. However, in some embodiments, additional surfaces that intersect the light from the air sensor can be flat. For example, at least a portion of the outer surfaces and the inner surfaces of the male end 9806 and at least a portion of the inner surfaces of the female end can also be flat. In some embodiments, each surface that the light for the air sensor passes through on the female end 9810 and the male end 9806 is a flat surface. In some embodiments, the male end 9806 and the female end 9808 can be substantially index matched when they are mated together, thereby reducing refraction, or other misdirection, of the light away from the corresponding sensor.

Returning now to FIG. 97, the target connector piece 8964 can align with the holes 8942a and 8944a which are associated with two optical sensors used for detecting an IV bag. In the illustrated embodiment, two optical sensors can be used to determine whether an IV bag is attached to the target connector piece 8964. As shown in FIG. 97 by the positions of the holes 8942a and 8944a, a first light path can pass through the target connector piece 8964 at a location above the outside surface of the plunger 8966, and a second light path can pass through the side wall of the plunger 8966. As similarly explained in connection with FIG. 19D, when no IV bag is attached to the target connector 8964, the valve member 8970 can be positioned in an open position, as shown in FIG. 97, to allow light to pass through the transparent components of the target connector piece 8964 to the corresponding light detectors. When the light detectors detect the light, they can provide a signal indicating that the no target container is attached to the target connector piece 8964. In response to that signal, a controller can stop or prevent the transfer of fluid thereby preventing fluid (e.g., hazardous chemotherapy drugs) from being sprayed out of the target connector piece 8964 when no IV bag is attached thereto. In a manner similar to that discussed in connection with FIG. 19E, when a connector of an IV bag assembly is attached to the target connector piece 8964, the valve member 8970 can be displaced to an open position in which an opaque portion of the valve member 8970 is positioned in between the holes 8942a and 8942b and also between the holes 8944a and 8944b, to block light of the optical sensors from reaching the light detectors. When the light detectors do not detect the light, they can provide a signal indicating that a target container is attached to the target connector piece 8964. In response to the signal, a controller can begin, resume, or allow the transfer of fluid through the connector.

In some embodiments, the connector 8810 can attach to the transfer station with some freedom of movement. Thus, in some instances, the light paths may not align at the precise locations shown. In some instances, one of the light paths may intersect the fluid pathway 8968 through the plunger 8966. Accordingly, a frequency of light can be used that is not blocked by the fluid (e.g., chemotherapy drugs) being transferred through the connector 8810. In some embodiments, a wavelength of light can be used that transmits well through water or saline, which can be used as a solvent or diluent for the drugs. In some embodiments, visible light can be used (e.g., red colored light). In some embodiments, light can be used for IV bag detection that has a wavelength of at least about 545 nanometers and/or no more than about 745 nanometers, or of at least about 615 nanometers and/or no more than about 675 nanometers, or of about 645 nanometers.

The embodiment of FIG. 97 includes two optical sensors for detecting an IV bag, and the controller can be configured to only allow fluid to be transferred through the target connector piece 8964 when both of the light detectors do not detect light from their corresponding light sources. While no IV bag is attached, if light from one of the optical sensors is unintentionally blocked or diverted away from the corresponding light detector, the light from the other optical sensor can reach its corresponding light detector, thereby preventing a false read in which the controller receives a signal that an IV bag is attached when no IV bag is present. Light from one of the optical sensors can be unintentionally blocked or diverted by various different causes.

As mentioned above, in some cases, the connector 8810 can connect to the fluid transfer station with some freedom of movement. Thus, in some instances, one of the light beams from one of the optical sensors may strike the curved housing 8972 of the target connector piece 8964 at a location other than at the locations shown in FIG. 97 associated with the holes 8942a and 8944a. If the connector is shifted enough from the position shown in FIG. 97, one of the light beams can strike the curved housing 8972 at a sufficiently oblique angle so that the light is reflected, refracted, or otherwise unintentionally diverted from its normal substantially linear path through the target connector piece 8964. Thus, the light can fail to reach the corresponding light detector even when the valve member 8970 is in the closed position.

The light path formed between the holes 8942a and 8942b can be spaced from the light path formed between the holes 8944a and 8944b in a direction transverse to the longitudinal axis of the target connector portion. The distance can be sufficient so that if one of the light paths intersects the curved housing 8972 at an angle that is oblique enough to divert the light, the other light path will travel through the target connector piece 8964 at a location close enough to the longitudinal axis so that the light strikes the curved housing 8972 at an angle that is close enough to normal so that the light is not diverted away from the corresponding light detector. For example, the holes 8944a and 8944b can be positioned substantially directly below the holes 8942a and 8942b. The hole 8944a can be spaced away from the hole 8942a by a distance of at least about 2 millimeters and/or no more than about 6 millimeters, or by about 4 millimeters. The hole 8944b can be spaced away from the hole 8942b by substantially the same distance.

As similarly discussed above, in some embodiments, the connector 8810 can be secured to the top connector 8816 such that it has little or no freedom of movement so that the connector 8810 can reliably be aligned with the optical sensors.

FIGS. 99-104 are cross sectional views of the target connector piece 8964 taken along the line 99-99 in FIG. 97. FIGS. 99-104 show how different rotational positions for the housing 8972 can affect the light of the two optical sensors. As previously discussed, the housing 8972 of the target connector piece 8964 can have gaps 8974*a-b* formed therein. In some embodiments, the light of one of the optical sensors can be scattered, reflected, refracted, or otherwise unintentionally blocked from reaching the corresponding light detector when an edge of one of the gaps 8974*a-b* is positioned between the light source and light detector. For example, the edges of the housing 8972 at the gaps 8974*a-b* can have a generally rough surface that scatters light so that the edges are substantially opaque to the light from the optical sensors.

The optical sensors and the corresponding holes 8942*a-b* and 8944*a-b* can be positioned such that if one light path is obstructed by one of the gaps 8974*a-b*, the other light path will not be obstructed. For example, in some embodiments, the light paths can be spaced from the center of the target connector piece 8964 by different amounts. For example, a first light path can be spaced about 3 millimeters from the center of the target connector piece 8964 and a second light path can be space about 1 millimeter from the center of the target connector piece 8964 in the opposite direction. Other orientations are also possible.

Figure 99:
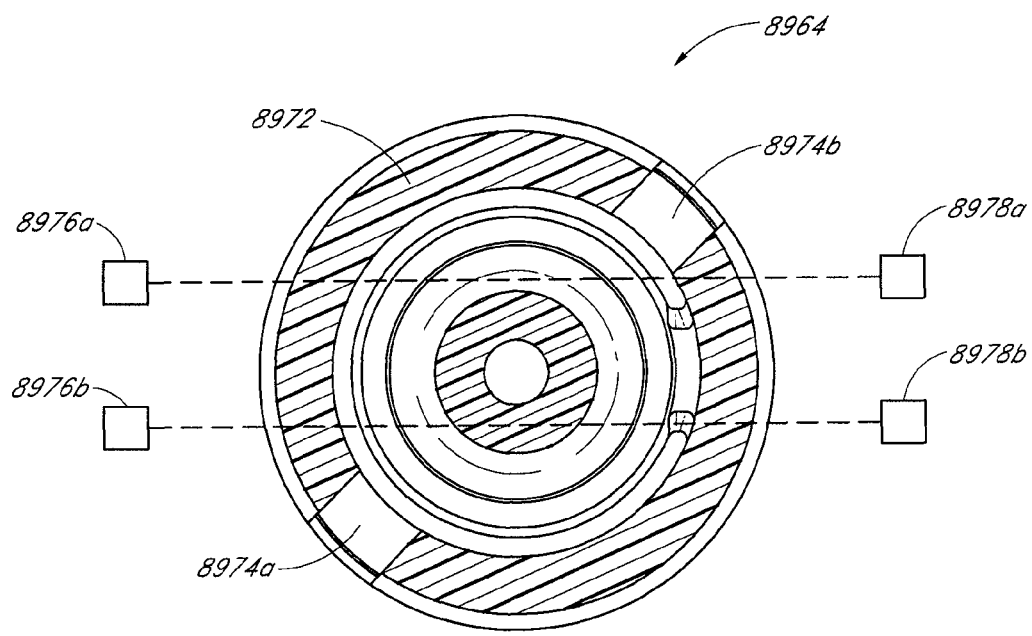
FIGS. 99-104 are cross sectional views of the target connector piece taken along the line 99-99 of FIG. 97 with the housing positioned as various different rotational positions.

When the housing 8972 is oriented as shown in FIG. 99, the light from the first light source 8976*a* can travel through the target connector piece 8964 to the first light detector 8978*a* without obstruction. Similarly, light from the second light source 8976*b* can travel through the target connector piece 8964 to the second light detector 8978*b* without obstruction. It will be understood that although the light can refract as it passes through certain surfaces of the target connector piece 8964, the light can follow a substantially linear pathway between the light sources 8976*a-b* and the corresponding light detectors 8978*a-b*, as shown by the dotted lines in FIG. 99.

Figure 100:
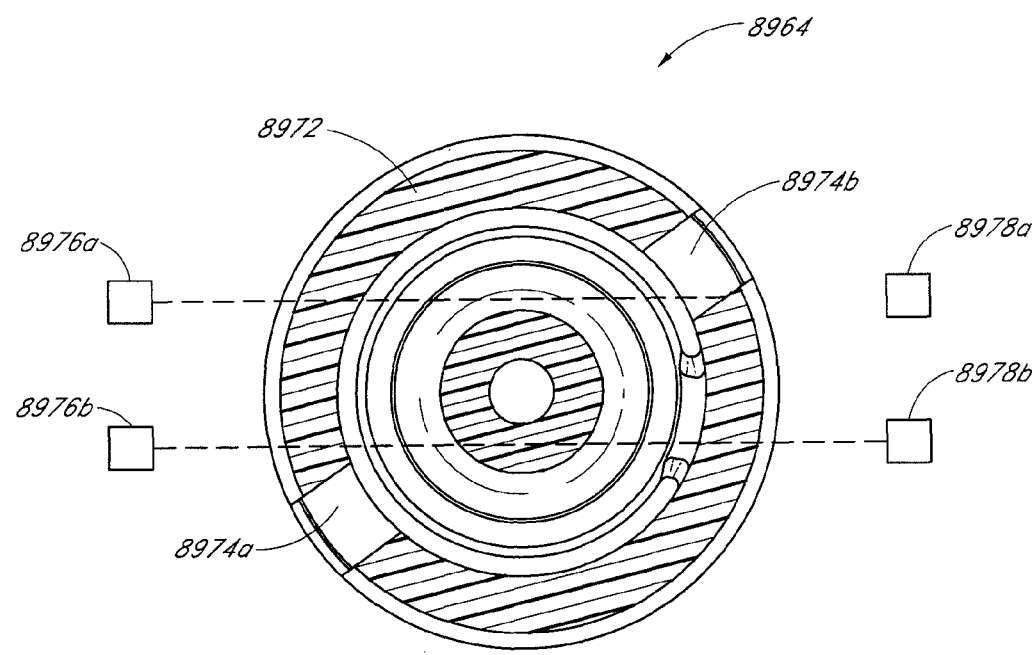

If the housing 8972 is rotated to the position shown in FIG. 100, the light from the first light source 8976*a* can strike an edge of the gap 8974*b* and be blocked from reaching the first light detector 8978*a*. However, the light from the second light source 8976*b* can pass through the target connector piece 8964 to the second light detector unobstructed.

Figure 101:
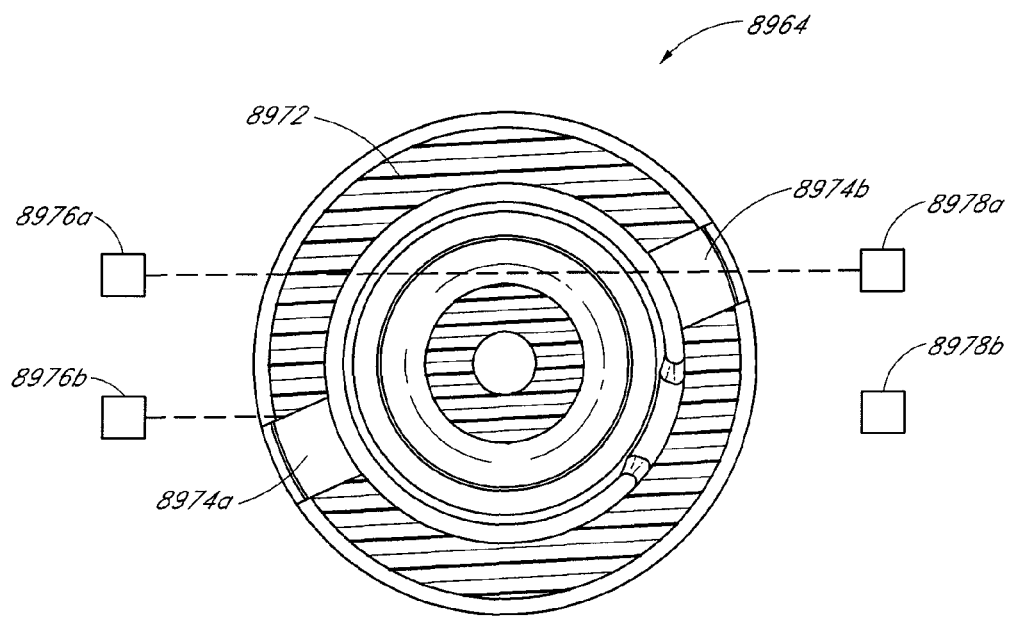

If the housing 8972 is further rotated to the position shown in FIG. 101, the light from the second light source 8976*b* can be obstructed by an edge of the gap 8974*a*. However, in this orientation, the light from the first light source 8976*a* can pass through the gap 8974*b* without being obstructed by the edges thereof.

Figure 102:
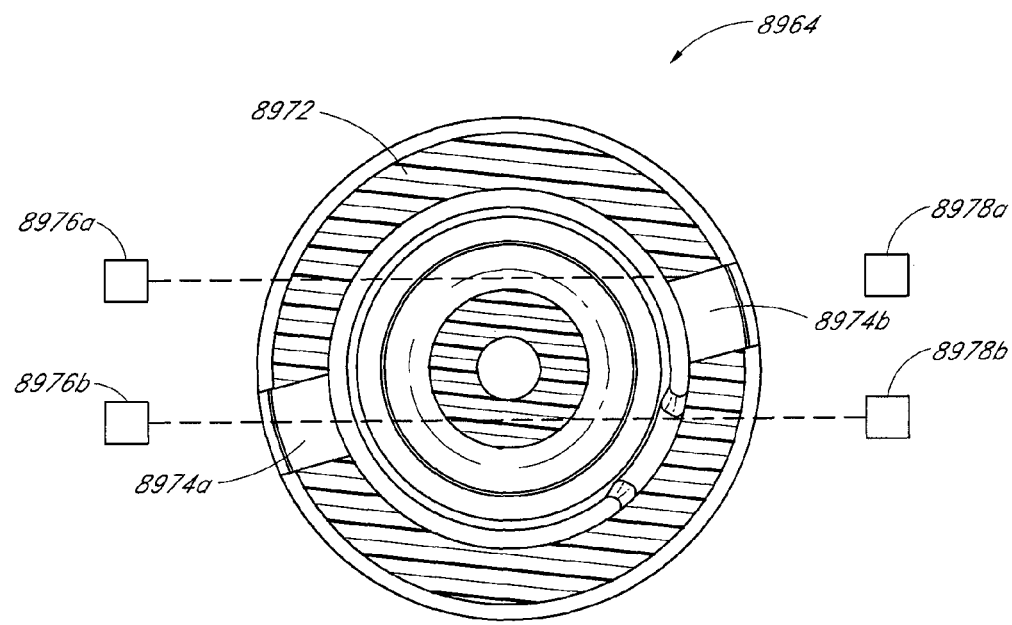

If the housing 8972 is further rotated to the position shown in FIG. 102, the light from the first light source 8976*a* can be obstructed by an edge of the gap 8974*b*. However, the light from the second light source 8976*b* can pass through the gap 8974*a* without being obstructed by the edges thereof.

Figure 103:
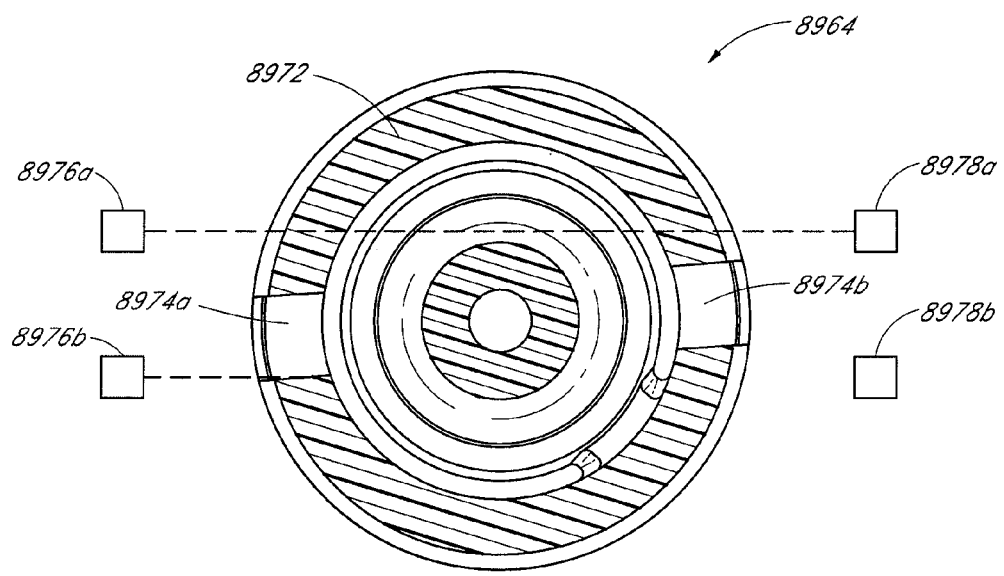

If the housing 8972 is further rotated to the position shown in FIG. 103, the light from the second light source 8976*b* is obstructed by an edge of the gap 8974*a*. However, the light from the first light source 8976*a* can pass through the target connector piece 8964 to the first light detector 8978*a* without being obstructed, as shown.

Figure 104:
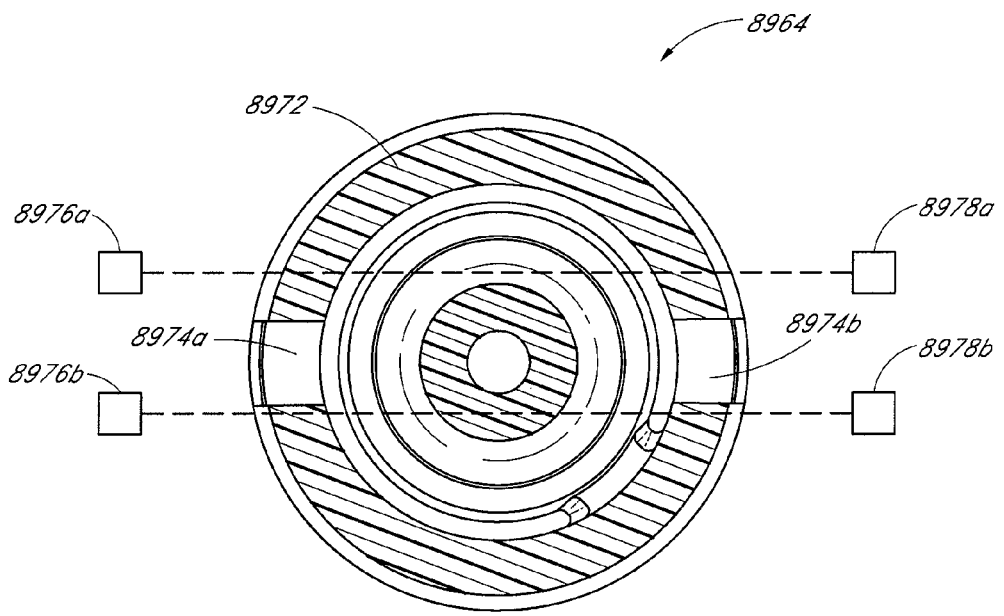

If the housing 8972 is further rotated to the position shown in FIG. 104, the light from both light sources 8976*a-b* can pass through the target connector portion 8964 to the corresponding light detectors 8978*a-b*, as shown.

In some embodiments, the target connector portion can be configured to be used with a single optical sensor for detecting whether the valve member is open or closed. For example, the target connector portion can be modified so that the gaps between the walls of the housing do not intersect the light path of the optical sensor.

Figure 105:
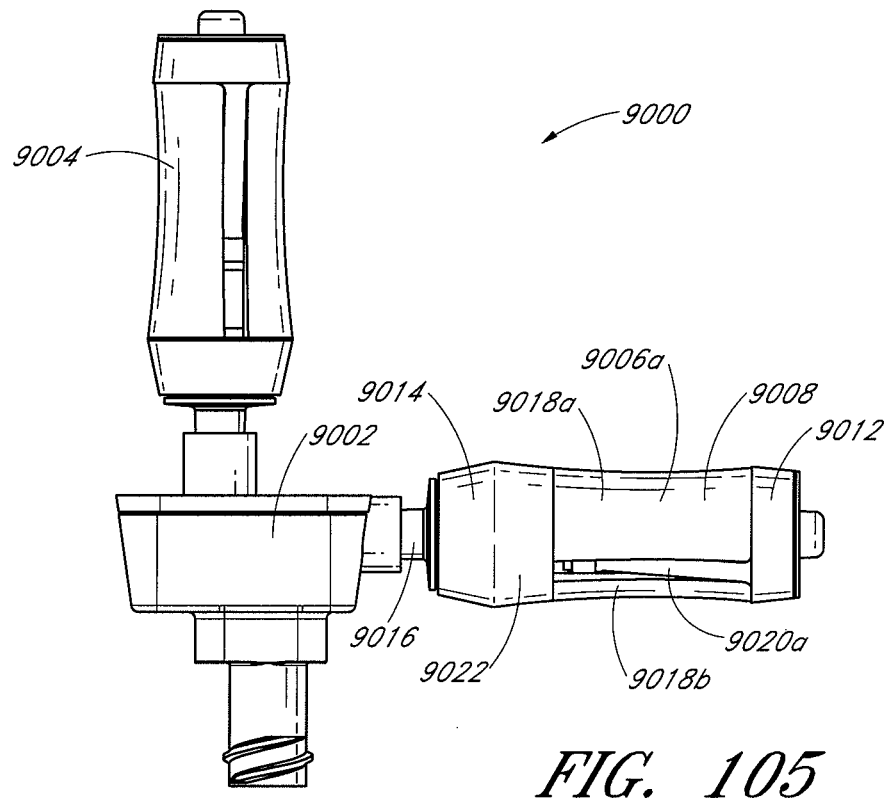
FIG. 105 is a side view of another example embodiment of a connector that can be used to transfer fluid.
Figure 106:
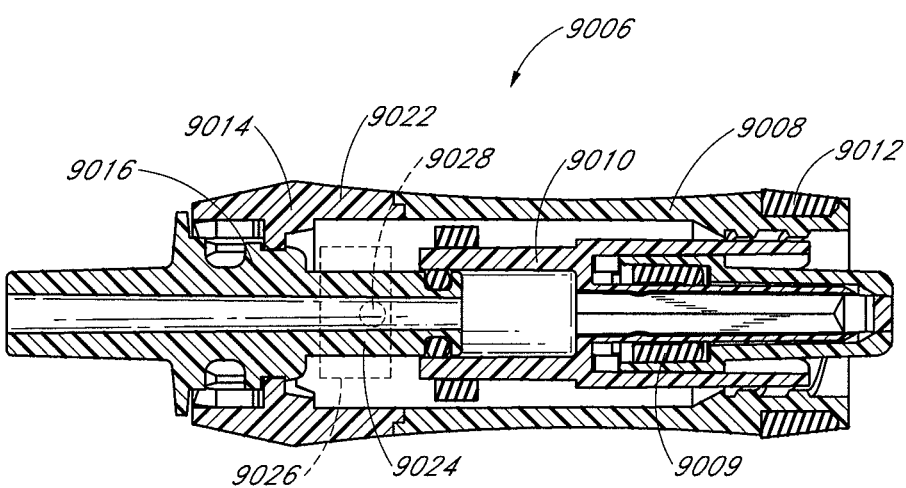
FIG. 106 is a cross sectional view of the target connector portion of the connector of FIG. 105.

FIG. 105 is a side view of another example embodiment of a connector 9000 which can be similar to, or the same as, the connector 8810, the connector 3910, the connector 320, or any other suitable connector discussed herein. The connector 9000 can include a main body portion 9002, a source connector portion 9004, and a target connector portion 9006, which can be similar to, or the same as, the corresponding components in, for example, the connector 8810, the connector 3910, or the connector 320. The target connector portion 9006 can be similar to the target connector portion 338 discussed above, and much of the disclosure relating to the target connector portion 338 also applies to the target connector portion 9006. FIG. 106 is a cross sectional view of the target connector portion 9006.

With further reference to FIGS. 105 and 106, the target connector portion 9006 can include a housing 9008, a sealing ring 9009, a valve member 9010, a resilient member 9012, a first end cap member 9014, and a second end cap member 9016. The sealing ring 9009, valve member 9010, resilient member 9012, and second end cap member 9016 can be the same as the corresponding components of the target connector portion 338. The first end cap member 9014 can be a modified version of the first end cap member 405 of the target connector portion 338. The first end cap member 9014 can have forward wall portion 9022 that surrounds a portion of the plunger 9024 on the second end cap member 9016 when assembled. The housing 9006 can include a first wall 9018*a* and a second wall 9018*b* with gaps 9020*a-b* formed therebetween to accommodate the elongate elastic members of the resilient member 9012.

The housing 9006 can attach to the ends of the forward wall portion 9022 by sonic welding, adhesive, mechanical attachments, or any other suitable manner. The target connector portion can be attached to a corresponding fluid transfer station that includes one or more optical sensors so that the light path of the optical sensor passes through the forward wall portion 9022. The first end cap member 9014 can be substantially transparent, and in some cases, the second end cap member 9016 can be substantially transparent as well. For example, the light path can pass through the target connector portion 9006 at a location within the area 9026 shown in dotted lines in FIG. 106. In some cases, the light path can pass through the target connector portion 9006 at about the centerline through the connector (e.g., at location 9028) such that the light enters and exits the curved surfaces of the forward wall portion 9022 at a direction that is substantially normal to the surfaces, thereby reducing the occurrence of unintentional redirecting of the light. Because the housing 9008 does not extend back into the light path, the gaps 9020*a-b* in the housing 9008 do not obstruct the light. The forward wall portion 9022 can be an unbroken, generally cylindrical wall, at least in the area that intersects the light path of the optical sensor. Thus, a single optical sensor can be used to determine whether the valve member 9010 is in the open or closed configuration.

Figure 107:
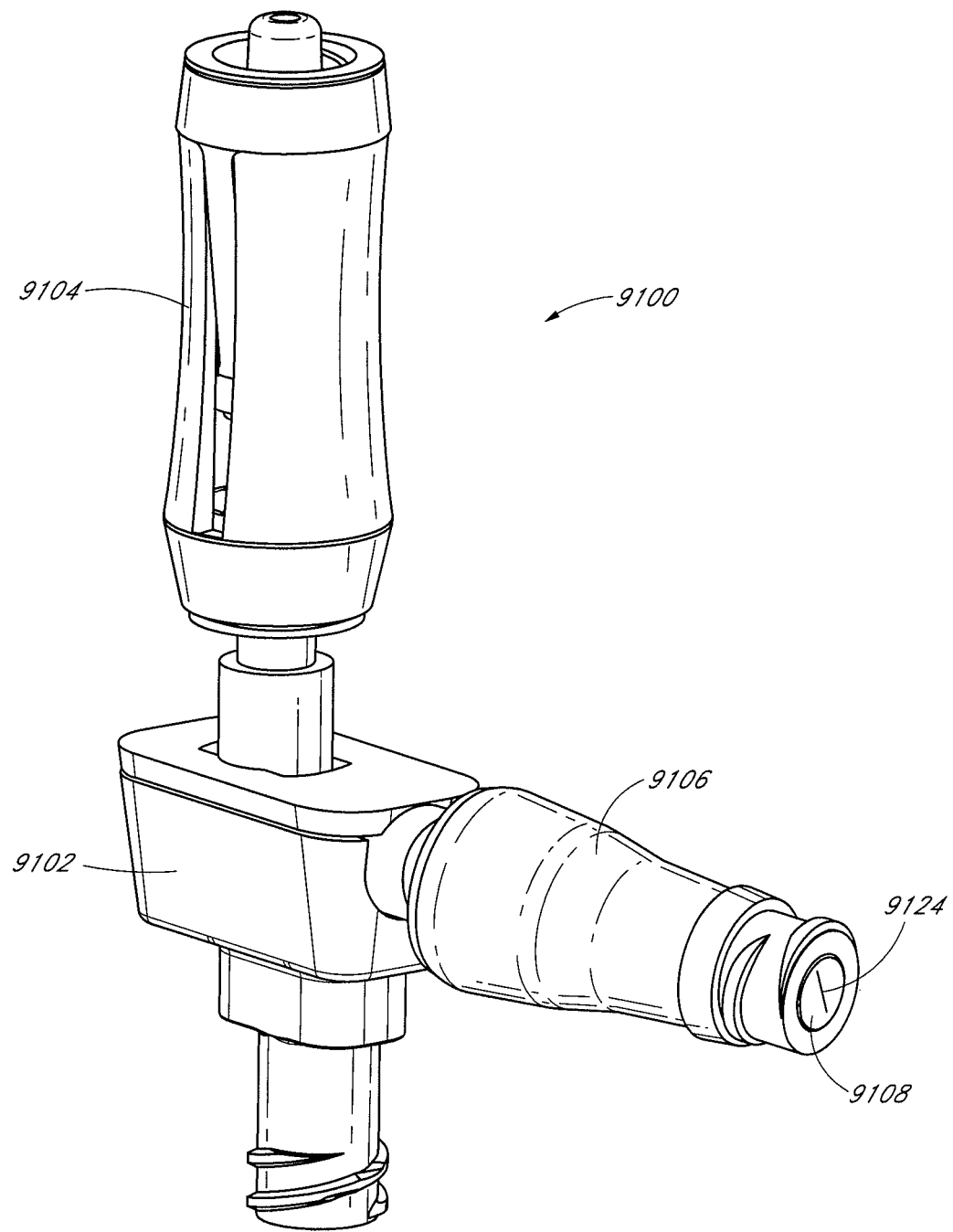
FIG. 107 is a perspective view of another example embodiment of a connector that can be used to transfer fluid.

Many different connector types can be used for the source connector portion and/or the target connector portion of the various connectors disclosed herein. Various other connector types can include a valve member, or other movable component, that can be transitioned in and out of the light path of an optical sensor to indicate whether an IV bag is attached to the connector. FIG. 107 is a perspective view of an example embodiment of a connector 9100. The connector 9100 can include a main body portion 9102, a source connector portion 9104, and a target connector portion 9106. The connector 9100 that can be similar to the connector 3910 or 8810 except that the target connector portion 9106 can be a version of the Clave® connector manufactured by ICU Medical, Inc., of San Clemente, Calif. Various embodiments of a connector of this type are described in the '866 patent. Additional details and alternatives are also provided in U.S. Provisional Patent Application No. 61/345,554, filed May 17, 2010, the entirety of which is hereby incorporated by reference herein.

The target connector portion 9106 can include a valve member 9108 disposed therein, which can transition between a closed position when no IV bag is attached thereto and an open position when an IV bag is attached thereto.

Figure 108:
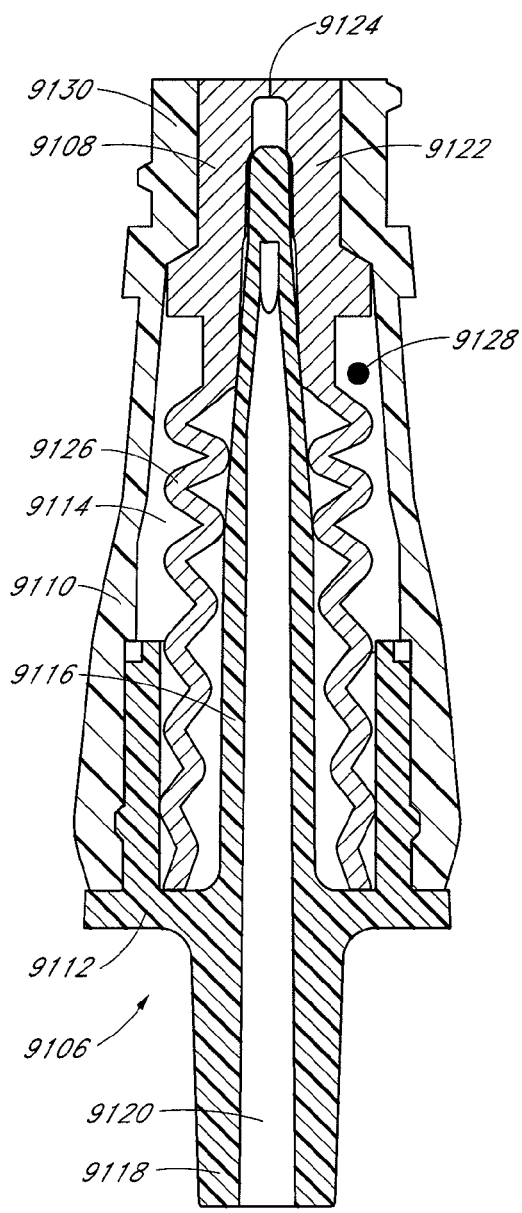
FIG. 108 is a cross sectional view of the target connector portion of the connector of FIG. 107 with the valve member in the closed position and an unobstructed light path.
Figure 109:
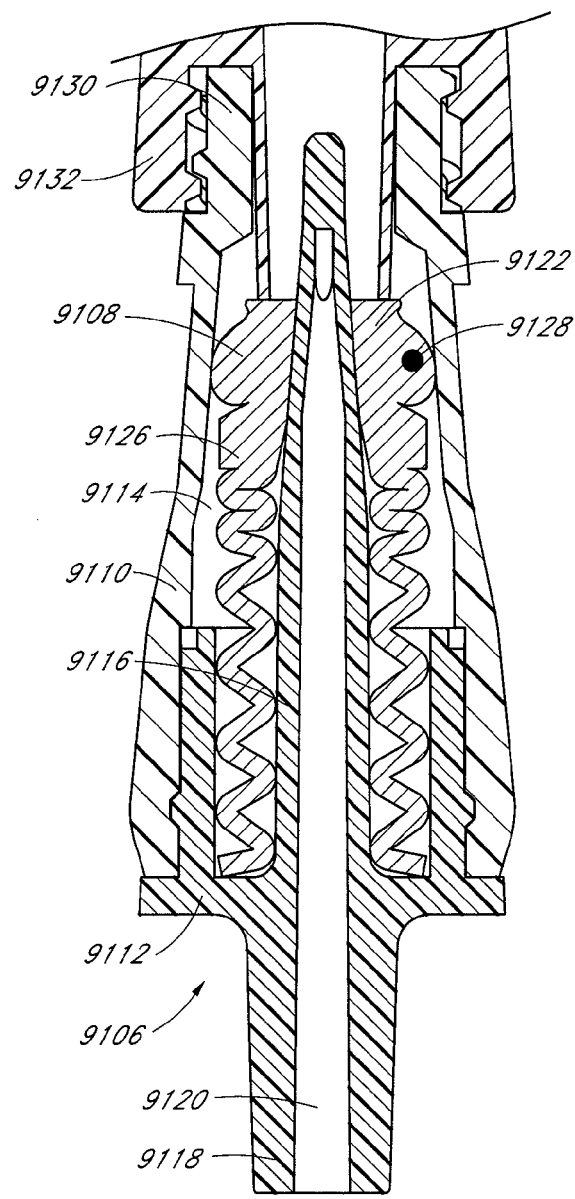

FIG. 108 is a cross sectional view of the target connector portion 9106 with the valve member 9108 in the closed configuration. FIG. 109 is a cross sectional view of the target connector portion 9106 with the valve member 9108 in the open configuration.

A housing member 9110 can attach to a base 9112 to define an interior chamber 9114 therein. The base can have a spike 9116 extending into the interior chamber 9114 and a male end 9118 extending generally opposite the spike 9116. A fluid pathway 9120 can run through the spike 9116 and male end 9118. The valve member 9108 can have a head 9122 that includes a slit 9124 therein. A resiliently compressible valve body 9126 can include a series of accordion sections or O-rings to bias the valve member 9108 toward the closed position. The end of the housing 9110 can be a female luer 9130 configured to receive a male luer end 9132 associated with, for example, an IV bag assembly.

In some embodiments, the housing member 9110, or at least a portion thereof, can be substantially transparent, and the valve member, or at least a portion thereof, can be substantially opaque. Light from an optical sensor can pass through the housing 9110 and the interior chamber 9114 at a location 9128. When the valve member 9108 is in the closed configuration, the light can travel through the target connector portion 9106 substantially unobstructed, to provide a signal indicating that the valve member 9108 is closed and no target container is attached. When the valve member 9108 is in the open configuration, it can be positioned in the light path such that the light is blocked from reaching the light detector. The light detector can then provide a signal indicating that the valve member 9108 is in the open configuration and a target container is attached thereto.

Figure 110:
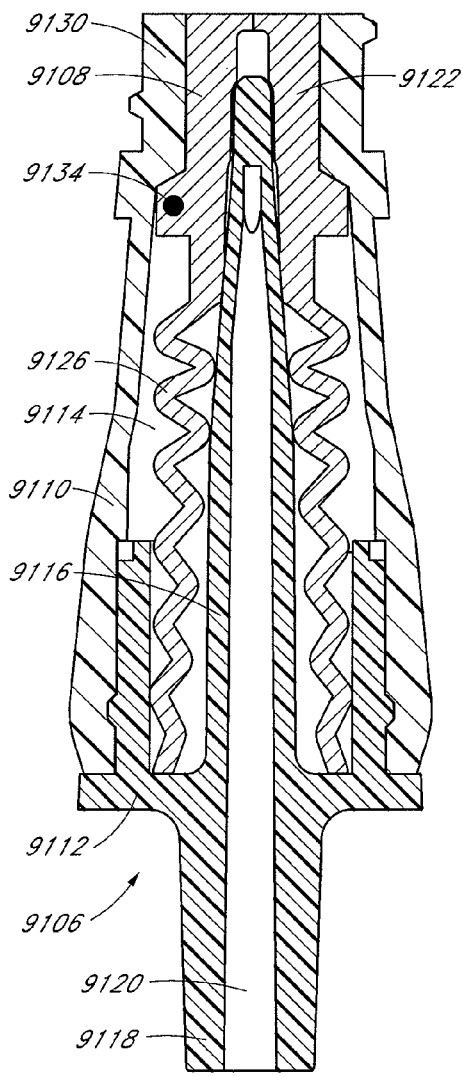
Figure 111:
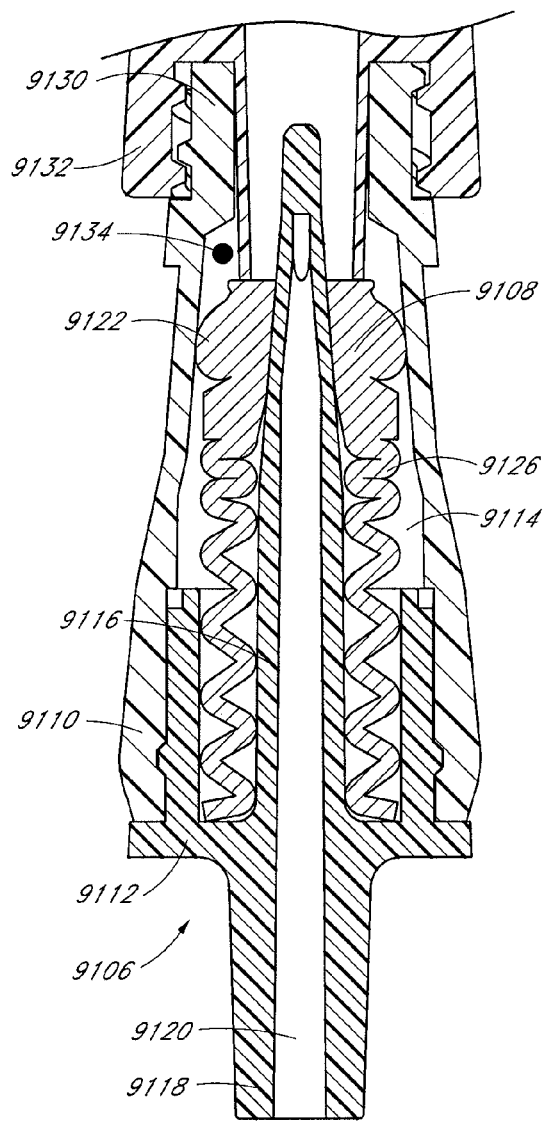

In some embodiments, the target connector portion can include an interaction portion. For example, in some embodiments, the interaction portion can comprise a generally opaque outer housing or can comprise a generally transparent outer housing and an internal generally opaque moveable portion. The optical sensor can be configured such that light is obstructed when the valve member is in the closed configuration and the light is permitted to pass to the light detector substantially unobstructed when the valve member is in the open configuration. For example, FIG. 110 is a cross sectional view of the target connector portion 9106 with the light path of the optical sensor passing through the target connector portion 9106 at a location 9134 that is blocked by the valve member 9108 when the valve member 9108 is closed (as shown in FIG. 110) and is substantially unobstructed when the valve member 9108 is open (as shown in FIG. 111). Accordingly, the controller can be configured to allow fluid transfer when the light detector is able to detect light transmitted through the target connector portion 9106 indicating that a source container is present, and the controller does not allow fluid transfer when the light detector does not detect the light.

It will be understood that various other types of connectors can be used for the target connector portion 9106 and can have a location where a light path is obstructed when the connector is in a first state (e.g., open or closed) and the light path is substantially unobstructed when the connector is in a second state (e.g., closed or open). Other variations are possible. In some embodiments, the optical sensor can be positioned to align with the connector of the IV bag assembly, or some other opaque portion of the IV bag assembly, such that when the IV bag assembly is present, the light is blocked from reaching the light detector to thereby generate a signal to allow fluid transfer.

Although many features of the embodiments shown in the Figures are specifically called out and described, it will be understood that additional features, dimensions, proportions, relational positions of elements, etc. shown in the drawings are intended to make up a part of this disclosure even when not specifically called out or described. Although forming part of the disclosure, it will also be understood that the specific dimensions, proportions, relational positions of elements, etc. can be varied from those shown in the illustrated embodiments.

Embodiments have been described in connection with the accompanying drawings. However, it should be understood that the foregoing embodiments have been described at a level of detail to allow one of ordinary skill in the art to make and use the devices, systems, etc. described herein. A wide variety of variation is possible. Components, elements, and/or steps may be altered, added, removed, or rearranged. Additionally, processing steps may be added, removed, or reordered. While certain embodiments have been explicitly described, other embodiments will also be apparent to those of ordinary skill in the art based on this disclosure.

Some aspects of the systems and methods described herein can advantageously be implemented using, for example, computer software, hardware, firmware, or any combination of software, hardware, and firmware. Software can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

While certain embodiments have been explicitly described, other embodiments will become apparent to those of ordinary skill in the art based on this disclosure. Therefore, the scope of the invention is intended to be defined by reference to the claims as ultimately published in one or more publications or issued in one or more patents and not simply with regard to the explicitly described embodiments.

The following is claimed:

1. A fluid transfer module for use with a substantially entirely closed system for the transfer of medical fluids between or among different medical fluid containers by an electronically controlled fluid dispensing system, the fluid transfer module comprising:
   a first interface configured to be connected in fluid communication with a fluid source container, the first interface comprising a first selectively openable and closeable aperture that is configured to substantially entirely prevent fluid within the fluid transfer module from escaping through the first aperture when the first aperture is closed;
   a second interface configured to be connected in fluid communication with a fluid destination container, the second interface comprising a second selectively openable and closeable aperture that is configured to substantially entirely prevent fluid within the fluid transfer module from escaping through the second aperture when the second aperture is closed;
   an intermediate container, or an intermediate interface configured to be connected to an intermediate container;
   a first valve configured to permit the passage of fluid from the fluid source container to the intermediate container and configured to generally obstruct the passage of fluid from the intermediate container to the fluid source container; and
   a second valve configured to permit the passage of fluid from the intermediate container to the fluid destination container and to generally obstruct the passage of fluid from the fluid destination container to the intermediate container;
   wherein the fluid transfer module is configured to be removably attachable to an electronically controlled fluid dispensing system;
   wherein an interaction portion of the fluid transfer module comprises a generally transparent housing portion and a generally opaque, generally rigid valve portion, the interaction portion being connected to the fluid transfer module such that the interaction portion is configured to permit the electronically controlled fluid dispensing system to detect that the second aperture is open when the valve portion moves into a light path in the electronically controlled fluid dispensing system; and
   wherein the fluid transfer module is configured to substantially prevent fluid within the fluid transfer module from escaping upon disconnection of the fluid transfer module from the fluid source container and the fluid destination container.

2. The combination of an electronically controlled fluid dispensing system and the fluid transfer module of claim 1 removably attached to the electronically controlled fluid dispensing system.

3. The fluid transfer module of claim 1, further comprising a fluid source container in fluid communication with the first interface.

4. The fluid transfer module of claim 1, further comprising a vial adapter configured to removably connect to the first interface between the fluid transfer module and the fluid source container, wherein the vial adapter comprises a selectively openable and closeable fluid passage that substantially prevents fluid within the vial adapter from escaping after the vial adapter is detached from the first interface.

5. The fluid transfer module of claim 1, further comprising a fluid destination container in fluid communication with the second interface.

6. The fluid transfer module of claim 1, wherein a second interaction portion of the fluid transfer module is configured to permit the electronically controlled fluid dispensing system to detect that at least a portion of the fluid transfer module is attached to the electronically controlled fluid dispensing system, and wherein the second interaction portion of the fluid transfer module comprises a generally opaque outer housing.

7. The electronically enabled fluid transfer system of claim 2, wherein the electronically controlled fluid dispensing system is capable of detecting air bubbles in the fluid transfer module.

8. The fluid transfer module of claim 1, wherein the first interface is a closeable male luer connector, or wherein the second interface is a closable male luer connector.

9. The fluid transfer module of claim 1, wherein the fluid transfer module is configured to transfer chemotherapy fluids.

10. The fluid transfer module of claim 1, further comprising an intermediate container configured to connect to the intermediate interface.

11. The fluid transfer module of claim 1, wherein the second interface comprises a valve member movable between a closed position and an open position, the valve member configured to be in the open position when the fluid destination container is attached to the second interface, and the valve member configured to close automatically when the fluid destination container is detached from the second interface.

12. A method of providing a disposable fluid transfer system for use with a substantially entirely closed system for the transfer of medical fluids between or among different medical fluid containers by an electronically controlled fluid dispensing system, the disposable fluid transfer system configured to be removably attachable to the electronically controlled fluid dispensing system, the method comprising:
   providing a fluid transfer system comprising:
      a first connector configured to be connected in fluid communication with a first fluid container, the first connector comprising a first sealing aperture that is configured to resist fluid within the disposable fluid transfer system from passing through the first sealing aperture when the first sealing aperture is closed;
      a second connector configured to be connected in fluid communication with a second fluid container, the second connector comprising a second sealing aperture that is configured to resist fluid within the disposable fluid transfer system from passing through the second sealing aperture when the second sealing aperture is closed;
      a measuring region, or an interface configured to be connected to a measuring region;
      a first valve configured to permit the passage of fluid from the first fluid container to the measuring region and configured to generally obstruct the passage of fluid from the measuring region to the first fluid container;
      a second valve configured to permit the passage of fluid from the measuring region to the second fluid container and to generally obstruct the passage of fluid from the second fluid container to the measuring region; and
      an interaction portion comprising a generally transparent housing portion and a generally opaque portion on a generally rigid valve portion, the interaction portion forming a portion of the disposable fluid transfer system such that the interaction portion is configured to permit the electronically controlled fluid dispensing system to detect the condition of the second sealing aperture when the valve portion moves into a light path in the electronically controlled fluid dispensing system; and instructing a user to removably attach the disposable fluid transfer system to an electronically controlled fluid dispensing system; and wherein the disposable fluid transfer system is configured to resist fluid within the disposable fluid transfer system from passing outside of the disposable fluid transfer system upon disconnection of the disposable fluid transfer system from the first fluid container and the second fluid container.

13. The method of claim 12, further comprising providing the electronically enabled fluid transfer system.

14. The method of claim 12, further comprising providing the first fluid container.

15. The method of claim 12, further comprising providing an adapter configured to removably connect to the first connector between the disposable fluid transfer system and the first fluid container, wherein the adapter comprises a sealing aperture that is configured to resist fluid within the adapter from passing through the sealing aperture of the adapter after the adapter is detached from the first connector.

16. The method of claim 12, further comprising providing the second fluid container.

17. The method of claim 12, further comprising providing a selectively closeable fluid connector configured to removably connect to the second connector between the disposable fluid transfer system and the IV bag, wherein the selectively closeable fluid connector is configured to resist fluid within the IV bag from passing through the selectively closeable fluid connector after the IV bag is detached from the second connector.

18. The method of claim 12, wherein the electronically controlled fluid dispensing system comprises a light emitter and a light detector, and wherein the electronically controlled fluid dispensing system is configured to detect the condition of the second sealing aperture is open by detecting that light emitted from the light emitter has not been detected by the light detector.

19. The method of claim 12, wherein the interaction portion of the disposable fluid transfer system comprises at least a portion of a closeable male luer connector.

20. The method of claim 12, further comprising connecting the first connector to the first fluid container, or further comprising connecting the second connector to the second fluid container.

21. The method of claim 12, wherein the electronically controlled fluid dispensing system is capable of detecting air bubbles in the disposable fluid transfer system.

22. The method of claim 12, further comprising providing the measuring region connected to the interface.

23. The method of claim 12, wherein the second connector comprises a valve member movable between a closed position and an open position, the valve member configured to be in the open position when the second fluid container is attached to the second connector, and the valve member configured to close automatically when the second fluid container is detached from the second connector.

* * * * *